United States Patent
Brizgys et al.

(10) Patent No.: US 11,851,419 B2
(45) Date of Patent: Dec. 26, 2023

(54) GLP-1R MODULATING COMPOUNDS

(71) Applicant: Gilead Sciences, Inc., Foster City, CA (US)

(72) Inventors: Gediminas J. Brizgys, San Carlos, CA (US); James S. Cassidy, San Francisco, CA (US); Chienhung Chou, Dublin, CA (US); Jeromy J. Cottell, Redwood City, CA (US); Chao-I Hung, San Mateo, CA (US); Kavoos Kolahdouzan, San Francisco, CA (US); James G. Taylor, Burlingame, CA (US); Nathan E. Wright, San Diego, CA (US); Zheng-Yu Yang, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 5 days.

(21) Appl. No.: 17/530,300

(22) Filed: Nov. 18, 2021

(65) Prior Publication Data

US 2022/0177449 A1 Jun. 9, 2022

Related U.S. Application Data

(60) Provisional application No. 63/134,505, filed on Jan. 6, 2021, provisional application No. 63/116,630, filed on Nov. 20, 2020.

(51) Int. Cl.
| | | |
|---|---|---|
| C07D 401/14 | (2006.01) | |
| A61K 45/06 | (2006.01) | |
| C07D 405/14 | (2006.01) | |

(52) U.S. Cl.
CPC ............ C07D 401/14 (2013.01); A61K 45/06 (2013.01); C07D 405/14 (2013.01)

(58) Field of Classification Search
CPC .......................... C07D 401/14; C07D 405/14
See application file for complete search history.

(56) References Cited

U.S. PATENT DOCUMENTS

| | | | |
|---|---|---|---|
| 10,208,019 B2* | 2/2019 | Aspnes | .............. A61P 19/02 |
| 10,543,212 B2 | 1/2020 | Matsunaga et al. | |
| 10,954,221 B2 | 3/2021 | Zhong et al. | |
| 2017/0035881 A1 | 2/2017 | Lannutti et al. | |
| 2018/0170908 A1 | 6/2018 | Aspnes et al. | |
| 2020/0325121 A1 | 10/2020 | Zhong et al. | |
| 2021/0023072 A1 | 1/2021 | Freeman et al. | |
| 2021/0171499 A1 | 6/2021 | Ammann et al. | |
| 2022/0288030 A1 | 9/2022 | Ammann et al. | |
| 2022/0298148 A1 | 9/2022 | Brizgys et al. | |
| 2022/0306614 A1 | 9/2022 | Brizgys et al. | |
| 2023/0021705 A1 | 1/2023 | Armstrong | |

FOREIGN PATENT DOCUMENTS

| | | |
|---|---|---|
| CN | 112409331 A | 2/2021 |
| CN | 113480534 A | 10/2021 |
| CN | 113493447 A | 10/2021 |
| CN | 113816948 A | 12/2021 |
| EP | 3438095 A1 | 2/2019 |
| EP | 4057055 A1 | 9/2022 |
| TW | 201904959 A | 2/2019 |
| TW | 202015683 A | 5/2020 |
| WO | WO-2000/08015 A2 | 2/2000 |
| WO | WO-2003/026587 A2 | 4/2003 |
| WO | WO-2004/099192 A2 | 11/2004 |
| WO | WO-2005/014543 A1 | 2/2005 |
| WO | WO-2006/055708 A2 | 5/2006 |
| WO | WO-2006/066879 A2 | 6/2006 |
| WO | WO-2007/031791 A1 | 3/2007 |
| WO | WO-2007/115077 A2 | 10/2007 |
| WO | WO-2008/033455 A2 | 3/2008 |
| WO | WO-2010/029299 A1 | 3/2010 |
| WO | WO-2010/029300 A1 | 3/2010 |
| WO | WO-2010/046780 A2 | 4/2010 |
| WO | WO-2011/163355 A1 | 12/2011 |
| WO | WO-2013/025733 A1 | 2/2013 |
| WO | WO-2013/056679 A1 | 4/2013 |
| WO | WO-2013/186229 A1 | 12/2013 |
| WO | WO-2016/018701 A1 | 2/2016 |
| WO | WO-2016/089060 A2 | 6/2016 |
| WO | WO-2016/118638 A1 | 7/2016 |
| WO | WO-2017/161028 A1 | 9/2017 |
| WO | WO-2018/109607 A1 | 6/2018 |
| WO | WO-2018/183112 A1 | 10/2018 |
| WO | WO-2019/055540 A1 | 3/2019 |
| WO | WO-2019/239319 A1 | 12/2019 |
| WO | WO-2019/239371 A1 | 12/2019 |
| WO | WO-2020/033413 A2 | 2/2020 |
| WO | WO-2020/103815 A1 | 5/2020 |

(Continued)

OTHER PUBLICATIONS

Camille G. Wermuth, Molecular Variations Based on Isosteric Replacements, The Practice of Medicinal Chemistry, (1996), 203-237 (Year: 1996).*

Andersen, A et al. (2018), "Glucagon-like peptide 1 in health and disease", Nat Rev Endocrinol., Jul.; 14(7):390-403.

Armstrong M J et al. (2016), "Liraglutide safety and efficacy in patients with non-alcoholic steatohepatitis (LEAN): a multicentre, double-blind, randomised, placebo-controlled phase 2 study", Lancet, 387(10019):679-690.

Armstrong, M et al. (2013), "Liraglutide efficacy and action in non-alcoholic steatohepatitis (LEAN): study protocol for a phase II multicentre, double-blinded, randomised, controlled trial", BMJ Open., 3(11):e003995, pp. 1-13.

(Continued)

*Primary Examiner* — Michael Barker
*Assistant Examiner* — Jed A Kucharczk
(74) *Attorney, Agent, or Firm* — Mintz, Levin, Cohn, Ferris, Glovsky and Popeo, P.C.

(57) ABSTRACT

The present disclosure provides GLP-1R agonists, and compositions, methods, and kits thereof. Such compounds are generally useful for treating a GLP-1R mediated disease or condition in a human.

4 Claims, No Drawings

(56) References Cited

FOREIGN PATENT DOCUMENTS

| WO | WO-2020/207474 A1 | 10/2020 |
|---|---|---|
| WO | WO-2020/263695 A1 | 12/2020 |
| WO | WO-2021/018023 A1 | 2/2021 |
| WO | WO-2021/018026 A1 | 2/2021 |
| WO | WO-2021/081207 A1 | 4/2021 |
| WO | WO-2021/096284 A1 | 5/2021 |
| WO | WO-2021/096304 A1 | 5/2021 |
| WO | WO-2021/112538 A1 | 6/2021 |
| WO | WO-2021/154796 A1 | 8/2021 |
| WO | WO-2021/155841 A1 | 8/2021 |
| WO | WO-2021/160127 A1 | 8/2021 |
| WO | WO-2021/187886 A1 | 9/2021 |
| WO | WO-2021/191812 A1 | 9/2021 |
| WO | WO-2021/197464 A1 | 10/2021 |
| WO | WO-2021/242817 A1 | 12/2021 |
| WO | WO-2021/244645 A1 | 12/2021 |
| WO | WO-2022/040600 A1 | 2/2022 |
| WO | WO-2022/068772 A1 | 4/2022 |
| WO | WO-2022/078152 A1 | 4/2022 |
| WO | WO-2022/111624 A1 | 6/2022 |
| WO | WO-2022/192428 A1 | 9/2022 |
| WO | WO-2022/192430 A1 | 9/2022 |
| WO | WO-2022/225914 A1 | 10/2022 |
| WO | WO-2022/225941 A1 | 10/2022 |

OTHER PUBLICATIONS

Armstrong, M J et al. (2016), "Glucagon-like peptide 1 decreases lipotoxicity in non-alcoholic steatohepatitis", Randomized Controlled Trial J Hepatol., 64(2):399-408.
Armstrong, M. J. (2017), "Glucagon-like peptide-1 analogues in nonalcoholic steatohepatitis: From bench to bedside", Review Clin Liver Dis (Hoboken), 10(2):32-35.
Ben-Shlomo, S et al. (2011), "Glucagon-like peptide-1 reduces hepatic lipogenesis via activation of AMP-activated protein kinase", J Hepatol. 54(6):1214-23.
Bernsmeier, C et al. (2014), "Glucose-Induced Glucagon-Like Peptide 1 Secretion Is Deficient in Patients with Non-Alcoholic Fatty Liver Disease", PLoS One, 9(1):e87488, 1-7.
Bueno, A B et al. (2016), "Positive Allosteric Modulation of the Glucagon-like Peptide-1 Receptor by Diverse Electrophiles", J Biol Chem, May 13, 2016; 291(20):10700-15.
Carbone L J et al. (2016), "Incretin-based therapies for the treatment of non-alcoholic fatty liver disease: A systemic review and meta-analysis", J Gastroenterol Hepatol, 31(1):23-31.
Chen D et al. (2007), "A nonpeptidic agonist of glucagon-like peptide 1 receptors with efficacy in diabetic db/db mice", Proc Natl Acad Sci USA, 104(3):943-948.
Chen, J et al. (2017), "GLP-1/GLP-1R Signaling in Regulation of Adipocyte Differentiation and Lipogenesis", Cell Physiol Biochem, 42(3):1165-1176.
Dalsgaard N B et al. (2018), "Effects of glucagon-like peptide-1 receptor agonists on cardiovascular risk factors: A narrative review of head-to-head comparisons", Diabetes Obes Metab, 20(3):508-519.
Davies, M et al. (2017), "Effect of Oral Semaglutide Compared With Placebo and Subcutaneous Semaglutide on Glycemic Control in Patients With Type 2 Diabetes: A Randomized Clinical Trial", JAMA, 318(15):1460-1470.
De Graaf C et al. (2016), "Glucagon-Like Peptide-1 and Its Class B G Protein-Coupled Receptors: A Long March to Therapeutic Successes", Pharmacol Rev., 68(4):954-1013.
Donnelly K L et al. (2005), "Sources of fatty acids stored in liver and secreted via lipoproteins in patients with nonalcoholic fatty liver disease", J Clin Invest, 115(5):1343-1351.
Edmonds, D J et al. (2013), "Oral GLP-1 Modulators for the Treatment of Diabetes", Annual Reports in Medicinal Chemistry, Chapter Nine, 48:119-130.

Eguchi Y et al. (2015), "Pilot study of liraglutide effects in non-alcoholic steatohepatitis and non-alcoholic fatty liver disease with glucose intolerance in Japanese patients (LEAN-J)", Hepatol Res, 45(3):269-278.
Gastaldelli A et al. (2016), "Exenatide improves both hepatic and adipose tissue insulin resistance: A dynamic positron emission tomography study", Hepatology, 64(6):2028-2037.
Jazayeri A et al. (2017), "Crystal structure of the GLP-1 receptor bound to a peptide agonist", Nature, 546(7657):254-258.
Jones, B et al. (2018), "Targeting GLP-1 receptor trafficking to improve agonist efficacy", Nature Communications, 9:1602, pp. 1-17.
Knudsen, L B et al. (2007), "Small-molecule agonists for the glucagon-like peptide 1 receptor", Proc Natl Acad Sci USA, 104(3):937-942.
Koole C et al. (2013), "Recent advances in understanding GLP-1R (glucagon-like peptide-1 receptor) function", Biochem Soc Trans, 41(1):172-179.
Ma H et al. (2020), "Structural insights into the activation of GLP-1R by a small molecule agonist", Cell Res 30, 1140-1142.
Mendez M et al. (2019), "Design, Synthesis and Pharmacological Evaluation of Potent Positive Allosteric Modulators of the Glucagon-like Peptide-1 Receptor (GLP-1R)", J. Med. Chem., Just Accepted Manuscript, Publication Date (Web): Oct. 9, 2019.
Nauck, M A et al. (2011), "Rapid tachyphylaxis of the glucagon-like peptide 1-induced deceleration of gastric emptying in humans", Diabetes, 60(5):1561-1565.
Nauck, M A et al. (2016), "A Phase 2, Randomized, Dose-Finding Study of the Novel Once-Weekly Human GLP-1 Analog, Semaglutide, Compared With Placebo and Open-Label Liraglutide in Patients With Type 2 Diabetes", Diabetes Care, 39(2):231-241.
Petit, J-M et al. (2017), "GLP-1 receptor agonists in NAFLD", Diabetes Metab., 43 Suppl 1:2S28-2S33.
Plisson F et al. (2017), "Helixconstraints and amino acid substitution in GLP-1 increase cAMP and insulin secretion but not beta-arrestin 2 signaling", Eur J Med Chem, 127:703-714.
Portillo-Sanchez P et al. (2016), "Treatment of Nonalcoholic Fatty Liver Disease (NAFLD) in patients with Type 2 Diabetes Mellitus", Clin Diabetes Endocrinol, 2:9.
Sloop K W et al. (2010), "Novel small molecule glucagon-like peptide-1 receptor agonist stimulates insulin secretion in rodents and from human islets", Diabetes, 59(12):3099-3107.
Song G et al. (2017), "Human GLP-1 receptor transmembrane domain structure in complex with allosteric modulators", Nature, 546(7657):312-315.
Svegliati-Baroni G et al. (2011), "Glucagon-like peptide-1 receptor activation stimulates hepatic lipid oxidation and restores hepatic signalling alteration induced by a high-fat diet in nonalcoholic steatohepatitis", Liver Int., 31(9):1285-1297.
Takayanagi R et al. (2018), "Evaluation of Drug Efficacy of GLP-1 Receptor Agonists and DPP-4 Inhibitors Based on Target Molecular Binding Occupancy", Biol Pharm Bull, 41(2):153-157.
Tong W et al. (2016), "Liraglutide ameliorates non-alcoholic fatty liver disease by enhancing mitochondrial architecture and promoting autophagy through the SIRT1/SIRT3-FOXO3a pathway", Hepatol Res., 46(9):933-943.
Umapathysivam M M et al. (2014), "Comparative effects of prolonged and intermittent stimulation of the glucagon-like peptide 1 receptor on gastric emptying and glycemia", Diabetes, 63(2):785-790.
Vendrell J et al. (2011), "Study of the potential association of adipose tissue GLP-1 receptor with obesity and insulin resistance", Endocrinology, 152(11):4072-4079.
Vilar-Gomez E et al. (2015), "Weight Loss Through Lifestyle Modification Significantly Reduces Features of Nonalcoholic Steatohepatitis", Gastroenterology, 149(2):367-378.e5.
Villanueva-Penacarrillo M L et al. (2001), "Effect of GLP-1 on lipid metabolism in human adipocytes", Horm Metab Res, 33(2):73-77.
VTv Therapeutics (2016), "Oral Small Molecule GLP-1 Receptor (GLP-1R) Agonists for Type 2 Diabetes (T2DM) with Negligible Nausea and Vomiting", Presentation from Keystone Symposia 2016.

(56) References Cited

OTHER PUBLICATIONS

Wang X-C et al. (2014), "Effects of glucagon-like peptide-1 receptor agonists on non-alcoholic fatty liver disease and inflammation", World J Gastroenterol, 20(40):14821-14830.

Wootten D et al. (2013), "Differential activation and modulation of the glucagon-like peptide-1 receptor by small molecule ligands", Mol Pharmacol, 83(4):822-834.

Wootten D et al. (2016), "A Hydrogen-Bonded Polar Network in the Core of the Glucagon-Like Peptide-1 Receptor Is a Fulcrum for Biased Agonism: Lessons from Class B Crystal Structures", Mol Pharmacol, 89(3):335-347.

Yang D et al. (2015), "Landmark studies on the glucagon subfamily of GPCRs: from small molecule modulators to a crystal structure", Acta Pharmacol Sin, 36(9):1033-42.

Intl. Search Report—Written Opinion dated Feb. 28, 2022 for Intl. Appl. No. PCT/US2021/059960.

Office Action dated Mar. 1, 2023 for Taiwan Appl. No. 110143097.

\* cited by examiner

GLP-1R MODULATING COMPOUNDS

CROSS-REFERENCES TO RELATED APPLICATIONS

This application claims the benefit under 35 U.S.C. § 119(e) of U.S. Provisional Application No. 63/116,630, filed on Nov. 20, 2020, and U.S. Provisional Application No. 63/134,505, filed on Jan. 6, 2021, which are hereby incorporated herein by reference in their entirety for all purposes.

FIELD

The present disclosure relates to compounds that bind to and act as agonists or modulators of the glucagon-like peptide-1 receptor (GLP-1R) and act as agonists or modulators of GLP-1R. The disclosure further relates to the use of the compounds for the treatment and/or prevention of diseases and/or conditions by said compounds.

BACKGROUND

Glucagon-like peptide-1 (GLP-1) is a peptide hormone that is secreted from the enteroendocrine cells in the gut in response to a meal. GLP-1 is believed to play a role in regulation of post-prandial glycemia, via directly augmenting meal-induced insulin secretion from the pancreatic beta-cells, as well as in promoting satiety by delaying the transit of food through the gut. GLP-1 mediates intracellular signaling via the GLP-1 receptor (GLP-1R) which belongs to a family of G-protein coupled receptors that are present on the cell membrane and can result in accumulation of the secondary messenger cyclic adenosine monophosphate (cAMP) upon activation. Non-alcoholic steatohepatitis (NASH) can be associated with features of metabolic syndrome, including obesity, type 2 diabetes, insulin resistance and cardiovascular disease.

GLP-1R agonists are currently being investigated in connection with diabetes, obesity, and NASH. GLP-1R agonists include peptides, such as exenatide, liraglutide, and dulaglutide, that have been approved for the management of type 2 diabetes. Such peptides are predominantly administered by subcutaneous injection. Oral GLP-1 agonists are also under investigation for treatment of type 2 diabetes. Some GLP-1R agonists, such as liraglutide, dulaglutide, and exenatide, are resistant to rapid degradation by dipeptidyl peptidase 4, resulting in longer half-lives than endogenous GLP-1.

There remains a need for compounds, such as agonists of GLP-1R, with desirable therapeutic properties, metabolic properties, and/or easy administration in the treatment of metabolic diseases and related diseases, including but not limited to NASH, obesity, and Type 2 diabetes.

SUMMARY

In one embodiment, the present disclosure provides a compound of Formula (I-A):

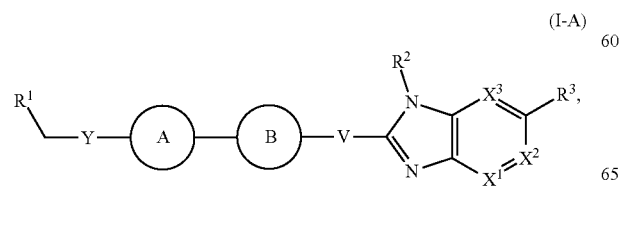

(I-A)

or a pharmaceutically acceptable salt thereof, wherein
R$^1$ is C$_{6-10}$ aryl or heteroaryl each optionally substituted with one to four Z$^1$;
ring A is

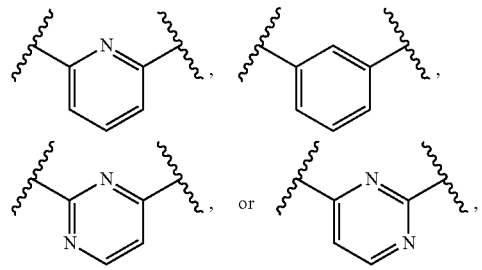

each of which is optionally substituted with 1 to 3 groups each independently C$_{1-6}$ alkyl, C$_{1-6}$ alkoxy, halogen, C$_{1-6}$ haloalkyl, C$_{1-6}$ haloalkoxy, —OH, —CN, or —N(R$^{4a}$)(R$^{4b}$);
ring B is

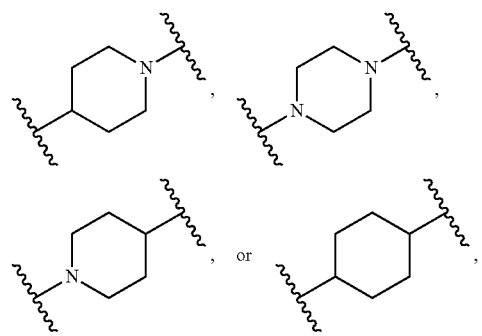

each of which is optionally substituted with 1 to 3 R$^B$ groups each independently C$_{1-6}$ alkyl or halogen,
alternatively, two R$^B$ groups on adjacent carbon ring members or the same carbon ring member can be combined with the atoms to which they are attached to form a C$_{3-6}$ cycloalkyl;
R$^2$ is H, C$_{1-6}$ alkyl, C$_{2-6}$ alkynyl, C$_{1-6}$ haloalkyl, C$_{3-10}$ cycloalkyl, heterocyclyl, C$_{1-6}$ alkyl-C$_{3-10}$ cycloalkyl, C$_{1-6}$ alkyl-heterocyclyl, or C$_{1-6}$ alkyl-heteroaryl,
wherein the alkyl, alkynyl, cycloalkyl, heterocyclyl or heteroaryl is each optionally substituted with one to four Z$^1$;
X$^1$ is —N=, —C(H)= or —C(R$^{11}$)=, X$^2$ and X$^3$ are each independently —N=, —C(H$^8$)=, or —C(R$^8$)=; wherein at least one of X$^2$ and X$^3$ is —C(R$^8$)= or X$^1$ is —C(R$^{11}$)=;
R$^3$ is COOR$^{3a}$;
R$^{3a}$ is H, C$_{1-4}$ alkyl-N(R$^{9a}$)(R$^{9b}$), —C$_{1-4}$ alkyl-N(R$^{9a}$)C(O)—O—C$_{1-4}$ alkyl-OP(O)(OR$^{9c}$)$_2$, C$_{1-4}$ alkyl-C(O)N(R$^{9a}$)(R$^{9b}$), —C$_{1-4}$ alkyl-O—C(O)—C$_{1-4}$ alkyl, —C$_{1-4}$ alkyl-O—C(O)—O—C$_{1-4}$ alkyl, —C$_{1-4}$ alkyl-O—C(O)—C$_{1-4}$ alkyl-N(R$^{9a}$)(R$^{9b}$), —C$_{1-4}$ alkyl-O—C(O)—C$_{1-4}$ alkyl-OP(O)(OR$^{9c}$)$_2$, —CH$_2$CH(N(R$^{9a}$)$_2$)C(O)OR$^{9b}$, —P(O)(OR$^{9c}$)$_2$, —OP(O)(OR$^{9c}$)$_2$, —CH$_2$P(O)(OR$^{9c}$)$_2$, —CH$_2$OP(O)(OR$^{9c}$)$_2$, —OCH$_2$P(O)(OR$^{9c}$)$_2$, —C(O)OCH$_2$P(O)(OR$^{9c}$)$_2$, —P(O)(R$^{9c}$)(OR$^{9d}$), —OP(O)(R$^{9c}$)(OR$^{9d}$), —CH$_2$P(O)(R$^{9c}$)(OR$^{9d}$)$_2$, —OCH$_2$P(O)(R$^{9c}$)(OR$^{9d}$), —C(O)OCH$_2$P(O)(R$^{9c}$)(OR$^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —OP(O)(N($R^{9c}$)$_2$)(O$R^{9d}$), —P(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), —C(O)OCH$_2$P(O)($R^{9c}$)(N($R^{9d}$)$_2$), or $C_{1-6}$ alkyl-heterocyclyl, wherein the alkyl or heterocyclyl is each optionally substituted with one to four halogens;

each $R^{9a}$ and $R^{9b}$ is independently H, $C_{1-6}$ alkyl, or $C_{1-6}$ haloalkyl, or $R^{9a}$ and $R^{9b}$ together form a 6-membered heterocyclyl;

V is —C($R^{6b}$)($R^{6c}$)—;

each $R^{6b}$ and $R^{6c}$ is independently —H, $C_{1-6}$ alkyl, or halogen;

alternatively, $R^{6b}$ is combined with the $R^B$ group attached to the carbon ring member to form a $C_{3-6}$ cycloalkyl;

Y is —O—;

$R^8$ and $R^{11}$ are each independently H, $C_{1-9}$ alkyl, $C_{1-8}$ haloalkyl, $C_{2-6}$ alkenyl, $C_{2-6}$ alkynyl, $C_{1-6}$ alkoxy, $C_{1-6}$ hydroxyalkyl, $C_{1-6}$ alkoxyalkyl, halogen, $C_{1-6}$ haloalkyl, $C_{1-6}$ haloalkoxy, halogen, $C_{1-6}$ haloalkyl, $C_{1-6}$ haloalkoxy, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein each alkyl, alkenyl, alkynyl, cycloalkyl, heterocyclyl, aryl, or heteroaryl is optionally substituted with 1 to 3 $Z^{1b}$;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—$R^{12a}$, —C(O)$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein each alkyl, haloalkyl, alkenyl, alkynyl, cycloalkyl, heterocyclyl, aryl, or heteroaryl is optionally substituted with 1 to 4 $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein each alkyl, haloalkyl, alkenyl, alkynyl, cycloalkyl, heterocyclyl, aryl, or heteroaryl is optionally substituted with 1 to 4 $Z^{1b}$;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N(C$_{1-9}$ alkyl)(C$_{6-10}$ aryl), —N(C$_{1-9}$ alkyl)(heteroaryl), —C(O)(C$_{1-9}$ alkyl), —C(O)(C$_{1-8}$ haloalkyl), —C(O)(C$_{2-6}$ alkenyl), —C(O)(C$_{2-6}$ alkynyl), —C(O)(C$_{3-15}$ cycloalkyl), —C(O)(heterocyclyl), —C(O)(C$_{6-10}$ aryl), —C(O)(heteroaryl), —C(O)O(C$_{1-9}$ alkyl), —C(O)O(C$_{1-8}$ haloalkyl), —C(O)O(C$_{2-6}$ alkenyl), —C(O)O(C$_{2-6}$ alkynyl), —C(O)O(C$_{3-15}$ cycloalkyl), —C(O)O(heterocyclyl), —C(O)O(C$_{6-10}$ aryl), —C(O)O(heteroaryl), —C(O)NH$_2$, —C(O)NH(C$_{1-9}$ alkyl), —C(O)NH(C$_{1-8}$ haloalkyl), —C(O)NH(C$_{2-6}$ alkenyl), —C(O)NH(C$_{2-6}$ alkynyl), —C(O)NH(C$_{3-15}$ cycloalkyl), —C(O)NH(heterocyclyl), —C(O)NH(C$_{6-10}$ aryl), —C(O)NH(heteroaryl), —C(O)N(C$_{1-9}$ alkyl)$_2$, —C(O)N(C$_{1-8}$ haloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(heterocyclyl)$_2$, —C(O)N(C$_{6-10}$ aryl)$_2$, —C(O)N(heteroaryl)$_2$, —NHC(O)(C$_{1-9}$ alkyl), —NHC(O)(C$_{1-8}$ haloalkyl), —NHC(O)(C$_{2-6}$ alkenyl), —NHC(O)(C$_{2-6}$ alkynyl), —NHC(O)(C$_{3-15}$ cycloalkyl), —NHC(O)(heterocyclyl), —NHC(O)(C$_{6-10}$ aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(heterocyclyl), —NHC(O)O(C$_{6-10}$ aryl), —NHC(O)O(heteroaryl), —NHC(O)NH(C$_{1-9}$ alkyl), —NHC(O)NH(C$_{1-8}$ haloalkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(heterocyclyl), —NHC(O)NH(C$_{6-10}$ aryl), —NHC(O)NH(heteroaryl), —NHS(O)(C$_{1-9}$ alkyl), —N(C$_{1-9}$ alkyl)(S(O)(C$_{1-9}$ alkyl), —S(C$_{1-9}$ alkyl), —S(C$_{1-8}$ haloalkyl), —S(C$_{2-6}$ alkenyl), —S(C$_{2-6}$ alkynyl), —S(C$_{3-15}$ cycloalkyl), —S(heterocyclyl), —S(C$_{6-10}$ aryl), —S(heteroaryl), —S(O)N(C$_{1-9}$ alkyl)$_2$, —S(O)(C$_{1-9}$ alkyl), —S(O)(C$_{1-8}$ haloalkyl), —S(O)(C$_{2-6}$ alkenyl), —S(O)(C$_{2-6}$ alkynyl), —S(O)(C$_{3-15}$ cycloalkyl), —S(O)(heterocyclyl), —S(O)(C$_{6-10}$ aryl), —S(O)(heteroaryl), —S(O)$_2$(C$_{1-9}$ alkyl), —S(O)$_2$(C$_{1-8}$ haloalkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein each alkyl, cycloalkyl, heterocyclyl, aryl, or heteroaryl is optionally substituted with 1 to 3 C$_{1-9}$ alkyl, C$_{1-8}$ haloalkyl, halogen, —OH, —NH$_2$, CO$_2$H, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$haloalkyl), —NHC(O)(C$_{3-15}$ cycloalkyl),
—NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

each R$^{2a}$, R$^{2b}$, R$^{4a}$, R$^{4b}$, R$^{9c}$, R$^{9d}$, R$^{12a}$, R$^{12b}$, and R$^{12c}$ is independently H, C$_{1-9}$ alkyl, C$_{2-6}$ alkenyl, C$_{2-6}$ alkynyl, C$_{3-15}$ cycloalkyl, heterocyclyl, C$_{6-10}$ aryl, or heteroaryl wherein the alkyl, alkenyl, alkynyl, cycloalkyl, heterocyclyl, aryl, or heteroaryl is each optionally substituted with 1 to 4 Z$^{1b}$; and wherein each heterocyclyl has 3 to 12 ring members and has 1 to 4 heteroatoms each independently N, O, or S; and wherein each heteroaryl has 5 to 12 ring members and 1 to 4 heteroatoms each independently N, O, or S.

In another embodiment, the present disclosure provides a compound of Formula (I-A):

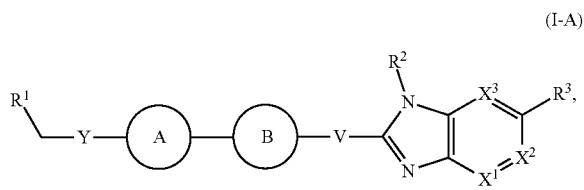

(I-A)

or a pharmaceutically acceptable salt thereof, wherein

R$^1$ is C$_6$ aryl or heteroaryl, wherein aryl and heteroaryl is each optionally substituted with 1 to 4 groups each independently C$_{1-6}$ alkyl, halogen, C$_{1-6}$ haloalkyl, —CN, —C(O)NH$_2$, —C(O)NH(C$_{1-6}$ alkyl), —C(O)N(C$_{1-6}$ alkyl)$_2$, —C(O)NH(C$_{3-6}$ cycloalkyl), —C(O)NH(heterocyclyl), heterocyclyl optionally substituted with 1 to 3 groups each independently C$_{1-6}$ alkyl, halogen, C$_{1-6}$ haloalkyl, or —OH, or heteroaryl optionally substituted with 1 to 3 groups each independently C$_{1-6}$ alkyl, halogen, C$_{1-6}$ haloalkyl, —OH, C$_{3-6}$ cycloalkyl, or heterocyclyl;

ring A is

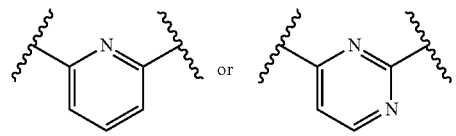 [SMILES: *c1cccc(*)n1 ; *c1ccnc(*)n1]

wherein each is optionally substituted with 1 to 3 groups each independently C$_{1-6}$ alkyl, C$_{1-6}$ alkoxy, halogen, C$_{1-6}$ haloalkyl, C$_{1-6}$ haloalkoxy, —OH or —NH$_2$;

ring B is

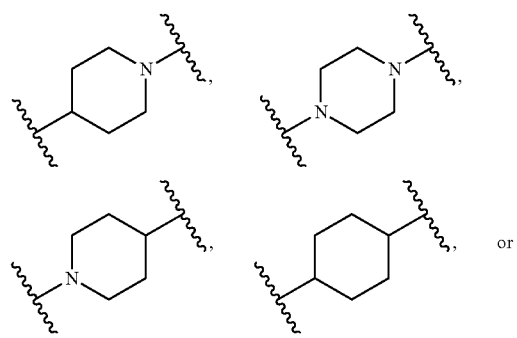

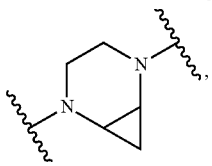

wherein each is optionally substituted with 1 to 3 $R^B$ groups each independently $C_{1-6}$ alkyl or halogen, alternatively, ring B is combined with V to form

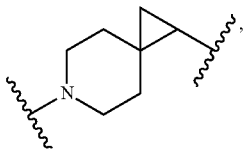

optionally substituted with 1 to 3 $R^B$ groups each independently $C_{1-6}$ alkyl or halogen;

$R^2$ is H, $C_{1-6}$ alkyl, $C_{3-10}$ cycloalkyl, $C_{1-6}$ alkyl-$C_{3-10}$ cycloalkyl, heterocyclyl, $C_{1-6}$ alkyl-heterocyclyl, or $C_{1-6}$ alkyl-heteroaryl, wherein each alkyl, cycloalkyl, heterocyclyl or heteroaryl is optionally substituted with 1 to 3 groups each independently $C_{1-6}$ alkyl, $C_{1-6}$ alkoxy, $C_{1-6}$ hydroxyalkyl, $C_{2-6}$ alkoxyalkyl, halogen, $C_{1-6}$ haloalkyl, $C_{1-6}$ haloalkoxy, —OH, —CN, $C_{1-6}$ alkyl-CN, —O—$C_{3-6}$ cycloalkyl or heteroaryl optionally substituted with 1 to 4 groups each independently $C_{1-6}$ alkyl, $C_{1-6}$ alkoxy, halogen, $C_{1-6}$ haloalkyl, or $C_{1-6}$ haloalkoxy;

$X^1$ is —N═, —C(H)═ or —C($R^{11}$)═;

$X^2$ and $X^3$ are each independently —N═, —C(H)═, or —C($R^8$)═, wherein at least one of $X^2$ and $X^3$ is —C($R^8$)═ or $X^1$ is —C($R^{11}$)═;

$R^3$ is COOR$^{3a}$;

$R^{3a}$ is H, $C_{1-4}$ alkyl-N($R^{9a}$)($R^{9b}$), —$C_{1-4}$ alkyl-N($R^{9a}$)C(O)—O—$C_{1-4}$ alkyl-OP(O)(OR$^{9c}$)$_2$, $C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-O—C(O)—$C_{1-4}$ alkyl-OP(O)(OR$^{9c}$)$_2$, —CH$_2$CH(N($R^{9a}$)$_2$)C(O)OR$^{9b}$, —P(O)(OR$^{9c}$)$_2$, —OP(O)(OR$^{9c}$)$_2$, —CH$_2$P(O)(OR$^{9c}$)$_2$, —CH$_2$OP(O)(OR$^{9c}$)$_2$, —OCH$_2$P(O)(OR$^{9c}$)$_2$, —C(O)OCH$_2$P(O)(OR$^{9c}$)$_2$, —P(O)(R$^{9c}$)(OR$^{9d}$), —OP(O)(R$^{9c}$)(OR$^{9d}$), —CH$_2$P(O)(R$^{9c}$)(OR$^{9d}$), —OCH$_2$P(O)(R$^{9c}$)(OR$^{9d}$), —C(O)OCH$_2$P(O)(R$^{9c}$)(OR$^{9d}$), —P(O)(N(R$^{9c}$)$_2$)$_2$, —OP(O)(N(R$^{9c}$)$_2$)$_2$, —CH$_2$P(O)(N(R$^{9c}$)$_2$)$_2$, —OCH$_2$P(O)(N(R$^{9c}$)$_2$)$_2$, —C(O)OCH$_2$P(O)(N(R$^{9c}$)$_2$)$_2$, —P(O)(N(R$^{9c}$)$_2$)(OR$^{9d}$), —OP(O)(N(R$^{9c}$)$_2$)(OR$^{9d}$), —CH$_2$P(O)(N(R$^{9c}$)$_2$)(OR$^{9d}$), —OCH$_2$P(O)(N(R$^{9c}$)$_2$)(OR$^{9d}$), —C(O)OCH$_2$P(O)(N(R$^{9c}$)$_2$)(OR$^{9d}$), —P(O)(R$^{9c}$)(N(R$^{9d}$)$_2$), —OP(O)(R$^{9c}$)(N(R$^{9d}$)$_2$), —CH$_2$P(O)(R$^{9c}$)(N(R$^{9d}$)$_2$), —OCH$_2$P(O)(R$^{9c}$)(N(R$^{9d}$)$_2$), —C(O)OCH$_2$P(O)(R$^{9c}$)(N(R$^{9d}$)$_2$), or $C_{1-6}$ alkyl-heterocyclyl, wherein the wherein the alkyl or heterocyclyl is each optionally substituted with one to four halogens;

each $R^{9a}$ and $R^{9b}$ is independently H, $C_{1-6}$ alkyl, or $C_{1-6}$ haloalkyl, or $R^{9a}$ and $R^{9b}$ together form a 6-membered heterocyclyl;

each $R^{9c}$ and $R^{9d}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with 1 to 4 $Z^{1b}$;

V is —C($R^{6b}$)($R^{6c}$)—;

each $R^{6b}$ and $R^{6c}$ is independently —H, $C_{1-6}$ alkyl, or halogen;

Y is —O—;

(i) If Ring A

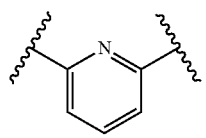

and ring B is

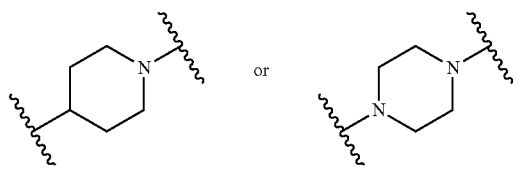 [SMILES: *C1CCN(*)CC1 ; *N1CCN(*)CC1]

and $R^1$ is phenyl substituted with $Z^1$ then $R^{11}$ is independently $C_{1-6}$ alkyl, $C_{2-6}$ alkenyl, $C_{2-6}$ alkynyl, $C_{1-6}$ alkoxy, $C_{1-6}$ hydroxyalkyl, $C_{2-6}$ alkoxyalkyl, halogen, $C_{1-6}$ haloalkyl, $C_{1-6}$ haloalkoxy, —CN, —OH, —NH$_2$, $C_{3-6}$ cycloalkyl, heterocyclyl, heteroaryl, —NH($C_{1-9}$ alkyl), —N($C_{1-9}$ alkyl)$_2$, —NH($C_{3-15}$ cycloalkyl), —NH(heterocyclyl), —NH($C_{6-10}$ aryl), or —NH(heteroaryl), wherein the alkyl, alkynyl, cycloalkyl, heterocyclyl, or heteroaryl in each instance is optionally substituted with one to three groups selected from $C_{1-6}$ alkyl, $C_{1-6}$ alkoxy, halogen, —$C_{1-6}$ haloalkyl, —OH, $C_{3-6}$ cycloalkyl optionally substituted with 1 to 3 groups each independently $C_{1-6}$ alkyl, $C_{1-6}$ alkoxy, halogen, $C_{1-6}$ haloalkyl, $C_{1-6}$ haloalkoxy, or —OH, or heterocyclyl optionally substituted with 1 to 3 groups each independently —$C_{1-6}$ alkyl, $C_{1-6}$ alkoxy, halogen, $C_{1-6}$ haloalkyl, $C_{1-6}$ haloalkoxy, or —OH;

$R^8$ is independently $C_{2-9}$ alkyl, $C_{2-6}$ alkenyl, $C_{2-6}$ alkynyl, $C_{1-6}$ alkoxy, $C_{1-6}$ hydroxyalkyl, $C_{1-6}$ alkoxyalkyl, $C_{1-6}$ haloalkyl, $C_{1-6}$ haloalkoxy, —CN, —OH, —NH$_2$, $C_{3-6}$ cycloalkyl, heterocyclyl, heteroaryl, —NH($C_{1-9}$ alkyl), —N($C_{1-9}$ alkyl)$_2$, —NH($C_{3-15}$ cycloalkyl), —NH(heterocyclyl), —NH($C_{6-10}$ aryl), or —NH(heteroaryl), wherein the alkyl, alkynyl, cycloalkyl, heterocyclyl, or heteroaryl in each instance is optionally substituted with 1 to 3 groups each independently $C_{1-6}$ alkyl, $C_{1-6}$ alkoxy, halogen, $C_{1-6}$ haloalkyl, —OH, $C_{3-6}$ cycloalkyl, heterocyclyl optionally substituted with 1 to 3 groups each independently $C_{1-6}$ alkyl, $C_{1-6}$ alkoxy, halogen, $C_{1-6}$ haloalkyl, —OH, $C_{3-6}$ cycloalkyl optionally substituted with 1 to 3 groups each independently $C_{1-6}$ alkyl, $C_{1-6}$ alkoxy, halogen, $C_{1-6}$ haloalkyl, $C_{1-6}$ haloalkoxy, —OH, and heterocyclyl optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH;

(ii) If ring A is

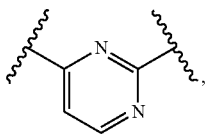 [SMILES: *c1ccnc(*)n1]

or
If ring B is

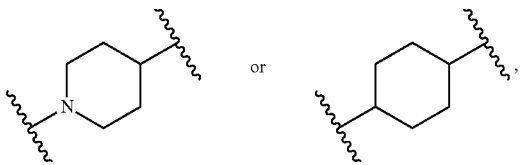 [SMILES: *C1CCN(*)CC1 ; *C1CCC(*)CC1]

or
If $R^1$ is not phenyl substituted with $Z^1$, then
$R^{11}$ and $R^8$ are independently $C_{2-6}$ alkynyl, $C_{1-6}$ hydroxyalkyl, $C_{2-6}$ alkoxyalkyl, $C_{3-6}$ cycloalkyl, heterocyclyl, heteroaryl, —NH($R^{12}$), —N($R^{12}$)$_2$, —NH($C_{3-15}$ cycloalkyl), —NH(heterocyclyl), —NH($C_{6-10}$ aryl), or —NH(heteroaryl),
wherein each alkynyl, cycloalkyl, heterocyclyl, or heteroaryl is optionally substituted with 1 to 3 groups each independently $C_{1-6}$ alkyl, $C_{1-6}$ alkoxy, halogen, $C_{1-6}$ haloalkyl, —OH,
$C_{3-6}$ cycloalkyl optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH, or heterocyclyl optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH;
each $R^{12}$ is $C_{1-6}$ alkyl substituted with 1 to 3 groups each independently halogen, —OH, —CN, or $C_{3-6}$ cycloalkyl;
each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —NR$^{12a}$S(O)$_2$N($R^{12b}$)($R^{12c}$), —NR$^{12a}$S(O)$_2$O($R^{12b}$), —OC(O)$R^{12a}$, —OC(O)OR$^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(NR$^{12a}$)$R^{12b}$, or —Si($R^{12a}$)$_3$;
wherein each alkyl, haloalkyl, alkenyl, alkynyl, cycloalkyl, heterocyclyl, aryl, or heteroaryl is optionally substituted with 1 to 4 $Z^{1a}$;
each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O
($R^{12b}$), —OC(O)$R^{12a}$, —OC(O)OR$^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(NR$^{12a}$)$R^{12b}$, or —Si($R^{12a}$)$_3$;
wherein each alkyl, haloalkyl, alkenyl, alkynyl, cycloalkyl, heterocyclyl, aryl, or heteroaryl is optionally substituted with 1 to 4 $Z^{1b}$;
each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl),
—NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein each alkyl, cycloalkyl, heterocyclyl, aryl, or heteroaryl is optionally substituted with 1 to 3 C$_{1-9}$ alkyl, C$_{1-8}$ haloalkyl, halogen, —OH, —NH$_2$, CO$_2$H, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$haloalkyl), —NHC(O)(C$_{3-15}$ cycloalkyl), —NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$ haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein each heterocyclyl has 3 to 12 ring members and 1 to 4 heteroatoms each independently N, O, or S; and wherein each heteroaryl has 5 to 12 ring members and 1 to 4 heteroatoms each independently N, O or S.

The present disclosure further provides pharmaceutical compositions, methods, and uses comprising the compound of Formula (I-A), or pharmaceutically acceptable salts thereof. For example, the compounds of the present disclosure are generally useful in a method of treating a GLP-1R-mediated disease or condition.

DETAILED DESCRIPTION

I. Definitions

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "C$_{u-v}$" or "C$_u$-C$_v$," indicates that the following group has from u to v carbon atoms, where u and v are integers. For example, "C$_{1-6}$ alkyl" or "C$_1$-C$_6$ alkyl" indicates that the alkyl group has from 1 to 6 carbon atoms.

"Alkyl" is a monovalent or divalent linear or branched saturated hydrocarbon radical. For example, an alkyl group can have 1 to 10 carbon atoms (i.e., C$_{1-10}$ alkyl) or 1 to 8 carbon atoms (i.e., C$_{1-8}$ alkyl) or 1 to 6 carbon atoms (i.e., C$_{1-6}$ alkyl) or 1 to 4 carbon atoms (i.e., C$_{1-4}$ alkyl). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), and octyl (—(CH$_2$)$_7$CH$_3$). Alkyl groups can be unsubstituted or substituted.

"Alkoxy" refers to the group —O-alkyl, where alkyl is as defined above. For example, C$_{1-4}$ alkoxy refers to an —O-alkyl group having 1 to 4 carbons. Alkoxy groups can be unsubstituted or substituted.

"Alkoxyalkyl" is an alkoxy group attached to an alkyl as defined above, such that the alkyl is divalent. For example, C$_{2-6}$ alkoxyalkyl includes —CH$_2$—OMe, —CH$_2$—O-iPr, —CH$_2$—CH$_2$—OMe, —CH$_2$—CH$_2$—O—CH$_2$—CH$_3$, and —CH$_2$—CH$_2$—O-tBu. Alkoxyalkyl groups can be unsubstituted or substituted.

"Hydroxyalkyl" is a hydroxy group attached to an alkyl as defined above, such that the alkyl is divalent. For example, C$_{1-6}$ hydroxyalkyl includes —CH$_2$—OH, and —CH$_2$—CH$_2$—OH. Hydroxyalkyl groups can be unsubstituted or substituted.

"Alkenyl" is a monovalent or divalent linear or branched hydrocarbon radical with at least one carbon-carbon double bond. For example, an alkenyl group can have 2 to 8 carbon atoms (i.e., C$_{2-8}$ alkenyl) or 2 to 6 carbon atoms (i.e., C$_{2-6}$ alkenyl) or 2 to 4 carbon atoms (i.e., C$_{2-4}$ alkenyl). Examples of alkenyl groups include, but are not limited to, ethenyl (—CH=CH$_2$), allyl (—CH$_2$CH=CH$_2$), and —CH$_2$—CH=CH—CH$_3$. Alkenyl groups can be unsubstituted or substituted.

"Alkynyl" is a monovalent or divalent linear or branched hydrocarbon radical with at least one carbon-carbon triple bond. For example, an alkynyl group can have 2 to 8 carbon atoms (i.e., C$_{2-8}$ alkynyl) or 2 to 6 carbon atoms (i.e., C$_{2-6}$ alkynyl) or 2 to 4 carbon atoms (i.e., C$_{2-4}$ alkynyl). Examples of alkynyl groups include, but are not limited to, acetylenyl (—C≡CH), propargyl (—CH$_2$C≡CH), and —CH$_2$—C≡C—CH$_3$. Alkynyl groups can be unsubstituted or substituted.

"Halogen" refers to fluoro (—F), chloro (—Cl), bromo (—Br) and iodo (—I).

"Haloalkyl" is an alkyl as defined herein, wherein one or more hydrogen atoms of the alkyl are independently replaced by a halogen, which may be the same or different, such that the alkyl is divalent. The alkyl group and the halogen can be any of those described above. In some embodiments, the haloalkyl defines the number of carbon atoms in the alkyl portion, e.g., C$_{1-4}$ haloalkyl includes CF$_3$, CH$_2$F, CHF$_2$, CH$_2$CF$_3$, CH$_2$CH$_2$CF$_3$, CCl$_2$CH$_2$CH$_2$CH$_3$, and C(CH$_3$)$_2$(CF$_2$H). Haloalkyl groups can be unsubstituted or substituted.

"Haloalkoxy" is an alkoxy as defined herein, wherein one or more hydrogen atoms of the alkyl in the alkyoxy are independently replaced by a halogen, which may be the same or different, such that the alkyl is divalent. The alkoxy group and the halogen can be any of those described above. In some embodiments, the haloalkoxy defines the number of carbon atoms in the alkyl portion, e.g., C$_{1-4}$ haloalkoxy includes OCF$_3$, OCH$_2$F, OCH$_2$CF$_3$, OCH$_2$CH$_2$CF$_3$, OCCl$_2$CH$_2$CH$_2$CH$_3$, and OC(CH$_3$)$_2$(CF$_2$H). Haloalkoxy groups can be unsubstituted or substituted.

"Cycloalkyl" is a monovalent or divalent single all carbon ring or a multiple condensed all carbon ring system wherein the ring in each instance is a non-aromatic saturated or unsaturated ring. For example, in some embodiments, a cycloalkyl group has 3 to 12 carbon atoms, 3 to 10 carbon atoms, 3 to 8 carbon atoms, 3 to 6 carbon atoms, 3 to 5 carbon atoms, or 3 to 4 carbon atoms. Exemplary single ring cycloalkyl groups include cyclopropyl, cyclobutyl, cyclopentyl, cyclohexyl, cyclohexenyl, cycloheptyl, cycloheptenyl, and cyclooctyl. Cycloalkyl also includes multiple condensed ring systems (e.g., ring systems comprising 2 rings) having about 7 to 12 carbon atoms. The rings of the multiple condensed ring system can be connected to each other via fused, spiro, or bridged bonds when allowed by valency requirements. Exemplary multiple ring cycloalkyl groups include octahydropentalene, bicyclo[2. 2. 1]heptane, bicyclo [2. 2. 2]octane, bicyclo[2. 2. 2]oct-2-ene, and spiro[2. 5]octane. Cycloalkyl groups can be unsubstituted or substituted.

"Alkylcycloalkyl" refers to an alkyl as defined herein, wherein one or more hydrogen atoms of the alkyl are independently replaced by a cycloalkyl group, which may be the same or different. The alkyl group and the cycloalkyl group can be any of those described above. In some embodiments, the number of carbon atoms in the alkyl and cycloalkyl portion can be designated separately, e.g., $C_{1-6}$ alkyl-$C_{3-12}$ cycloalkyl. Alkylcycloalkyl groups can be unsubstituted or substituted.

"Aryl" as used herein refers to a monovalent or divalent single all carbon aromatic ring or a multiple condensed all carbon ring system wherein the ring is aromatic. For example, in some embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which multiple rings are aromatic. The rings of the multiple condensed ring system can be connected to each other via fused bonds when allowed by valency requirements. It is also understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl. Non-limiting examples of aryl groups include, but are not limited to, phenyl, naphthyl, anthracenyl, and the like. Aryl groups can be unsubstituted or substituted.

"Alkylaryl" refers to an alkyl as defined herein, wherein one or more hydrogen atoms of the alkyl are independently replaced by an aryl group, which may be the same or different. The alkyl group and the aryl group can be any of those described above, such that the alkyl is divalent. In some embodiments, an alkylaryl group has 7 to 24 carbon atoms, 7 to 16 carbon atoms, 7 to 13 carbon atoms, or 7 to 11 carbon atoms. An alkylaryl group defined by the number of carbon atoms refers to the total number of carbon atoms present in the constitutive alkyl and aryl groups combined. For example, $C_7$ alkylaryl refers to benzyl, while $C_{11}$ alkylaryl includes 1-methylnaphthyl and n-pentylphenyl. In some embodiments the number of carbon atoms in the alkyl and aryl portion can be designated separately, e.g., $C_{1-6}$ alkyl-$C_{6-10}$ aryl. Non-limiting examples of alkylaryl groups include, but are not limited to, benzyl, 2,2-dimethylphenyl, n-pentylphenyl, 1-methylnaphthyl, 2-ethylnaphthyl, and the like. Alkylaryl groups can be unsubstituted or substituted.

"Heterocyclyl" or "heterocycle" or "heterocycloalkyl" as used herein refers to a single saturated or partially unsaturated non-aromatic ring or a non-aromatic multiple ring system that has at least one heteroatom in the ring (i.e., at least one annular (i.e., ring-shaped) heteroatom selected from oxygen, nitrogen, and sulfur). Unless otherwise specified, a heterocyclyl group has from 3 to about 20 annular atoms, for example from 3 to 12 annular atoms, for example from 4 to 12 annular atoms, 4 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g., bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3. 3]heptan-6-yl, 6-oxa-1-azaspiro[3. 3]heptan-1-yl, 2-thia-6-azaspiro[3. 3]heptan-6-yl, 2,6-diazaspiro[3. 3]heptan-2-yl, 2-azabicyclo[3. 1. 0]hexan-2-yl, 3-azabicyclo [3. 1. 0]hexanyl, 2-azabicyclo[2. 1. 1]hexanyl, 2-azabicyclo [2. 2. 1]heptan-2-yl, 4-azaspiro[2. 4]heptanyl, 5-azaspiro[2. 4]heptanyl, and the like. Heterocyclyl groups can be unsubstituted or substituted.

"Alkylheterocyclyl" refers to an alkyl as defined herein, wherein one or more hydrogen atoms of the alkyl are independently replaced by a heterocyclyl group, which may be the same or different. The alkyl group and the heterocyclyl group can be any of those described above, such that the alkyl is divalent. In some embodiments, the number of atoms in the alkyl and heterocyclyl portion can be designated separately, e.g., $C_{1-6}$ alkyl-3 to 12 membered heterocyclyl having one to three heteroatoms each independently N, O, or S. Alkylheterocyclyl groups can be unsubstituted or substituted.

"Heteroaryl" refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl) and aryls (to form, for example, benzimidazolyl or indazolyl) to form the multiple condensed ring system. Thus, a heteroaryl (a single aromatic ring or multiple condensed ring system) can have about 1-20 carbon atoms and about 1-6 heteroatoms within the heteroaryl ring. For example, tetrazolyl has 1 carbon atom and 4 nitrogen heteroatoms within the ring. The rings of the multiple condensed ring system can be connected to each other via fused bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. It is also to be understood that the rings of the multiple condensed ring system may include an aryl ring fused to a heterocyclic ring with saturated or partially unsaturated bonds (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. For example, a 5-membered heteroaryl includes thiazolyl and a 10-membered heteroaryl includes quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, benzofuranyl, benzimidazolyl, thianaphthenyl, pyrrolo[2,3-b]pyridinyl, quinazolinyl-4(3H)-one, triazolyl, and tetrazolyl. Heteroaryl groups can be unsubstituted or substituted.

"Alkylheteroaryl" refers to an alkyl as defined herein, wherein one or more hydrogen atoms of the alkyl are independently replaced by a heteroaryl group, which may be the same or different, such that the alkyl is divalent. The alkyl group and the heteroaryl group can be any of those described above. In some embodiments, the number of atoms in the alkyl and heteroaryl portion are designated separately, e.g., $C_{1-6}$ alkyl-5 to 10 membered heteroaryl having one to four heteroatoms each independently N, O, or S. Alkylheteroaryl groups can be unsubstituted or substituted.

"Oxo" as used herein refers to =O.

"Substituted" as used herein refers to wherein one or more hydrogen atoms of the group are independently replaced by one or more substituents (e.g., 1, 2, 3, or 4 or more) as indicated.

A "compound of the present disclosure" includes compounds disclosed herein, for example a compound of the present disclosure includes compounds of Formula (I-A), including the compounds of the Examples. In some embodiments, a "compound of the present disclosure" includes compounds of Formula (I-A).

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Therapeutically effective amount" or "effective amount" as used herein refers to an amount that is effective to elicit the desired biological or medical response, including the amount of a compound that, when administered to a subject for treating a disease, is sufficient to affect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the subject.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $N(C_1$≡$C_4$ alkyl$)_4{}^+$. Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (I-A) can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Stereoisomer" as used herein refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Tautomer" as used herein refers to a proton shift from one atom of a molecule to another atom of the same molecule. In some embodiments, the present disclosure includes tautomers of said compounds.

"Solvate" as used herein refers to the result of the interaction of a solvent and a compound. Solvates of salts of the compounds described herein are also provided. Hydrates of the compounds described herein are also provided.

"Hydrate" as used herein refers to a compound of the disclosure that is chemically associated with one or more molecules of water.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Prodrug" as used herein refers to a derivative of a drug that upon administration to the human body is converted to the parent drug according to some chemical or enzymatic pathway. In some embodiments, a prodrug is a biologically inactive derivative of a drug that upon administration to the human body is converted to the biologically active parent drug according to some chemical or enzymatic pathway.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival. "At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

II. Compounds

In one embodiment, the present disclosure provides a compound of Formula (I-A):

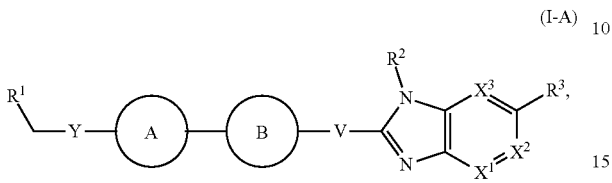

(I-A)

or a pharmaceutically acceptable salt thereof, wherein
$R^1$ is $C_{6-10}$ aryl or heteroaryl each optionally substituted with one to four $Z^1$;
ring A is

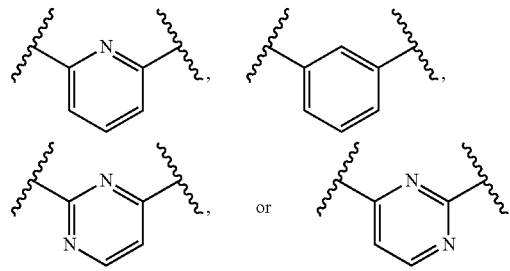

each of which is optionally substituted with 1 to 3 groups each independently $C_{1-6}$ alkyl, $C_{1-6}$ alkoxy, halogen, $C_{1-6}$ haloalkyl, $C_{1-6}$ haloalkoxy, —OH, —CN, or —N($R^{4a}$)($R^{4b}$);
ring B is

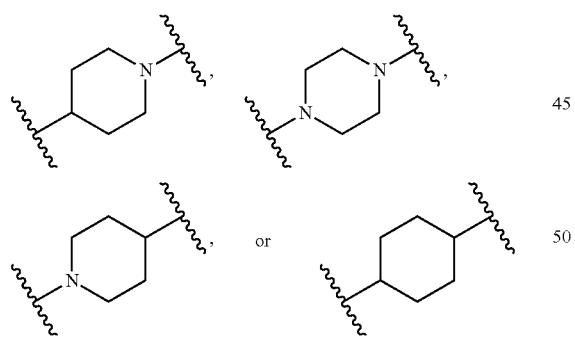

each of which is optionally substituted with 1 to 3 $R^B$ groups each independently $C_{1-6}$ alkyl or halogen, alternatively, two $R^B$ groups on adjacent carbon ring members or the same carbon ring member can be combined with the atoms to which they are attached to form a $C_{3-6}$ cycloalkyl;
$R^2$ is H, $C_{1-6}$ alkyl, $C_{2-6}$ alkynyl, $C_{1-6}$ haloalkyl, $C_{3-10}$ cycloalkyl, heterocyclyl, $C_{1-6}$ alkyl-$C_{3-10}$ cycloalkyl, $C_{1-6}$ alkyl-heterocyclyl, or $C_{1-6}$ alkyl-heteroaryl, wherein the alkyl, alkynyl, cycloalkyl, heterocyclyl or heteroaryl is each optionally substituted with one to four $Z^1$;

$X^1$ is —N═, —C(H)═ or —C($R^{11}$)═, $X^2$ and $X^3$ are each independently —N═, —C(H)═, or —C($R^8$)═; wherein at least one of $X^2$ and $X^3$ is —C($R^8$)═ or $X^1$ is —C($R^{11}$)═;
$R^3$ is COOR$^{3a}$;
$R^{3a}$ is H, $C_{1-4}$ alkyl-N($R^{9a}$)($R^{9b}$), —$C_{1-4}$ alkyl-N($R^{9a}$)C(O)—O—$C_{1-4}$ alkyl-OP(O)(OR$^{9c}$)$_2$, $C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-O—C(O)—$C_{1-4}$ alkyl-OP(O)(OR$^9$)$_2$, —CH$_2$CH(N($R^{9a}$)$_2$)C(O)OR$^{9b}$, —P(O)(OR$^{9c}$)$_2$, —OP(O)(OR$^{9c}$)$_2$, —CH$_2$P(O)(OR$^{9c}$)$_2$, —CH$_2$OP(O)(OR$^{9c}$)$_2$, —OCH$_2$P(O)(OR$^{9c}$)$_2$, —C(O)OCH$_2$P(O)(OR$^9$)$_2$, —P(O)(R$^{9c}$)(OR$^{9d}$), —OP(O)(R$^{9c}$)(OR$^{9d}$), —CH$_2$P(O)(R$^{9c}$)(OR$^{9d}$), —OCH$_2$P(O)(R$^{9c}$)(OR$^{9d}$), —C(O)OCH$_2$P(O)(R$^{9c}$)(OR$^{9d}$), —P(O)(N(R$^{9c}$)$_2$)$_2$, —OP(O)(N(R$^{9c}$)$_2$)$_2$, —CH$_2$P(O)(N(R$^{9c}$)$_2$)$_2$, —OCH$_2$P(O)(N(R$^{9c}$)$_2$)$_2$, —C(O)OCH$_2$P(O)(N(R$^{9c}$)$_2$)$_2$, —P(O)(N(R$^{9c}$)$_2$)(OR$^{9d}$), —OP(O)(N(R$^{9c}$)$_2$)(OR$^{9d}$), —CH$_2$P(O)(N(R$^{9c}$)$_2$)(OR$^{9d}$), —OCH$_2$P(O)(N(R$^{9c}$)$_2$)(OR$^{9d}$), —C(O)OCH$_2$P(O)(N(R$^{9c}$)$_2$)(OR$^{9d}$), —P(O)(R$^{9c}$)(N(R$^{9d}$)$_2$), —OP(O)(R$^{9c}$)(N(R$^{9d}$)$_2$), —CH$_2$P(O)(R$^{9c}$)(N(R$^{9d}$)$_2$), —OCH$_2$P(O)(R$^{9c}$)(N(R$^{9d}$)$_2$), —C(O)OCH$_2$P(O)(R$^{9c}$)(N(R$^{9d}$)$_2$), or $C_{1-6}$ alkyl-heterocyclyl, wherein the alkyl or heterocyclyl is each optionally substituted with one to four halogens;
each $R^{9a}$ and $R^{9b}$ is independently H, $C_{1-6}$ alkyl, or $C_{1-6}$ haloalkyl, or $R^{9a}$ and $R^{9b}$ together form a 6-membered heterocyclyl;
V is —C($R^{6b}$)($R^{6c}$)—;
each $R^{6b}$ and $R^{6c}$ is independently —H, $C_{1-6}$ alkyl, or halogen;
alternatively, $R^{6b}$ is combined with the $R^B$ group attached to the carbon ring member to form a $C_{3-6}$ cycloalkyl;
Y is —O—;
$R^8$ and $R^{11}$ are each independently H, $C_{1-9}$ alkyl, $C_{1-8}$ haloalkyl, $C_{2-6}$ alkenyl, $C_{2-6}$ alkynyl, $C_{1-6}$ alkoxy, $C_{1-6}$ hydroxyalkyl, $C_{1-6}$ alkoxyalkyl, halogen, $C_{1-6}$ haloalkyl, $C_{1-6}$ haloalkoxy, halogen, $C_{1-6}$ haloalkyl, $C_{1-6}$ haloalkoxy, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl),
—NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein each alkyl, alkenyl, alkynyl, cycloalkyl, heterocyclyl, aryl, or heteroaryl is optionally substituted with 1 to 3 $Z^{1b}$;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—R$^{12a}$, —C(O)—R$^{12a}$, —C(O)O—R$^{12a}$, —C(O)—N(R$^{12a}$)(R$^{12b}$), —N(R$^{12a}$)(R$^{12b}$), —N(R$^{12a}$)$_2$(R$^{12b}$)$^+$, —N(R$^{12a}$)C(O)—R$^{12b}$, —N(R$^{12a}$)C(O)O—R$^{12b}$, —N(R$^{12a}$)C(O)N(R$^{12b}$)(R$^{12c}$), —N(R$^{12a}$)S(O)$_2$(R$^{12b}$), —NR$^{12a}$S(O)$_2$N(R$^{12b}$)(R$^{12c}$), —NR$^{12a}$S(O)$_2$O(R$^{12b}$), —OC(O)R$^{12a}$, —OC(O)OR$^{12a}$, —OC(O)—N(R$^{12a}$)(R$^{12b}$), —S—R$^{12a}$, —S(O)R$^{12a}$, —S(O)(NH)R$^{12a}$, —S(O)$_2$R$^{12a}$, —S(O)$_2$N(R$^{12a}$)(R$^{12b}$), —S(O)(NR$^{12a}$)R$^{12b}$, or —Si(R$^{12a}$)$_3$;

wherein each alkyl, haloalkyl, alkenyl, alkynyl, cycloalkyl, heterocyclyl, aryl, or heteroaryl is optionally substituted with 1 to 4 $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—R$^{12a}$, —C(O)R$^{12a}$, —C(O)O—R$^{12a}$, —C(O)N(R$^{12a}$)(R$^{12b}$), —N(R$^{12a}$)(R$^{12b}$), —N(R$^{12a}$)$_2$(R$^{12b}$)$^+$, —N(R$^{12a}$)—C(O)R$^{12b}$, —N(R$^{12a}$)C(O)O(R$^{12b}$), —N(R$^{12a}$)C(O)N(R$^{12b}$)(R$^{12c}$), —N(R$^{12a}$)S(O)$_2$(R$^{12b}$), —N(R$^{12a}$)S(O)$_2$—N(R$^{12b}$)(R$^{12c}$), —N(R$^{12a}$)S(O)$_2$O(R$^{12b}$), —OC(O)R$^{12a}$, —OC(O)OR$^{12a}$, —OC(O)—N(R$^{12a}$)(R$^{12b}$), —S—R$^{12a}$, —S(O)R$^{12a}$, —S(O)(NH)R$^{12a}$, —S(O)$_2$R$^{12a}$, —S(O)$_2$N(R$^{12a}$)(R$^{12b}$), —S(O)(NR$^{12a}$)R$^{12b}$, or —Si(R$^{12a}$)$_3$;

wherein each alkyl, haloalkyl, alkenyl, alkynyl, cycloalkyl, heterocyclyl, aryl, or heteroaryl is optionally substituted with 1 to 4 $Z^{1b}$;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein each alkyl, cycloalkyl, heterocyclyl, aryl, or heteroaryl is optionally substituted with 1 to 3 $C_{1-9}$ alkyl, $C_{1-8}$ haloalkyl, halogen, —OH, —NH$_2$, CO$_2$H, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$haloalkyl), —NHC(O)(C$_{3-15}$ cycloalkyl), —NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$ haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

each R$^{2a}$, R$^{2b}$, R$^{4a}$, R$^{4b}$, R$^{9c}$, R$^{9d}$, R$^{12a}$, R$^{12b}$, and R$^{12c}$ is independently H, C$_{1-9}$ alkyl, C$_{2-6}$ alkenyl, C$_{2-6}$ alkynyl, C$_{3-15}$ cycloalkyl, heterocyclyl, C$_{6-10}$ aryl, or heteroaryl wherein the alkyl, alkenyl, alkynyl, cycloalkyl, heterocyclyl, aryl, or heteroaryl is each optionally substituted with 1 to 4 Z$^{1b}$; and wherein each heterocyclyl has 3 to 12 ring members and has 1 to 4 heteroatoms each independently N, O, or S; and wherein each heteroaryl has 5 to 12 ring members and 1 to 4 heteroatoms each independently N, O, or S.

In some embodiments of the compound of Formula (I-A), or pharmaceutically acceptable salt thereof, (i) if Ring A is

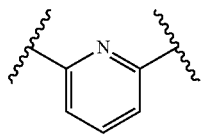 [SMILES: *c1cccc(*)n1]

and ring B is

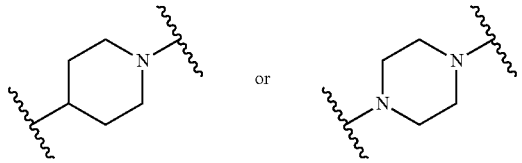 [SMILES: *C1CCN(*)CC1 ; *N1CCN(*)CC1]

and R$^1$ is phenyl optionally substituted with Z$^1$ then

R$^8$ is independently C$_{2-9}$ alkyl, R$^{12}$, C$_{1-8}$ haloalkyl, C$_{2-6}$ alkenyl, C$_{2-6}$ alkynyl, C$_{3-15}$ cycloalkyl, heterocyclyl, C$_{6-10}$ aryl, heteroaryl, oxo, —OH, —CN, —NO$_2$, —NH$_2$, —N$_3$, —SH, —O(C$_{1-9}$ alkyl), —O(C$_{1-8}$ haloalkyl), —O(C$_{2-6}$ alkenyl), —O(C$_{2-6}$ alkynyl), —O(C$_{3-15}$ cycloalkyl), —O(heterocyclyl), —O(C$_{6-10}$ aryl), —O(heteroaryl), —NH(C$_{1-9}$ alkyl), —NH(C$_{1-8}$ haloalkyl), —NH(C$_{2-6}$ alkenyl), —NH(C$_{2-6}$ alkynyl), —NH(C$_{3-15}$ cycloalkyl), —NH(heterocyclyl), —NH(C$_{6-10}$ aryl), —NH(heteroaryl), —N(C$_{1-9}$ alkyl)$_2$, —N(C$_{1-8}$haloalkyl)$_2$, —N(C$_{2-6}$ alkenyl)$_2$, —N(C$_{2-6}$ alkynyl)$_2$, —N(C$_{3-15}$ cycloalkyl)$_2$, —N(heterocyclyl)$_2$, —N(C$_{6-10}$ aryl)$_2$, —N(heteroaryl)$_2$, —N(C$_{1-9}$ alkyl)(C$_{1-8}$ haloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(heterocyclyl), —N(C$_{1-9}$ alkyl)(C$_{6-10}$ aryl), —N(C$_{1-9}$ alkyl)(heteroaryl), —C(O)(C$_{1-9}$ alkyl), —C(O)(C$_{1-8}$ haloalkyl), —C(O)(C$_{2-6}$ alkenyl), —C(O)(C$_{2-6}$ alkynyl), —C(O)(C$_{3-15}$ cycloalkyl), —C(O)(heterocyclyl), —C(O)(C$_{6-10}$ aryl), —C(O)(heteroaryl), —C(O)O(C$_{1-9}$ alkyl), —C(O)O(C$_{1-8}$ haloalkyl), —C(O)O(C$_{2-6}$ alkenyl), —C(O)O(C$_{2-6}$ alkynyl), —C(O)O(C$_{3-15}$ cycloalkyl), —C(O)O(heterocyclyl), —C(O)O(C$_{6-10}$ aryl), —C(O)O(heteroaryl), —C(O)NH$_2$, —C(O)NH(C$_{1-9}$ alkyl), —C(O)NH(C$_{1-8}$haloalkyl), —C(O)NH(C$_{2-6}$ alkenyl), —C(O)NH(C$_{2-6}$ alkynyl), —C(O)NH(C$_{3-15}$ cycloalkyl), —C(O)NH(heterocyclyl), —C(O)NH(C$_{6-10}$ aryl), —C(O)NH(heteroaryl), —C(O)N(C$_{1-9}$ alkyl)$_2$, —C(O)N(C$_{1-8}$ haloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(heterocyclyl)$_2$, —C(O)N(C$_{6-10}$ aryl)$_2$, —C(O)N(heteroaryl)$_2$, —NHC(O)(C$_{1-9}$ alkyl), —NHC(O)(C$_{1-8}$ haloalkyl), —NHC(O)(C$_{2-6}$ alkenyl), —NHC(O)(C$_{2-6}$ alkynyl), —NHC(O)(C$_{3-15}$ cycloalkyl), —NHC(O)(heterocyclyl), —NHC(O)(C$_{6-10}$ aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(heterocyclyl), —NHC(O)O(C$_{6-10}$ aryl), —NHC(O)O(heteroaryl), —NHC(O)NH(C$_{1-9}$ alkyl), —NHC(O)NH(C$_{1-8}$ haloalkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(heterocyclyl), —NHC(O)NH(C$_{6-10}$ aryl), —NHC(O)NH(heteroaryl), —NHS(O)(C$_{1-9}$ alkyl), —N(C$_{1-9}$ alkyl)(S(O)(C$_{1-9}$ alkyl), —S(C$_{1-9}$ alkyl), —S(C$_{1-8}$ haloalkyl), —S(C$_{2-6}$ alkenyl), —S(C$_{2-6}$ alkynyl), —S(C$_{3-15}$ cycloalkyl), —S(heterocyclyl), —S(C$_{6-10}$ aryl), —S(heteroaryl), —S(O)N(C$_{1-9}$ alkyl)$_2$, —S(O)(C$_{1-9}$ alkyl), —S(O)(C$_{1-8}$ haloalkyl), —S(O)(C$_{2-6}$ alkenyl), —S(O)(C$_{2-6}$ alkynyl), —S(O)(C$_{3-15}$ cycloalkyl), —S(O)(heterocyclyl), —S(O)(C$_{6-10}$ aryl), —S(O)(heteroaryl), —S(O)$_2$(C$_{1-9}$ alkyl), —S(O)$_2$(C$_{1-8}$ haloalkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein each alkyl, alkenyl, alkynyl, cycloalkyl, heterocyclyl, aryl, or heteroaryl is optionally substituted with 1 to 3 Z$^{1b}$; and R$^{11}$ is independently C$_{1-9}$ alkyl, C$_{1-8}$ haloalkyl, C$_{2-6}$ alkenyl, C$_{2-6}$ alkynyl, halogen, C$_{3-15}$ cycloalkyl, heterocyclyl, C$_{6-10}$ aryl, heteroaryl, oxo, —OH, —CN, —NO$_2$, —NH$_2$, —N$_3$, —SH, —O(C$_{1-9}$ alkyl), —O(C$_{1-8}$ haloalkyl), —O(C$_{2-6}$ alkenyl), —O(C$_{2-6}$ alkynyl), —O(C$_{3-15}$ cycloalkyl), —O(heterocyclyl), —O(C$_{6-10}$ aryl), —O(heteroaryl), —NH(C$_{1-9}$ alkyl), —NH(C$_{1-8}$ haloalkyl), —NH(C$_{2-6}$ alkenyl), —NH(C$_{2-6}$ alkynyl), —NH(C$_{3-15}$ cycloalkyl), —NH(heterocyclyl), —NH(C$_{6-10}$ aryl), —NH(heteroaryl), —N(C$_{1-9}$ alkyl)$_2$, —N(C$_{1-8}$ haloalkyl)$_2$, —N(C$_{2-6}$ alkenyl)$_2$, —N(C$_{2-6}$ alkynyl)$_2$, —N(C$_{3-15}$ cycloalkyl)$_2$, —N(heterocyclyl)$_2$, —N(C$_{6-10}$ aryl)$_2$, —N(heteroaryl)$_2$, —N(C$_{1-9}$ alkyl)(C$_{1-8}$ haloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(heterocyclyl), —N(C$_{1-9}$ alkyl)(C$_{6-10}$ aryl), —N(C$_{1-9}$ alkyl)(heteroaryl), —C(O)(C$_{1-9}$ alkyl), —C(O)(C$_{1-8}$ haloalkyl), —C(O)(C$_{2-6}$ alkenyl), —C(O)(C$_{2-6}$ alkynyl), —C(O)(C$_{3-15}$ cycloalkyl), —C(O)(heterocyclyl), —C(O)(C$_{6-10}$ aryl), —C(O)(heteroaryl), —C(O)O(C$_{1-9}$ alkyl), —C(O)O(C$_{1-8}$haloalkyl), —C(O)O(C$_{2-6}$ alkenyl), —C(O)O ($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heterocyclyl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein each alkyl, alkenyl, alkynyl, cycloalkyl, heterocyclyl, aryl, or heteroaryl is optionally substituted with 1 to 3 $Z^{1b}$, or (ii) if ring A is

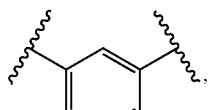 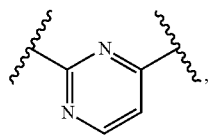 , or

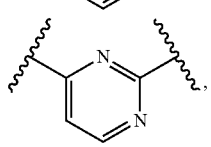 , or
if ring B is

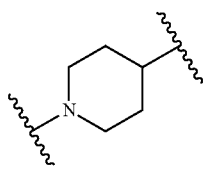 or 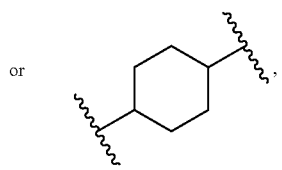 ;

or
if $R^1$ is not phenyl optionally substituted with $Z^1$, then $R^{11}$ and $R^8$ are independently selected from $R^{13}$, $C_{2-6}$ alkenyl, $C_{2-6}$ alkynyl, $C_{3-15}$ cycloalkyl, heterocyclyl, $C_{6-10}$ aryl, heteroaryl, oxo, —NO$_2$, —N$_3$, —SH, —OR$^{13}$, —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($R^{12}$), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($R^{12}$)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($R^{13}$), —C(O)($C_{2-6}$ alkenyl), —C(O)($C_{2-6}$ alkynyl), —C(O)(heterocyclyl), —C(O)($C_{6-10}$ aryl), —C(O)(heteroaryl), —C(O)O($C_{1-9}$ alkyl), —C(O)O($C_{1-8}$haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein each alkyl, alkenyl, alkynyl, cycloalkyl, heterocyclyl, aryl, or heteroaryl is optionally substituted with 1 to 3 $Z^{1b}$;

each $R^{12}$ is $C_{1-9}$ alkyl substituted with 1 to 3 $Z^{1b}$;

each $R^{13}$ is $C_{1-9}$ alkyl optionally substituted with $Z^{1b}$ and necessarily substituted with at least one group selected from C$_{2-6}$ alkenyl, C$_{2-6}$ alkynyl, heterocyclyl, C$_{6-10}$ aryl, heteroaryl, —OH, —NO$_2$, —NH$_2$, —N$_3$, —SH, —O(C$_{1-9}$ alkyl), —O(C$_{1-8}$ haloalkyl), —O(C$_{2-6}$ alkenyl), —O(C$_{2-6}$ alkynyl), —O(C$_{3-15}$ cycloalkyl), —O(heterocyclyl), —O(C$_{6-10}$ aryl), —O(heteroaryl), —NH(C$_{1-9}$ alkyl), —NH(C$_{1-8}$ haloalkyl), —NH(C$_{2-6}$ alkenyl), —NH(C$_{2-6}$ alkynyl), —NH(C$_{3-15}$ cycloalkyl), —NH(heterocyclyl), —NH(C$_{6-10}$ aryl), —NH(heteroaryl), —N(C$_{1-9}$ alkyl)$_2$, —N(C$_{1-8}$ haloalkyl)$_2$, —N(C$_{2-6}$ alkenyl)$_2$, —N(C$_{2-6}$ alkynyl)$_2$, —N(C$_{3-15}$ cycloalkyl)$_2$, —N(heterocyclyl)$_2$, —N(C$_{6-10}$ aryl)$_2$, —N(heteroaryl)$_2$, —N(C$_{1-9}$ alkyl)(C$_{1-8}$ haloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(heterocyclyl), —N(C$_{1-9}$ alkyl)(C$_{6-10}$ aryl), —N(C$_{1-9}$ alkyl)(heteroaryl), —C(O)(C$_{1-9}$ alkyl), —C(O)(C$_{1-8}$ haloalkyl), —C(O)(C$_{2-6}$ alkenyl), —C(O)(C$_{2-6}$ alkynyl), —C(O)(C$_{3-15}$ cycloalkyl), —C(O)(heterocyclyl), —C(O)(C$_{6-10}$ aryl), —C(O)(heteroaryl), —C(O)O(C$_{1-9}$ alkyl), —C(O)O(C$_{1-8}$haloalkyl), —C(O)O(C$_{2-6}$ alkenyl), —C(O)O(C$_{2-6}$ alkynyl), —C(O)O(C$_{3-15}$ cycloalkyl), —C(O)O(heterocyclyl), —C(O)O(C$_{6-10}$ aryl), —C(O)O(heteroaryl), —C(O)NH$_2$, —C(O)NH(C$_{1-9}$ alkyl), —C(O)NH(C$_{1-8}$ haloalkyl), —C(O)NH(C$_{2-6}$ alkenyl), —C(O)NH(C$_{2-6}$ alkynyl), —C(O)NH(C$_{3-15}$ cycloalkyl), —C(O)NH(heterocyclyl), —C(O)NH(C$_{6-10}$ aryl), —C(O)NH(heteroaryl), —C(O)N(C$_{1-9}$ alkyl)$_2$, —C(O)N(C$_{1-8}$ haloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(heterocyclyl)$_2$, —C(O)N(C$_{6-10}$ aryl)$_2$, —C(O)N(heteroaryl)$_2$, —NHC(O)(C$_{1-9}$ alkyl), —NHC(O)(C$_{1-8}$ haloalkyl), —NHC(O)(C$_{2-6}$ alkenyl), —NHC(O)(C$_{2-6}$ alkynyl), —NHC(O)(C$_{3-15}$ cycloalkyl), —NHC(O)(heterocyclyl), —NHC(O)(C$_{6-10}$ aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(heterocyclyl), —NHC(O)O(C$_{6-10}$ aryl), —NHC(O)O(heteroaryl), —NHC(O)NH(C$_{1-9}$ alkyl), —NHC(O)NH(C$_{1-8}$ haloalkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(heterocyclyl), —NHC(O)NH(C$_{6-10}$ aryl), —NHC(O)NH(heteroaryl), —NHS(O)(C$_{1-9}$ alkyl), —N(C$_{1-9}$ alkyl)(S(O)(C$_{1-9}$ alkyl), —S(C$_{1-9}$ alkyl), —S(C$_{1-8}$ haloalkyl), —S(C$_{2-6}$ alkenyl), —S(C$_{2-6}$ alkynyl), —S(C$_{3-15}$ cycloalkyl), —S(heterocyclyl), —S(C$_{6-10}$ aryl), —S(heteroaryl), —S(O)N(C$_{1-9}$ alkyl)$_2$, —S(O)(C$_{1-9}$ alkyl), —S(O)(C$_{1-8}$ haloalkyl), —S(O)(C$_{2-6}$ alkenyl), —S(O)(C$_{2-6}$ alkynyl), —S(O)(C$_{3-15}$ cycloalkyl), —S(O)(heterocyclyl), —S(O)(C$_{6-10}$ aryl), —S(O)(heteroaryl), —S(O)$_2$(C$_{1-9}$ alkyl), —S(O)$_2$(C$_{1-8}$ haloalkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein each alkyl, cycloalkyl, heterocyclyl, aryl, or heteroaryl is optionally substituted with 1 to 3 groups each independently C$_{1-9}$ alkyl, C$_{1-8}$ haloalkyl, halogen, —OH, —NH$_2$, CO$_2$H, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$ haloalkyl), —NHC(O)(C$_{3-15}$ cycloalkyl), —NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$.

In some embodiments of the compound of Formula (I-A), the present disclosure provides a compound of Formula (I-A):

(I-A)

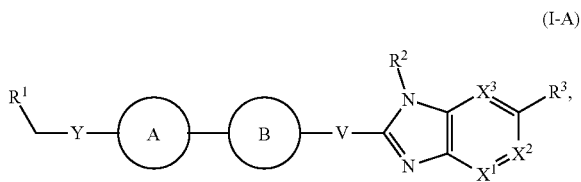

or a pharmaceutically acceptable salt thereof, wherein

R$^1$ is C$_6$ aryl or heteroaryl, wherein aryl and heteroaryl is each optionally substituted with 1 to 4 groups each independently C$_{1-6}$ alkyl, halogen, C$_{1-6}$ haloalkyl, —CN, —C(O)NH$_2$, —C(O)NH(C$_{1-6}$ alkyl), —C(O)N(C$_{1-6}$ alkyl)$_2$, —C(O)NH(C$_{3-6}$ cycloalkyl), —C(O)NH(heterocyclyl), heterocyclyl optionally substituted with 1 to 3 groups each independently C$_{1-6}$ alkyl, halogen, C$_{1-6}$ haloalkyl, or —OH, or heteroaryl optionally substituted with 1 to 3 groups each independently C$_{1-6}$ alkyl, halogen, C$_{1-6}$ haloalkyl, —OH, C$_{3-6}$ cycloalkyl, or heterocyclyl;

ring A is

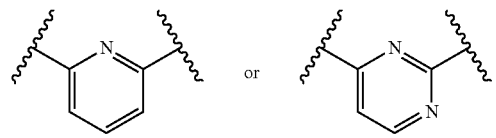 [SMILES: *c1cccc(*)n1 ; *c1ccnc(*)n1]

wherein each is optionally substituted with 1 to 3 groups each independently C$_{1-6}$ alkyl, C$_{1-6}$ alkoxy, halogen, C$_{1-6}$ haloalkyl, C$_{1-6}$ haloalkoxy, —OH or —NH$_2$;

ring B is

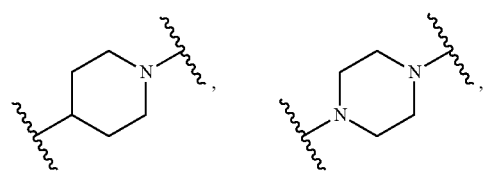

-continued

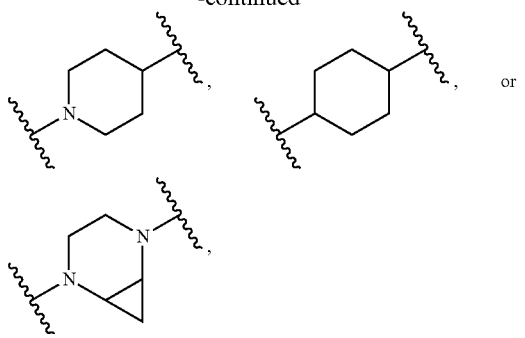

wherein each is optionally substituted with 1 to 3 $R^B$ groups each independently $C_{1-6}$ alkyl or halogen, alternatively, ring B is combined with V to form

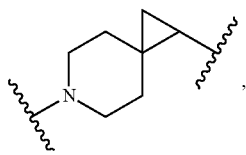 [SMILES: *C1CC12CCN(*)CC2]

optionally substituted with 1 to 3 $R^B$ groups each independently $C_{1-6}$ alkyl or halogen;

$R^2$ is H, $C_{1-6}$ alkyl, $C_{3-10}$ cycloalkyl, $C_{1-6}$ alkyl-$C_{3-10}$ cycloalkyl, heterocyclyl, $C_{1-6}$ alkyl-heterocyclyl, or $C_{1-6}$ alkyl-heteroaryl, wherein each alkyl, cycloalkyl, heterocyclyl or heteroaryl is optionally substituted with 1 to 3 groups each independently $C_{1-6}$ alkyl, $C_{1-6}$ alkoxy, $C_{1-6}$ hydroxyalkyl, $C_{2-6}$ alkoxyalkyl, halogen, $C_{1-6}$ haloalkyl, $C_{1-6}$ haloalkoxy, —OH, —CN, $C_{1-6}$ alkyl-CN, —O—$C_{3-6}$ cycloalkyl or heteroaryl optionally substituted with 1 to 4 groups each independently $C_{1-6}$ alkyl, $C_{1-6}$ alkoxy, halogen, $C_{1-6}$ haloalkyl, or $C_{1-6}$ haloalkoxy;

$X^1$ is —N=, —C(H)= or —C($R^{11}$)=;

$X^2$ and $X^3$ are each independently —N=, —C(H)=, or —C($R^8$)=, wherein at least one of $X^2$ and $X^3$ is —C($R^8$)= or $X^1$ is —C($R^{11}$)=;

$R^3$ is COO$R^{3a}$;

$R^{3a}$ is H, $C_{1-4}$ alkyl-N($R^{9a}$)($R^{9b}$), —$C_{1-4}$ alkyl-N($R^{9a}$)C(O)—O—$C_{1-4}$ alkyl-OP(O)(O$R^{9c}$)$_2$, $C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-O—C(O)—$C_{1-4}$ alkyl-OP(O)(O$R^{9c}$)$_2$, —CH$_2$CH(N($R^{9a}$)$_2$)C(O)O$R^{9b}$, —P(O)(O$R^{9c}$)$_2$, —OP(O)(O$R^{9c}$)$_2$, —CH$_2$P(O)(O$R^{9c}$)$_2$, —CH$_2$OP(O)(O$R^{9c}$)$_2$, —OCH$_2$P(O)(O$R^{9c}$)$_2$, —C(O)OCH$_2$P(O)(O$R^{9c}$)$_2$, —P(O)($R^{9c}$)(O$R^{9d}$), —OP(O)($R^{9c}$)(O$R^{9d}$), —CH$_2$P(O)($R^{9c}$)(O$R^{9d}$), —OCH$_2$P(O)($R^{9c}$)(O$R^{9d}$), —C(O)OCH$_2$P(O)($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), —C(O)OCH$_2$P(O)($R^{9c}$)(N($R^{9d}$)$_2$), or $C_{1-6}$ alkyl-heterocyclyl, wherein the wherein the alkyl or heterocyclyl is each optionally substituted with one to four halogens;

each $R^{9a}$ and $R^{9b}$ is independently H, $C_{1-6}$ alkyl, or $C_{1-6}$ haloalkyl, or $R^{9a}$ and $R^{9b}$ together form a 6-membered heterocyclyl;

each $R^{9c}$ and $R^{9d}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with 1 to 4 $Z^{1b}$;

V is —C($R^{6b}$)($R^{6c}$)—;

each $R^{6b}$ and $R^{6c}$ is independently —H, $C_{1-6}$ alkyl, or halogen;

Y is —O—;

(i) If Ring A is

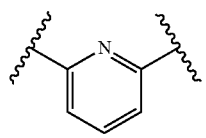 [SMILES: *c1cccc(*)n1]

and ring B is

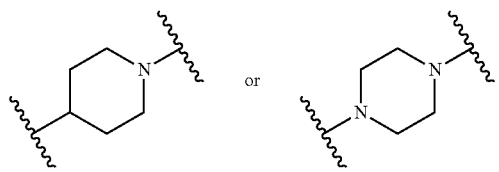 [SMILES: *C1CCN(*)CC1 ; *N1CCN(*)CC1]

and $R^1$ is phenyl optionally substituted with $Z^1$ then $R^8$ is independently $C_{2-9}$ alkyl, $C_{2-6}$ alkenyl, $C_{2-6}$ alkynyl, $C_{1-6}$ alkoxy, $C_{1-6}$ hydroxyalkyl, $C_{1-6}$ alkoxyalkyl, $C_{1-6}$ haloalkyl, $C_{1-6}$ haloalkoxy, —CN, —OH, —NH$_2$, $C_{3-6}$ cycloalkyl, heterocyclyl, heteroaryl, —NH($C_{1-9}$ alkyl), —N($C_{1-9}$ alkyl)$_2$, —NH($C_{3-15}$ cycloalkyl), —NH(heterocyclyl), —NH($C_{6-10}$ aryl), or —NH(heteroaryl), wherein the alkyl, alkynyl, cycloalkyl, heterocyclyl, or heteroaryl in each instance is optionally substituted with 1 to 3 groups each independently $C_{1-6}$ alkyl, $C_{1-6}$ alkoxy, halogen, $C_{1-6}$ haloalkyl, —OH, $C_{3-6}$ cycloalkyl, heterocyclyl optionally substituted with 1 to 3 groups each independently $C_{1-6}$ alkyl, $C_{1-6}$ alkoxy, halogen, $C_{1-6}$ haloalkyl, —OH, $C_{3-6}$ cycloalkyl optionally substituted with 1 to 3 groups each independently $C_{1-6}$ alkyl, $C_{1-6}$ alkoxy, halogen, $C_{1-6}$ haloalkyl, $C_{1-6}$ haloalkoxy, —OH, and heterocyclyl optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH;

$R^{11}$ is independently $C_{1-6}$ alkyl, $C_{2-6}$ alkenyl, $C_{2-6}$ alkynyl, $C_{1-6}$ alkoxy, $C_{1-6}$ hydroxyalkyl, $C_{2-6}$ alkoxyalkyl, halogen, $C_{1-6}$ haloalkyl, $C_{1-6}$ haloalkoxy, —CN, —OH, —NH$_2$, $C_{3-6}$ cycloalkyl, heterocyclyl, heteroaryl, —NH($C_{1-9}$ alkyl), —N($C_{1-9}$ alkyl)$_2$, —NH($C_{3-15}$ cycloalkyl), —NH(heterocyclyl), —NH($C_{6-10}$ aryl), or —NH(heteroaryl), wherein the alkyl, alkynyl, cycloalkyl, heterocyclyl, or heteroaryl in each instance is optionally substituted with one to three groups selected from $C_{1-6}$ alkyl, $C_{1-6}$ alkoxy, halogen, —$C_{1-6}$ haloalkyl, —OH, each $C_{3-6}$ cycloalkyl is optionally substituted with 1 to 3 groups each independently $C_{1-6}$ alkyl, $C_{1-6}$ alkoxy, halogen, $C_{1-6}$ haloalkyl, $C_{1-6}$ haloalkoxy, or —OH, and each heterocyclyl is optionally substituted with 1 to 3 groups each independently —$C_{1-6}$ alkyl, $C_{1-6}$ alkoxy, halogen, $C_{1-6}$ haloalkyl, $C_{1-6}$ haloalkoxy, or —OH;

(ii) If ring A is

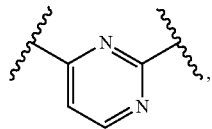 [SMILES: *c1ccnc(*)n1]

or

If ring B is

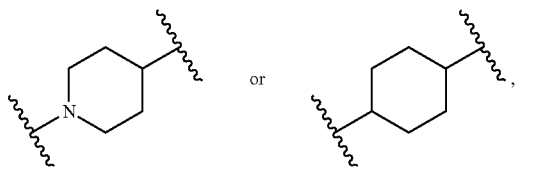 [SMILES: *C1CCN(*)CC1 ; *C1CCC(*)CC1]

or

If $R^1$ is not phenyl optionally substituted with $Z^1$, then $R^{11}$ and $R^8$ are independently $C_{2-6}$ alkynyl, $C_{1-6}$ hydroxyalkyl, $C_{2-6}$ alkoxyalkyl, $C_{3-6}$ cycloalkyl, heterocyclyl, heteroaryl, —NH($R^{12}$), —N($R^{12}$)$_2$, —NH($C_{3-15}$ cycloalkyl), —NH(heterocyclyl), —NH($C_{6-10}$ aryl), or —NH(heteroaryl), wherein each alkynyl, cycloalkyl, heterocyclyl, or heteroaryl is optionally substituted with 1 to 3 groups each independently $C_{1-6}$ alkyl, $C_{1-6}$ alkoxy, halogen, $C_{1-6}$ haloalkyl, —OH, each $C_{3-6}$ cycloalkyl is optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH, and each heterocyclyl is optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH;

each $R^{12}$ is $C_{1-6}$ alkyl substituted with 1 to 3 groups each independently halogen, —OH, —CN, or $C_{3-6}$ cycloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —NR$^{12a}$S(O)$_2$N($R^{12b}$)($R^{12c}$), —NR$^{12a}$S(O)$_2$O($R^{12b}$), —OC(O)$R^{12a}$, —OC(O)OR$^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(NR$^{12a}$)R$^{12b}$, or —Si($R^{12a}$)$_3$;

wherein each alkyl, haloalkyl, alkenyl, alkynyl, cycloalkyl, heterocyclyl, aryl, or heteroaryl is optionally substituted with 1 to 4 $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{12a}$, —C(O)$R^{12a}$, —C(O)O—$R^{12a}$, —C(O)N ($R^{12a}$)($R^{12b}$), —N($R^{12a}$)($R^{12b}$), —N($R^{12a}$)$_2$($R^{12b}$)$^+$, —N($R^{12a}$)—C(O)R$^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O ($R^{12b}$), —OC(O)$R^{12a}$, —OC(O)OR$^{12a}$, —OC(O)—N ($R^{12a}$)($R^{12b}$), —S—$R^{12a}$, —S(O)$R^{12a}$, —S(O)(NH) $R^{12a}$, —S(O)$_2R^{12a}$, —S(O)$_2$N($R^{12a}$)($R^{12b}$), —S(O)(NR$^{12a}$)R$^{12b}$, or —Si($R^{12a}$)$_3$;

wherein each alkyl, haloalkyl, alkenyl, alkynyl, cycloalkyl, heterocyclyl, aryl, or heteroaryl is optionally substituted with 1 to 4 $Z^{1b}$;

each $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O ($C_{1-9}$ alkyl), —C(O)O($C_{1-8}$haloalkyl), —C(O)O ($C_{2-6}$ alkenyl), —C(O)O($C_{2-6}$ alkynyl), —C(O)O ($C_{3-15}$ cycloalkyl), —C(O)O(heterocyclyl), —C(O) O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N (heterocyclyl)$_2$, —C(O)N($C_{6-10}$ aryl)$_2$, —C(O)N (heteroaryl)$_2$, —NHC(O)($C_{1-9}$ alkyl), —NHC(O) ($C_{1-8}$ haloalkyl), —NHC(O)($C_{2-6}$ alkenyl), —NHC (O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O) O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O) NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O) N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$(C$_{1-9}$ alkyl), —S(O)$_2$(C$_{1-8}$ haloalkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein each alkyl, cycloalkyl, heterocyclyl, aryl, or heteroaryl is optionally substituted with 1 to 3 C$_{1-9}$ alkyl, C$_{1-8}$ haloalkyl, halogen, —OH, —NH$_2$, CO$_2$H, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$haloalkyl), —NHC(O)(C$_{3-15}$ cycloalkyl), —NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein each heterocyclyl has 3 to 12 ring members and 1 to 4 heteroatoms each independently N, O, or S; and wherein each heteroaryl has 5 to 12 ring members and 1 to 4 heteroatoms each independently N, O or S.

In some embodiments of the compound of Formula (I-A), or pharmaceutically acceptable salt thereof, R$^1$ is phenyl optionally substituted with 1 to 4 groups each independently C$_{1-6}$ alkyl, halogen, C$_{1-6}$ haloalkyl, —CN, —C(O)NH$_2$, —C(O)NH(C$_{1-6}$ alkyl), —C(O)N(C$_{1-6}$ alkyl)$_2$, —C(O)NH(C$_{3-6}$ cycloalkyl), —C(O)NH(heterocyclyl), heterocyclyl optionally substituted with 1 to 3 groups each independently C$_{1-6}$ alkyl, halogen, C$_{1-6}$ haloalkyl, or —OH, or heteroaryl optionally substituted with 1 to 3 groups each independently C$_{1-6}$ alkyl, halogen, C$_{1-6}$ haloalkyl, —OH, C$_{3-6}$ cycloalkyl, or heterocyclyl.

In some embodiments of the compound of Formula (I-A), or pharmaceutically acceptable salt thereof, ring A is

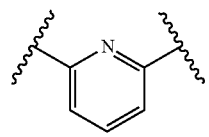 [SMILES: *c1cccc(*)n1]

optionally substituted with 1 to 3 groups each independently C$_{1-6}$ alkyl, C$_{1-6}$ alkoxy, halogen, C$_{1-6}$ haloalkyl, C$_{1-6}$ haloalkoxy, —OH or —NH$_2$.

In some embodiments of the compound of Formula (I-A), or pharmaceutically acceptable salt thereof, ring A is

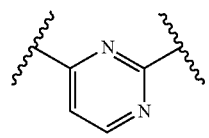 [SMILES: *c1ccnc(*)n1]

optionally substituted with 1 to 3 groups each independently C$_{1-6}$ alkyl, C$_{1-6}$ alkoxy, halogen, C$_{1-6}$ haloalkyl, C$_{1-6}$ haloalkoxy, —OH or —NH$_2$.

In some embodiments of the compound of Formula (I-A), or pharmaceutically acceptable salt thereof, ring B is

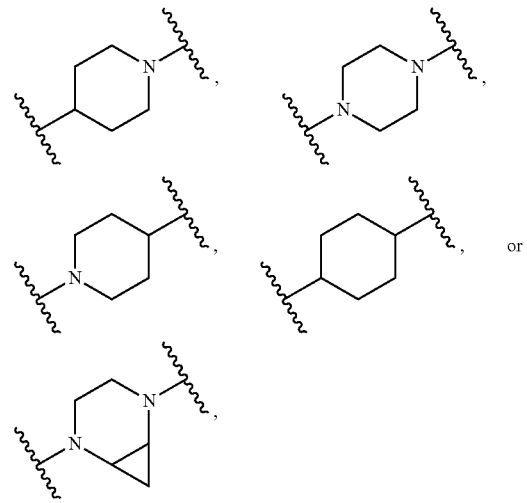

wherein each is optionally substituted with 1 to 3 R$^B$ groups each independently C$_{1-6}$ alkyl or halogen, alternatively, ring B is combined with V to form

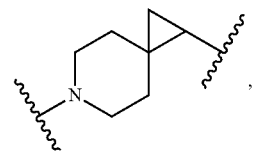 [SMILES: *C1CC12CCN(*)CC2]

optionally substituted with 1 to 3 R$^B$ groups each independently C$_{1-6}$ alkyl or halogen.

In some embodiments of the compound of Formula (I-A), or pharmaceutically acceptable salt thereof, R$^2$ is C$_{1-6}$ alkyl, heterocyclyl, or C$_{1-6}$ alkyl-heterocyclyl, wherein each alkyl or heterocyclyl is optionally substituted with 1 to 3 groups each independently C$_{1-6}$ alkyl, C$_{1-6}$ alkoxy, C$_{1-6}$ hydroxyalkyl, C$_{2-6}$ alkoxyalkyl, halogen, C$_{1-6}$ haloalkyl, C$_{1-6}$ haloalkoxy, —OH, —CN, C$_{1-6}$ alkyl-CN, —O—C$_{3-6}$ cycloalkyl or heteroaryl optionally substituted with 1 to 4 groups each independently C$_{1-6}$ alkyl, C$_{1-6}$ alkoxy, halogen, C$_{1-6}$ haloalkyl, or C$_{1-6}$ haloalkoxy.

In some embodiments of the compound of Formula (I-A), or pharmaceutically acceptable salt thereof, R$^2$ is C$_{1-6}$ alkyl, heterocyclyl, or C$_{1-6}$ alkyl-heterocyclyl, wherein each alkyl or heterocyclyl is optionally substituted with 1 to 3 groups each independently C$_{1-6}$ alkyl, C$_{1-6}$ alkoxy, C$_{1-6}$ hydroxyalkyl, C$_{2-6}$ alkoxyalkyl, or halogen.

In some embodiments of the compound of Formula (I-A), or pharmaceutically acceptable salt thereof, R$^2$ is C$_{1-6}$ alkyl, optionally substituted with 1 to 3 groups each independently C$_{1-6}$ alkoxy, C$_{1-6}$ hydroxyalkyl, or C$_{2-6}$ alkoxyalkyl.

In some embodiments of the compound of Formula (I-A), or pharmaceutically acceptable salt thereof, R$^2$ is C$_{1-6}$ alkyl-heterocyclyl.

In some embodiments of the compound of Formula (I-A), or pharmaceutically acceptable salt thereof, R² is heterocyclyl, optionally substituted with 1 to 3 groups each independently $C_{1-6}$ alkyl, $C_{1-6}$ alkoxy, $C_{1-6}$ hydroxyalkyl, $C_{2-6}$ alkoxyalkyl, or halogen;

wherein the heterocyclyl has 4 to 6 ring members and 1 to 2 heteroatoms each O.

In some embodiments of the compound of Formula (I-A), or pharmaceutically acceptable salt thereof, R² is

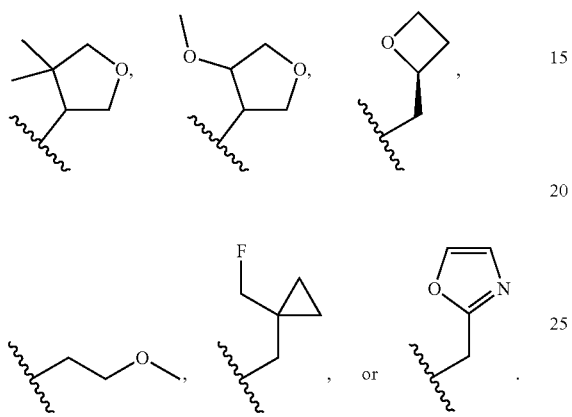

In some embodiments of the compound of Formula (I-A), or pharmaceutically acceptable salt thereof, $X^1$ is —C(R¹¹)═; and $X^2$ and $X^3$ are each independently —N═, —C(H)═, or —C(R⁸)═.

In some embodiments of the compound of Formula (I-A), or pharmaceutically acceptable salt thereof, $X^1$ is —N═, —C(H)═ or —C(R¹¹)═;

$X^2$ is —C(R⁸)═; and $X^3$ is —N═, —C(H)═, or —C(R⁸)═.

In some embodiments of the compound of Formula (I-A), or pharmaceutically acceptable salt thereof, $X^1$ is —N═, —C(H)═ or —C(R¹¹)═;

$X^2$ is —N═, —C(H)═, or —C(R⁸)═; and $X^3$ is —C(R⁸)═.

In some embodiments of the compound of Formula (I-A), or pharmaceutically acceptable salt thereof, R³ is —COOH.

In some embodiments of the compound of Formula (I-A), or pharmaceutically acceptable salt thereof, R³ is

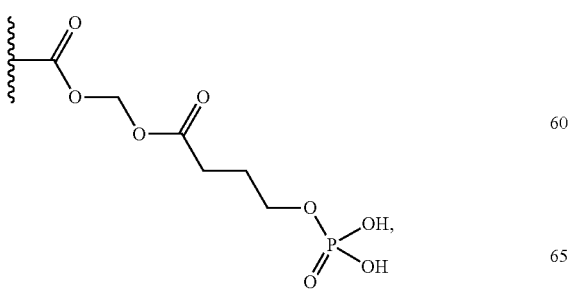

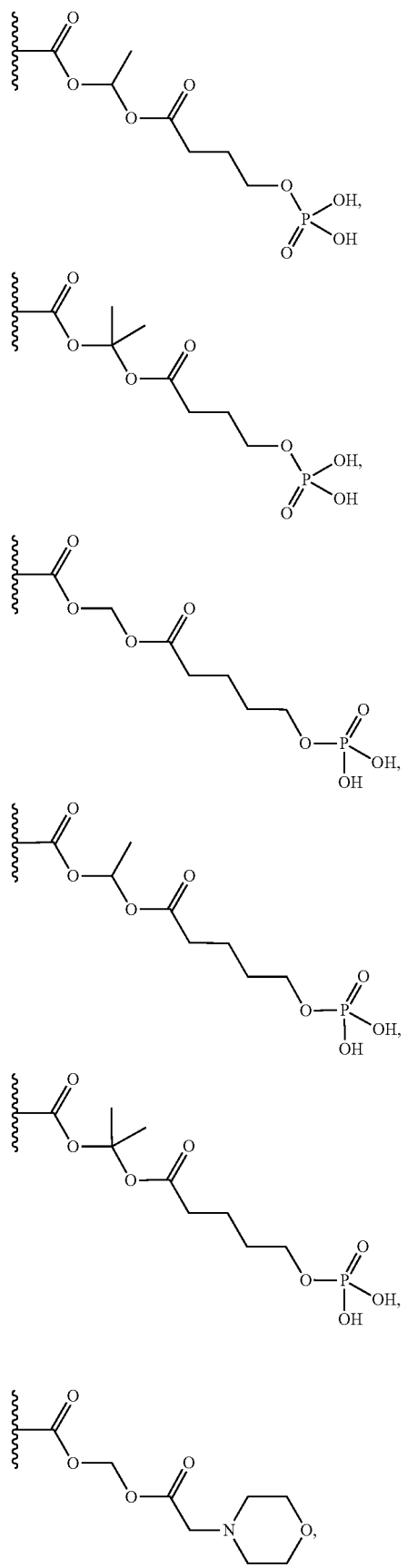

37
-continued
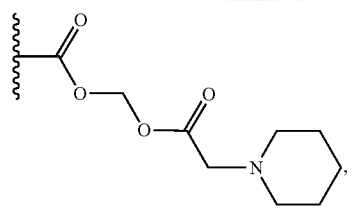
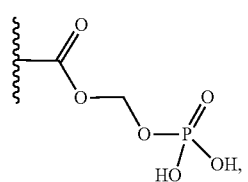
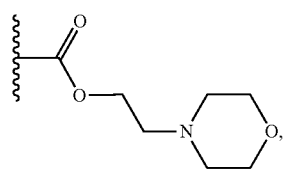
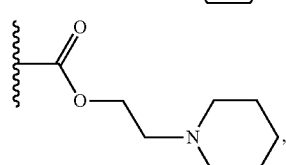
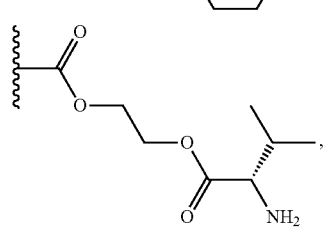
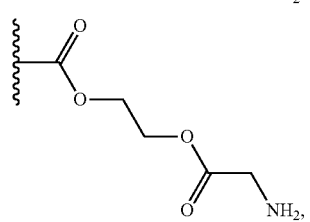
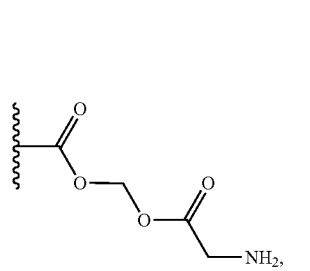
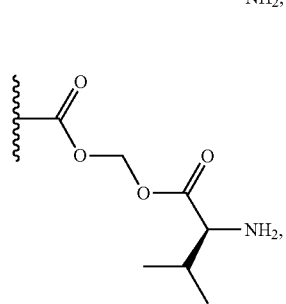
38
-continued
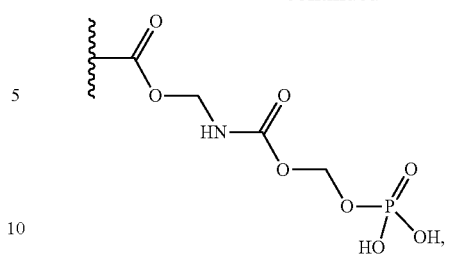
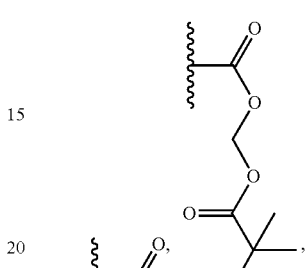
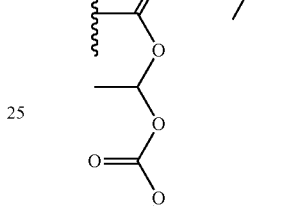
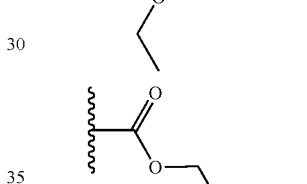
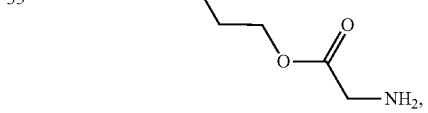
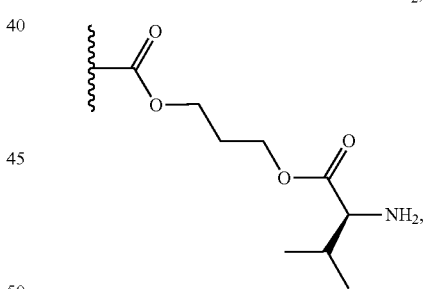
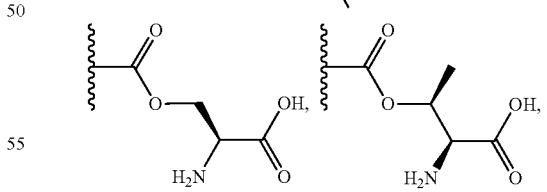
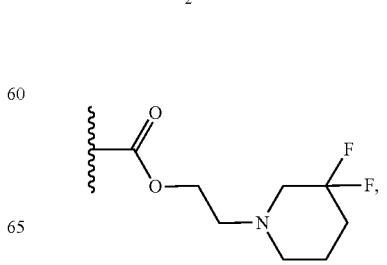

-continued

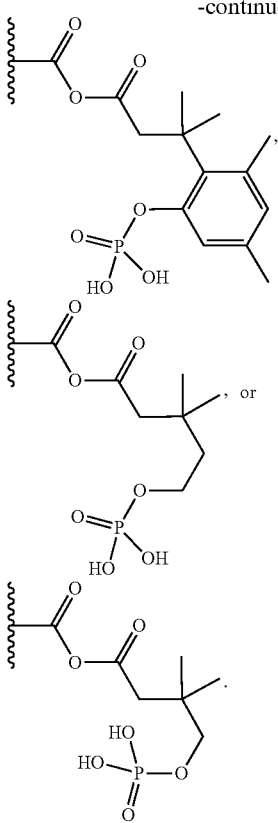

In some embodiments of the compound of Formula (I-A), or pharmaceutically acceptable salt thereof, V is —CH$_2$—.

In some embodiments of the compound of Formula (I-A), or pharmaceutically acceptable salt thereof, wherein at least one of $R^8$ and $R^{11}$ is C$_{2-6}$ alkynyl, C$_{1-6}$ hydroxyalkyl, C$_{2-6}$ alkoxyalkyl, C$_{3-6}$ cycloalkyl, heterocyclyl, heteroaryl, —NH($R^{12}$), —N($R^{12}$)$_2$, —NH(C$_{3-15}$ cycloalkyl), —NH(heterocyclyl), —NH(C$_{6-10}$ aryl), or —NH(heteroaryl), wherein each alkynyl, cycloalkyl, heterocyclyl, or heteroaryl is optionally substituted with 1 to 3 groups each independently C$_{1-6}$ alkyl, C$_{1-6}$ alkoxy, halogen, C$_{1-6}$ haloalkyl, —OH, each C$_{3-6}$ cycloalkyl is optionally substituted with 1 to 3 groups each independently C$_{1-6}$ alkyl, C$_{1-6}$ alkoxy, halogen, C$_{1-6}$ haloalkyl, C$_{1-6}$ haloalkoxy or —OH, and each heterocyclyl is optionally substituted with 1 to 3 groups each independently C$_{1-6}$ alkyl, C$_{1-6}$ alkoxy, halogen, C$_{1-6}$ haloalkyl, C$_{1-6}$ haloalkoxy or —OH.

In some embodiments of the compound of Formula (I-A), or pharmaceutically acceptable salt thereof, $R^1$ is phenyl optionally substituted with 1 to 4 groups each independently C$_{1-6}$ alkyl, halogen, C$_{1-6}$ haloalkyl, —CN, —C(O)NH$_2$, —C(O)NH(C$_{1-6}$ alkyl), —C(O)N(C$_{1-6}$ alkyl)$_2$, —C(O)NH(C$_{3-6}$ cycloalkyl), —C(O)NH(heterocyclyl), heterocyclyl optionally substituted with 1 to 3 groups each independently C$_{1-6}$ alkyl, halogen, C$_{1-6}$ haloalkyl, or —OH, or heteroaryl optionally substituted with 1 to 3 groups each independently C$_{1-6}$ alkyl, halogen, C$_{1-6}$ haloalkyl, —OH, C$_{3-6}$ cycloalkyl, or heterocyclyl;

Ring A is

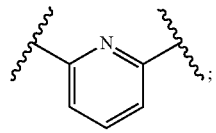 [SMILES: *c1cccc(*)n1]

ring B is

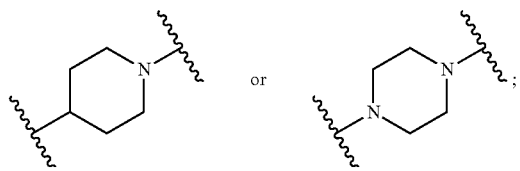 [SMILES: *C1CCN(*)CC1 ; *N1CCN(*)CC1]

$R^8$ is independently C$_{2-9}$ alkyl, C$_{2-6}$ alkenyl, C$_{2-6}$ alkynyl, C$_{1-6}$ alkoxy, C$_{1-6}$ hydroxyalkyl, C$_{1-6}$ alkoxyalkyl, C$_{1-6}$ haloalkyl, C$_{1-6}$ haloalkoxy, —CN, —OH, —NH$_2$, C$_{3-6}$ cycloalkyl, heterocyclyl, heteroaryl, —NH(C$_{1-9}$ alkyl), —N(C$_{1-9}$ alkyl)$_2$, —NH(C$_{3-15}$ cycloalkyl), —NH(heterocyclyl), —NH(C$_{6-10}$ aryl), or —NH(heteroaryl), wherein the alkyl, alkynyl, cycloalkyl, heterocyclyl, or heteroaryl in each instance is optionally substituted with 1 to 3 groups each independently C$_{1-6}$ alkyl, C$_{1-6}$ alkoxy, halogen, C$_{1-6}$ haloalkyl, —OH, C$_{3-6}$ cycloalkyl, heterocyclyl optionally substituted with 1 to 3 groups each independently C$_{1-6}$ alkyl, C$_{1-6}$ alkoxy, halogen, C$_{1-6}$ haloalkyl, —OH, C$_{3-6}$ cycloalkyl optionally substituted with 1 to 3 groups each independently C$_{1-6}$ alkyl, C$_{1-6}$ alkoxy, halogen, C$_{1-6}$ haloalkyl, C$_{1-6}$ haloalkoxy, —OH, and heterocyclyl optionally substituted with 1 to 3 groups each independently C$_{1-6}$ alkyl, C$_{1-6}$ alkoxy, halogen, C$_{1-6}$ haloalkyl, C$_{1-6}$ haloalkoxy or —OH; and $R^{11}$ is independently C$_{1-6}$ alkyl, C$_{2-6}$ alkenyl, C$_{2-6}$ alkynyl, C$_{1-6}$ alkoxy, C$_{1-6}$ hydroxyalkyl, C$_{2-6}$ alkoxyalkyl, halogen, C$_{1-6}$ haloalkyl, C$_{1-6}$ haloalkoxy, —CN, —OH, —NH$_2$, C$_{3-6}$ cycloalkyl, heterocyclyl, heteroaryl, —NH(C$_{1-9}$ alkyl), —N(C$_{1-9}$ alkyl)$_2$, —NH(C$_{3-15}$ cycloalkyl), —NH(heterocyclyl), —NH(C$_{6-10}$ aryl), or —NH(heteroaryl), wherein the alkyl, alkynyl, cycloalkyl, heterocyclyl, or heteroaryl in each instance is optionally substituted with one to three groups selected from C$_{1-6}$ alkyl, C$_{1-6}$ alkoxy, halogen, —C$_{1-6}$ haloalkyl, —OH, each C$_{3-6}$ cycloalkyl is optionally substituted with 1 to 3 groups each independently C$_{1-6}$ alkyl, C$_{1-6}$ alkoxy, halogen, C$_{1-6}$ haloalkyl, C$_{1-6}$ haloalkoxy, or —OH, and each heterocyclyl is optionally substituted with 1 to 3 groups each independently —C$_{1-6}$ alkyl, C$_{1-6}$ alkoxy, halogen, C$_{1-6}$ haloalkyl, C$_{1-6}$ haloalkoxy, or —OH.

In some embodiments of the compound of Formula (I-A), or pharmaceutically acceptable salt thereof, $R^1$ is not phenyl optionally substituted with 1 to 4 groups each independently C$_{1-6}$ alkyl, halogen, C$_{1-6}$ haloalkyl, —CN, —C(O)NH$_2$, —C(O)NH(C$_{1-6}$ alkyl), —C(O)N(C$_{1-6}$ alkyl)$_2$, —C(O)NH(C$_{3-6}$ cycloalkyl), —C(O)NH(heterocyclyl), heterocyclyl optionally substituted with 1 to 3 groups each independently C$_{1-6}$ alkyl, halogen, C$_{1-6}$ haloalkyl, or —OH, or heteroaryl optionally substituted with 1 to 3 groups each independently $C_{1-6}$ alkyl, halogen, $C_{1-6}$ haloalkyl, —OH, $C_{3-6}$ cycloalkyl, or heterocyclyl; and $R^{11}$ and $R^8$ are independently $C_{2-6}$ alkynyl, $C_{1-6}$ hydroxyalkyl, $C_{2-6}$ alkoxyalkyl, $C_{3-6}$ cycloalkyl, heterocyclyl, heteroaryl, —NH($R^{12}$), —N($R^{12}$)$_2$, —NH($C_{3-15}$ cycloalkyl), —NH(heterocyclyl), —NH($C_{6-10}$ aryl), or —NH(heteroaryl), wherein each alkynyl, cycloalkyl, heterocyclyl, or heteroaryl is optionally substituted with 1 to 3 groups each independently $C_{1-6}$ alkyl, $C_{1-6}$ alkoxy, halogen, $C_{1-6}$ haloalkyl, —OH, each $C_{3-6}$ cycloalkyl is optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH, and each heterocyclyl is optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH.

In some embodiments of the compound of Formula (I-A), or pharmaceutically acceptable salt thereof,
ring A is

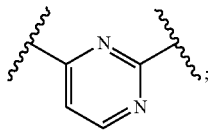 [SMILES: *c1ccnc(*)n1]

and $R^{11}$ and $R^8$ are independently $C_{2-6}$ alkynyl, $C_{1-6}$ hydroxyalkyl, $C_{2-6}$ alkoxyalkyl, $C_{3-6}$ cycloalkyl, heterocyclyl, heteroaryl, —NH($R^{12}$), —N($R^{12}$)$_2$, —NH($C_{3-15}$ cycloalkyl), —NH(heterocyclyl), —NH($C_{6-10}$ aryl), or —NH(heteroaryl), wherein each alkynyl, cycloalkyl, heterocyclyl, or heteroaryl is optionally substituted with 1 to 3 groups each independently $C_{1-6}$ alkyl, $C_{1-6}$ alkoxy, halogen, $C_{1-6}$ haloalkyl, —OH, each $C_{3-6}$ cycloalkyl is optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH, and each heterocyclyl is optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH.

In some embodiments of the compound of Formula (I-A), or pharmaceutically acceptable salt thereof,
ring B is

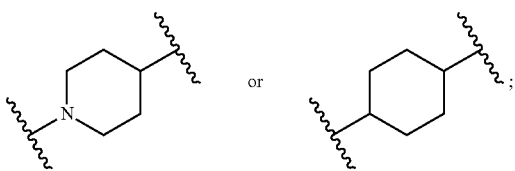 [SMILES: *C1CCN(*)CC1 ; *C1CCC(*)CC1]

and $R^{11}$ and $R^8$ are independently $C_{2-6}$ alkynyl, $C_{1-6}$ hydroxyalkyl, $C_{2-6}$ alkoxyalkyl, $C_{3-6}$ cycloalkyl, heterocyclyl, heteroaryl, —NH($R^{12}$), —N($R^{12}$)$_2$, —NH($C_{3-15}$ cycloalkyl), —NH(heterocyclyl), —NH($C_{6-10}$ aryl), or —NH(heteroaryl), wherein each alkynyl, cycloalkyl, heterocyclyl, or heteroaryl is optionally substituted with 1 to 3 groups each independently $C_{1-6}$ alkyl, $C_{1-6}$ alkoxy, halogen, $C_{1-6}$ haloalkyl, —OH, each $C_{3-6}$ cycloalkyl is optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH, and each heterocyclyl is optionally substituted with 1 to 3 groups each independently $C_{1-6}$ alkyl, $C_{1-6}$ alkoxy, halogen, $C_{1-6}$ haloalkyl, $C_{1-6}$ haloalkoxy or —OH.

In some embodiments of the compound of Formula (I-A), or pharmaceutically acceptable salt thereof, each $R^{12}$ is $C_{1-3}$ alkyl substituted with 1 to 3 groups each independently halogen, —OH, —CN, or $C_{3-6}$ cycloalkyl.

In some embodiments of the compound of Formula (I-A), or pharmaceutically acceptable salt thereof, having the structure of a compound in Table 2.

Also disclosed herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabeled (e.g., $^{14}$C or $^3$H) compound, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products can be easily isolated since they are labeled (others are isolated by the use of antibodies capable of binding epitopes surviving in the metabolite). The metabolite structures are determined in conventional fashion, e.g., by MS or NMR analysis. In general, analysis of metabolites can be done in the same way as conventional drug metabolism studies well-known to those skilled in the art. The conversion products, so long as they are not otherwise found in vivo, can be useful in diagnostic assays for therapeutic dosing of the compounds even if they possess no GLP-1R activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

II. Methods of Preparing Compounds

The compounds of the present disclosure can be prepared by any method known in the art. The following exemplary general methods illustrate routes that may be used to obtain a compound of the present disclosure.

Scheme 1

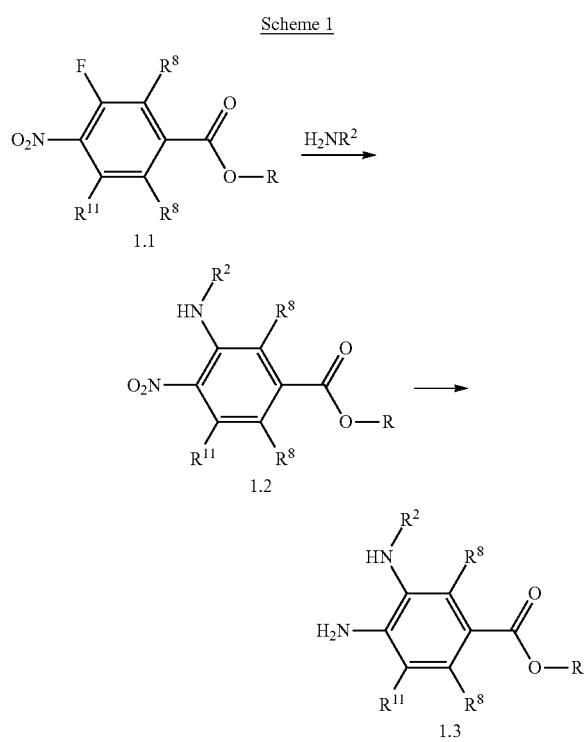

Intermediate 1.3 may be assembled by reacting an amine with Intermediate 1.1, wherein R is an alkyl, alkylaryl, or aryl, in the presence of a suitable base (e.g., DIPEA, KOtBu, etc.) to give Intermediate 1.2. Intermediate 1.2 can be converted to Intermediate 1.3 using suitable reducing conditions (e.g., $H_2$ and Pd/C, Fe and HCl, etc.).

Scheme 2

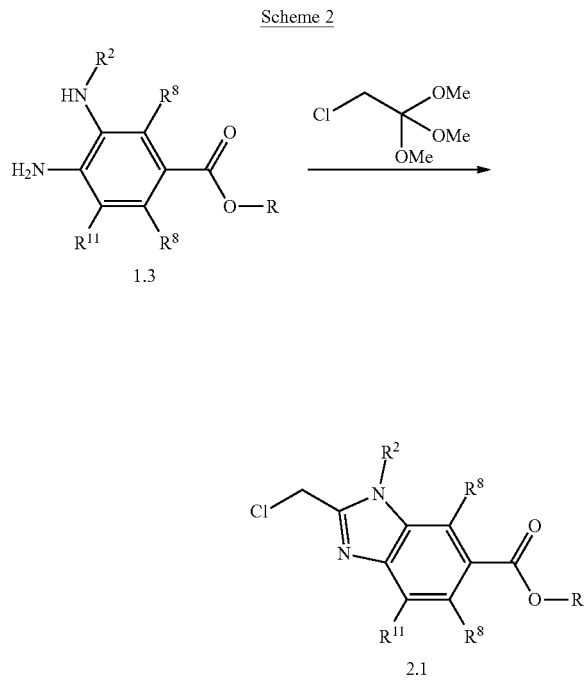

Intermediate 2.1 may be assembled by reacting an intermediate of the type 1.3 with 2-chloro-1,1,1-trimethoxyethane in the presence of a suitable acid (e.g., pTSA, HCl, AcOH, etc.).

Scheme 3

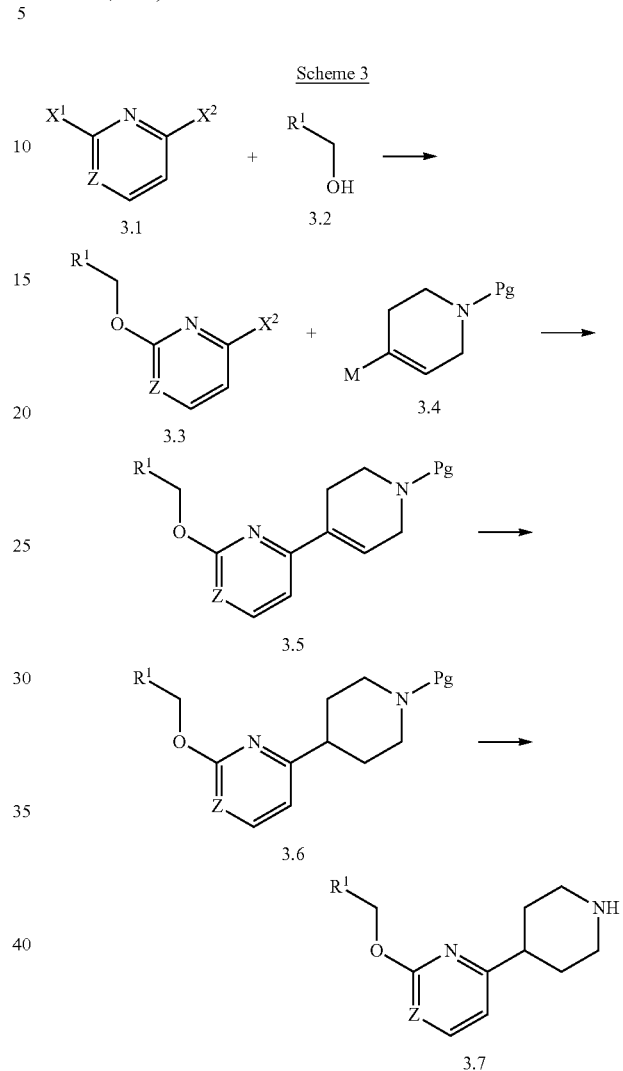

Intermediate 3.7 may be assembled by first reacting an intermediate of the type 3.1 where Z is —CH═, —CX═, or —N═, $X^1$ is a halogen or suitable leaving group (e.g., —$SO^2Me$), and $X^2$ is a halogen with a suitable alcohol of the type 3.2 in the presence of a suitable base (e.g., DIPEA, KOtBu, NaH, $Cs_2CO_3$ etc.) or transition metal catalyst (e.g., RockPhos Pd G3, JohnPhos and Pd(OAc)$_2$, etc.) with a base (e.g., $Cs_2CO_3$, $K_2CO_3$, etc) to give intermediate 3.3. 3.3 can then be converted to 3.5 via coupling with an intermediate of the type 3.4 where M is a suitable metal species (e.g., —B(OH)$_2$, —B-pinacol, —SnBu$_3$, etc.) and Pg is a suitable amine protecting group (e.g., Boc) using a transition metal catalyst (e.g., Pd(dppf)Cl$_2$, Pd(PPh$_3$)$_4$, etc.) and a suitable base (e.g., $Cs_2CO_3$, $K_2CO_3$, etc). 3.5 can then be converted to 3.6 via $H_2$ atmosphere and a suitable reduction catalyst (e.g., Pd/C, Pd(OH)$_2$, PtO$_2$, etc.) which can then be deprotected to intermediate 3.7 via acid treatment (e.g., TFA, HCl, etc.).

Scheme 4

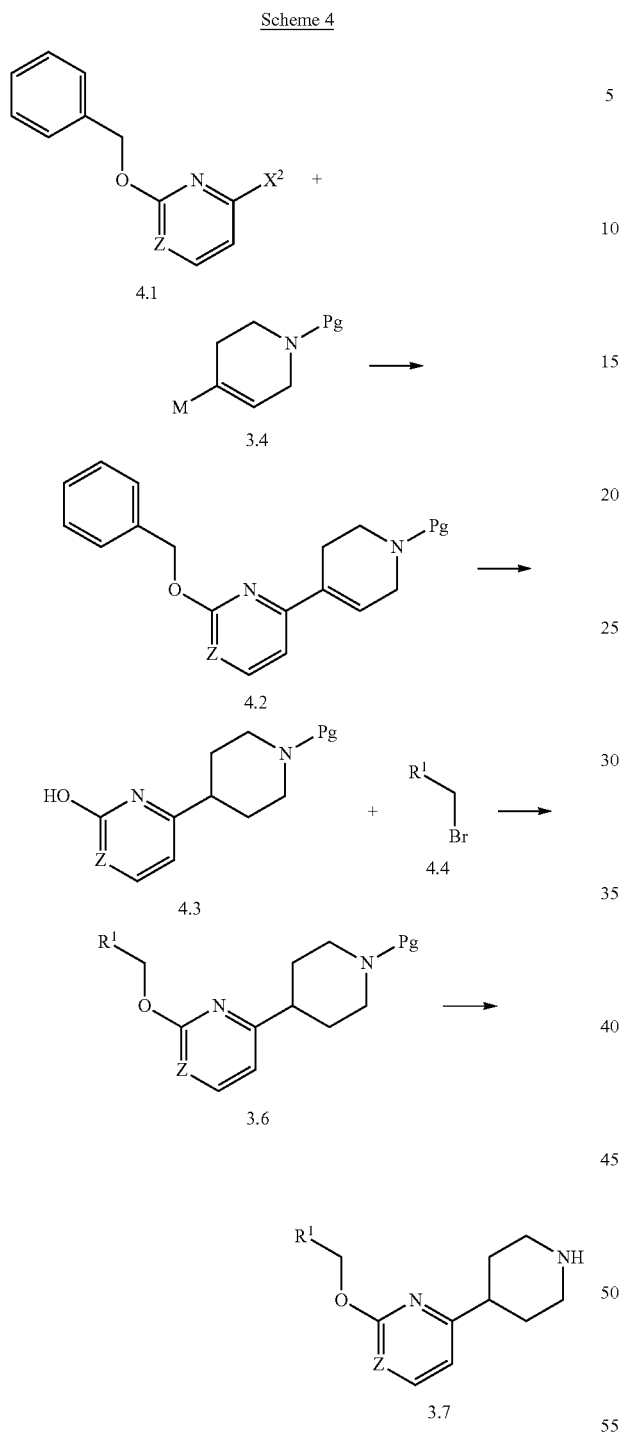

Scheme 5

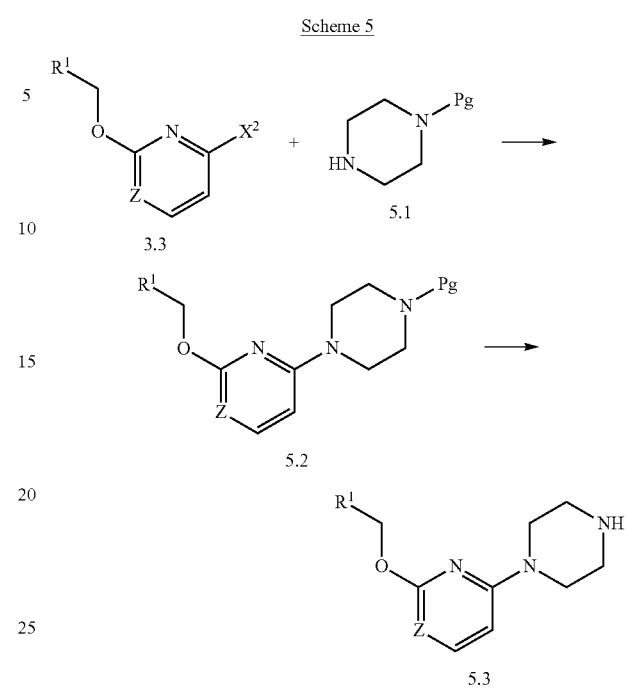

Intermediate 5.3 may first be assembled by reacting an intermediate of the type 3.3 where $X^2$ is a halogen with a suitably protected (e.g., Boc) piperazine of the type 5.1 in the presence of a suitable base (e.g., $Cs_2CO_3$), transition metal catalyst (e.g., $Pd_2(dba)_3$)) and a ligand (e.g., BINAP) to give intermediate 5.2. 5.2 can then be deprotected to intermediate 5.3 via acid treatment (e.g., TFA, HCl, etc.).

Scheme 6

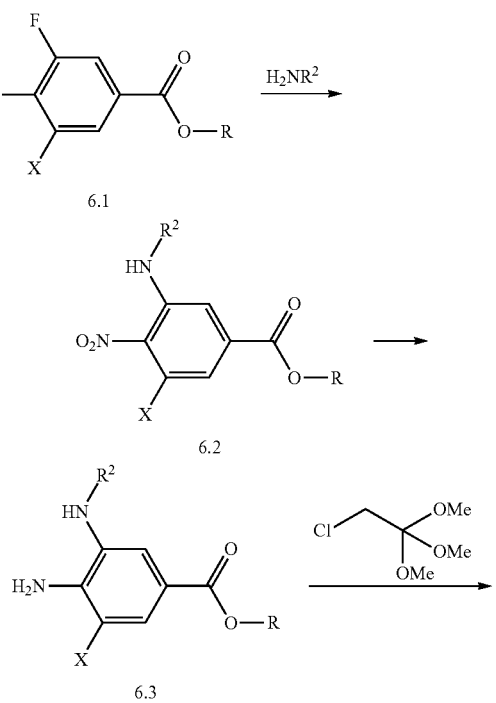

Alternately, intermediate 3.7 may be assembled by first converting 4.1 and 3.4 to intermediate 4.2 using a transition metal catalyst (e.g., $Pd(dppf)Cl_2$, $Pd(PPh_3)_4$, etc.) and a suitable base (e.g., $Cs_2CO_3$, $K_2CO_3$, etc). 4.2 can be converted to 4.3 via $H_2$ atmosphere and a suitable reduction catalyst (e.g., Pd/C, $Pd(OH)_2$, $PtO_2$, etc.) after which intermediate 3.6 can be obtained through the reaction of 4.3 with intermediate 4.4 in the presence of a suitable base (e.g., $Cs_2CO_3$, $Ag_2CO_3$, etc.). 3.7 can be obtained from 3.6 as previously described.

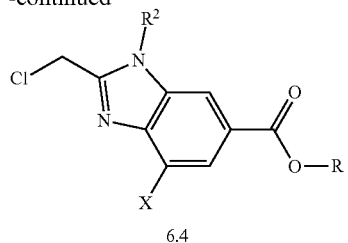

6.4

Intermediate 6.4 may be assembled by reacting an amine with Intermediate 6.1, wherein X is a halide R is an alkyl, alkylaryl, or aryl, in the presence of a suitable base (e.g., DIPEA, KOtBu, etc.) to give Intermediate 6.2. Intermediate 6.2 can be converted to Intermediate 6.3 using suitable reducing conditions (e.g., $H_2$ and Pd/C, Fe and HCl, etc.). Intermediate 6.4 can then be obtained through the reaction of 6.3 with 2-chloro-1,1,1-trimethoxyethane in the presence of a suitable acid (e.g., pTSA, HCl, AcOH, etc.).

Scheme 7

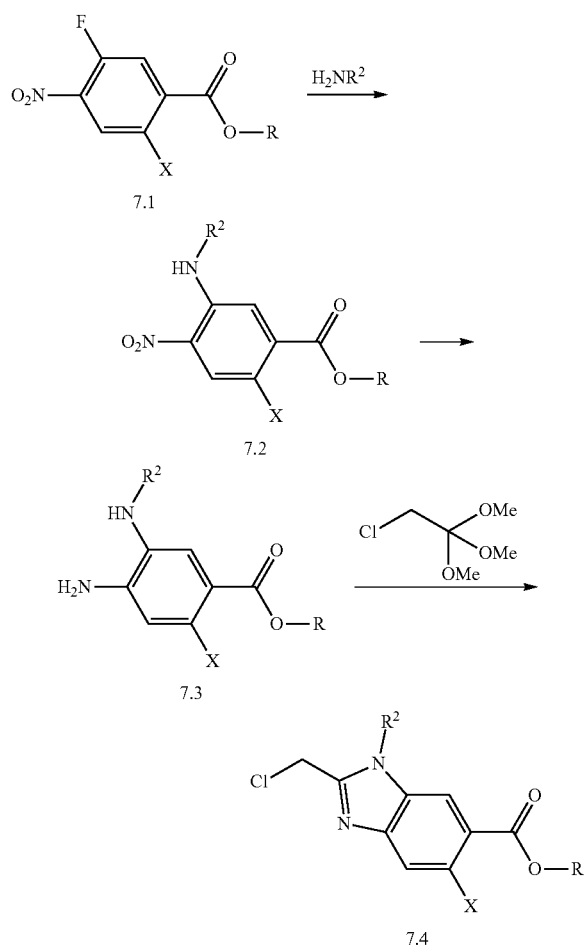

Intermediate 7.4 may be assembled by reacting an amine with Intermediate 7.1, wherein X is a halide R is an alkyl, alkylaryl, or aryl, in the presence of a suitable base (e.g., DIPEA, KOtBu, etc.) to give Intermediate 7.2. Intermediate 7.2 can be converted to Intermediate 7.3 using suitable reducing conditions (e.g., $H_2$ and Pd/C, Fe and HCl, etc.). Intermediate 7.4 can then be obtained through the reaction of 7.3 with 2-chloro-1,1,1-trimethoxyethane in the presence of a suitable acid (e.g., pTSA, HCl, AcOH, etc.).

Scheme 8

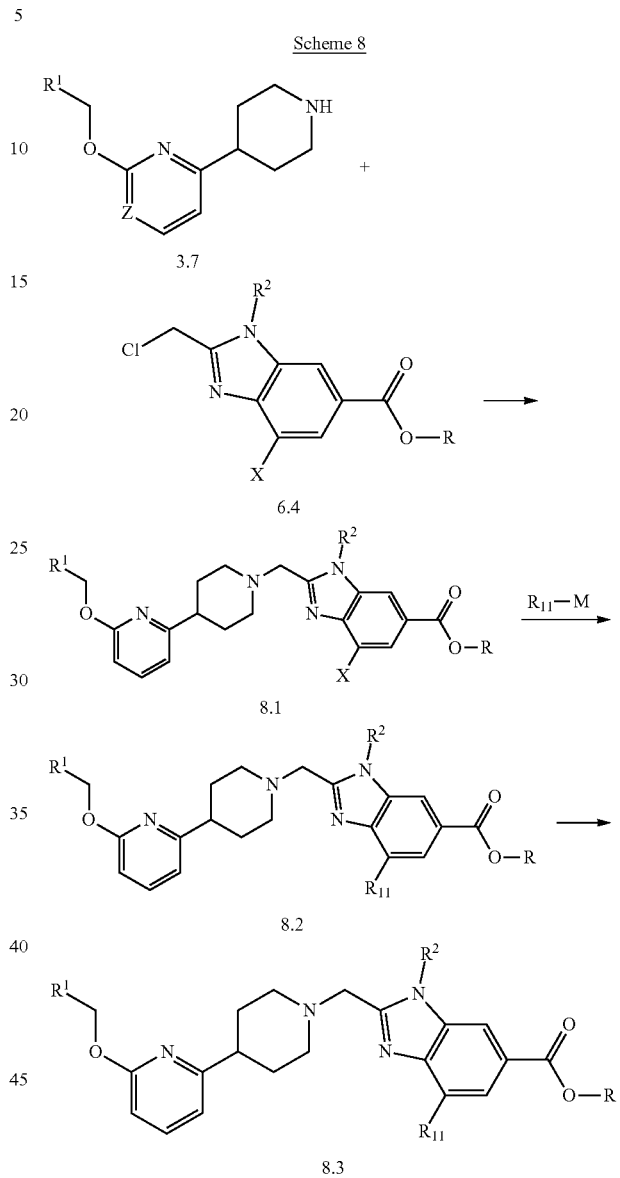

Compounds of the 8.3 may be assembled by first reacting intermediates of the type 3.7 and 6.4 the presence of a suitable base (e.g., $Cs_2CO_3$, $K_2CO^3$, etc.) to give intermediate 8.1. 8.1 can then be coupled with a metallated species of the type R 11-M wherein M represents a suitable metal (e.g., —B(OH)$_2$, —B-pinacol, —SnBu$_3$, etc.) in the presence of a suitable transition metal catalyst (e.g., Pd(dppf)Cl$_2$, Pd(PPh$_3$)$_4$, etc.) and a suitable base (e.g., $Cs_2CO_3$, $K_2CO_3$, etc) to give intermediate 8.2. Filly treatment of 8.2 with a suitable source of —OH (e.g., KOH, LiOH, etc.) when R is -Me or -Et or with a suitable acid (e.g., HCl, TFA, etc.) when R is -tBu will yield compound 8.3.

IV. Pharmaceutical Formulations

In some embodiments, the present disclosure provides a pharmaceutical composition comprising a compound of the present disclosure (e.g., a compound of Formula (I-A)), or a pharmaceutically acceptable salt thereof, and a pharmaceutically acceptable excipient.

In some embodiments of the disclosure, the pharmaceutical composition comprises a compound of Formula (I-A), or a pharmaceutically acceptable salt thereof, and one or more additional therapeutic agents, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. In some embodiments, compositions may contain excipients such as those set forth in the Rowe et al, Handbook of Pharmaceutical Excipients, $6^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In some embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if desired, shaping the product. Techniques and formulations generally are found in Remington: The Science and Practice of Pharmacy, $21^{st}$ Edition, Lippincott Wiliams and Wilkins, Philadelphia, Pa., 2006.

Compositions described herein that are suitable for oral administration may be presented as discrete units (a unit dosage form) including but not limited to capsules, sachets or tablets each containing a predetermined amount of the active ingredient. In one embodiment, the pharmaceutical composition of the disclosure is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the mode of administration. For example, in some embodiments, a dosage form for oral administration to humans may contain approximately 1 to 1000 mg of active material formulated with an appropriate and convenient amount of a pharmaceutically acceptable excipient. In some embodiments, the pharmaceutically acceptable excipient varies from about 5 to about 95% of the total compositions (weight:weight).

In some embodiments, a composition comprising a compound of the present disclosure, or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

In some embodiments, the pharmaceutical compositions described above are for use in a human or an animal.

The disclosure further includes a compound of the present disclosure for administration as a single active ingredient of a pharmaceutically acceptable composition which can be prepared by conventional methods known in the art, for example by binding the active ingredient to a pharmaceutically acceptable, therapeutically inert organic and/or inorganic carrier or excipient, or by mixing therewith.

In one aspect, provided herein is the use of a compound of the present disclosure as a second or other active ingredient having a synergistic effect with other active ingredients in known drugs, or administration of the compound of the present disclosure together with such drugs.

The compound of the present disclosure may also be used in the form of a prodrug or other suitably modified form which releases the active ingredient in vivo.

V. Routes of Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Kits that comprise a compound of the present disclosure, or an enantiomer, or pharmaceutically acceptable salt thereof, or a pharmaceutical composition containing any of the above, are also included in the present disclosure. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, such as the diseases or conditions, described herein. In one embodiment, kits comprising a compound of the present disclosure, or a pharmaceutically acceptable salt thereof, in combination with one or more (e.g., one, two, three, four, one or two, or one to three, or one to four) additional therapeutic agents are provided.

Provided herein are also articles of manufacture that include a compound of the present disclosure or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

VI. Combination Therapy

In some embodiments, a compound of the present disclosure, or a pharmaceutically acceptable salt thereof, can be combined with a therapeutically effective amount of one or more (e.g., one, two, three, four, one or two, one to three, or one to four) additional therapeutic agents. In some embodiments, the additional therapeutic agent comprises an apoptotic signal-regulating kinase (ASK-1) inhibitor, a farnesoid X receptor (FXR) agonist, a peroxisome proliferator-activated receptor alpha (PPARα) agonist, fish oil, an acetyl-coA carboxylase (ACC) inhibitor, a TGFβ antagonist, a LPAR antagonist, a SGLT2 inhibitor, a Tpl2 inhibitor, or a GLP-1 agonist combination thereof.

The benefit of combination may be increased efficacy and/or reduced side effects for a component as the dose of that component may be adjusted down to reduce its side effects while benefiting from its efficacy augmented by the efficacy of the compound of the present disclosure.

In some embodiments, the therapeutic agent, or combination of therapeutic agents, are a(n) ACE inhibitor, 2-Acylglycerol O-acyltransferase 2 (DGAT2) inhibitor, Acetaldehyde dehydrogenase inhibitor, Acetyl CoA carboxylase inhibitor, Adrenergic receptor agonist, Alstrom syndrome protein 1(ALMS1)/PKC alpha protein interaction inhibitor, Apelin receptor agonist, Diacylglycerol O acyltransferase 2 inhibitor, Adenosine A3 receptor agonist, Adenosine A3 receptor antagonist, Adiponectin receptor agonist, Aldehyde dehydrogenase 2 stimulator, AKT protein kinase inhibitor, AMP-activated protein kinases (AMPK), AMP kinase activator, ATP citrate lyase inhibitor, AMP activated protein kinase stimulator, Endothelial nitric oxide synthase stimulator, NAD-dependent deacetylase sirtuin-1 stimulator, Adrenergic receptor antagonist, Androgen receptor agonist, Amylin receptor agonist, Angiotensin II AT-1 receptor antagonist, Apical sodium-dependent bile acid transport inhibitor, Autophagy protein modulator, Autotaxin inhibitors, Axl tyrosine kinase receptor inhibitor, Bax protein stimulator, Beta-catenin inhibitor, Bioactive lipid, Calcitonin agonist, Cannabinoid receptor modulator, Caspase inhibitor, Caspase-3 stimulator, Cathepsin inhibitor, Caveolin 1 inhibitor, CCK receptor antagonist, CCL26 gene inhibitor, CCR2 chemokine antagonist, CCR2 chemokine antagonist, Angiotensin II AT-1 receptor antagonist, CCR3 chemokine antagonist, CCR5 chemokine antagonist, CD3 antagonist, CDGSH iron sulfur domain protein modulator, chitinase inhibitor, Chloride channel stimulator, Chitotriosidase 1 inhibitor, CNR1 inhibitor, Connective tissue growth factor ligand inhibitor, COT protein kinase inhibitor, Cyclin D1 inhibitor, Cytochrome P450 7A1 inhibitor, Cytochrome P450 reductase inhibitors, DGAT1/2 inhibitor, Diacylglycerol O acyltransferase 1 inhibitor (DGAT1), Cytochrome P450 2E1 inhibitor (CYP2E1), CXCR3 chemokine antagonist, CXCR4 chemokine antagonist, Dihydroceramide delta 4 desaturase inhibitor, Dihydroorotate dehydrogenase inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, fibroblast activation protein inhibitor, Free fatty acid receptor 1 agonist, Galectin-3 inhibitor, GDNF family receptor alpha like agonist, Glucagon receptor agonist, Glucagon-like peptide 1 agonist, Glucocorticoid receptor antagonist, Glucose 6-phosphate 1-dehydrogenase inhibitor, G-protein coupled bile acid receptor 1 agonist, G-protein coupled receptor-119 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, STAT-3 modulator, HMG CoA reductase inhibitor, HSD17B13 gene inhibitor, 5-HT 2a receptor antagonist, Hydrolase inhibitor, Hypoxia inducible factor-2 alpha inhibitor, IL-10 agonist, IL-17 antagonist, IL-22 agonist, Ileal sodium bile acid cotransporter inhibitor, Insulin sensitizer, Insulin ligand agonist, Insulin receptor agonist, integrin modulator, Integrin Antagonist, Integrin alpha-V/beta-1 antagonist, Integrin alpha-V/beta-6 antagonist, intereukin-1 receptor-associated kinase 4 (IRAK4) inhibitor, IL-6 receptor agonist, interleukin 17 ligand inhibitor, Jak2 tyrosine kinase inhibitor, Jun N terminal kinase-1 inhibitor, Kelch like ECH associated protein 1 modulator, Ketohexokinase (KHK) inhibitor, Klotho beta stimulator, Leukotriene A4 hydrolase inhibitor, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, LXR inverse agonists, Macrophage mannose receptor 1 modulator, Matrix metalloproteinases (MMPs) inhibitor, MEKK-5 protein kinase inhibitor, MCH receptor-1 antagonist, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21(miR-21) inhibitor, Mitochondrial uncoupler, Mixed lineage kinase-3 inhibitor, Motile sperm domain protein 2 inhibitor, Myelin basic protein stimulator, NACHT LRR PYD domain protein 3 (NLRP3) inhibitor, NAD-dependent deacetylase sirtuin stimulator, NADPH oxidase inhibitor (NOX), NFE2L2 gene inhibitor, Nicotinic acid receptor 1 agonist, Opioid receptor mu antagonist, P2Y13 purinoceptor stimulator, Nuclear erythroid 2-related factor 2 stimulator, Nuclear receptor modulators, Nuclear transport of transcription factor modulator, P2X7 purinoceptor modulator, PACAP type I receptor agonist, PDE 3 inhibitor, PDE 4 inhibitor, PDE 5 inhibitor, PDGF receptor beta modulator, Phenylalanine hydroxylase stimulator, Phospholipase C inhibitor, Phosphoric diester hydrolase inhibitor, PPAR alpha agonist, PPAR delta agonist, PPAR gamma agonist, Peptidyl-prolyl cis-trans isomerase A inhibitor, PNPLA3 gene inhibitor, PPAR gamma modulator, Protease-activated receptor-2 antagonist, Protein kinase modulator, Protein NOV homolog modulator, PTGS2 gene inhibitor, renin inhibitor, Resistin/CAP1 (adenylyl cyclase associated protein 1) interaction inhibitor, Rho associated protein kinase inhibitor, RNA polymerase inhibitors, S-nitrosoglutathione reductase (GSNOR) enzyme inhibitor, Sodium glucose transporter-2 inhibitor, Sphingolipid delta 4 desaturase DES1 inhibitor, SREBP transcription factor inhibitor, STAT-1 inhibitor, Stearoyl CoA desaturase-1 inhibitor, STK25 inhibitor, Suppressor of cytokine signalling-1 stimulator, Suppressor of cytokine signalling-3 stimulator, Taste receptor type 2 agonist, Telomerase stimulator, TERT gene modulator, TGF beta (TGFB1) ligand inhibitor, TNF antagonist, Transforming growth factor β (TGF-β), Transforming growth factor R activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, TLR-9 antagonist, VDR agonist, Vitamin D3 receptor modulators, WNT modulators, YAP/TAZ modulator or a Zonulin inhibitor, and combinations thereof.

Non-limiting examples of the one or more additional therapeutic agents include:

ACE inhibitors, such as enalapril;

Acetaldehyde dehydrogenase inhibitors, such as ADX-629;

Acetyl CoA carboxylase (ACC) inhibitors, such as NDI-010976 (firsocostat), DRM-01, gemcabene, GS-834356, PF-05175157, QLT-091382, PF-05221304;

Acetyl CoA carboxylase/Diacylglycerol O acyltransferase 2 inhibitors, such as PF-07055341;

Adenosine receptor agonists, such as CF-102 (namodenoson), CF-101 (piclidenoson), CF-502, CGS21680;

Adenosine A3 receptor antagonist, such as FM-101;

Adiponectin receptor agonists, such as ADP-355, ADP-399, ALY668-SR;

Adrenergic receptor antagonist, such as bromocriptine, phentermine, VI-0521;

Aldehyde dehydrogenase 2 stimulators, such as FP-045;

Amylin/calcitonin receptor agonists, such as KBP-042, KBP-089;

AMP activated protein kinase stimulators, such as C-455, PXL-770, O-304;

AMP kinase activators/ATP citrate lyase inhibitors, such as bempedoic acid (ETC-1002, ESP-55016);

AMP activated protein kinase/Endothelial nitric oxide synthase/NAD-dependent deacetylase sirtuin-1 stimulators, such as NS-0200 (leucine+metformin+sildenafil);

Androgen receptor agonists, such as LPCN-1144, LPCN-1148, testosterone prodrug;

Angiotensin II AT-1 receptor antagonists, such as irbesartan; Angiopoietin-related protein-3 inhibitors, such as vupanorsen (IONIS-ANGPTL3-LRx);

Apelin receptor agonist, such as CB-5064, MBT-2;

Apical sodium-dependent bile acid transport inhibitors, such as A-3907; Autophagy protein modulators, such as A-2906, GM-90194;

Autotaxin (ectonucleotide pyrophosphatase/phosphodiesterase 2 (NPP2 or ENPP2)) inhibitors, such as FP10.47, PAT-505, PAT-048, GLPG-1690, X-165, PF-8380, TJC-0265, TJC-0316, AM-063, BBT-877;

Axl tyrosine kinase receptor inhibitors, such as bemcentinib (BGB-324, R-428);

Bax protein stimulators, such as CBL-514;

Bioactive lipids, such as DS-102;

Cannabinoid receptor modulators, such as namacizumab (nimacimab), GWP-42004, REV-200, CRB-4001, INV-101, SCN-002;

Caspase inhibitors, such as emricasan;

Pan cathepsin B inhibitors, such as VBY-376;

Pan cathepsin inhibitors, such as VBY-825;

CCK receptor antagonist, such as proglumide;

CCL26 gene inhibitor, such as mosedipimod, KDDF-201410-10;

CCR2/CCR5 chemokine antagonists, such as BMS-687681, cenicriviroc, maraviroc, CCX-872, leronlimab, WXSH-0213;

CCR2/CCR5 chemokine antagonists and FXR agonists, such as LJC-242 (tropifexor+cenivriviroc);
CCR2 chemokine antagonists, such as propagermanium;
CCR2 chemokine/Angiotensin II AT-I receptor antagonists, such as DMX-200, DMX-250;
CCR3 chemokine antagonists, such as bertilimumab;
CD3 antagonists, such as NI-0401 (foralumab);
CDGSH iron sulfur domain protein modulators, such as EYP-002;
Chitinase inhibitor, such as OATD-01;
Chitotriosidase 1 inhibitors, such as OAT-2068;
Chloride channel stimulators, such as cobiprostone, and lubiprostone;
Casein kinase-1 (CK1) delta/epsilon inhibitors, such as PF-05006739;
Connective tissue growth factor ligand inhibitor, such as PBI-4050;
COT protein kinase inhibitors, such as GS-4875, GS-5290;
CXCR4 chemokine antagonists, such as AD-214;
Cytochrome P450 reductase inhibitors, such as SNP-630;
Diglyceride acyltransferase 2 (DGAT2) inhibitors, such as IONIS-DGAT2Rx, PF-06865571;
Diglyceride acyltransferase 1 (DGAT1) inhibitors, such as GSK-3008356;
Diacylglycerol 0 acyltransferase 1 (DGAT1)/Cytochrome P450 2E1 inhibitors (CYP2E1), such as SNP-610;
Dihydroorotate dehydrogenase inhibitor, such as vidofludimus;
Dipeptidyl peptidase IV inhibitors, such as linagliptin, evogliptin;
Eotaxin ligand inhibitors, such as bertilimumab, CM-101;
Extracellular matrix protein modulators, such as CNX-024;
Farnesoid X receptor (FXR) agonists, such as AGN-242266, AGN-242256, ASC-42, EDP-297 (EP-024297), RDX-023, BWL-200, AKN-083, EDP-305, GNF-5120, cilofexor tromethamine (GS-9674), HPG-1860, IOT-022, LMB-763, obeticholic acid, Px-102, Px-103, M790, M780, M450, M-480, MET-409, MET-642, PX20606, SYHA-1805, vonafexor (EYP-001), TERN-101, TC-100, INT-2228, TQA-3526, ZG-5266, HPD-001, alendronate;
Farnesoid X receptor (FXR)/G-protein coupled bile acid receptor 1(TGR5) agonists, such as INT-767;
Fatty acid synthase inhibitors, such as TVB-2640, FT-8225;
Fibroblast growth factor 19 (rhFGF19)/cytochrome P450 (CYP) 7A1 inhibitors, such as aldafermin (NGM-282);
Fibroblast growth factor 21(FGF-21) ligand modulators, such as AP-025, BMS-986171, B-1654, BI089-100, BOS-580, Pegbelfermin (BMS-986036), B-1344, NN-9499;
Fibroblast growth factor 21 (FGF-21)/glucagon like peptide 1 (GLP-1) agonists, such as YH-25723 (YH-25724; YH-22241), efruxifermin (AKR-001);
FGF receptor agonists/Klotho beta stimulators, such as BFKB-8488A (RG-7992);
Free fatty acid receptor 1 agonist, such as SCO-267;
Galectin-3 inhibitors, such as belapectin (GR-MD-02), GB-1107 (Gal-300), GB-1211 (Gal-400), IMT-001;
GDNF family receptor alpha like agonist, such as NGM-395;
Glucagon-like peptide 1 (GLP1R) agonists, such as ALT-801, AC-3174, liraglutide, cotadutide (MEDI-0382), SAR-425899, LY-3305677, HM-15211, YH-25723, YH-GLP1, RPC-8844, PB-718, PF-06882961, semaglutide;
Glucagon-like peptide 1 receptor agonist; Oxyntomodulin ligand; Glucagon receptor agonist, such as efinopegdutide;
Gastric inhibitory polypeptide/Glucagon-like peptide-1 (GIP/GLP-1) receptor co-agonist, such as tirzepatide (LY-3298176);
PEGylated long-acting glucagon-like peptide-1/glucagon (GLP-1R/GCGR) receptor dual agonist, such as DD-01;
Glucagon/GLP1-receptor agonist, such as BI-456906, NN-6177;
Glucocorticoid receptor antagonists, such as CORT-118335 (miricorilant);
Glucose 6-phosphate 1-dehydrogenase inhibitors, such as ST001;
Glucokinase stimulator, such as dorzagliatin, sinogliatin (RO-5305552);
G-protein coupled bile acid receptor 1(TGR5) agonists, such as RDX-009, INT-777, HY-209;
G-protein coupled receptor 84 antagonist, such as PBI-4547;
G-protein coupled receptor-119 agonist, such as DA-1241;
Heat shock protein 47 (HSP47) inhibitors, such as ND-L02-s0201;
Hedgehog protein TGF beta ligand inhibitors, such as Oxy-210;
Histone deacetylase inhibitors/STAT-3 modulators, such as SFX-01;
HMG CoA reductase inhibitors, such as atorvastatin, fluvastatin, pitavastatin, pravastatin, rosuvastatin, simvastatin;
HSD17B13 gene inhibitor, such as ALN-HSD, ARO-HSD;
Hydrolase inhibitor, such as ABD-X;
Hypoxia inducible factor-2 alpha inhibitors, such as PT-2567;
IL-10 agonists, such as peg-ilodecakin;
Ileal sodium bile acid cotransporter inhibitors, such as odevixibat (A-4250), volixibat potassium ethanolate hydrate (SHP-262), GSK2330672, CJ-14199, elobixibat (A-3309);
Insulin sensitizers, such as, KBP-042, azemiglitazone potassium (MSDC-0602K), ION-224, MSDC-5514, Px-102, RG-125 (AZD4076), Tolimidone, VVP-100X, CB-4211, ETI-101;
Insulin ligand/dsInsulin receptor agonists, such as ORMD-0801;
Integrin antagonists, such as IDL-2965;
IL-6 receptor agonists, such as KM-2702;
Integrin alpha-V/beta-6 and alpha-V/beta-1 dual inhibitor; such as PLN-74809;
Interleukin 17 ligand inhibitor, such as netakimab;
Jak1/2 tyrosine kinase inhibitor, such as baricitinib;
Jun N terminal kinase-1 inhibitor, such as CC-90001;
Kelch like ECH associated protein 1 modulator, such as alpha-cyclodextrin-stabilized sulforaphane;
Ketohexokinase (KHK) inhibitors, such as PF-06835919, LY-3478045, LY-3522348;
beta Klotho (KLB)-FGF1c agonists, such as MK-3655 (NGM-313);
Leukotriene A4 hydrolase inhibitor, such as LYS-006;
5-Lipoxygenase inhibitors, such as tipelukast (MN-001), epeleuton (DS-102,AF-102);

Lipoprotein lipase inhibitors, such as CAT-2003;

LPL gene stimulators, such as alipogene tiparvovec;

Liver X receptor (LXR) inhibitors, such as PX-665, PX-L603, PX-L493, BMS-852927, T-0901317, GW-3965, SR-9238;

Lysophosphatidate-1 receptor antagonists, such as BMT-053011, UD-009 (CP-2090), AR-479, ITMN-10534, BMS-986020, KI-16198;

Lysyl oxidase homolog 2 inhibitors, such as simtuzumab, PXS-5382A (PXS-5338);

Macrophage mannose receptor 1 modulators, such as tilmanocept-Cy3 (technetium Tc 99m tilmanocept);

Matrix metalloprotease inhibitors, such as ALS-L1023;

Membrane copper amine oxidase (VAP-1) inhibitors, such as TERN-201, TT-01025;

MEKK-5 protein kinase (ASK-1) inhibitors, such as CJ-16871, CS-17919, selonsertib (GS-4997), SRT-015, GS-444217, GST-HG-151, TERN-301;

MCH receptor-1 antagonists, such as CSTI-100 (ALB-127158);

Semicarbazide-Sensitive Amine Oxidase/Vascular Adhesion Protein-1 (SSAO/VAP-1) Inhibitors, such as PXS-4728A (BI-1467335);

Methionine aminopeptidase-2 inhibitors, such as ZGN-1061, ZGN-839, ZN-1345;

Methyl CpG binding protein 2 modulators, such as mercaptamine;

Mineralocorticoid receptor antagonists (MCRA), such as MT-3995 (apararenone);

Mitochondrial uncouplers, such as 2,4-dinitrophenol, HU6, Mito-99-0053;

Mixed lineage kinase-3 inhibitors, such as URMC-099-C;

Motile sperm domain protein 2 inhibitors, such as VB-601;

Myelin basic protein stimulators, such as olesoxime;

Myeloperoxidase inhibitors, such as PF-06667272, AZM-198;

NADPH oxidase inhibitors, such as GKT-831, GenKyoTex, APX-311, setanaxib;

Nicotinic acid receptor 1 agonists, such as ARI-3037MO;

NACHT LRR PYD domain protein 3 (NLRP3) inhibitors, such as KDDF-201406-03, NBC-6, IFM-514, JT-194 (JT-349);

NFE2L2 gene inhibitor, such as GeRP-amiR-144;

Nuclear transport of transcription factor modulators, such as AMTX-100;

Nuclear receptor modulators, such as DUR-928 (DV-928);

Opioid receptor mu antagonists, such as methylnaltrexone;

P2X7 purinoceptor modulators, such as SGM-1019;

P2Y13 purinoceptor stimulators, such as CER-209;

PDE 3/4 inhibitors, such as tipelukast (MN-001);

PDE 5 inhibitors, such as sildenafil, MSTM-102;

PDGF receptor beta modulators, such as BOT-191, BOT-509;

Peptidyl-prolyl cis-trans isomerase inhibitors, such as CRV-431 (CPI-432-32), NVP-018, NV-556 (NVP-025);

Phenylalanine hydroxylase stimulators, such as HepaStem;

Phosphoric diester hydrolase inhibitor, such as ZSP-1601;

PNPLA3 gene inhibitor, such as AZD-2693;

PPAR agonists, such as Chiglitazar, elafibranor (GFT-505), seladelpar lysine (MBX-8025), deuterated pioglitazone R-enantiomer, pioglitazone, PXL-065 (DRX-065), saroglitazar, lanifibranor (IVA-337), CHS-131, pemafibrate (K-877), ZG-0588, ZSP-0678; ZSYM-008;

Protease-activated receptor-2 antagonists, such as PZ-235;

Protein kinase modulators, such as CNX-014;

Protein NOV homolog modulators, such as BLR-200;

PTGS2 gene inhibitors, such as STP-705, STP-707;

Renin inhibitors, such as PRO-20;

Resistin/CAP1 (adenylyl cyclase associated protein 1) interaction inhibitors, such as DWJ-211;

Rev protein modulator, such as ABX-464;

Rho associated protein kinase (ROCK) inhibitors, such as REDX-10178 (REDX-10325), KD-025, RXC-007, TDI-01;

RNA polymerase inhibitors, such as rifaximin;

Snitrosoglutathione reductase (GSNOR) enzyme inhibitors, such as SL-891;

Sodium glucose transporter-2 (SGLT2) inhibitors, such as ipragliflozin, remogliflozin etabonate, ertugliflozin, dapagliflozin, tofogliflozin, sotagliflozin;

Sodium glucose transporter-1/2 (SGLT 1/2) inhibitors, such as licogliflozin bis(prolinate) (LIK-066);

SREBP transcription factor inhibitors, such as CAT-2003, HPN-01, MDV-4463;

Stearoyl CoA desaturase-1 inhibitors, such as aramchol;

Taste receptor type 2 agonists, such as ARD-101;

Thyroid hormone receptor beta agonists, such as ALG-009, ASC-41, CNPT-101101; CNPT-101207, CS-27186, KY-41111, resmetirom (MGL-3196), MGL-3745, TERN-501, VK-2809, HP-515;

TLR-2/TLR-4 antagonists, such as VB-201 (CI-201);

TLR-4 antagonists, such as JKB-121, JKB-122, naltrexone;

Tyrosine kinase receptor modulators, such as CNX-025, GFE-2137 (repurposed nitazoxanide);

TLR-9 antagonist, such as GNKS-356, AVO-101;

TNF antagonist, such as ALF-421;

GPCR modulators, such as CNX-023;

Nuclear hormone receptor modulators, such as Px-102;

VDR agonist, such as CK-15;

Xanthine oxidase inhibitors, such as ACQT-1127;

Xanthine oxidase/Urate anion exchanger 1 (URAT1) inhibitors, such as RLBN-1001, RLBN-1127; or Zonulin Inhibitors, such as larazotide acetate (INN-202).

In certain specific embodiments, the one or more additional therapeutic agents are selected from A-4250, AC-3174, acetylsalicylic acid, AK-20, alipogene tiparvovec, AMX-342, AN-3015, anti-CXCR3 antibodies, anti-TAGE antibody, aramchol, ARI-3037MO, ASP-8232, AXA-1125, bertilimumab, Betaine anhydrous, BI-1467335, BMS-986036, BMS-986171, BMT-053011, BOT-191, BTT-1023, budesonide, BX-003, CAT-2003, cenicriviroc, CBW-511, CER-209, CF-102, CGS21680, CNX-014, CNX-023, CNX-024, CNX-025, cobiprostone, colesevelam, dabigatran etexilate mesylate, dapagliflozin, DCR-LIV1, deuterated pioglitazone R-enantiomer, 2,4-dinitrophenol, DRX-065, DS-102, DUR-928, edaravone (TTYP-01), EDP-305, elafibranor (GFT-505), emricasan, enalapril, ertugliflozin, evogliptin, F-351, fluasterone (ST-002), FT-4101, GDD-3898, GH-509, GKT-831, GNF-5120, GRI-0621, GR-MD-02, GS-300, GS-4997, GS-9674, GS-4875, GS-5290, HEC-96719, HTD-1801, HS-10356, HSG-4112, HST-202, HST-201, HU-6, hydrochlorothiazide, icosabutate (PRC-4016), icosapent ethyl ester, IMM-124-E, INT-767, INV-240, ION-455, IONIS-DGAT2Rx, ipragliflozin, Irbesarta, propagermanium, IVA-337, J2H-1702, JKB-121, KB-GE-001, KBLP-004, KBLP-009, KBP-042, KD-025, M790, M780, M450, metformin, sildenafil, LB-700, LC-280126, linagliptin, liraglutide, (LJN-452) tropifexor, LM-011, LM-002 (CVI-LM-002), LMB-763, LYN-100, MB-N-008, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-011, NP-135, NP-160, norursodeoxycholic acid, NV-422, NVP-022, O-304, obeticholic acid (OCA), 25HC3S, olesoxime, PAT-505, PAT-048, peg-ilodecakin, pioglitazone, pirfenidone, PRI-724, PX20606, Px-102, PX-L603, PX-L493, PXS-4728A, PZ-235, PZH-2109, RCYM-001, RDX-009, remogliflozin etabonate, RG-125 (AZD4076), RP-005, RPI-500, 5-723595, saroglitazar, SBP-301, semaglutide, SH-2442, SHC-028, SHC-023, simtuzumab, solithromycin, sotagliflozin, statins (atorvastatin, fluvastatin, pitavastatin, pravastatin, rosuvastatin, simvastatin), TCM-606F, TEV-45478, TQA-3526, TQA-3563, tipelukast (MN-001), TLY-012, TRX-318, TVB-2640, TXR-611, TXR-612, TS-20004, UD-009, UN-03, ursodeoxycholic acid, VBY-376, VBY-825, VK-2809, vismodegib, volixibat potassium ethanolate hydrate (SHP-626), VVP-100X, WAV-301, WNT-974, WXSH-0038, WXSH-0078, XEN-103, XRx-117, XTYW-003, XW-003, XW-004, XZP-5610, ZGN-839, ZG-5216, ZSYM-008, or ZYSM-007.

In some embodiments, the compound of the present disclosure is combined with one or more thereapeutic agents selected from an anti-obesity agent including but not limited to peptide YY or an analogue thereof, a neuropeptide Y receptor type 2 (NPYR2) agonist, a NPYR1 agonist, an NPYR5 antagonist, a cannabinoid receptor type 1 (CB1 R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g., obeticholic acid), apoptotic signal-regulating kinase (ASK-1) inhibitor, zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1 R agonist, e.g., liraglutide, exenatide, dulaglutide, albiglutide, lixisenatide, or semaglutide), an insulin sensitizer such as thiazolidinediones (TZDs), a peroxisome proliferator-activated receptor alpha (PPARα) agonist, fish oil, an acetyl-coA carboxylase (ACC) inhibitor, a transforming growth factor beta (TGFβ) antagonist, a GDNF family receptor alpha like (GFRAL) agonist, a melanocortin-4 receptor (MC4R) agonist, including the pharmaceutically acceptable salts of the specifically named agents and the pharmaceutically acceptable solvates of said agents and salts.

VII. Methods of Treatment

In some embodiments, compounds of Formula (I-A), or pharmaceutically acceptable salt thereof, are useful in a method of treating and/or preventing a GLP-1R mediated disease or condition. In some embodiments, a method for treating and/or preventing a GLP-1R mediated disease or condition includes administering to a subject in need thereof a pharmaceutically effective amount of a compound of the present disclosure or pharmaceutically acceptable salt thereof.

In some embodiments, the disease or condition comprises a liver disease or related diseases or conditions, e.g., liver fibrosis, non-alcoholic fatty liver disease (NAFLD), non-alcoholic steatohepatitis (NASH), liver cirrhosis, compensated liver fibrosis, decompensated liver fibrosis, hepatocellular carcinoma, Primary Biliary Cirrhosis (PBC), or Primary Sclerosing Cholangitis (PSC). In some embodiments, the disease or condition comprises a metabolic disease or related diseases or conditions, such as diabetes mellitus, obesity, or cardiometabolic diseases.

GLP-1R agonists are currently being investigated in connection with certain disorders and conditions, including for example diabetes. GLP-1 analogs that are DPP4 resistant and have longer half-lives than endogenous GLP-1 have been reported to be associated with weight loss and improved insulin action. Liraglutide, a peptide GLP-1R agonist approved in connection with treatment of diabetes, has been reported to show favorable improvements in outcomes in NASH subjects.

In some embodiments, the present disclosure relates to the use of compounds of Formula (I-A), or a pharmaceutically acceptable salt thereof in the preparation of a medicament for the prevention and/or treatment of a disease or condition mediated by GLP-1R, such as a liver disease or metabolic disease. In some embodiments, the present disclosure relates to the use of compounds of Formula (I-A), or a pharmaceutically acceptable salt thereof in the preparation of a medicament for the prevention and/or treatment of a disease or condition mediated by GLP-1R, such as a liver disease or metabolic disease. For example, some embodiments provide a compound of Formula (I-A), or a pharmaceutically acceptable salt thereof, or a use thereof, for treatment and/or prevention of chronic intrahepatic or some forms of extrahepatic cholestatic conditions, of liver fibrosis, of acute intraheptic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of type II diabetes and clinical complications of type I and type II diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistent infections by intracellular bacteria or parasitic protozoae, of non-malignant hyperproliferative disorders, of malignant hyperproliferative disorders, of colon adenocarcinoma and hepatocellular carcinoma for instance, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis, of type I diabetes, pre-diabetes, idiopathic type 1 diabetes, latent autoimmune diabetes, maturity onset diabetes of the young, early onset diabetes, malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, obesity, eating disorders, sleep apnea, weight gain, sugar craving, dyslipidemia, hyperinsulinemia, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, left ventricular hypertrophy, Parkinson's Disease, peripheral arterial disease, macular degeneration, cataract, glomerulosclerosis, chronic renal failure, metabolic syndrome, angina pectoris, premenstrual syndrome, thrombosis, atherosclerosis, impaired glucose metabolism, or vascular restenosis.

In some embodiments, a method of treating and/or preventing a non-alcoholic fatty liver disease (NAFLD), comprises administering to a subject in need thereof a compound of the present disclosure or a pharmaceutically acceptable salt thereof.

The disclosure also relates to a compound according to Formula (I-A) or a pharmaceutical composition comprising said compound for preventive and posttraumatic treatment of a cardiovascular disorder, such as acute myocardial infarction, acute stroke, or thrombosis which occur as an endpoint of chronic obstructive atherosclerosis. In some embodiments, a method for treating and/or preventing cardiovascular disorder comprises administering a compounds of Formula (I-A) to a subject in need thereof.

The disclosure further relates to a compound or pharmaceutical composition for the treatment and/or prevention of obesity and associated disorders such as metabolic syndrome (combined conditions of dyslipidemias, diabetes and abnormally high body-mass index) which can be overcome by GLP1R-mediated lowering of serum triglycerides, blood glucose and increased insulin sensitivity and GLP1R-mediated weight loss. In some embodiments, a method for treating and/or preventing a metabolic disease comprises administering a compounds of Formula (I-A) to a subject in need thereof. In some embodiments, a method for treating and/or preventing a metabolic disease comprises administering a compounds of Formula (I-A), to a subject in need thereof.

In a further embodiment, the compounds or pharmaceutical composition of the present disclosure are useful in preventing and/or treating clinical complications of Type I and Type II Diabetes. Examples of such complications include diabetic nephropathy, diabetic retinopathy, diabetic neuropathies, or Peripheral Arterial Occlusive Disease (PAOD). Other clinical complications of diabetes are also encompassed by the present disclosure. In some embodiments, a method for treating and/or preventing complications of Type I and Type II Diabetes comprises administering a compounds of Formula (I-A) to a subject in need thereof. In some embodiments, a method for treating and/or preventing complications of Type I and Type II Diabetes comprises administering a compounds of Formula (I-A) to a subject in need thereof.

Furthermore, conditions and diseases which result from chronic fatty and fibrotic degeneration of organs due to enforced lipid and/or triglyceride accumulation and subsequent activation of profibrotic pathways may also be prevented and/or treated by administering the compounds or pharmaceutical composition of the present disclosure. Such conditions and diseases can include NASH and chronic cholestatic conditions in the liver, Glomerulosclerosis and Diabetic Nephropathy in the kidney, Macular Degeneration and Diabetic Retinopathy in the eye and neurodegenerative diseases, such as Alzheimer's Disease in the brain, or Diabetic Neuropathies in the peripheral nervous system. In some embodiments, a method for treating and/or preventing conditions and diseases which result from chronic fatty and fibrotic degeneration of organs due to enforced lipid and/or triglyceride accumulation and subsequent activation of profibrotic pathways comprises administering a compounds of Formula (I-A) to a subject in need thereof. In some embodiments, a method for treating and/or preventing conditions and diseases which result from chronic fatty and fibrotic degeneration of organs due to enforced lipid and/or triglyceride accumulation and subsequent activation of profibrotic pathways comprises administering a compounds of Formula (I-A) to a subject in need thereof. In some embodiments, a method for treating and/or preventing NASH comprises administering a compounds of Formula (I-A) to a subject in need thereof. In some embodiments, a method for treating and/or preventing NASH comprises administering a compounds of Formula (I-A) to a subject in need thereof.

Further provided herein is a pharmaceutical composition for use in treating a GLP-1R mediated disease or condition described herein, comprising a compound of the present disclosure or a pharmaceutically acceptable salt thereof.

The present disclosure also describes a use for the manufacture of a medicament in treating a GLP-1R mediated disease or condition comprising a compound of the present disclosure or a pharmaceutically acceptable salt thereof. Medicaments as referred to herein may be prepared by conventional processes, including the combination of a compound according to the present disclosure and a pharmaceutically acceptable carrier.

Also disclosed is a compound of the present disclosure or a pharmaceutically acceptable salt thereof for the treatment of a GLP-1R mediated disease or condition. Also disclosed is a compound of the present disclosure or a pharmaceutically acceptable salt thereof for the prevention of a GLP-1R mediated disease or condition.

VIII. Examples

Many general references providing commonly known chemical synthetic schemes and conditions useful for synthesizing the disclosed compounds are available (see, e.g., Smith, March's Advanced Organic Chemistry: Reactions, Mechanisms, and Structure, $7^{th}$ edition, Wiley-Interscience, 2013.).

Compounds as described herein can be purified by any of the means known in the art, including chromatographic means, such as high-performance liquid chromatography (HPLC), preparative thin layer chromatography, flash column chromatography and ion exchange chromatography. Any suitable stationary phase can be used, including normal and reversed phases as well as ionic resins. For example, the disclosed compounds can be purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the pendant groups. Each of the reactions depicted in the general schemes can be run at a temperature from about 0° C. to the reflux temperature of the organic solvent used.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The embodiments are also directed to processes and intermediates useful for preparing the subject compounds or pharmaceutically acceptable salts thereof. The following description is, therefore, not intended to limit the scope of the present disclosure.

In some embodiments, the present disclosure generally provides a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in schemes below, and the examples that follow.

The compounds detailed in the Examples were synthesized according to the general synthetic methods described below. Compounds were named using ChemDraw version 18. 1. 0. 535 (PerkinElmer Informatics, Inc.) unless otherwise indicated.

Abbreviations

Certain abbreviations and acronyms are used in describing the experimental details. Although most of these would be understood by one skilled in the art, Table 1 contains a list of many of these abbreviations and acronyms.

TABLE 1

List of Abbreviations and Acronyms

| Abbreviation | Meaning |
|---|---|
| Ac | acetate |
| ACN | acetonitrile |
| AmPhos | di-tert-butyl(4-dimethylaminophenyl)phosphine |
| Bn | benzyl |
| Bpin | (pinacolato)boron |
| $B_2Pin_2$ | bis(pinacolato)diboron |
| Bu | butyl |
| Bz | benzoyl |
| BzCl | benzoyl chloride |
| cataCXium ® A Pd G3 | Mesylate[(di(1-adamantyl)-n-butylphosphine)-2-(2'-amino-1,1'-biphenyl)]palladium(II) |
| DBA | dibenzalacetone |
| DBU | 1,8-Diazabicyclo |
| DCM | dichloromethane |
| DCE | dichlorethane |
| DEA | diethylamine |
| Deoxofluor | Bis(2-methoxyethyl)aminosulfur trifluoride |
| DIPEA | diisopropylethylamine |
| DME | dimethoxyethane |
| DMEM | Dulbecco's Modified Eagle Medium |
| DMF | dimethylformamide |
| DMSO | dimethylsulfoxide |
| dppf | 1,1'-Ferrocenediyl-bis(diphenylphosphine) |
| EDCI | N-(3-dimethylaminopropyl)-N'-ethylcarbodiimide hydrochloride |
| ES/MS | electron spray mass spectrometry |
| Et | ethyl |
| FBS | fetal bovine serum |
| HATU | 1-[Bis(dimethylamino)methylene]-1H-1,2,3-triazolo[4,5-b]pyridinium 3-oxide hexafluorophosphate |
| IPA | isopropanol |
| JohnPhos | (2-Biphenyl)di-tert-butylphosphine |
| KOtBu | potassium tert-butoxide |
| LC | liquid chromatography |

TABLE 1-continued

List of Abbreviations and Acronyms

| Abbreviation | Meaning |
| --- | --- |
| LCMS | liquid chromatography/mass spectrometry |
| MCPBA | meta-chloroperbenzoic acid |
| Me | methyl |
| m/z | mass to charge ratio |
| MS or ms | mass spectrum |
| NMP | N-methyl-2-pyrrolidone |
| Pd Rockphos G3 | [(2-Di-tert-butylphosphino-3-methoxy-6-methyl-2',4',6'-triisopropyl-1,1'-biphenyl)-2-(2-aminobiphenyl)]palladium(II)methanesulfonate |
| Ph | phenyl |
| Ph$_3$P | triphenylphosphine |
| pin | pinacol |
| Pyr | pyridine |
| RBF | round bottom flask |
| RP-HPLC | reverse phase high performance liquid chromatography |
| RT | room temperature |
| SFC | supercritical fluid chromatography |
| tBuXPhos Pd G3 | [(2-Di-tert-butylphosphino-2',4',6'-triisopropyl-1,1'-biphenyl)-2-(2'-amino-1,1'-biphenyl)]palladium(II)methanesulfonate |
| TEA | triethylamine |
| TFA | trifluoroacetic acid |
| THF | tetrahydrofuran |
| Ts | 4-toluenesulfonyl |
| XPhos Pd G2 | Chloro(2-dicyclohexylphosphino-2',4',6'-triisopropyl-1,1'-biphenyl)[2-(2'-amino-1,1'-biphenyl)]palladium(II) |
| δ | parts per million referenced to residual solvent peak |

A. Synthesis of Intermediates

Intermediate I-1

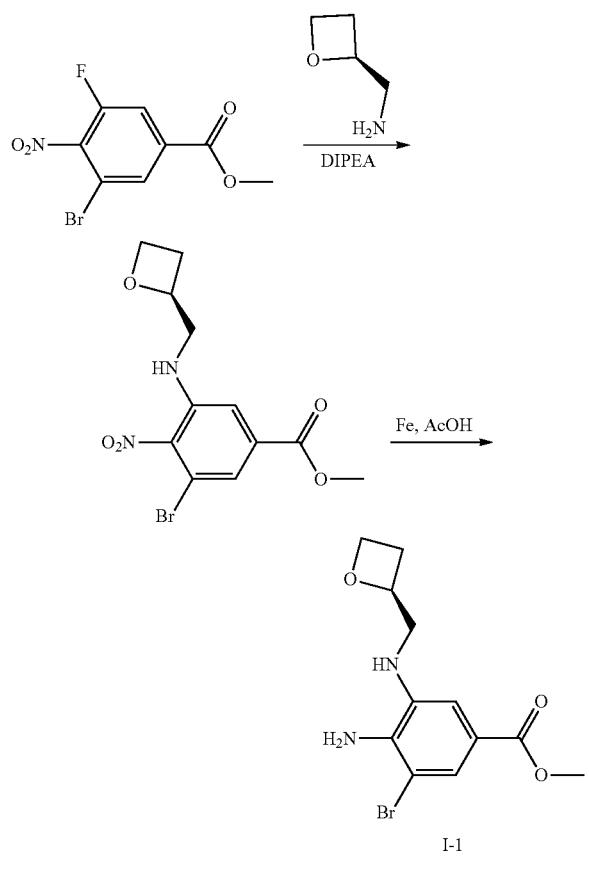

Methyl (S)-3-bromoo-4-nitro-5-((oxetan-2-ylmethyl)amino)benzoate

Methyl 3,5-difluoro-4-nitro-benzoate (3.00 g, 10.8 mmol) and (S)-oxetan-2-ylmethanamine (1034 mg, 11.9 mol) were taken up in N,N-dimethylformamide (10.0 mL), and N,N-diisopropylethylamine (3.68 mL, 21.1 mmol) was added. The mixture was heated to 60° C. for 3 hours. Following this time, the mixture was poured into water (15 mL) and extracted by EtOAc (2×25 mL). The combined organic layers were washed with brine (10 mL), dried over MgSO$_4$, filtered and concentrated to afford the crude product, which was used without further purification. ES/MS: 345.0 (M+H$^+$).

Methyl (S)-4-amino-3-bromo-5-((oxetan-2-ylmethyl)amino)benzoate (I-1)

Methyl (S)-3-bromoo-4-nitro-5-((oxetan-2-ylmethyl)amino)benzoate (3.72 g, 10.8 mmol) was dissolved in acetic acid (25 mL) in a 100 mL round bottom flask with a stir bar and reflux condenser after which iron (6.03 g, 108 mmol) was added and the resulting mixture placed in a 100° C. heating block for 1 hour. The crude mixture was cooled to room temperature, diluted with EtOAc and filtered through a pad of Celite rinsing with EtOAc for a final organic volume of 100 mL. The filtrate was then washed with water (2×25 mL) and saturated aqueous NaHCO$_3$ (2×25 mL), brine (1×20 mL) dried over MgSO4, filtered and concentrated. The crude residue was then purified by column chromatography (eluent: EtOAc/Hexanes) to afford the desired product. ES/MS: 315.1 (M+H$^+$).

Intermediate I-2

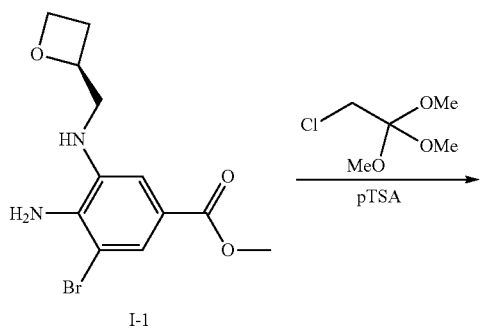

Methyl (S)-4-bromo-2-(chloromethyl)-1-(oxetan-2-ylmethyl)-1H-benzo[d]imidazole-6-carboxylate (I-2)

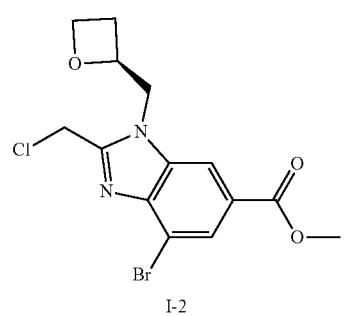

Methyl (S)-4-bromo-2-(chloromethyl)-1-(oxetan-2-ylmethyl)-1H-benzo[d]imidazole-6-carboxylate (I-2)

To a solution of methyl (S)-4-amino-3-bromo-5-((oxetan-2-ylmethyl)amino)benzoate (I-1) (1640 mg, 5.20 mmol) in acetonitrile (15 mL) was added 2-chloro-1,1,1-trimethoxy ethane (0.77 mL, 5.72 mmol) and para-toluenesulfonic acid monohydrate (69 mg, 0.36 mmol) after which the mixture was heated to 60° C. for 1 hour. The resultant solution was concentrated directly then purified by column chromatography (eluent: EtOAc/Hexanes) to afford the desired product. ES/MS: 374.0 (M+H+).

Intermediate I-3

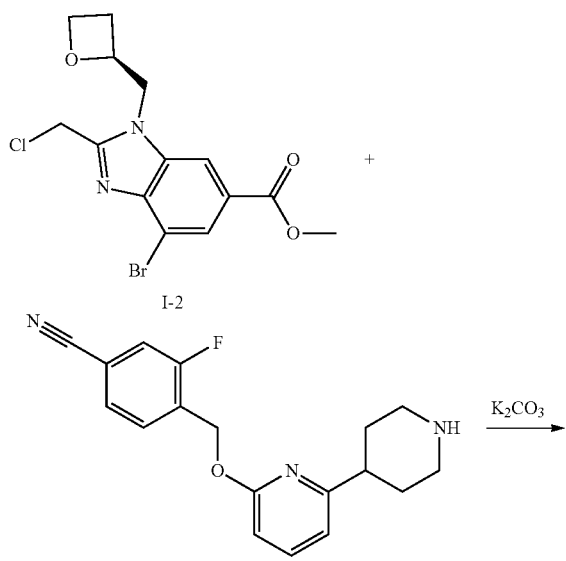

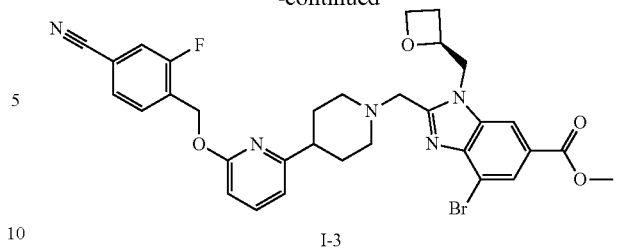

Methyl (S)-4-bromo-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylate (I-3)

Methyl (S)-4-bromo-2-(chloromethyl)-1-(oxetan-2-ylmethyl)-1H-benzo[d]imidazole-6-carboxylate (I-2) (291 mg, 0.78 mmol), 3-fluoro-4-[[6-(4-piperidyl)-2-pyridyl]oxymethyl]benzonitrile bis(4-methylbenzenesulfonate) (511 mg, 0.78 mmol), potassium carbonate (538 mg, 3.9 mmol) and acetonitrile (10 mL) were combined in a sealed 40 mL vial and heated to 50° C. for 16 hours. Upon completion the reaction mixture was poured into water (10 mL) and extracted with EtOAc (2×25 mL). The combined organic layers were washed with brine (10 mL), dried over MgSO4, filtered, concentrated and purified by column chromatography (eluent: EtOAc/Hexanes) to afford the desired product. ES/MS: 649.1 (M+H+).

Intermediate I-4

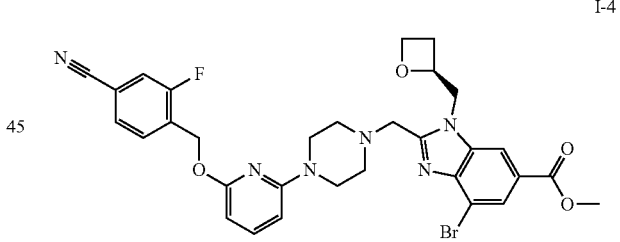

Methyl (S)-4-bromo-2-((4-(6-((4-cyano-2-fluorobenzyl)oxy)pyridin-2-yl)piperazin-1-yl)methyl)-1-(oxetan-2-ylmethyl)-1H-benzo[d]imidazole-6-carboxylate (I-4)

This intermediate was made in an identical manner as described for I-3 substituting 3-fluoro-4-[[6-(4-piperidyl)-2-pyridyl]oxymethyl]benzonitrile bis(4-methylbenzenesulfonate) with 3-fluoro-4-(((6-(piperazin-1-yl)pyridin-2-yl)oxy)methyl)benzonitrile bis hydrochloride.

ES/MS: 650.2 (M+H+).

Intermediate I-5

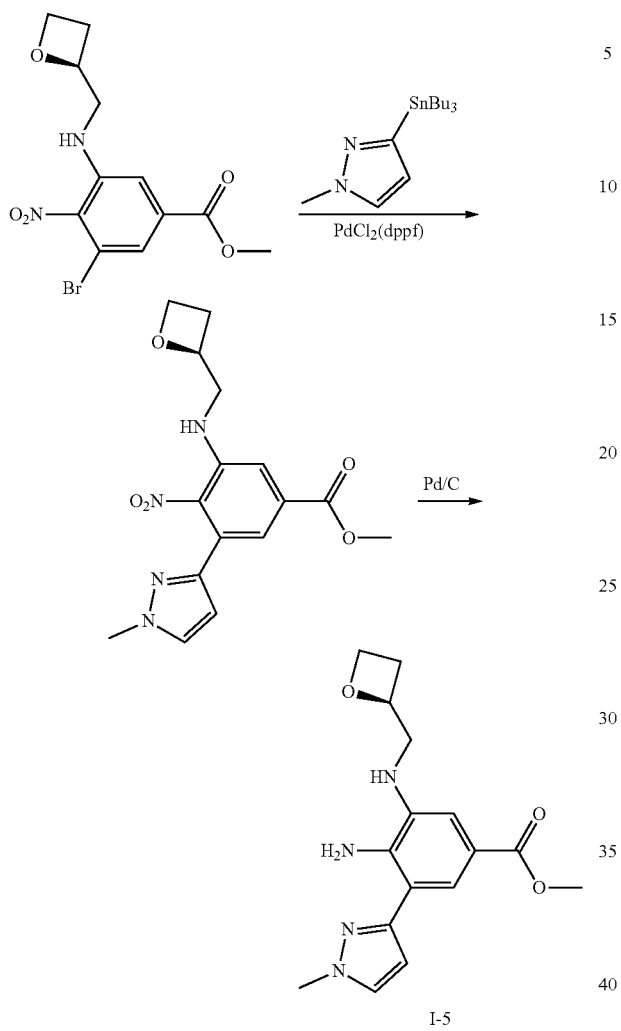

Methyl (S)-3-(1-methyl-1H-pyrazol-3-yl)-4-nitro-5-((oxetan-2-ylmethyl)amino)benzoate To a solution of methyl (S)-3-bromo-4-nitro-5-((oxetan-2-ylmethyl)amino)benzoate (140 mg, 0.41 mmol) in DMF (4 mL) was added cesium carbonate (396 mg, 1.2 mmol), 1,1'-Bis(diphenylphosphino)ferrocene] dichloropalladium (II) (29 mg, 0.096 mmol) and tributyl-(1-methylpyrazol-3-yl)stannane (244 mg, 0.66 mmol). The resulting solution was degassed with argon for 2 min and heated to 100° C. in a microwave for 30 min. The reaction was then diluted with EtOAc, filtered through Celite, and concentrated to dryness. The crude material was then purified by SiO₂ column chromatography (eluent:EtOAc/hexanes) to provide methyl (S)-3-(1-methyl-1H-pyrazol-3-yl)-4-nitro-5-((oxetan-2-ylmethyl)amino)benzoate. ES/MS m/z: 347.048 (M+H+).

Methyl (S)-4-amino-3-(1-methyl-1H-pyrazol-3-yl)-5-((oxetan-2-ylmethyl)amino)benzoate (I-5)

To a solution of methyl (S)-3-(1-methyl-1H-pyrazol-3-yl)-4-nitro-5-((oxetan-2-ylmethyl)amino)benzoate (101 mg, 0.29 mmol) in a mixture of EtOAc (2 mL) and EtOH (1 mL) was added palladium on carbon (10%, 48.5 mg, 0.05 mmol). The resulting solution was stirred at room temperature under an atmosphere of hydrogen for 18 hours. The slurry was filtered through Celite and then concentrated to dryness to provide methyl (S)-4-amino-3-(1-methyl-1H-pyrazol-3-yl)-5-((oxetan-2-ylmethyl)amino)benzoate (I-5). ES/MS m/z: 317.201 (M+H+).

Intermediate I-6

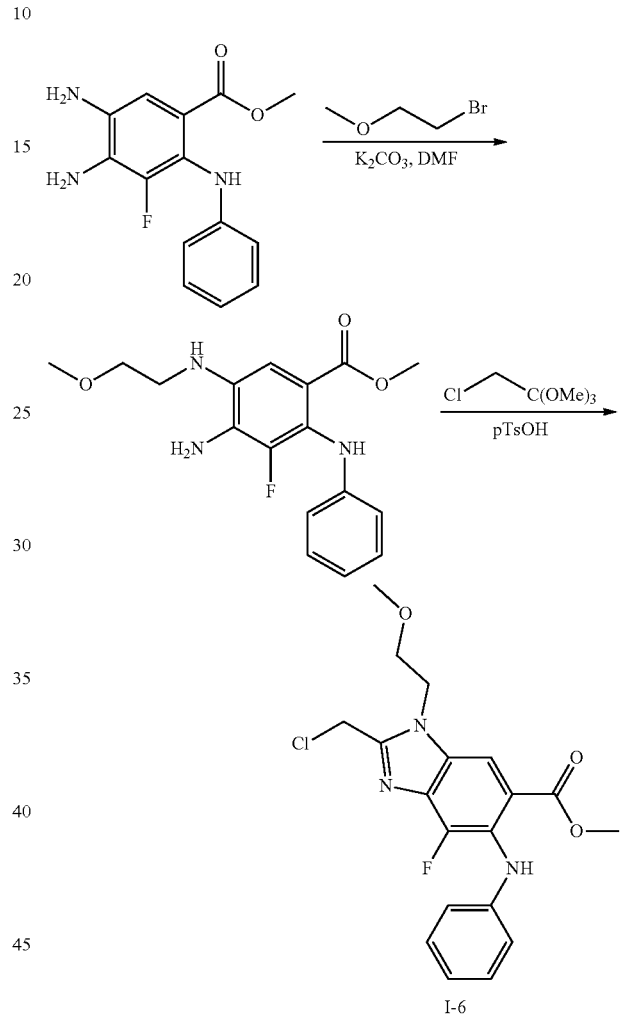

Methyl 4-amino-3-fluoro-5-((2-methoxyethyl)amino)-2-(phenylamino)benzoate

To a solution of methyl 4,5-diamino-3-fluoro-2-(phenylamino)benzoate (100 mg, 0.36 mmol) in DMF (1.25 mL) was added 1-bromo-2-methoxy-ethane (0.04 mL, 0.43 mmol) and potassium carbonate (98 mg, 0.71 mmol). The resulting slurry was heated to 80° C. for 2 days, at which time most of the starting material was consumed. The mixture was diluted with EtOAc and washed twice with aqueous ammonium chloride and then brine. The aqueous layers were back-extracted with EtOAc and the combined organic layers were dried over magnesium sulfate and concentrated to dryness to provide methyl 4-amino-3-fluoro-5-((2-methoxyethyl)amino)-2-(phenylamino)benzoate. ES/MS m/z: 334.323 (M+H+).

Methyl 2-(chloromethyl)-4-fluoro-1-(2-methoxy-ethyl)-5-(phenylamino)-1H-benzo[d]imidazole-6-carboxylate (I-6)

To a solution of methyl 4-amino-3-fluoro-5-((2-methoxyethyl)amino)-2-(phenylamino)benzoate (121 mg, 0.363 mmol) in acetonitrile (2.5 mL) was added 2-chloro-1,1,1-trimthoxy-ethane (0.07 mL, 0.52 mmol) and p-toluenesulfonic acid, monohydrate (7 mg, 0.04 mmol). The mixture was heated to 50° C. for 2 hours and then cooled to room temperature. The resulting solution was diluted with EtOAc and washed with $H_2O$ and brine. The aqueous layers were back-extracted with EtOAc and the combined organic layers were dried over magnesium sulfate and concentrated to dryness. The crude material was then purified by $SiO_2$ column chromatography (eluent:EtOAc/hexanes) to provide methyl 2-(chloromethyl)-4-fluoro-1-(2-methoxyethyl)-5-(phenylamino)-1H-benzo[d]imidazole-6-carboxylate (I-6. ES/MS m/z: 392.225 (M+H+).

Intermediate I-7

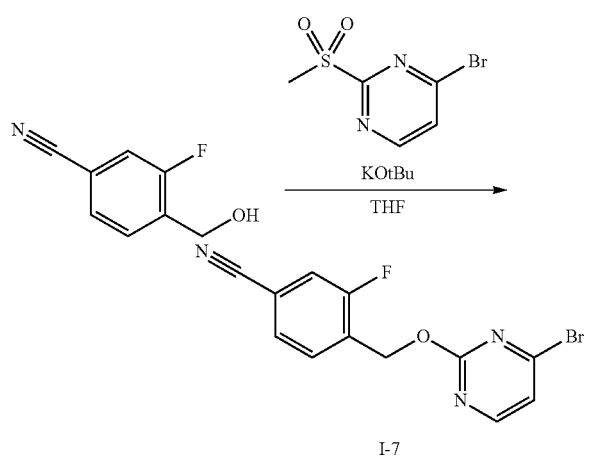

4-(((4-Bromopyrimidin-2-yl)oxy)methyl)-3-fluorobenzonitrile (I-7)

3-Fluoro-4-(hydroxymethyl)benzonitrile (7.01 g, 46.4 mmol) was taken up in THF (120 mL). This solution was cooled to 0° C. and potassium tert-butoxide (1.0 M in THF, 42.2 mL, 42.2 mmol) was added slowly dropwise. The mixture was stirred at 0° C. for 15 min. The solution of deprotonated alcohol was added slowly to a suspension of 4-bromo-2-methylsulfonyl-pyrimidine (10.0 g, 42.2 mol) in THF (120 mL) cooled to −78° C. The reaction was stirred −78° C. for 2 hours and, following this time, the reaction was quenched by addition of water (20 mL), allowed to warm to room temperature, and partitioned between EtOAc (200 mL) and saturated aqueous $NH_4Cl$ (200 mL). The organic phase was collected and the aqueous phase extracted with EtOAc (1×200 mL). The combined organics were dried over $MgSO_4$, concentrated in vacuo, and purified by normal phase column chromatography (eluent: EtOAc/hexanes gradient) to afford the product as a solid.

ES/MS: 309.2 (M+H$^+$).

Intermediate I-8

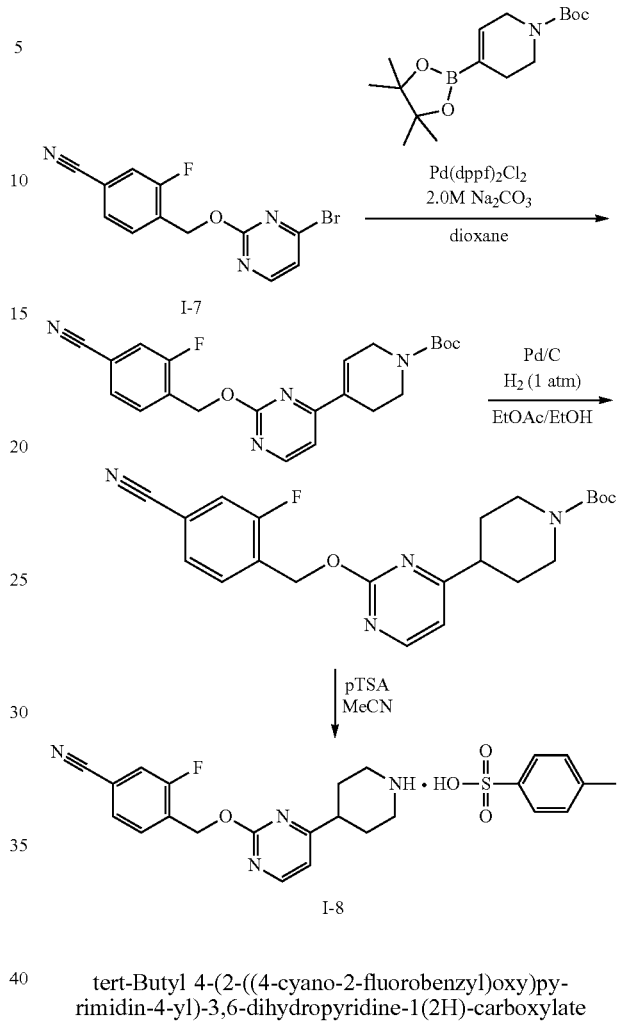

tert-Butyl 4-(2-((4-cyano-2-fluorobenzyl)oxy)pyrimidin-4-yl)-3,6-dihydropyridine-1(2H)-carboxylate tert-Butyl 4-(4,4,5,5-tetramethyl-1,3,2-dioxaborolan-2-yl)-3,6-dihydropyridine-1(2H)-carboxylate (3.0 g, 9.9 mmol), I-7 (3.04 g, 9.9 mmol), and $Pd(dppf)_2Cl_2$ (690 mg, 0.99 mmol) were taken up in dioxane (20 mL) and aqueous $Na_2CO_3$ (2.0 M, 9.9 mL, 20 mmol) was added. The mixture was sparged with argon for 10 minutes then heated to 90° C. for 4 hours. Following this time, the mixture was filtered through Celite and concentrated in vacuo. The resulting residue was loaded onto $SiO_2$ and purified by normal phase column chromatography (eluent: EOAc/hexanes gradient) to afford the desired product as an oil. ES/MS: 411.2 (M+H$^+$).

tert-Butyl 4-(2-((4-cyano-2-fluorobenzyl)oxy)pyrimidin-4-yl)piperidine-1-carboxylate tert-Butyl 4-(2-((4-cyano-2-fluorobenzyl)oxy)pyrimidin-4-yl)-3,6-dihydropyridine-1(2H)-carboxylate (1.5 g, 3.6 mmol) was taken up in ethanol (7.5 mL) and EtOAc (7.5 mL) and the mixture was sparged with nitrogen for 5 minutes. Pd/C (10% loading, 380 mg) was then added and sparging continued for 5 minutes. $H_2$ was then bubbled through the mixture for 2 minutes and then the reaction was set up under balloon $H_2$ atmosphere. After 1.5 hours the mixture was heated to 45° C. and stirred for an additional 1.5 hours. Upon reaction completion, the mixture was filtered through Celite and the filter washed with EtOAc (3×20 mL).

The resulting solution was concentrated to dryness then loaded directly onto SiO$_2$ for purification by column chromatography (eluent: EtOAc/hexanes gradient) to afford the desired product. ES/MS: 413.2 (M+H$^+$).

3-fluoro-4-(((4-(piperidin-4-yl)pyrimidin-2-yl)oxy) methyl)benzonitrile•p-toluenesulfonic acid salt (I-8)

tert-Butyl 4-(2-((4-cyano-2-fluorobenzyl)oxy)pyrimidin-4-yl)piperidine-1-carboxylate (414 mg, 1.00 mmol) was taken up in EtOAc (4.0 mL) and p-toluenesulfonic acid monohydrate (518 mg, 3.01 mmol) was added. The mixture was heated to 60° C. for 2 hours. Following reaction completion, the mixture was cooled to room temperature and filtered. The resulting solid was washed with EtOAc (2×10 mL) and then dried under high vacuum to yield to desired product as the p-toluenesulfonic acid salt. ES/MS: 313.2 (M+H$^+$).

Intermediate I-9

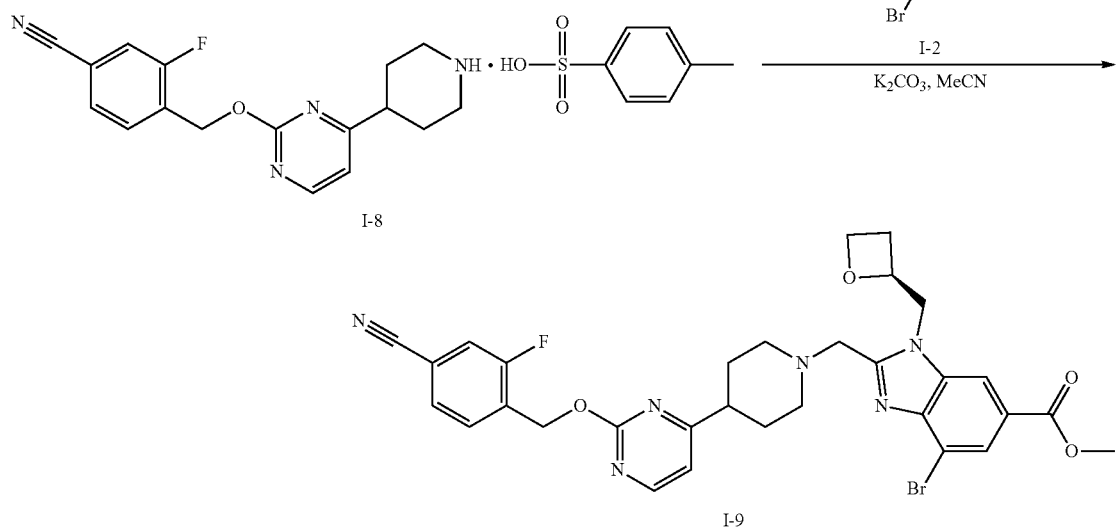

I-8

Methyl (S)-4-bromo-2-((4-(2-((4-cyano-2-fluorobenzyl)oxy)pyrimidin-4-yl)piperidin-1-yl)methyl)-1-(oxetan-2-ylmethyl)-1H-benzo[d]imidazole-6-carboxylate (I-9)

I-8 (300 mg, 0.62 mmol), I-2 (300 mg, 0.80 mmol), and K$_2$CO$_3$ (428 mg, 3.10 mmol) were combined in acetonitrile (4.0 mL) and the reaction was heated to 60° C. for 9 hours. Following this time, the mixture was filtered to remove K$_2$CO$_3$ and the filter washed with EtOAc (2×10 mL). The resulting solution was concentrated in vacuo and purified by normal phase column chromatography (eluent: EtOAc/hexanes gradient) to provide the desired product as a solid. ES/MS: 650.0 (M+H$^+$).

Intermediate I-10

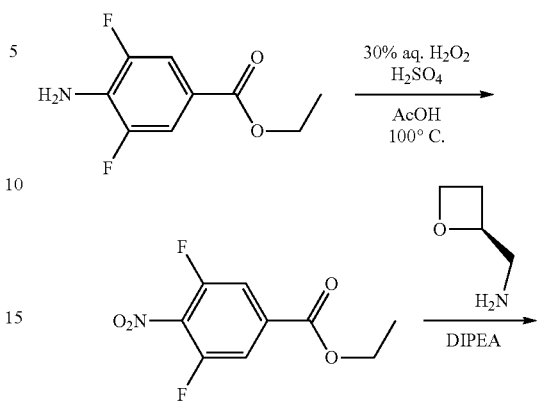

-continued

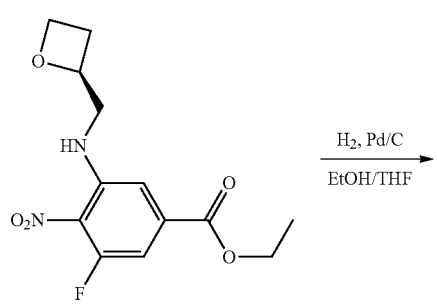

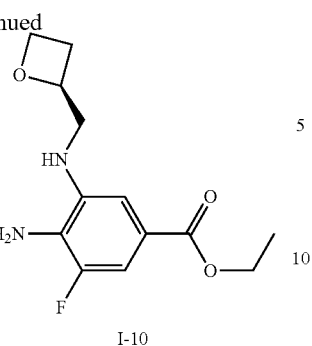

I-10

Ethyl 3,5-difluoro-4-nitrobenzoate

Ethyl 4-amino-3,5-difluorobenzoate (5.00 g, 24.9 mmol) was taken up in acetic acid (50.0 mL) and sulfuric acid (12.1 M, 2.05 mL, 24.9 mmol) and hydrogen peroxide (30% aqueous solution, 46.7 mL, 74.6 mmol) were added sequentially. The mixture was heated to 100° C. for 1 hour. The mixture was then cooled to room temperature and then slowly poured into 300 mL of ice water while swirling. The mixture was then diluted with EtOAc (200 mL), transferred to a separatory funnel, and the organic phase collected. The aqueous phase was extracted with EtOAc (2×100 mL) and the combined organics were dried over MgSO$_4$ and concentrated in vacuo. The residue was purified by column chromatography (eluent: EtOAc/Hexanes gradient) to afford the product.

Ethyl (S)-3-fluoro-4-nitro-5-((oxetan-2-ylmethyl)amino)benzoate

Ethyl 3,5-difluoro-4-nitrobenzoate (2.50 g, 10.8 mmol) and (S)-oxetan-2-ylmethanamine (989 mg, 11.4 mol) were taken up in tetrahydrofuran (12.0 mL) and N,N-dimethylformamide (6.0 mL), and N,N-diisopropylethylamine (9.42 mL, 54.1 mmol) was added. The mixture was heated to 50° C. for 16 hours. Following this time, the mixture was concentrated in vacuo and the residue purified by column chromatography (eluent: 0-25% EtOAc/Hexanes) to afford the product. ES/MS: 299.2 (M+H$^+$).

Ethyl (S)-4-amino-3-fluoro-5-((oxetan-2-ylmethyl)amino)benzoate (1-10)

Ethyl (S)-3-fluoro-4-nitro-5-((oxetan-2-ylmethyl)amino)benzoate (2.20 g, 7.38 mmol) was taken up in ethanol (10 mL) and tetrahydrofuran (5 mL) and the mixture sparged with nitrogen for 5 minutes. Palladium on carbon (10 wt. % loading, 785 mg, 0.74 mmol) was then added and sparging continued for 5 minutes. Hydrogen was then bubbled through the solution for one minute and then the mixture was set up under balloon hydrogen atmosphere for 21 hours. Following this time, the reaction was stopped and the mixture was filtered through Celite. The filter was washed with EtOAc (2×20 mL) and methanol (2×10 mL) and the filtrate concentrated in vacuo to afford ethyl (S)-4-amino-3-fluoro-5-((oxetan-2-ylmethyl)amino)benzoate (1-10). ES/MS: 269.2 (M+H$^+$); $^1$H NMR (400 MHz, chloroform) δ 7.44-7.30 (m, 2H), 5.13 (qd, J=7.1, 3.4 Hz, 1H), 4.72 (ddd, J=8.7, 7.4, 6.0 Hz, 1H), 4.62 (dt, J=9.1, 6.1 Hz, 1H), 4.33 (q, J=7.1 Hz, 2H), 3.58-3.30 (m, 2H), 2.76 (dtd, J=11.4, 8.0, 6.1 Hz, 1H), 2.56 (ddt, J=11.3, 9.0, 7.1 Hz, 1H), 1.37 (t, J=7.1 Hz, 3H).

Intermediate I-11

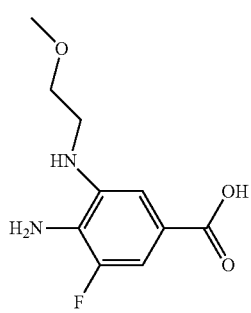 [SMILES: COCCNc1cc(C(=O)O)cc(F)c1N]

4-amino-3-fluoro-5-(2-methoxyethylamino)benzoic acid (I-11)

To a solution of 3,5-difluoro-4-nitro-benzoic acid (1 g, 4.9 mmol) and N-ethyldiisopropylamine (2.14 mL, 12.3 mmol) in 10 mL of THF, 2-Methoxyethylamine (0.43 mL, 4.9 mmol) was added dropwise to the mixture. The mixture was heated to 55° C. overnight. The solvent was removed and 10 mL of water was added to the mixture. The suspension was stirred for 1 hour and filtered. The crude solid was dissolved in 10 mL of EtOAc and 10 mL of ethanol. 300 mg of 10 wt. % palladium on activated carbon suspension in 10 mL of EtOAc and 10 mL of ethanol was added to the mixture. The reaction was charged with hydrogen balloon and stirred for 3 hours. The reaction was bubbled with nitrogen air for 10 minutes and filtered. The filtrated was concentrated, and sed without further purification. ES/MS: 229.1 (M+H$^+$).

Intermediate I-12

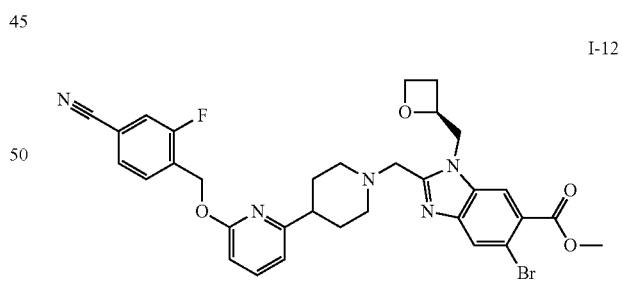

Methyl (S)-5-bromo-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylate (I-12)

The title compound was prepared according to the general procedure described for Intermediates I-1 to I-3 substituting methyl 3-bromo-5-fluoro-4-nitrobenzoate with methyl 2-bromo-5-fluoro-4-nitrobenzoate: ES/MS: 650.0 (M+H+).

Intermediate I-13

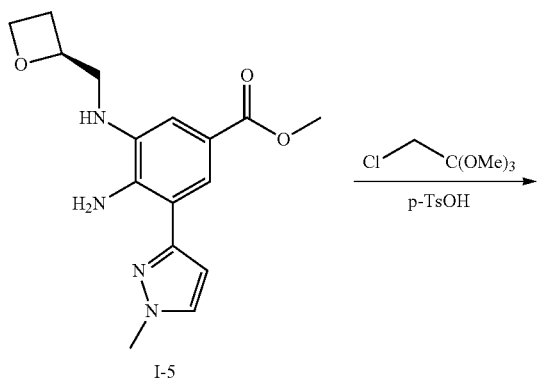

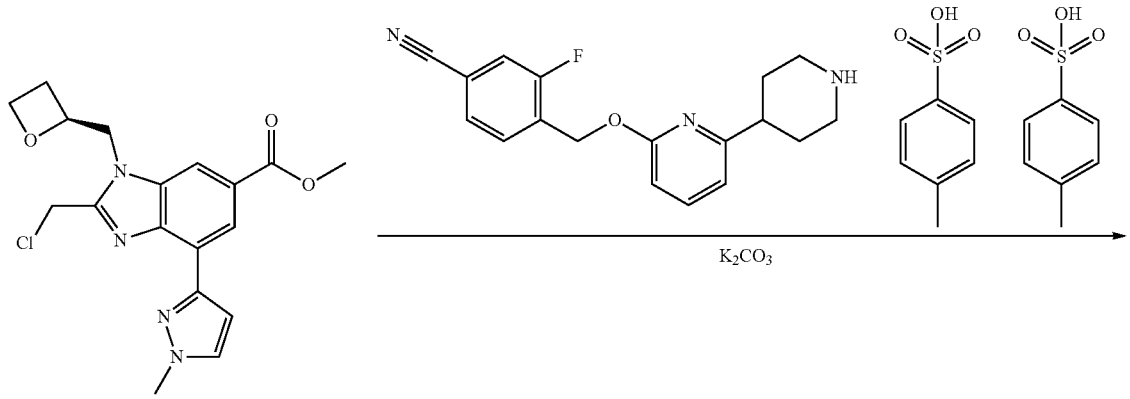

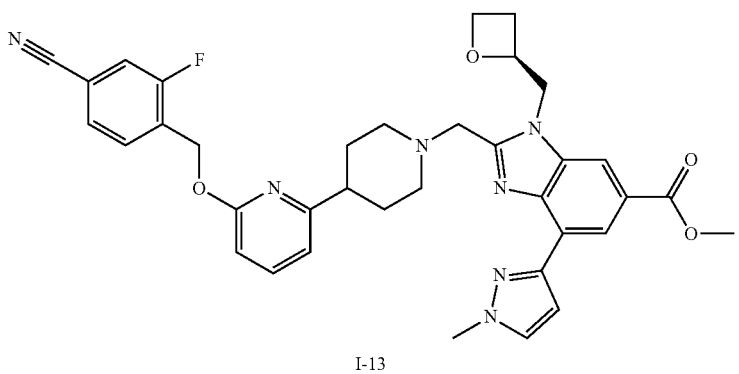

Methyl 2-[[4-[6-[(4-cyano-2-fluoro-phenyl)methoxy]-2-pyridyl]-1-piperidyl]methyl]-7-(1-methylpyrazol-3-yl)-3-[[(2 S)-oxetan-2-yl]methyl]benzimidazole-5-carboxylate (I-13)

To a solution of methyl 4-amino-3-(1-methylpyrazol-3-yl)-5-[[(2S)-oxetan-2-yl]methylamino]benzoate (42.0 mg, 0.13 mmol) in acetonitrile (6 mL) was added 2-chloro-1,1,1-trimethoxyethane (0.02 mL, 0.02 mmol) followed by p-Toluenesulfonic Acid, monohydrate (1.14 mg, 6.64e-3 mmol). The solution was heated to 60° C. for 2.5 h, then cooled to rt. To the rt solution was added 3-fluoro-4-[[6-(4-piperidyl)-2-pyridyl]oxymethyl]benzonitrile; 4-methylbenzenesulfonic acid (87.0 mg, 0.13 mmol) and potassium carbonate (91.7 mg, 0.66 mmol). The solution was stirred overnight at rt. The following day the solution was partitioned between EtOAc, and H$_2$O. The aqueous layer was extracted twice with EtOAc, washed with brine, dried over MgSO4, filtered, and concentrated in vacuo. The crude material was purified by SiO$_2$ column chromatography with a gradient of 30-100% EtOAc/Hexanes to give methyl 2-[[4-[6-[(4-cyano-2-fluoro-phenyl)methoxy]-2-pyridyl]-1-piperidyl]methyl]-7-(1-methylpyrazol-3-yl)-3-[[(2S)-oxetan-2-yl]methyl]benzimidazole-5-carboxylate (I-13). ES/MS m/z. 650.2 (M+H+).

Intermediate I-14

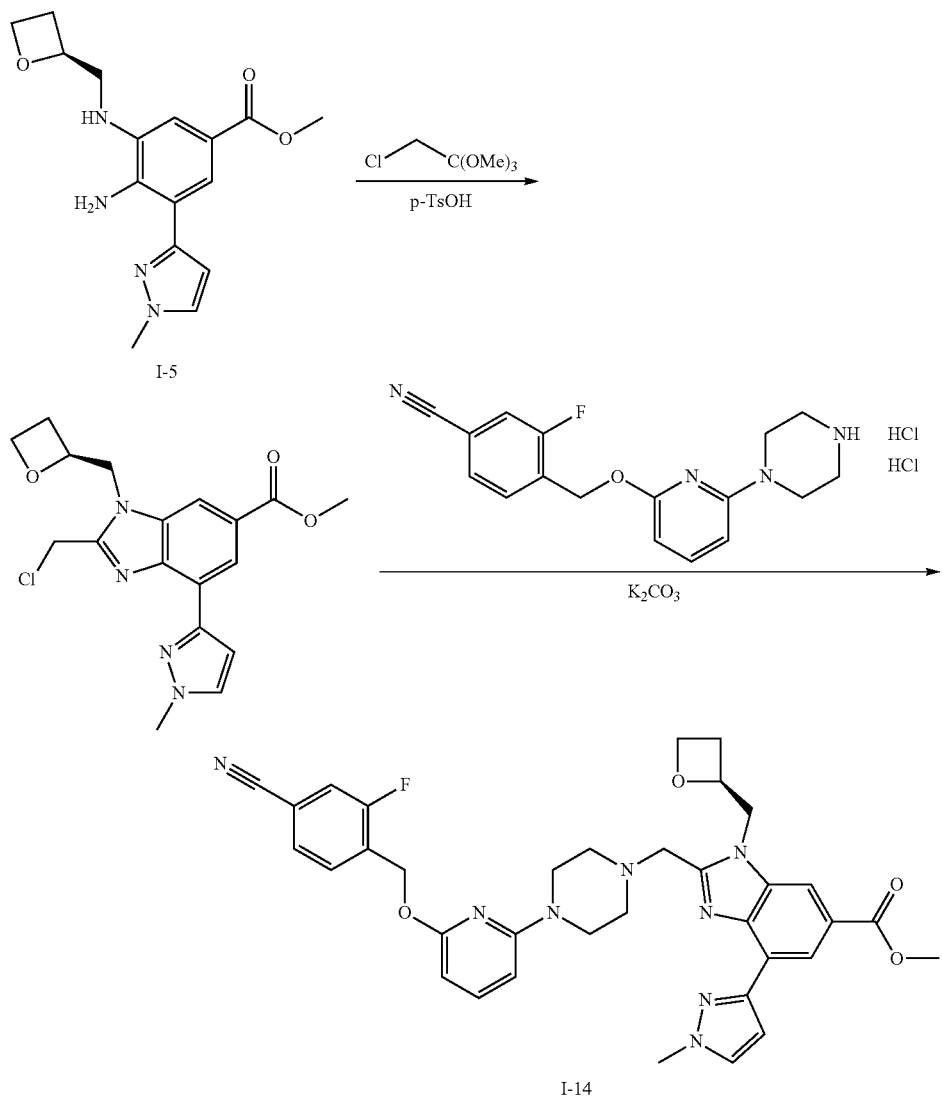

Methyl 2-[[4-[6-[(4-cyano-2-fluoro-phenyl)methoxy]-2-pyridyl]piperazin-1-yl]methyl]-7-(1-methylpyrazol-3-yl)-3-[[(2S)-oxetan-2-yl]methyl]benzimidazole-5-carboxylate (I-14)

To a solution of methyl 4-amino-3-(1-methylpyrazol-3-yl)-5-[[(2S)-oxetan-2-yl]methylamino]benzoate (42.0 mg, 0.13 mmol) in acetonitrile (6 mL) was added 2-chloro-1,1,1-trimethoxyethane (0.02 mL, 0.02 mmol) followed by p-toluenesulfonic Acid, monohydrate (1.14 mg, 6.64e$^{-3}$ mmol). The solution was heated to 60° C. for 2.5 h, then cooled to rt. To the rt solution was added 3-fluoro-4-[(6-piperazin-1-yl-2-pyridyl)oxymethyl]benzonitrile; dihydrochloride (51.1 mg, 0.13 mmol) and potassium carbonate (91.7 mg, 0.66 mmol). The solution was stirred overnight at rt. The following day the solution was partitioned between EtOAc, and H$_2$O. The aqueous layer was extracted twice with EtOAc, washed with brine, dried over MgSO$_4$, filtered, and concentrated in vacuo. The crude material was purified by SiO$_2$ column chromatography with a gradient of 30-100% EtOAc/Hexanes to give methyl 2-[[4-[6-[(4-cyano-2-fluoro-phenyl)methoxy]-2-pyridyl]piperazin-1-yl]methyl]-7-(1-methylpyrazol-3-yl)-3-[[(2S)-oxetan-2-yl]methyl]benzimidazole-5-carboxylate (I-14). ES/MS m/z: 651.2 (M+H+).

Intermediate I-15

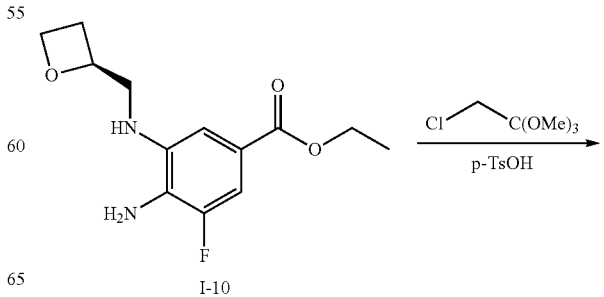

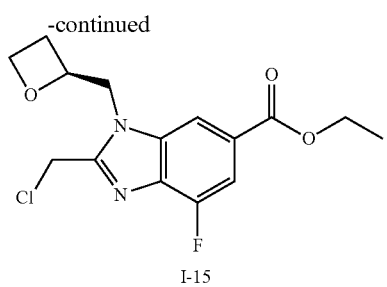

I-15 ethyl 2-(chloromethyl)-7-fluoro-3-[[(2S)-oxetan-2-yl]methyl]benzimidazole-5-carboxylate (I-15)

To a solution of ethyl 4-amino-3-fluoro-5-[[(2S)-oxetan-2-yl]methylamino]benzoate (500 mg, 1.86 mmol) in acetonitrile (20 mL) was added 2-chloro-1,1,1-trimethoxyethane (0.255 mL, 2.42 mmol) and p-toluenesulfonic Acid, monohydrate (16.0 mg, 0.09 mmol). The solution was heated to 60° C. for 3 h before cooling to rt. The solution was then partitioned between EtOAc and water, extracting the aqueous twice with EtOAc, washing with brine, drying over $MgSO_4$, filter, and concentrate. Purification by $SiO_2$ column chromatography using a gradient of 30-100% EtOAc gave ethyl 2-(chloromethyl)-7-fluoro-3-[[(2S)-oxetan-2-yl]methyl]benzimidazole-5-carboxylate (I-15). ES/MS m/z: 327.2 (M+H+).

Intermediate I-16

[Reaction scheme]

I-16

2-benzyloxy-6-bromo-3-fluoro-pyridine (I-16)

To a solution of 6-bromo-2-chloro-3-fluoro-pyridine (3.0 g, 14.3 mmol) and benzyl alcohol (1.59 g, 14.7 mmol) in acetonitrile (20 mL) was added cesium carbonate (9.29 g, 28.5 mmol). The mixture was stirred at 60° C. overnight before being cooled to rt. The reaction was diluted with water, extracted three times with EtOAc, washed with brine, dried over sodium sulfate, filtered, and concentrated. Purification by $SiO_2$ column chromatography using 50-100% EtOAc/Hexanes yielded 2-benzyloxy-6-bromo-3-fluoro-pyridine (I-16). ES/MS m/z: 280.00 and 282.0 (M−H)⁻.

Intermediate I-17

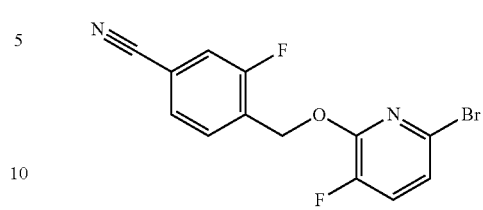

I-17

I-17 was prepared in an identical manner as described for I-16 substituting benzyl alcohol with 3-fluoro-4-(hydroxymethyl)benzonitrile.

Intermediate I-18

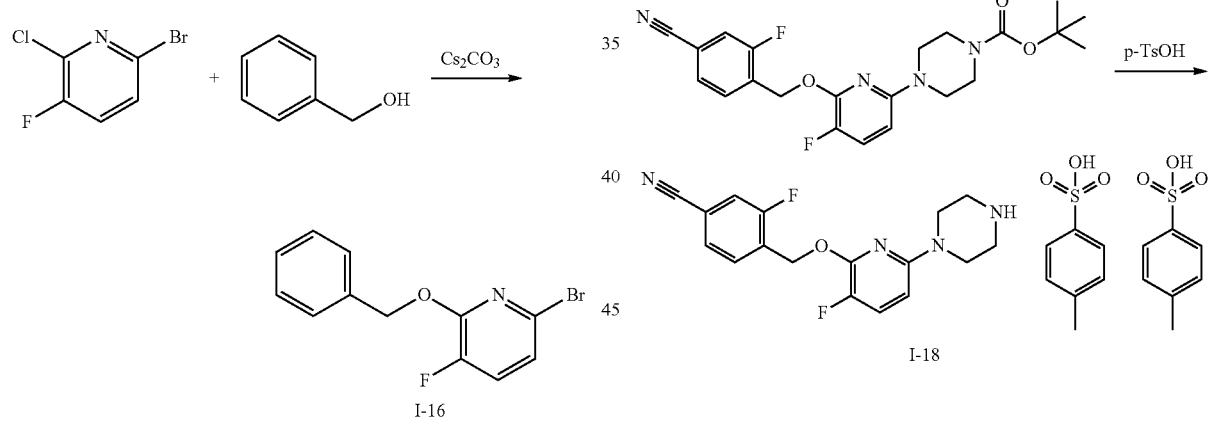

I-18 tert-butyl 4-[6-[(4-cyano-2-fluoro-phenyl)methoxy]-5-fluoro-2-pyridyl]piperazine-1-carboxylate To a solution of 4-[(6-bromo-3-fluoro-2-pyridyl)oxymethyl]-3-fluoro-benzonitrile (I-17, 500 mg, 1.54 mmol), tert-butyl piperazine-1-carboxylate (315 mg, 1.69 mmol), cesium carbonate (1.00 g, 3.08 mmol), and 2,2'-Bis(diphenylphosphino)-1,1'-binaphthalene (95.8 mg, 0.15 mmol), tris(dibenzylideneacetone)dipalladium(0) (94.4 mg, 0.10 mmol) was added in 8 mL of toluene. The mixture had argon bubbled through for 5 minutes followed by heating to 120° C. overnight. The following day, the mixture was diluted with EtOAc, filtered, concentrated, and purified by $SiO_2$ column chromatography using a gradient of 20-80% EtOAc/Hex to give tert-butyl 4-[6-[(4-cyano-2-fluoro-phenyl)methoxy]-5-fluoro-2-pyridyl]piperazine-1-carboxylate. ES/MS m/z: 431.2 (M+H+).

3-fluoro-4-[(3-fluoro-6-piperazin-1-yl-2-pyridyl)oxymethyl]benzonitrile; 4-methylbenzenesulfonic acid (I-18)

To a solution of tert-butyl 4-[6-[(4-cyano-2-fluoro-phenyl)methoxy]-5-fluoro-2-pyridyl]piperazine-1-carboxylate (374 mg, 0.869 mmol) in =EtOAc (5 mL) was added p-toluenesulfonic acid monohydrate (538 mg, 2.83 mmol). The solution was heated for 2 h at 60° C. before cooling to rt. Concentrating to dryness provided 3-fluoro-4-[(3-fluoro-6-piperazin-1-yl-2-pyridyl)oxymethyl]benzonitrile; 4-methylbenzenesulfonic acid (I-18). ES/MS m/z: 331.2 (M+H+). Intermediate I-19

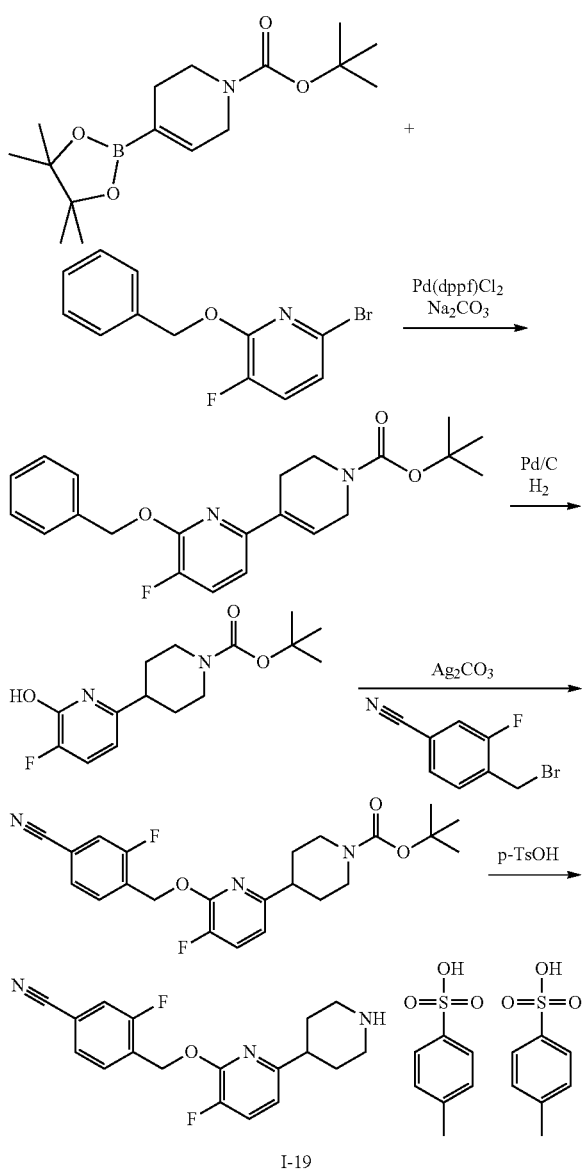

I-19 tert-butyl 4-(6-benzyloxy-5-fluoro-2-pyridyl)-3,6-dihydro-2H-pyridine-1-carboxylate (1-19)

To a solution of tert-butyl 4-(4,4,5,5-tetramethyl-1,3,2-dioxaborolan-2-yl)-3,6-dihydro-2H-pyridine-1-carboxylate (950 mg, 3.10 mmmol), 2-benzyloxy-6-bromo-3-fluoro-pyridine (1-16, 867 mg, 3.10 mmol), and (1,1'-Bis(diphenylphosphino)ferrocene)dichloropalladium(II) (215 mg, 0.31 mmol) in 1,4-dioxane was added sodium carbonate (3.1 mL, 6.1 mmol, 2 M). Argon was bubbled through the mixture for 5 minutes then it was heated to 110° C. for 1 h. The mixture was diluted in EtOAc, filtered, and concentrated. Purification by $SiO_2$ column chromatography usinga 0-50% EtOAc/Hex gradient gave of tert-butyl 4-(6-benzyloxy-5-fluoro-2-pyridyl)-3,6-dihydro-2H-pyridine-1-carboxylate. ES/MS m/z: 385.2 (M+H+).

tert-butyl 4-(5-fluoro-6-hydroxy-2-pyridyl)piperidine-1-carboxylate

To a solution of tert-butyl 4-(6-benzyloxy-5-fluoro-2-pyridyl)-3,6-dihydro-2H-pyridine-1-carboxylate (863 mg, 2.20 mmol) in EtOAc (7.5 mL) was added 10% Palladium on carbon (239 mg, 2.2 mmol). The mixture was vacuumed and backfilled with hydrogen gas before being left under an atmosphere of hydrogen to stir at rt for 3 h. The mixture was filtered through Celite, washed with EtOAc and concentrated to yield tert-butyl 4-(5-fluoro-6-hydroxy-2-pyridyl)piperidine-1-carboxylate. ES/MS m/z: 319.2 (M+Na+).

tert-butyl 4-[6-[(4-cyano-2-fluoro-phenyl)methoxy]-5-fluoro-2-pyridyl]piperidine-1-carboxylate To a solution of tert-butyl 4-(5-fluoro-6-hydroxy-2-pyridyl)piperidine-1-carboxylate (377 mg, 1.30 mmol) and 4-(bromomethyl)-3-fluoro-benzonitrile (297 mg, 1.4 mmol) in acetonitrile (11 mL) was added silver carbonate (690 mg, 2.5 mmol). The mixture was heated to 50° C. for 2 h before being cooled to rt, diluted with EtOAc, filtered, and concentrated to give tert-butyl 4-[6-[(4-cyano-2-fluoro-phenyl)methoxy]-5-fluoro-2-pyridyl]piperidine-1-carboxylate which was used without further purification. ES/MS m/z: 452.2 (M+Na+).

3-fluoro-4-[[3-fluoro-6-(4-piperidyl)-2-pyridyl]oxymethyl]benzonitrile; 4-methylbenzenesulfonic Acid To a solution of tert-butyl 4-[6-[(4-cyano-2-fluoro-phenyl)methoxy]-5-fluoro-2-pyridyl]piperidine-1-carboxylate (546 mg, 1.27 mmol) in EtOAc (5 mL) was added p-toluenesulfonic acid monohydrate (788 mg, 4.14 mmol). The solution was heated to 50° C. for 1 h before being concentrated to dryness to yield 3-fluoro-4-[[3-fluoro-6-(4-piperidyl)-2-pyridyl]oxymethyl]benzonitrile; 4-methylbenzenesulfonic acid (I-19) which was used without further purification. ES/MS m/z: 330.2 (M+H$^+$).
Intermediate I-20

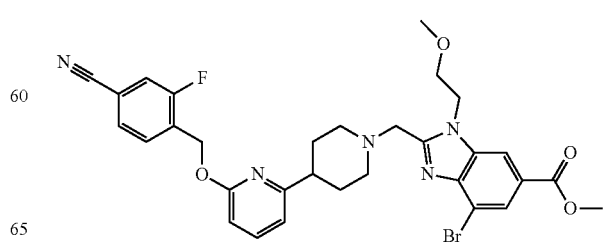

I-20

I-20 was prepared according to the general procedure described for Intermediates I-1 to I-3 substituting (S)-oxetan-2-ylmethanamine with 2-methoxyethylamine. ES/MS m/z: 637.3 (M+H+).

Intermediate I-21

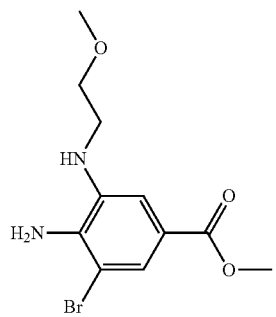

I-21

I-21 was prepared in an identical manner as described for I-2 substituting (S)-oxetan-2-ylmethanamine with 2-methoxyethylamine.

Intermediate I-22

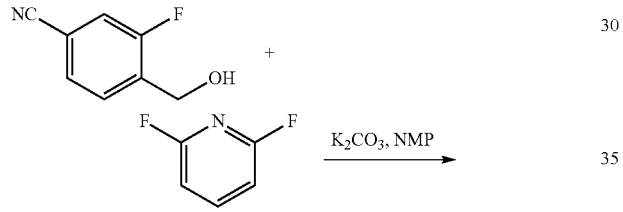

I-22

3-fluoro-4-[(6-fluoro-2-pyridyl)oxymethyl]benzonitrile (I-22)

A suspension of 2,6-difluoropyridine (0.39 ml, 4.34 mmol), 3-fluoro-4-(hydroxymethyl)benzonitrile (0.72 g, 4.78 mmol), and Potassium carbonate (1.8 g, 13.03 mmol) in NMP (10 mL) was heated at 100 deg overnight. The reaction was diluted with EtOAc and washed with 5% LiCi solution 3x. The organic extract was dried over sodium sulfate, concentrated and purified by silica gel column chromatography (eluent: EtOAc/hexanes) to afford the title product. ES/MS: 247.0 (M+H$^+$). $^1$H NMR (400 MHz, Chloroform-d) δ 7.73 (q, J=8.0 Hz, 1H), 7.67 (t, J=7.5 Hz, 1H), 7.50 (dd, J=7.9, 1.6 Hz, 1H), 7.41 (dd, J=9.3, 1.6 Hz, 1H), 6.73 (dd, J=8.0, 1.6 Hz, 1H), 6.56 (dd, J=7.8, 2.4 Hz, 1H), 5.48 (d, J=1.2 Hz, 2H). $^{19}$F NMR (376 MHz, Chloroform-d) 6-70.47 (d, J=8.7 Hz), −112.50-−117.78 (m).

B. Compound Examples

Example 1. 2-((4-(6-((4-cyano-2-fluorobenzyl)oxy)pyridin-2-yl)piperidin-1-yl)methyl)-4-fluoro-1-(2-methoxyethyl)-5-(phenylamino)-1H-benzo[d]imidazole-6-carboxylic acid Example 2. 2-((4-(6-((4-carbamoyl-2-fluorobenzyl)oxy)pyridin-2-yl)piperidin-1-yl)methyl)-4-fluoro-1-(2-methoxyethyl)-5-(phenylamino)-1H-benzo[d]imidazole-6-carboxylic Acid Procedure 1

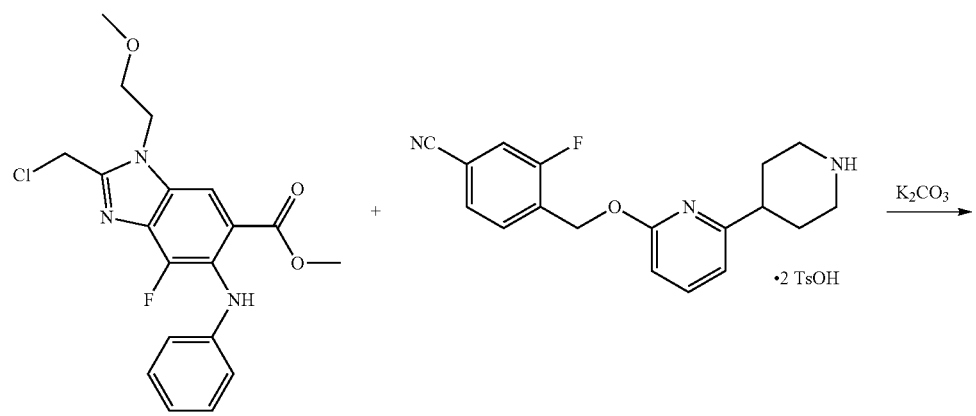

-continued

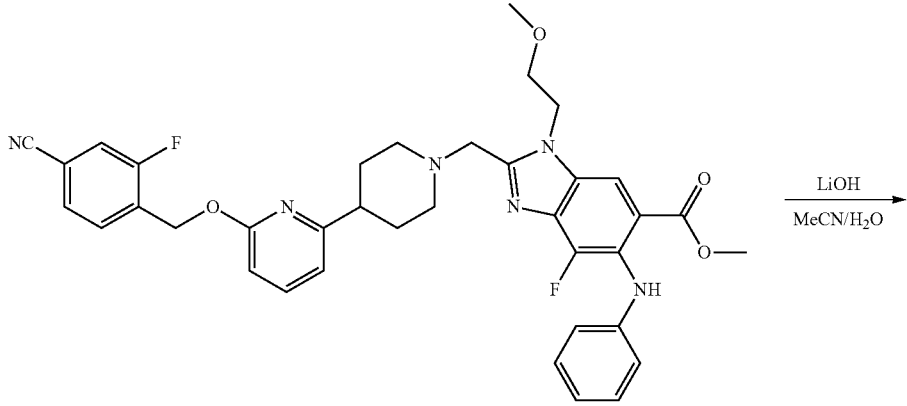

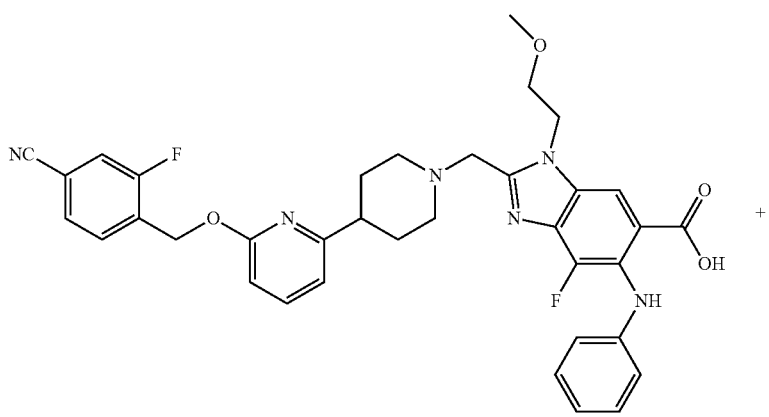

Example 1

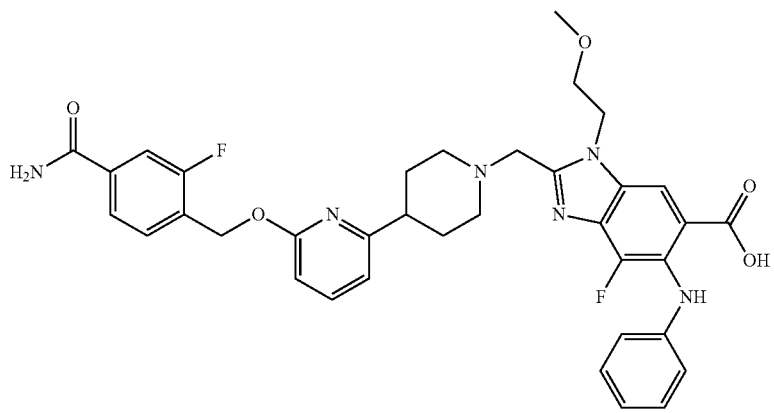

Example 2

Methyl 2-((4-(6-((4-cyano-2-fluorobenzyl)oxy)pyridin-2-yl)piperidin-1-yl)methyl)-4-fluoro-1-(2-methoxyethyl)-5-(phenylamino)-1H-benzo[d]imidazole-6-carboxylate To a solution of methyl 2-(chloromethyl)-4-fluoro-1-(2-methoxyethyl)-5-(phenylamino)-1H-benzo[d]imidazole-6-carboxylate (I-6) (47 mg, 0.121 mmol) in acetonitrile (2 mL) was added 3-fluoro-4-(((6-(piperidin-4-yl)pyridin-2-yl)oxy)methyl)benzonitrile bis 4-methylbenzenesulfonic acid (95 mg, 0.15 mmol) and potassium carbonate (59 mg, 0.43 mmol). The resulting slurry was heated to 50° C. for 2 h. The mixture was diluted with EtOAc and washed with $H_2O$ and brine. The aqueous layers were back-extracted with EtOAc and the combine organic layers were dried over magnesium sulfate and concentrated to dryness. The crude material was then purified by $SiO_2$ column chromatography (eluent: EtOAc/hexanes) to provide methyl 2-((4-(6-((4-cyano-2-fluorobenzyl)oxy)pyridin-2-yl)piperidin-1-yl)methyl)-4-fluoro-1-(2-methoxyethyl)-5-(phenylamino)-1H-benzo[d]imidazole-6-carboxylate. ES/MS m/z: 667.587 (M+H+).

2-((4-(6-((4-cyano-2-fluorobenzyl)oxy)pyridin-2-yl)piperidin-1-yl)methyl)-4-fluoro-1-(2-methoxyethyl)-5-(phenylamino)-1H-benzo[d]imidazole-6-carboxylic Acid. (Example 1) and 2-((4-(6-((4-carbamoyl-2-fluorobenzyl)oxy)pyridin-2-yl)piperidin-1-yl)methyl)-4-fluoro-1-(2-methoxyethyl)-5-(phenylamino)-1H-benzo[d]imidazole-6-carboxylic Acid (Example 2)

To a solution of methyl 2-((4-(6-((4-cyano-2-fluorobenzyl)oxy)pyridin-2-yl)piperidin-1-yl)methyl)-4-fluoro-1-(2-methoxyethyl)-5-(phenylamino)-1H-benzo[d]imidazole-6-carboxylate (49 mg, 0.074 mmol) in a mixture of acetonitrile (1.5 mL) and water (0.25 mL) was added lithium hydroxide (1M aqueous, 0.23 mL. 0.23 mmol). The reaction vessel was sealed and then heated to 100° C. for 3 min. The mixture was then rapidly cooled and the resulting solution was diluted with MeCN and DMF and neutralized with TFA. Purification via reverse phase HPLC (eluent:MeCN/H$_2$O/0.1% TFA), followed by lyophilization, provided 2-((4-(6-((4-cyano-2-fluorobenzyl)oxy)pyridin-2-yl)piperidin-1-yl)methyl)-4-fluoro-1-(2-methoxyethyl)-5-(phenylamino)-1H-benzo[d]imidazole-6-carboxylic acid (Example 1) as a trifluoroacetate salt and 2-((4-(6-((4-carbamoyl-2-fluorobenzyl)oxy)pyridin-2-yl)piperidin-1-yl)methyl)-4-fluoro-1-(2-methoxyethyl)-5-(phenylamino)-1H-benzo[d]imidazole-6-carboxylic acid (Example 2) as a trifluoroacetate salt.

Example 1. ES/MS m/z: 653.427 (M+H$^+$); 1H NMR (400 MHz, MeOD) δ 8.22 (s, 1H), 7.76-7.67 (m, 2H), 7.65-7.56 (m, 2H), 7.26-7.18 (m, 2H), 6.98 (d, J=7.3 Hz, 1H), 6.93-6.87 (m, 1H), 6.87-6.83 (m, 2H), 6.81 (d, J=8.2 Hz, 1H), 5.58 (s, 2H), 4.84 (s, 2H), 4.62 (t, J=4.8 Hz, 2H), 3.94 (s, 2H), 3.78 (t, J=4.7 Hz, 2H), 3.44 (s, 2H), 3.36 (s, 3H), 3.09 (s, 1H), 2.26 (d, J=18.3 Hz, 4H).

Example 2. ES/MS m/z: 671.209 (M+H$^+$); 1H NMR (400 MHz, MeOD) δ 8.16 (s, 1H), 7.64 (t, J=8.5 Hz, 2H), 7.56 (dd, J=14.4, 6.5 Hz, 2H), 7.16 (t, J=7.8 Hz, 2H), 6.90 (d, J=7.4 Hz, 1H), 6.87-6.76 (m, 3H), 6.74 (d, J=8.3 Hz, 1H), 5.50 (s, 2H), 4.76 (s, 2H), 4.56 (s, 2H), 3.87 (s, 2H), 3.72 (s, 2H), 3.42-3.34 (m, 2H), 3.30 (d, J=2.5 Hz, 3H), 3.03 (s, 1H), 2.19 (s, 4H).

Example 3. 2-((4-(6-((4-cyano-2-fluorobenzyl)oxy)pyridin-2-yl)piperazin-1-yl)methyl)-4-fluoro-1-(2-methoxyethyl)-5-(phenylamino)-1H-benzo[d]imidazole-6-carboxylic acid Procedure 2

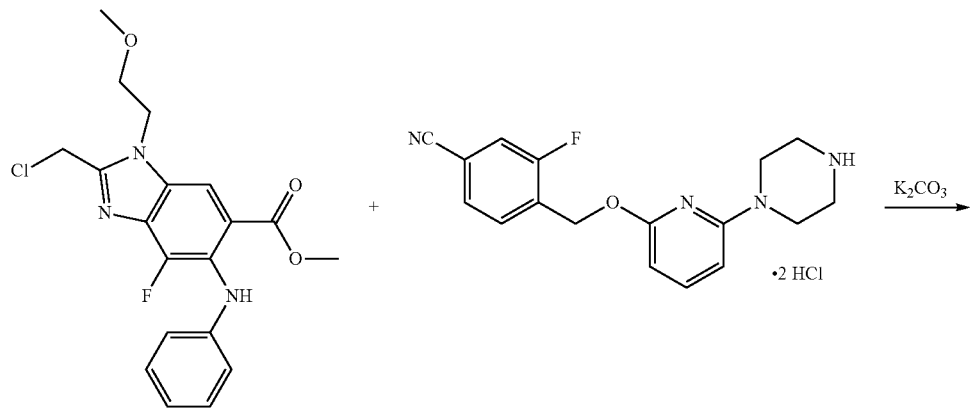

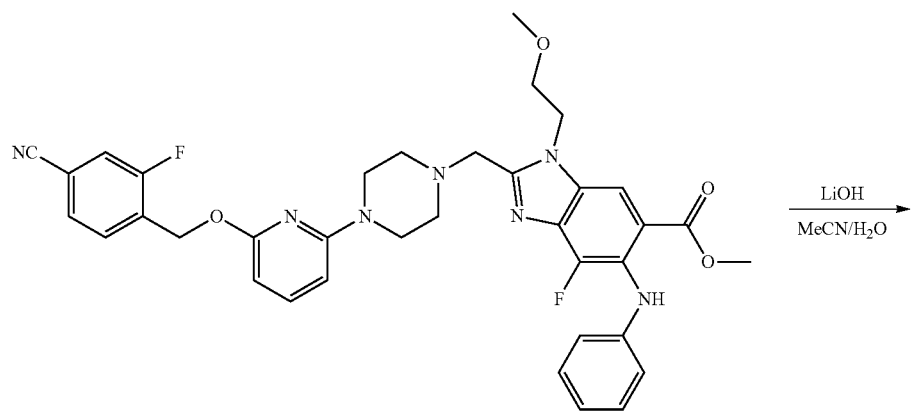

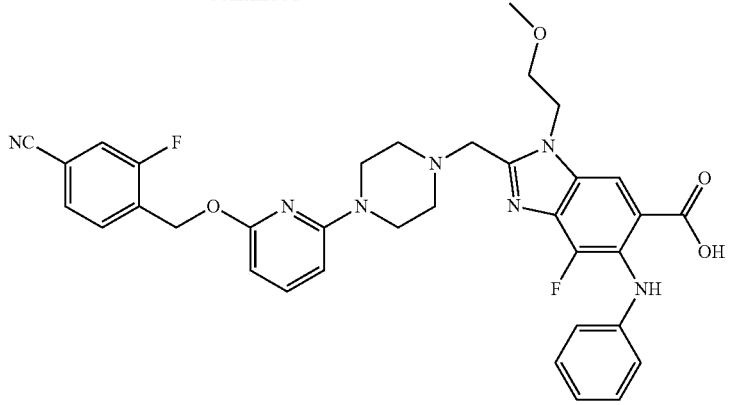

Example 3

Methyl 2-((4-(6-((4-cyano-2-fluorobenzyl)oxy)pyridin-2-yl)piperazin-1-yl)methyl)-4-fluoro-1-(2-methoxyethyl)-5-(phenylamino)-1H-benzo[d]imidazole-6-carboxylate To a solution of methyl 2-(chloromethyl)-4-fluoro-1-(2-methoxyethyl)-5-(phenylamino)-1H-benzo[d]imidazole-6-carboxylate (I-6) (47 mg, 0.121 mmol) in acetonitrile (2 mL) was added 3-fluoro-4-(((6-(piperazin-1-yl)pyridin-2-yl)oxy)methyl)benzonitrile bis hydrochloric acid (56 mg, 0.15 mmol) and potassium carbonate (59 mg, 0.43 mmol). The resulting slurry was heated to 50° C. for 18 h. The mixture was diluted with EtOAc and washed with H₂O and brine. The aqueous layers were back-extracted with EtOAc and the combine organic layers were dried over magnesium sulfate and concentrated to dryness. The crude material was then purified by SiO₂ column chromatography (eluent:EtOAc/hexanes) to provide methyl 2-((4-(6-((4-cyano-2-fluorobenzyl)oxy)pyridin-2-yl)piperazin-1-yl)methyl)-4-fluoro-1-(2-methoxyethyl)-5-(phenylamino)-1H-benzo[d]imidazole-6-carboxylate. ES/MS m/z: 668.2 (M+H+).

2-((4-(6-((4-cyano-2-fluorobenzyl)oxy)pyridin-2-yl)piperazin-1-yl)methyl)-4-fluoro-1-(2-methoxyethyl)-5-(phenylamino)-1H-benzo[d]imidazole-6-carboxylic acid (Example 3)

To a solution of methyl 2-((4-(6-((4-cyano-2-fluorobenzyl)oxy)pyridin-2-yl)piperazin-1-yl)methyl)-4-fluoro-1-(2-methoxyethyl)-5-(phenylamino)-1H-benzo[d]imidazole-6-carboxylate (51 mg, 0.081 mmol) in a mixture of acetonitrile (1.5 mL) and water (0.25 mL) was added lithium hydroxide (1M aqueous, 0.20 mL. 0.20 mmol). The reaction vessel was sealed and then heated to 80° C. for 3 min. The mixture was then rapidly cooled and the resulting solution was diluted with MeCN and DMF and neutralized with TFA. Purification via reverse phase HPLC (eluent:MeCN/H₂O/0.1% TFA), followed by lyophilization, provided 2-((4-(6-((4-cyano-2-fluorobenzyl)oxy)pyridin-2-yl)piperazin-1-yl)methyl)-4-fluoro-1-(2-methoxyethyl)-5-(phenylamino)-1H-benzo[d]imidazole-6-carboxylic acid (Example 3) as a trifluoroacetate salt. ES/MS m/z: 654.688 (M+H⁺); 1H NMR (400 MHz, MeOD) δ 8.22 (d, J=0.9 Hz, 1H), 7.68 (t, J=7.5 Hz, 1H), 7.63-7.54 (m, 3H), 7.27-7.17 (m, 2H), 6.90 (tt, J=7.4, 1.1 Hz, 1H), 6.85 (dq, J=8.5, 1.1 Hz, 2H), 6.46 (d, J=8.0 Hz, 1H), 6.31 (d, J=7.9 Hz, 1H), 5.49 (s, 2H), 4.76 (s, 2H), 4.61 (t, J=4.8 Hz, 2H), 3.85 (s, 4H), 3.80-3.73 (m, 2H), 3.52 (d, J=6.2 Hz, 4H), 3.34 (s, 3H).

Example 4. (S)-2-((4-(2-((4-cyano-2-fluorobenzyl)oxy)pyrimidin-4-yl)piperidin-1-yl)methyl)-4-(1-methyl-1H-pyrazol-3-yl)-1-(oxetan-2-ylmethyl)-1H-benzo[d]imidazole-6-carboxylic Acid Procedure 3

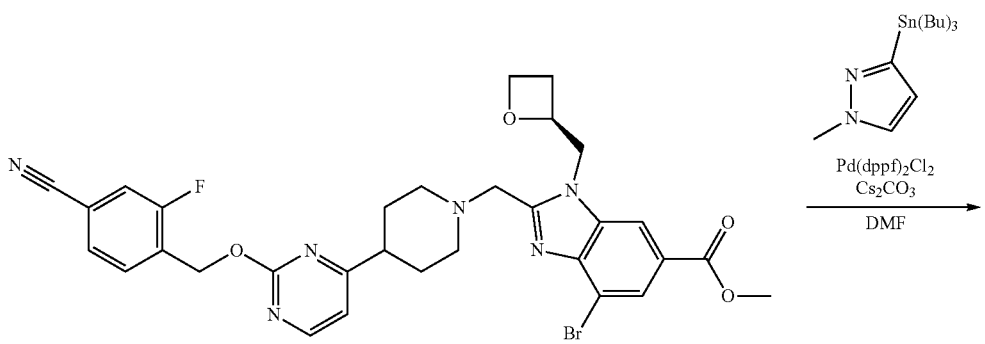

I-9

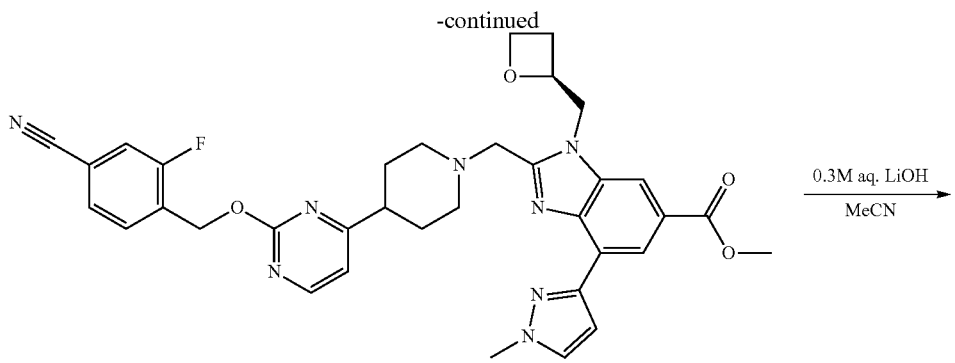

Methyl (S)-2-((4-(2-((4-cyano-2-fluorobenzyl)oxy)pyrimidin-4-yl)piperidin-1-yl)methyl)-4-(1-methyl-1H-pyrazol-3-yl)-1-(oxetan-2-ylmethyl)-1H-benzo[d]imidazole-6-carboxylate In a 5 mL microwave vial, I-9 (150 mg, 0.23 mmol), 1-methyl-3-(tributylstannyl)-1H-pyrazole (214 mg, 0.58 mmol), $Cs_2CO_3$ (226 mg, 0.69 mmol), and $Pd(dppf)_2Cl_2$ (17 mg, 0.023 mmol) were taken up in DMF (1.2 mL). The mixture was sparged with argon for 5 minutes and then the vial was sealed and heated to 110° C. for 20 minutes. Following this time, the reaction was complete by LC/MS analysis. The mixture was loaded directly onto $SiO_2$ for purification (normal phase column chromatography, eluent: EtOAc/hexanes gradient) which yielded the desired product. ES/MS: 651.2 (M+H+).

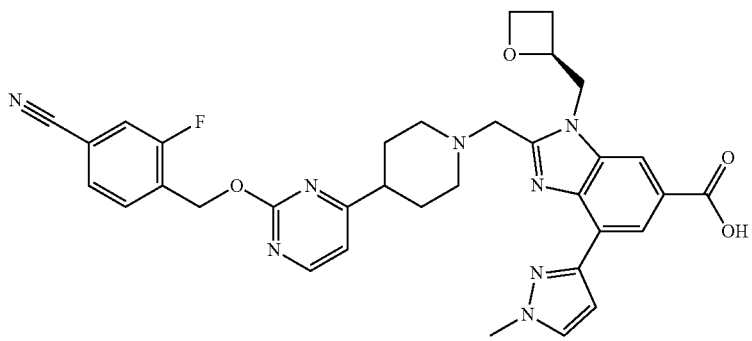

Example 4

(S)-2-((4-(2-((4-cyano-2-fluorobenzyl)oxy)pyrimidin-4-yl)piperidin-1-yl)methyl)-4-(1-methyl-1H-pyrazol-3-yl)-1-(oxetan-2-ylmethyl)-1H-benzo[d]imidazole-6-carboxylic Acid (Example 4)

Methyl (S)-2-((4-(2-((4-cyano-2-fluorobenzyl)oxy)pyrimidin-4-yl)piperidin-1-yl)methyl)-4-(1-methyl-1H-pyrazol-3-yl)-1-(oxetan-2-ylmethyl)-1H-benzo[d]imidazole-6-carboxylate (109 mg, 0.17 mmol) was taken up in acetonitrile (0.84 mL) and aqueous LiOH (0.3 M, 0.84 mL, 0.25 mmol) was added. The reaction was heated to 100° C. for 10 minutes. Following this time, the mixture was diluted with DMF (1.5 mL) and acetic acid (0.2 mL) and purified directly by RP-HPLC (eluent: MeCN/water gradient with 0.1% TFA). The product was afforded as the bis-trifluoroacetate salt following lyophilization of the isolated RP-HPLC fractions. ES/MS: 637.2 (M+H+). H NMR (400 MHz, MeOH-d4) δ 8.59-8.51 (m, 2H), 8.28 (d, J=1.5 Hz, 1H), 7.80-7.71 (m, 2H), 7.66-7.57 (m, 2H), 7.33 (d, J=2.3 Hz, 1H), 7.16 (d, J=5.1 Hz, 1H), 5.62 (s, 2H), 5.25 (qd, J=7.0, 2.4 Hz, 1H), 4.95 (s, 2H), 4.79 (dd, J=15.8, 6.7 Hz, 1H), 4.75-4.63 (m, 2H), 4.45 (dt, J=9.3, 5.9 Hz, 1H), 4.04 (s, 3H), 4.04-3.90 (m, 2H), 3.58-3.40 (m, 2H), 3.17 (tt, J=10.3, 4.7 Hz, 1H), 2.83 (dtd, J=11.5, 8.2, 6.0 Hz, 1H), 2.52 (ddt, J=11.5, 9.2, 7.4 Hz, 1H), 2.27 (d, J=10.5 Hz, 4H).

Example 5. Methyl 2-[[4-[6-[(4-cyano-2-fluoro-phenyl)methoxy]-2-pyridyl]-1-piperidyl]methyl]-3-[[(2S)-oxetan-2-yl]methyl]-7-(2-pyridyl)benzimidazole-5-carboxylic Acid

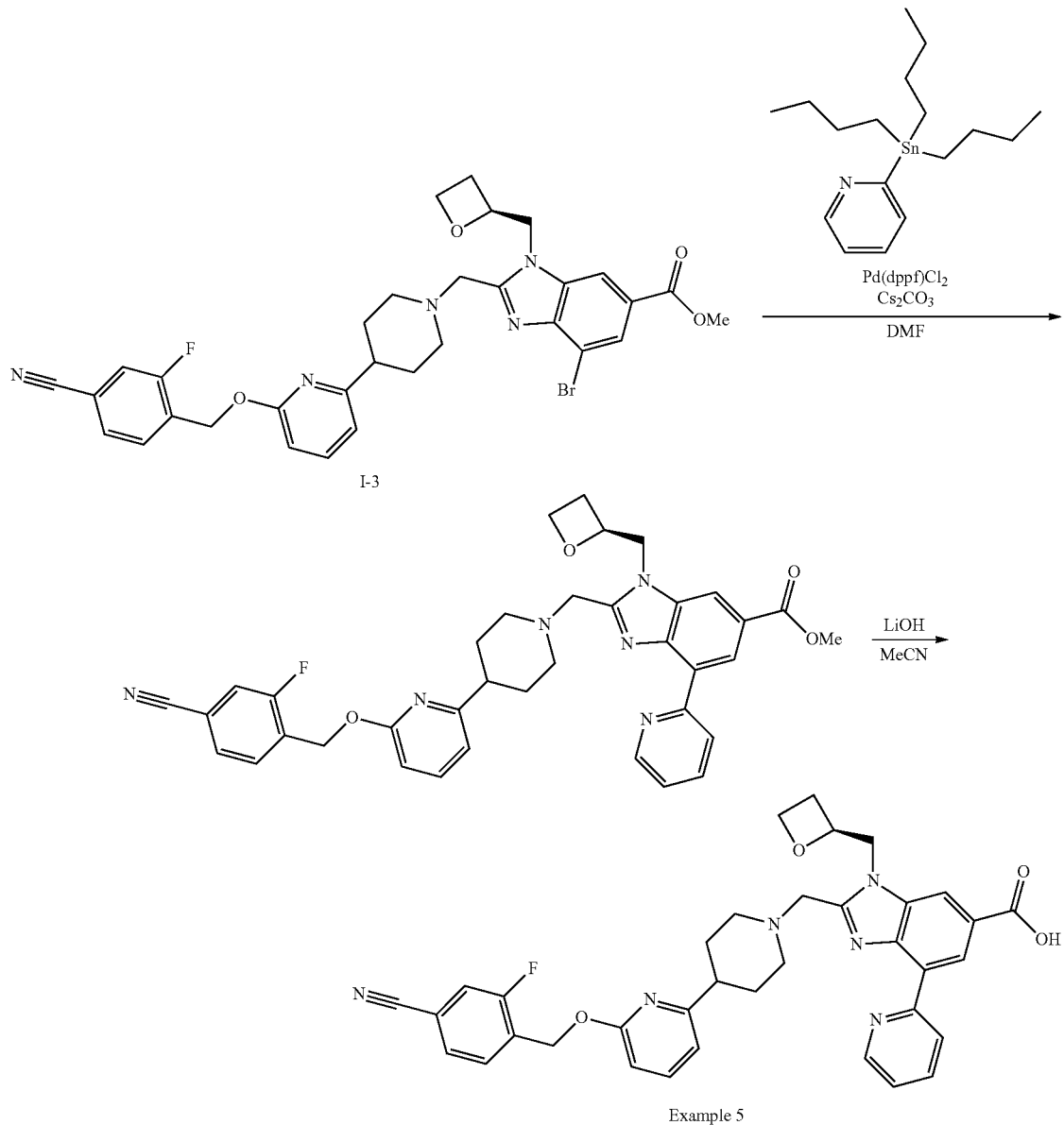

methyl 2-[[4-[6-[(4-cyano-2-fluoro-phenyl)methoxy]-2-pyridyl]-1-piperidyl]methyl]-3-[[(2S)-oxetan-2-yl]methyl]-7-(2-pyridyl)benzimidazole-5-carboxylate A solution of I-3 (50.0 mg, 0.07 mmol), tributyl(2-pyridyl)stannane (43 mg, 0.1 mmol), Cs₂CO₃ (45 mg, 0.2 mmol) and Pd (dppf)Cl₂ (13.4 mg, 0.01 mmol) in DMF (2 mL) was degassed for 10 minutes, followed heating overnight at 100° C. Upon completion the mixture was injected straight on to silica for flash column chromatography. The product was purified and carried through to the next step. ES/MS: 647.2 (M+H⁺).

methyl 2-[[4-[6-[(4-cyano-2-fluoro-phenyl)methoxy]-2-pyridyl]-1-piperidyl]methyl]-3-[[(2S)-oxetan-2-yl]methyl]-7-(2-pyridyl)benzimidazole-5-carboxylic Acid (Example 5)

To a solution of methyl 2-[[4-[6-[(4-cyano-2-fluoro-phenyl)methoxy]-2-pyridyl]-1-piperidyl]methyl]-3-[[(2S)-oxetan-2-yl]methyl]-7-(2-pyridyl)benzimidazole-5-carboxylate (30.0 mg, 0.04 mmol) in MeCN (1 mL) was added LiOH (1.6 mg, 0.225 mL, 0.3 M) and the solution was heated for 5 minutes at 100° C. Upon completion, the reaction mixture was purified by a RP-HPLC column to yield the product as a TFA salt. ES/MS: 633.2 (M+H$^+$). 1H NMR (400 MHz, DMSO-d6) δ 9.03 (d, J=8.0 Hz, 1H), 8.87 (d, J=1.5 Hz, 1H), 8.81-8.75 (m, 1H), 8.45 (d, J=1.6 Hz, 1H), 7.97 (td, J=7.8, 1.9 Hz, 1H), 7.91 (d, J=9.9 Hz, 1H), 7.74 (d, J=5.8 Hz, 3H), 7.48-7.42 (m, 1H), 6.97 (d, J=7.4 Hz, 1H), 6.81 (d, J=8.2 Hz, 1H), 5.50 (s, 2H), 5.13-5.04 (m, 1H), 4.93 (m, 3H), 4.78 (m, 2H), 2.96 (m, 1H), 2.75 (m, 1H), 2.39 (m, 2H), 2.08 (m, 5H).

Example 7. 2-[6-[6-[(4-cyano-2-fluoro-phenyl)methoxy]-2-pyridyl]-6-azaspiro[2.5]octan-2-yl]-7-fluoro-3-(2-methoxyethyl)benzimidazole-5-carboxylic Acid Procedure 5

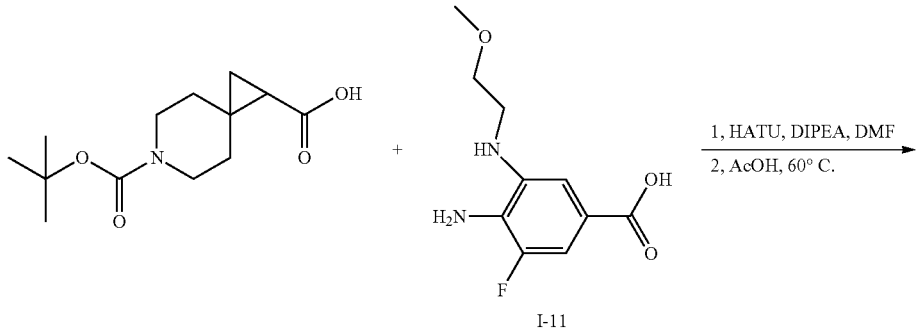

I-11

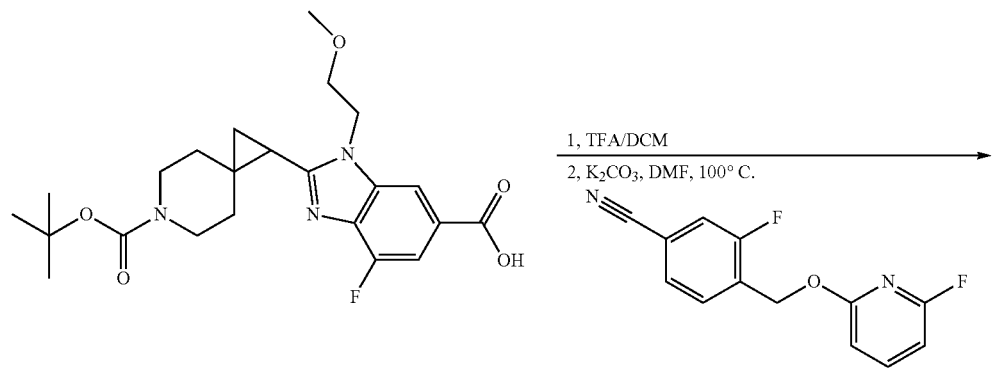

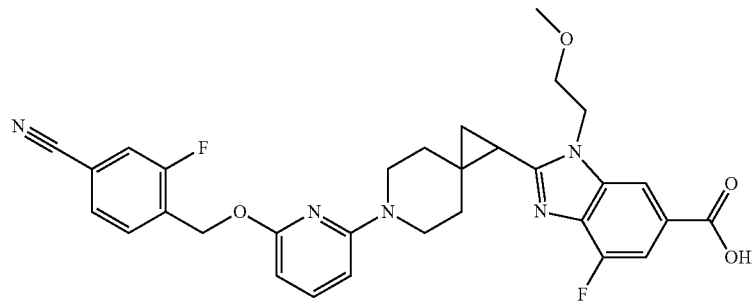

Example 7

2-(6-tert-butoxycarbonyl-6-azaspiro[2.5]octan-2-yl)-7-fluoro-3-(2-methoxyethyl)benzimidazole-5-carboxylic Acid To a solution of 6-tert-butoxycarbonyl-6-azaspiro[2.5]octane-2-carboxylic acid (200 mg, 0.78 mmol), o-(7-Azabenzotriazol-1-yl)-N,N,N',N'-tetramethyluronium hexafluorophosphate (298 mg, 0.78 mmol), and DIPEA (0.41 mL, 2.4 mmol) in DMF (3 mL), 4-amino-3-fluoro-5-(2-methoxyethylamino)benzoic acid (I-11) (197 mg, 0.86 mmol) was added to the solution after 15 minutes. The resulting solution was stirred at room temperature for 1 hour after which the reaction contents were poured into 25 mL of saturated sodium bicarbonate solution and extracted with EtOAc (2×50 mL). The combined organic extracts were washed with brine (20 mL), dried over MgSO4, and concentrated. The crude product was dissolved in 2 mL of acetic acid and heated to 60° C. for overnight. The mixture was cooled down and filtered. The filtrate was purified by RP-HPLC (eluent: water/MeCN*0.1% TFA). ES/MS: 448.2 (M+H$^+$).

2-[6-[6-[(4-cyano-2-fluoro-phenyl)methoxy]-2-pyridyl]-6-azaspiro[2.5]octan-2-yl]-7-fluoro-3-(2-methoxyethyl)benzimidazole-5-carboxylic Acid (Example 7)

2-(6-tert-butoxycarbonyl-6-azaspiro[2.5]octan-2-yl)-7-fluoro-3-(2-methoxyethyl)benzimidazole-5-carboxylic acid (140 mg, 0.3 mmol) was dissolved in 2 mL of trifluoroacetic acid in 1 mL of DCM. After 2 hours, the solvent was removed. The crude product was dissolved in 2 mL of DMF, potassium carbonate (129 mg, 0.93 mmol) and 3-fluoro-4-(((6-fluoropyridin-2-yl)oxy)methyl)benzonitrile (I-22) (76.5 g, 0.3 mmol) was added to the suspension. It was heated at 100° C. overnight. The mixture was cooled down and filtered. The filtrate was purified by RP-HPLC (eluent: water/MeCN*0.1% TFA). ES/MS: 574.5 (M+H$^+$). 1H NMR (400 MHz, Methanol-d4) δ 8.15 (d, J=1.2 Hz, 1H), 7.74 (dd, J=11.1, 1.1 Hz, 1H), 7.59 (t, J=7.6 Hz, 1H), 7.55-7.45 (m, 2H), 7.41 (t, J=8.0 Hz, 1H), 6.29 (d, J=8.2 Hz, 1H), 6.10 (d, J=7.8 Hz, 1H), 5.50-5.29 (m, 2H), 4.73-4.51 (m, 2H), 4.02 (dt, J=13.2, 4.5 Hz, 1H), 3.84-3.64 (m, 3H), 3.39-3.32 (m, 1H), 3.21 (ddd, J=13.1, 9.9, 3.2 Hz, 1H), 3.10 (s, 3H), 2.44 (dd, J=8.3, 5.7 Hz, 1H), 1.91 (ddd, J=13.4, 9.8, 3.8 Hz, 1H), 1.79 (t, J=5.5 Hz, 1H), 1.53 (ddd, J=13.6, 9.7, 3.8 Hz, 1H), 1.40 (ddd, J=13.6, 8.9, 4.8 Hz, 2H), 1.24 (td, J=11.9, 10.0, 7.0 Hz, 1H).

Example 10. 2-((4-(6-((4-cyano-2-fluorobenzyl)oxy)pyridin-2-yl)piperidin-1-yl)methyl)-4,5-difluoro-1-(2-methoxyethyl)-1H-benzo[d]imidazole-6-carboxylic Acid Procedure 6

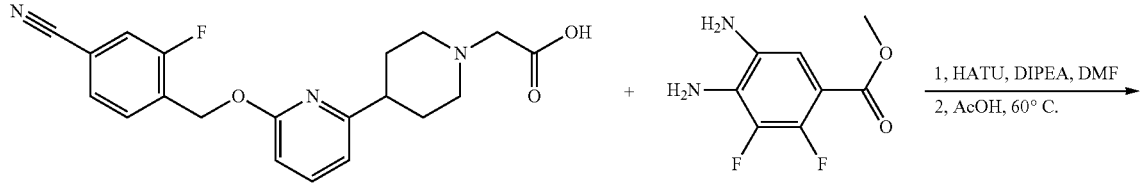

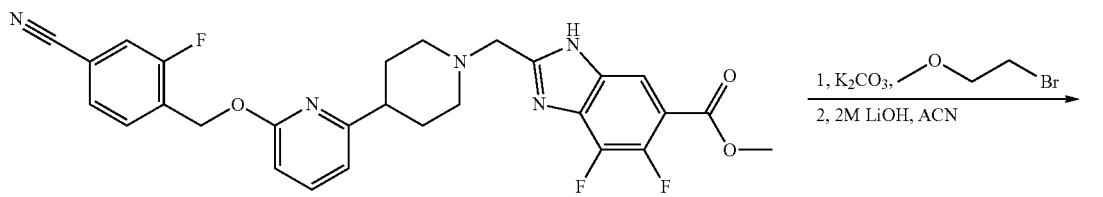

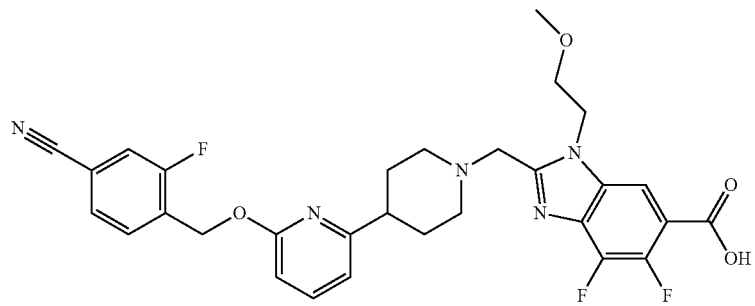

Example 10 methyl 2-((4-(6-((4-cyano-2-fluorobenzyl)oxy)pyridin-2-yl)piperidin-1-yl)methyl)-4,5-difluoro-1H-benzo[d]imidazole-6-carboxylate To a solution of 2-[4-[6-[(4-cyano-2-fluoro-phenyl)methoxy]-2-pyridyl]-1-piperidyl]acetic acid (100 mg, 0.78 mmol), o-(7-Azabenzotriazol-1-yl)-N,N,N',N'-tetramethyluronium hexafluorophosphate (154 mg, 0.4 mmol), and DIPEA (0.24 mL, 1.35 mmol) in DMF (1 mL), was added methyl 4,5-diamino-2,3-difluorobenzoate (93.3 mg, 0.46 mmol). The resulting solution was stirred at room temperature for 1 hour after which the reaction contents were poured into 25 mL of saturated sodium bicarbonate solution and extracted with EtOAc (2×50 mL). The combined organic extracts were washed with brine (20 mL), dried over MgSO4, and concentrated. The crude product was dissolved in 2 mL of acetic acid and heated to 60° C. overnight. The mixture was cooled down and filtered. The filtrate was purified by RP-HPLC (eluent: water/MeCN*0.1% TFA). ES/MS: 536.5 (M+H$^+$).

2-((4-(6-((4-cyano-2-fluorobenzyl)oxy)pyridin-2-yl)piperidin-1-yl)methyl)-4,5-difluoro-1-(2-methoxyethyl)-1H-benzo[d]imidazole-6-carboxylic Acid (Example 10)

To a solution of methyl 2-[[4-[6-[(4-cyano-2-fluoro-phenyl)methoxy]-2-pyridyl]-1-piperidyl]methyl]-6,7-difluoro-3H-benzimidazole-5-carboxylate (140 mg, 0.26 mmol) and potassium carbonate (108 mg, 0.78 mmol) was dissolved in 2 mL of DMF, 1-bromo-2-methoxy-ethane (50 mg, 0.36 mmol) was added to the solution. It was stirred for 2 hours. Diluted with 50 mL of EtOAc and washed with brine (25 mL twice). The organic layer was dried and concentrated. Dissolved in 1 mL of ACN and 0.3 mL of LiOH (2M) was added to the solution. The mixture was heated to 50° C. for 3 hours. 0.3 mL of acetic acid was added to the mixture and purified by RP-HPLC (eluent: water/MeCN 0.1% TFA) to yield the product. ES/MS: 580.2 (M+H+). 1H NMR (400 MHz, Methanol-d4) δ 8.07 (dd, J=5.0, 1.6 Hz, 1H), 7.78-7.64 (m, 2H), 7.64-7.53 (m, 2H), 6.97 (d, J=7.4 Hz, 1H), 6.81 (d, J=8.2 Hz, 1H), 5.58 (s, 2H), 4.84 (s, 2H), 4.61 (t, J=4.8 Hz, 2H), 3.95 (s, 2H), 3.75 (t, J=4.8 Hz, 2H), 3.56-3.37 (m, 3H), 3.20-3.04 (m, 1H), 2.23 (s, 4H).

Example 11. 2-[[4-[6-[(4-cyano-2-fluoro-phenyl)methoxy]-2-pyridyl]piperazin-1-yl]methyl]-7-(3-hydroxy-3-methyl-but-1-ynyl)-3-[[(2S)-oxetan-2-yl]methyl]benzimidazole-5-carboxylic Acid Example 13. 2-[[4-[6-[(4-carbamoyl-2-fluoro-phenyl)methoxy]-2-pyridyl]piperazin-1-yl]methyl]-7-(3-hydroxy-3-methyl-but-1-ynyl)-3-[[(2S)-oxetan-2-yl]methyl]benzimidazole-5-carboxylic Acid Procedure 7

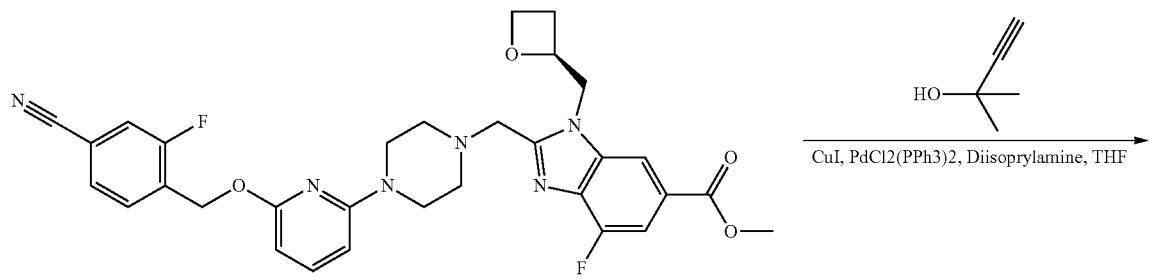

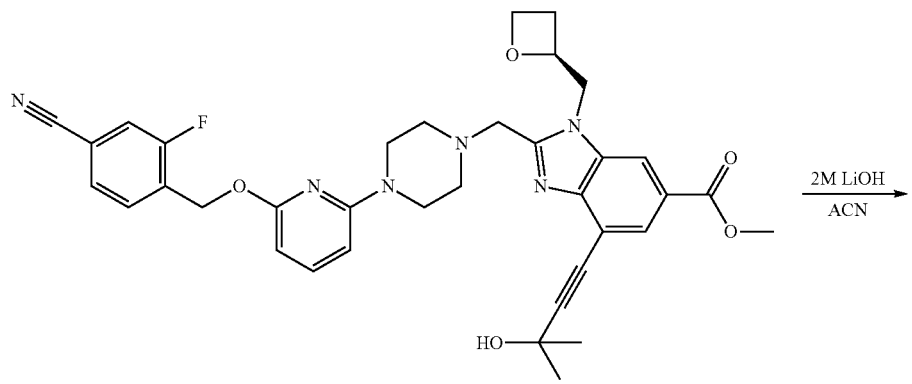

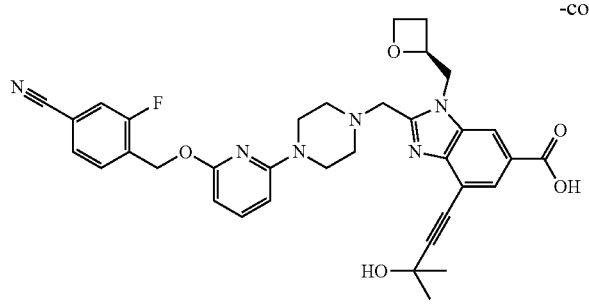

Example 11

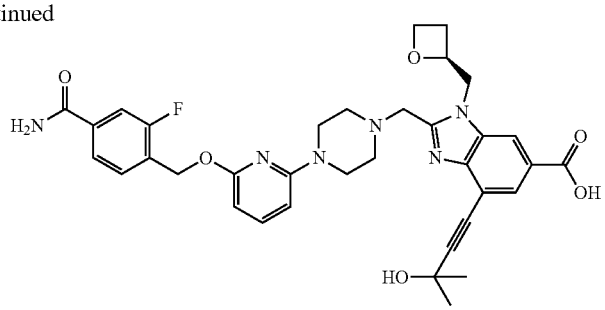

Example 13

Methyl 2-[[4-[6-[(4-cyano-2-fluoro-phenyl)methoxy]-2-pyridyl]piperazin-1-yl]methyl]-7-(3-hydroxy-3-methyl-but-1-ynyl)-3-[[(2S)-oxetan-2-yl]methyl]benzimidazole-5-carboxylate To a flask of methyl 7-bromo-2-[[4-[6-[(4-cyano-2-fluoro-phenyl)methoxy]-2-pyridyl]piperazin-1-yl]methyl]-3-[[(2S)-oxetan-2-yl]methyl]benzimidazole-5-carboxylate (I-4) (100 mg, 0.15 mmol), was added 2-methylbut-3-yn-2-ol (130 mg, 1.5 mmol), Bis(triphenylphosphine)palladium Chloride (21.6 mg, 0.03 mmol) copper(I) iodide (6 mg, 0.03 mmol) and diisopropylamine (0.22 mL, 1.5 mmol) in 1 mL of THF. The mixture was heated at 80° C. for 1 hour. The mixture was filtered and the filtrate was then purified by RP-HPLC (eluent: water/MeCN*0.1% TFA). ES/MS: 653.6 (M+H$^+$).

2-[[4-[6-[(4-cyano-2-fluoro-phenyl)methoxy]-2-pyridyl]piperazin-1-yl]methyl]-7-(3-hydroxy-3-methyl-but-1-ynyl)-3-[[(2S)-oxetan-2-yl]methyl]benzimidazole-5-carboxylic Acid (Example 11) and 2-[[4-[6-[(4-carbamoyl-2-fluoro-phenyl)methoxy]-2-pyridyl]piperazin-1-yl]methyl]-7-(3-hydroxy-3-methyl-but-1-ynyl)-3-[[(2S)-oxetan-2-yl]methyl]benzimidazole-5-carboxylic Acid (Example 13)

Methyl 2-[[4-[6-[(4-cyano-2-fluoro-phenyl)methoxy]-2-pyridyl]piperazin-1-yl]methyl]-7-(3-hydroxy-3-methyl-but-1-ynyl)-3-[[(2S)-oxetan-2-yl]methyl]benzimidazole-5-carboxylate (50 mg, 0.27 mmol) was dissolved in acetonitrile (1 mL), after which 0.3 mL of 2 N LiOH was added and the resulting mixture stirred at 80° C. for 20 minutes. To the mixture was added 0.3 mL of acetic acid. The organic layer was concentrated, then purified by RP-HPLC (eluent: water/MeCN*0.1% TFA) to yield the products as trifluoroacetate salts.

Example 11. ES/MS: 639.5 (M+H$^+$). 1H NMR (400 MHz, Methanol-d4) δ 8.34 (d, J=1.5 Hz, 1H), 8.08 (d, J=1.4 Hz, 1H), 7.68 (t, J=7.5 Hz, 1H), 7.64-7.50 (m, 3H), 6.46 (d, J=8.1 Hz, 1H), 6.32 (d, J=7.9 Hz, 1H), 5.49 (s, 2H), 5.22 (td, J=7.7, 5.3 Hz, 1H), 4.85-4.75 (m, 3H), 4.68 (ddd, J=13.7, 6.1, 3.1 Hz, 2H), 4.43 (dt, J=9.2, 5.9 Hz, 1H), 3.83 (s, 4H), 3.52 (d, J=18.8 Hz, 4H), 2.82 (dq, J=13.8, 7.8 Hz, 1H), 2.61-2.29 (m, 1H), 1.65 (s, 6H).

Example 13. ES/MS: 657.4 (M+H+). 1H NMR (400 MHz, Methanol-d4) δ 8.35 (d, J=1.5 Hz, 1H), 8.09 (d, J=1.4 Hz, 1H), 7.74-7.61 (m, 2H), 7.61-7.50 (m, 2H), 6.46 (d, J=8.1 Hz, 1H), 6.32 (d, J=7.9 Hz, 1H), 5.48 (s, 2H), 5.22 (q, J=6.2 Hz, 1H), 4.87 (s, 2H), 4.79 (dd, J=15.8, 6.9 Hz, 1H), 4.73-4.58 (m, 2H), 4.44 (dt, J=9.2, 5.9 Hz, 1H), 3.87 (s, 4H), 3.58 (s, 4H), 2.89-2.71 (m, 1H), 2.49 (dt, J=17.9, 8.1 Hz, 1H), 1.66 (s, 7H).

Example 14. 2-(6-(6-((4-cyano-2-fluorobenzyl)oxy)pyridin-2-yl)-6-azaspiro[2.5]octan-1-yl)-1-(2-methoxyethyl)-1H-benzo[d]imidazole-6-carboxylic Acid Procedure 8

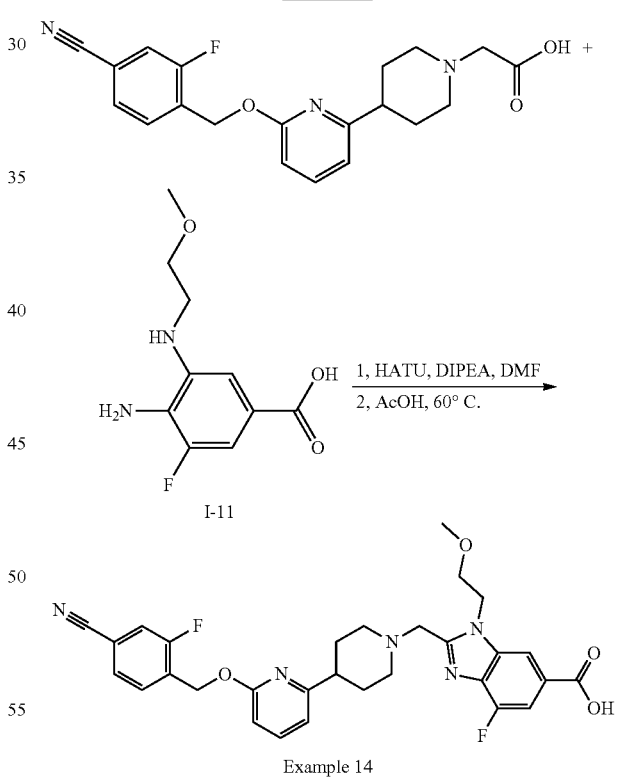

Example 14

2-[[4-[6-[(4-cyano-2-fluoro-phenyl)methoxy]-2-pyridyl]-1-piperidyl]methyl]-7-fluoro-3-(2-methoxyethyl)benzimidazole-5-carboxylic Acid (Example 14)

To a solution of 2-[4-[6-[(4-cyano-2-fluoro-phenyl)methoxy]-2-pyridyl]-1-piperidyl]acetic acid (200 mg, 0.54 mmol), o-(7-Azabenzotriazol-1-yl)-N,N,N',N'-tetramethyluronium hexafluorophosphate (206 mg, 0.54 mmol), and DIPEA (0.28 mL, 1.6 mmol) in DMF (3 mL), 4-amino-3-fluoro-5-(2-methoxyethylamino)benzoic acid (136 mg, 0.6 mmol) was added to the solution after 15 minutes. The resulting solution was stirred at room temperature for 1 hour after which the reaction contents were poured into 25 mL of saturated sodium bicarbonate solution and extracted with EtOAc (2×50 mL). The combined organic extracts were washed with brine (20 mL), dried over MgSO4, and concentrated. The crude product was dissolved in 2 mL of acetic acid and heated to 60° C. overnight. The mixture was cooled down and filtered. The filtrate was purified by RP-HPLC (eluent: water/MeCN*0.1% TFA). ES/MS: 562.4 (M+H⁺). 1H NMR (400 MHz, Methanol-d4) δ 8.17 (d, J=1.2 Hz, 1H), 7.69 (q, J=6.4 Hz, 3H), 7.64-7.51 (m, 2H), 6.95 (d, J=7.3 Hz, 1H), 6.79 (d, J=8.3 Hz, 1H), 5.56 (s, 3H), 4.61 (t, J=4.9 Hz, 2H), 3.91 (s, 2H), 3.74 (t, J=4.8 Hz, 2H), 3.09 (d, J=29.2 Hz, 2H), 2.20 (s, 5H), 1.43-1.19 (m, 2H).

Example 16. (S)-2-((4-(6-((4-cyano-2-fluorobenzyl)oxy)pyridin-2-yl)piperidin-1-yl)methyl)-5-(3-hydroxy-3-methylbut-1-yn-1-yl)-1-(oxetan-2-ylmethyl)-1H-benzo[d]imidazole-6-carboxylic Acid Procedure 9

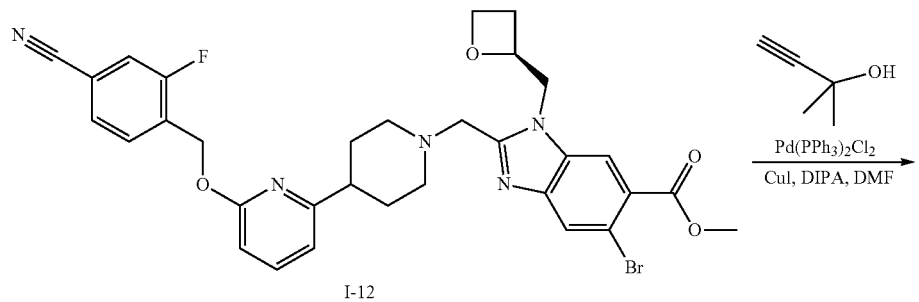

I-12

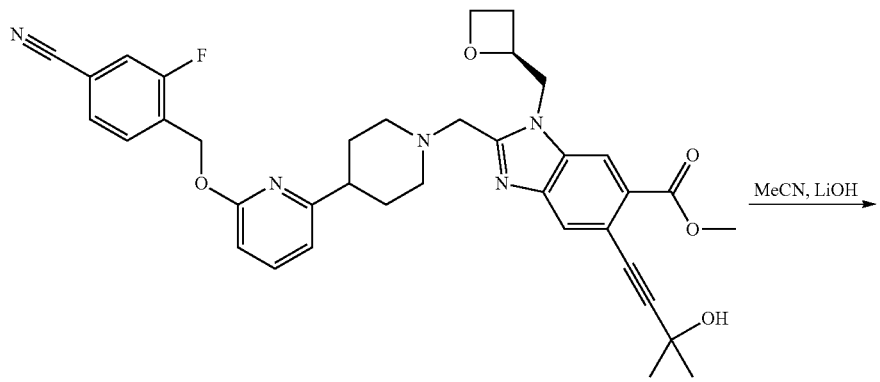

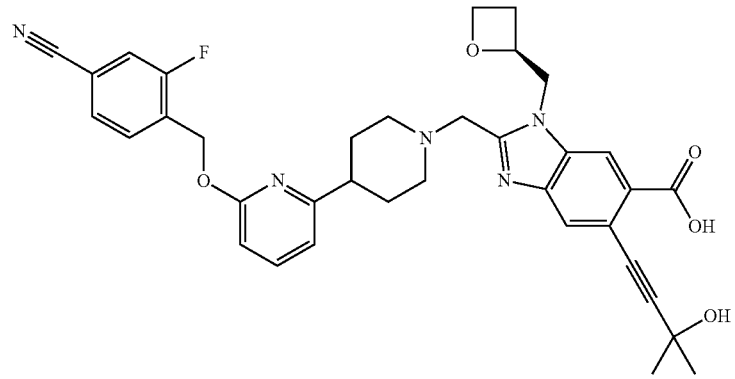

Example 16

Methyl (S)-2-((4-(6-((4-cyano-2-fluorobenzyl)oxy)pyridin-2-yl)piperidin-1-yl)methyl)-5-(3-hydroxy-3-methylbut-1-yn-1-yl)-1-(oxetan-2-ylmethyl)-1H-benzo[d]imidazole-6-carboxylate Methyl (S)-5-bromo-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylate (60 mg, 0.093 mmol), 2-methylbut-3-yn-2-ol (78 mg, 0.93 mmol), bis(triphenylphosphine)palladium chloride (33 mg, 0.046 mmol), and copper iodide (9 mg, 0.046 mmol) were taken up in DMF (1.6 mL). Diisopropylamine (0.27 mL, 1.85 mmol) was added and the resulting mixture was purged with argon and heated to 105° C. After 3 hours, the mixture was diluted with EtOAc (5 mL) and H₂O (5 mL). The organic phase was collected, and the aqueous phase was extracted with EtOAc (2×5 mL). The combined organics were dried over MgSO₄, concentrated in vacuo, and purified by silica gel column chromatography (eluent: EtOAc/hexanes) to afford the product: ES/MS: 652.2 (M+H⁺).

(S)-2-((4-(6-((4-cyano-2-fluorobenzyl)oxy)pyridin-2-yl)piperidin-1-yl)methyl)-5-(3-hydroxy-3-methylbut-1-yn-1-yl)-1-(oxetan-2-ylmethyl)-1H-benzo[d]imidazole-6-carboxylic Acid (Example 16)

Methyl (S)-2-((4-(6-((4-cyano-2-fluorobenzyl)oxy)pyridin-2-yl)piperidin-1-yl)methyl)-5-(3-hydroxy-3-methylbut-1-yn-1-yl)-1-(oxetan-2-ylmethyl)-1H-benzo[d]imidazole-6-carboxylate (48 mg, 0.074 mmol) was taken up in acetonitrile (0.75 mL) and aqueous lithium hydroxide (0.3 M, 0.75 mL, 0.22 mmol) was added. The mixture was heated to 105° C. for 4 minutes. Following this time, the mixture was diluted with water (5 mL), the pH adjusted to ~5 with 1M aqueous citric acid solution and the mixture extracted with EtOAc (3×5 mL). The combined organics were dried over MgSO₄, concentrated in vacuo, and purified by RP-HPLC (eluent: MeCN/water) to yield the product (Example 16). ES/MS: 638.2 (M+H⁺); ¹H NMR (400 MHz, DMSO-d6) δ 8.15 (s, 1H), 7.90 (d, J=10.0 Hz, 1H), 7.77-7.58 (m, 4H), 6.89 (d, J=7.4 Hz, 1H), 6.73 (d, J=8.2 Hz, 1H), 5.48 (s, 2H), 5.10 (d, J=5.5 Hz, 1H), 4.80 (dd, J=15.1, 7.3 Hz, 1H), 4.65 (d, J=14.1 Hz, 1H), 4.49 (q, J=7.7, 7.0 Hz, 1H), 4.39 (dt, J=8.9, 5.9 Hz, 1H), 3.94 (d, J=13.5 Hz, 1H), 3.77 (d, J=13.5 Hz, 1H), 2.98 (d, J=11.0 Hz, 1H), 2.83 (d, J=11.2 Hz, 1H), 2.76-2.65 (m, 1H), 2.42 (dd, J=18.3, 8.5 Hz, 1H), 2.20 (dt, J=25.0, 11.4 Hz, 2H), 1.84-1.57 (m, 4H), 1.48 (s, 6H), 1.42-1.28 (m, 1H).

Example 17. (S)-2-((4-(6-((4-cyano-2-fluorobenzyl)oxy)pyridin-2-yl)piperidin-1-yl)methyl)-5-(1-methyl-1H-pyrazol-4-yl)-1-(oxetan-2-ylmethyl)-1H-benzo[d]imidazole-6-carboxylic Acid Procedure 10

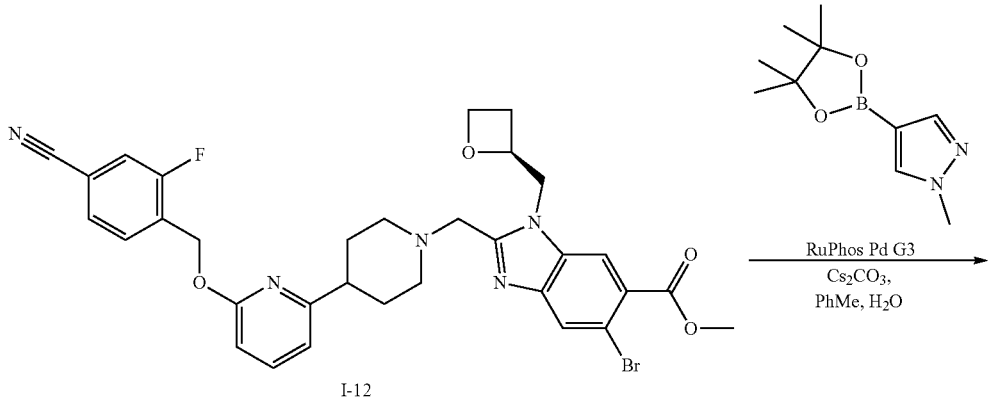

I-12

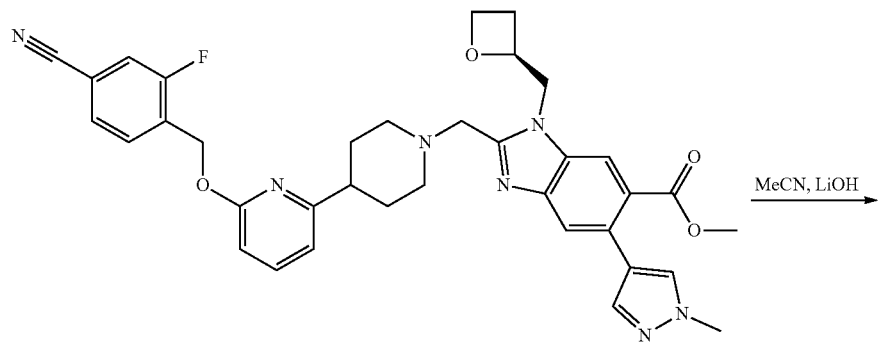

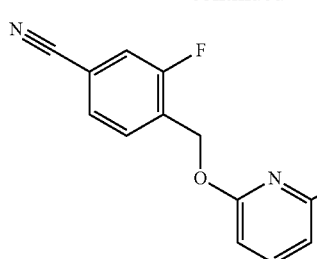
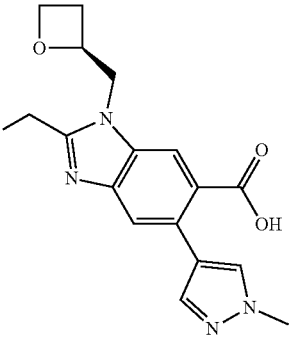

Example 17

Methyl (S)-2-((4-(6-((4-cyano-2-fluorobenzyl)oxy)pyridin-2-yl)piperidin-1-yl)methyl)-5-(1-methyl-1H-pyrazol-4-yl)-1-(oxetan-2-ylmethyl)-1H-benzo[d]imidazole-6-carboxylate Methyl (S)-5-bromo-2-((4-(6-((4-cyano-2-fluorobenzyl)oxy)pyridin-2-yl)piperidin-1-yl)methyl)-1-(oxetan-2-ylmethyl)-1H-benzo[d]imidazole-6-carboxylate (60 mg, 0.093 mmol), 1-methyl-4-(4,4,5,5-tetramethyl-1,3,2-dioxaborolan-2-yl)pyrazole (29 mg, 0.14 mmol), RuPhos Pd G3 (16 mg, 0.019 mmol), and cesium carbonate (90 mg, 0.28 mmol) were taken up in toluene (1.5 mL) and water (0.3 mL). The resulting mixture was purged with argon and heated to 105° C. After 3 hours, the mixture was diluted with EtOAc (5 mL) and H$_2$O (5 mL). The organic phase was collected, and the aqueous phase was extracted with EtOAc (2×5 mL). The combined organics were dried over MgSO$_4$, concentrated in vacuo, and purified by silica gel column chromatography (eluent: EtOAc/hexanes) to afford the product: ES/MS: 650.2 (M+H$^+$).

(S)-2-((4-(6-((4-cyano-2-fluorobenzyl)oxy)pyridin-2-yl)piperidin-1-yl)methyl)-5-(1-methyl-1H-pyrazol-4-yl)-1-(oxetan-2-ylmethyl)-1H-benzo[d]imidazole-6-carboxylic Acid (Example 17)

Methyl (S)-2-((4-(6-((4-cyano-2-fluorobenzyl)oxy)pyridin-2-yl)piperidin-1-yl)methyl)-5-(1-methyl-1H-pyrazol-4-yl)-1-(oxetan-2-ylmethyl)-1H-benzo[d]imidazole-6-carboxylate (50 mg, 0.077 mmol) was taken up in acetonitrile (0.64 mL) and aqueous lithium hydroxide (0.3 M, 0.64 mL, 0.19 mmol) was added. The mixture was heated to 105° C. for 6 minutes. Following this time, the mixture was diluted with water (5 mL), the pH adjusted to −5 with 1M aqueous citric acid solution and the mixture extracted with EtOAc (3×5 mL). The combined organics were dried over MgSO$_4$, concentrated in vacuo, and purified by RP-HPLC (eluent: MeCN/water with 0.1% TFA) to yield the product as a bis-trifluoroacetic acid salt (Example 17). ES/MS: 636.2 (M+H$^+$); $^1$H NMR (400 MHz, DMSO-d6) δ 8.06 (s, 1H), 7.98-7.88 (m, 1H), 7.85 (s, 1H), 7.78-7.66 (m, 4H), 7.55 (s, 1H), 6.96 (d, J=7.4 Hz, 1H), 6.81 (d, J=8.2 Hz, 1H), 5.51 (s, 2H), 5.05 (d, J=8.0 Hz, 1H), 4.94-4.73 (m, 3H), 4.64 (d, J=15.3 Hz, 1H), 4.50 (q, J=7.1 Hz, 1H), 4.40-4.27 (m, 1H), 3.88 (s, 3H), 3.32 (s, 3H), 2.95 (s, 1H), 2.80-2.69 (m, 1H), 2.40-2.28 (m, 1H), 2.08 (s, 4H), one signal overlapping with water.

Example 18. 2-[[4-[6-[(4-cyano-2-fluoro-phenyl)methoxy]-2-pyridyl]-1-piperidyl]methyl]-7-(1-methylpyrazol-3-yl)-3-[[(2S)-oxetan-2-yl]methyl]benzimidazole-5-carboxylic Acid Procedure 11

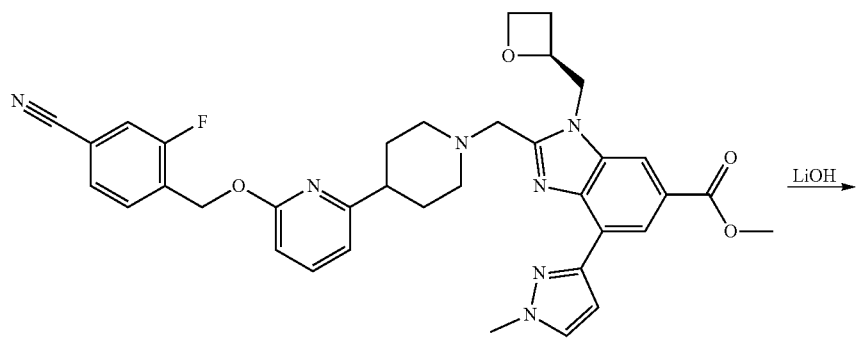

I-13

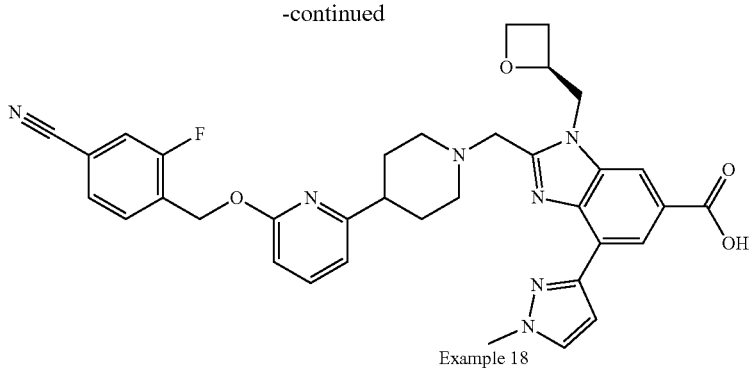

Example 18

2-[[4-[6-[(4-cyano-2-fluoro-phenyl)methoxy]-2-pyridyl]-1-piperidyl]methyl]-7-(1-methylpyrazol-3-yl)-3-[[(2S)-oxetan-2-yl]methyl]benzimidazole-5-carboxylic Acid (Example 18)

To a solution of methyl 2-[[4-[6-[(4-cyano-2-fluoro-phenyl)methoxy]-2-pyridyl]-1-piperidyl]methyl]-7-(1-methylpyrazol-3-yl)-3-[[(2S)-oxetan-2-yl]methyl]benzimidazole-5-carboxylate (I-13) (32.1 mg, 0.05 mmol) in a mixture of acetonitrile (3 mL) and water (1 mL) was added LiOH (3.55 mg, 0.15 mmol). The solution was then heated in a sealed vial to 100° C. for 3 minutes. The solution was cooled to rt, a drop of TFA and DMF (1 mL) was added, and the solution concentrated to remove the acetonitrile. The crude material was purified by reverse phase chromatography 10-58% ACN/water with 0.1% TFA added. The product containing fractions were combined, diluted with EtOAc, and 1 mg of sodium bicarbonate was added per mL of HPLC solvent. The aqueous layer was separated and the organic washed twice with water, then brine. The organic layer was dried over $MgSO_4$, filtered, and concentrated to give 2-[[4-[6-[(4-cyano-2-fluoro-phenyl)methoxy]-2-pyridyl]-1-piperidyl]methyl]-7-(1-methylpyrazol-3-yl)-3-[[(2S)-oxetan-2-yl]methyl]benzimidazole-5-carboxylic acid (Example 18). ES/MS m/z: 636.5 (M+H$^+$); $^1$H NMR (400 MHz, CD3CN) δ 8.50 (s, 1H), 8.16 (s, 1H), 7.96 (s, 1H), 7.65 (t, J=7.5 Hz, 1H), 7.62-7.56 (m, 2H), 7.52 (d, J=8.9 Hz, 2H), 7.44 (d, J=2.1 Hz, 1H), 6.81 (d, J=7.2 Hz, 1H), 6.66 (d, J=8.1 Hz, 1H), 5.48 (s, 2H), 5.16 (d, J=7.3 Hz, 1H), 4.79 (dd, J=14.7, 7.0 Hz, 1H), 4.71-4.51 (m, 2H), 4.44 (dd, J=9.4, 5.6 Hz, 1H), 4.22-4.00 (m, 2H), 3.97 (s, 3H), 3.32-3.08 (m, 2H), 2.92 (s, 2H), 2.80 (d, J=0.6 Hz, 2H), 2.78-2.61 (m, 1H), 2.48 (s, 3H), 1.85 (dt, J=12.4, 7.8 Hz, 2H).

Example 19. 2-[[4-[6-[(4-cyano-2-fluoro-phenyl)methoxy]-2-pyridyl]piperazin-1-yl]methyl]-7-(1-methylpyrazol-3-yl)-3-[[(2S)-oxetan-2-yl]methyl]benzimidazole-5-carboxylic Acid Procedure 12

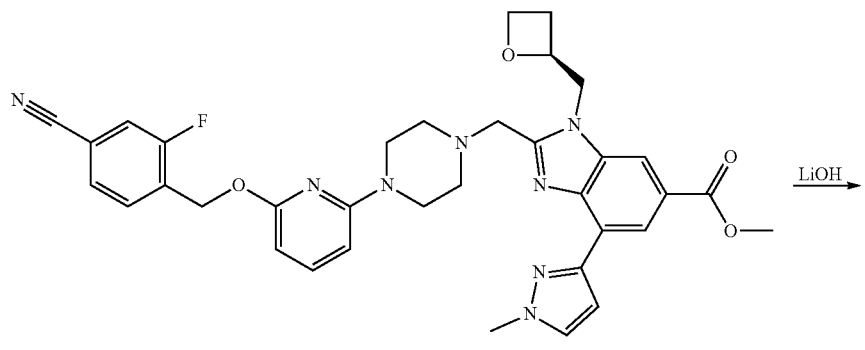

I-14

-continued

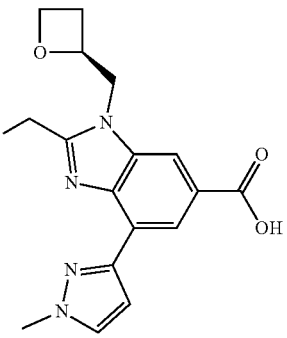

Example 19

2-[[4-[6-[(4-cyano-2-fluoro-phenyl)methoxy]-2-pyridyl]piperazin-1-yl]methyl]-7-(1-methylpyrazol-3-yl)-3-[[(2S)-oxetan-2-yl]methyl]benzimidazole-5-carboxylic Acid (Example 19)

To a solution of methyl 2-[[4-[6-[(4-cyano-2-fluoro-phenyl)methoxy]-2-pyridyl]piperazin-1-yl]methyl]-7-(1-methylpyrazol-3-yl)-3-[[(2S)-oxetan-2-yl]methyl]benzimidazole-5-carboxylate (I-14) (55.7 mg, 0.08 mmol) in a mixture of acetonitrile (3 mL) and water (1 mL) was added LiOH (6.15 mg, 0.26 mmol). The solution was then heated in a sealed vial to 100° C. for 3 minutes. The solution was cooled to rt, a drop of TFA and DMF (1 mL) was added, and the solution was concentrated to remove the acetonitrile. The crude material was purified by reverse phase chromatography 10-58% ACN/water with 0.1% TFA added. The product containing fractions were combined, diluted with EtOAc, and 1 mg of sodium bicarbonate was added per mL of HPLC solvent. The aqueous layer was separated and the organic washed twice with water, then brine. The organic layer was dried over $MgSO_4$, filtered, and concentrated to give 2-[[4-[6-[(4-cyano-2-fluoro-phenyl)methoxy]-2-pyridyl]piperazin-1-yl]methyl]-7-(1-methylpyrazol-3-yl)-3-[[(2S)-oxetan-2-yl]methyl]benzimidazole-5-carboxylic acid (Example 19). ES/MS m/z: 637.5 (M+H$^+$); $^1$H NMR (400 MHz, CD3CN) δ 8.49 (s, 1H), 8.17 (s, 1H), 7.65-7.55 (m, 2H), 7.55-7.41 (m, 3H), 7.38 (d, J=2.1 Hz, 1H), 6.25 (d, J=8.0 Hz, 1H), 6.14 (d, J=7.8 Hz, 1H), 5.42 (s, 2H), 5.15 (d, J=7.2 Hz, 1H), 4.77 (dd, J=15.4, 7.0 Hz, 1H), 4.68-4.50 (m, 2H), 4.43 (dt, J=8.7, 5.7 Hz, 1H), 4.24-4.01 (m, 2H), 3.99 (s, 3H), 3.50 (d, J=5.1 Hz, 4H), 2.73 (s, 5H), 2.55-2.33 (m, 1H).

Example 20. 2-[[4-[6-[(4-cyano-2-fluoro-phenyl)methoxy]-5-fluoro-2-pyridyl]-1-piperidyl]methyl]-7-fluoro-3-[[(2S)-oxetan-2-yl]methyl]benzimidazole-5-carboxylic Acid Procedure 13

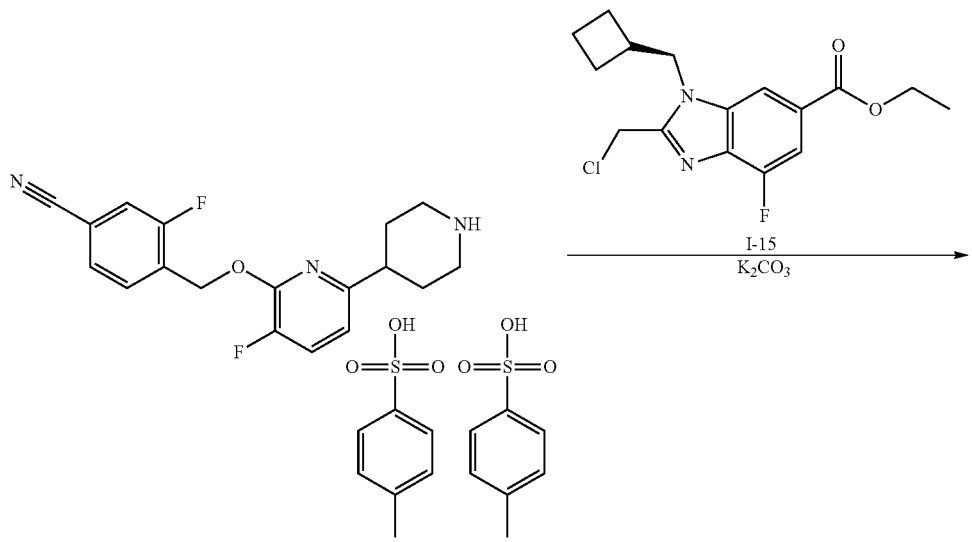

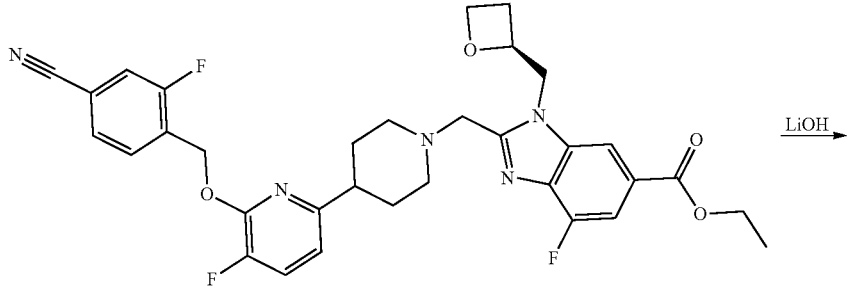

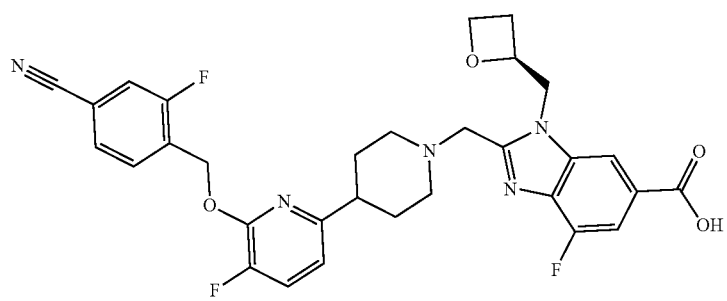

Example 20

Ethyl 2-[[4-[6-[(4-cyano-2-fluoro-phenyl)methoxy]-5-fluoro-2-pyridyl]-1-piperidyl]methyl]-7-fluoro-3-[[(2S)-oxetan-2-yl]methyl]benzimidazole-5-carboxylate To a solution of ethyl 2-(chloromethyl)-7-fluoro-3-[[(2S)-oxetan-2-yl]methyl]benzimidazole-5-carboxylate (I-15) (83.0 mg, 0.25 mmol) and 3-fluoro-4-[[3-fluoro-6-(4-piperidyl)-2-pyridyl]oxymethyl]benzonitrile; 4-methylbenzenesulfonic acid (205 mg, 0.31 mmol) in acetonitrile (6 mL) was added potassium carbonate (176 mg, 1.27 mmol). The mixture was stirred at rt overnight. The reaction was partitioned between EtOAc and water, extracted twice with EtOAc, washed with brine, dried over MgSO$_4$, filtered, and concentrated. The crude material was purified by SiO$_2$ column chromatography with a gradient of 30-100% EtOAc/Hex to yield ethyl 2-[[4-[6-[(4-cyano-2-fluoro-phenyl)methoxy]-5-fluoro-2-pyridyl]-1-piperidyl]methyl]-7-fluoro-3-[[(2S)-oxetan-2-yl]methyl]benzimidazole-5-carboxylate. ES/MS m/z: 620.2 (M+H$^+$).

2-[[4-[6-[(4-cyano-2-fluoro-phenyl)methoxy]-5-fluoro-2-pyridyl]-1-piperidyl]methyl]-7-fluoro-3-[[(2S)-oxetan-2-yl]methyl]benzimidazole-5-carboxylic Acid (Example 20)

To a solution of ethyl 2-[[4-[6-[(4-cyano-2-fluoro-phenyl)methoxy]-5-fluoro-2-pyridyl]-1-piperidyl]methyl]-7-fluoro-3-[[(2S)-oxetan-2-yl]methyl]benzimidazole-5-carboxylate (108 mg, 0.174 mmol) in acetonitrile (3 mL) and water (1 mL) was added lithium hydroxide (12.5 mg, 0.52 mmol). The solution was heated to 100° C. for 3 minutes before being cooled to rt, having 1 drop of TFA and DMF (1 mL) added, and the solution was concentrated to remove acetonitrile. Purification by reverse phase chromatography 10-58% ACN/H$_2$O with 0.1% TFA to yielded 2-[[4-[6-[(4-cyano-2-fluoro-phenyl)methoxy]-5-fluoro-2-pyridyl]-1-piperidyl]methyl]-7-fluoro-3-[[(2S)-oxetan-2-yl]methyl]benzimidazole-5-carboxylic acid (JSC-3) as a mono TFA salt. Example 20. ES/MS m/z: 592.2 (M+H$^+$); $^1$H NMR (400 MHz, DMSO) δ 8.28 (s, 2H), 7.93 (d, J=9.9 Hz, 1H), 7.77 (d, J=5.8 Hz, 2H), 7.73-7.66 (m, 1H), 7.63 (d, J=11.1 Hz, 1H), 7.00 (s, 1H), 5.60 (s, 2H), 5.05 (d, J=7.0 Hz, 2H), 4.85 (d, J=15.6 Hz, 4H), 4.71 (d, J=15.3 Hz, 1H), 4.49 (s, 2H), 4.43-4.23 (m, 2H), 2.92 (d, J=16.8 Hz, 1H), 2.80-2.63 (m, 2H), 2.33 (s, 2H).

Example 22. 2-[[4-[6-[(4-cyano-2-fluoro-phenyl)methoxy]-5-fluoro-2-pyridyl]piperazin-1-yl]methyl]-7-fluoro-3-[[(2S)-oxetan-2-yl]methyl]benzimidazole-5-carboxylic Acid

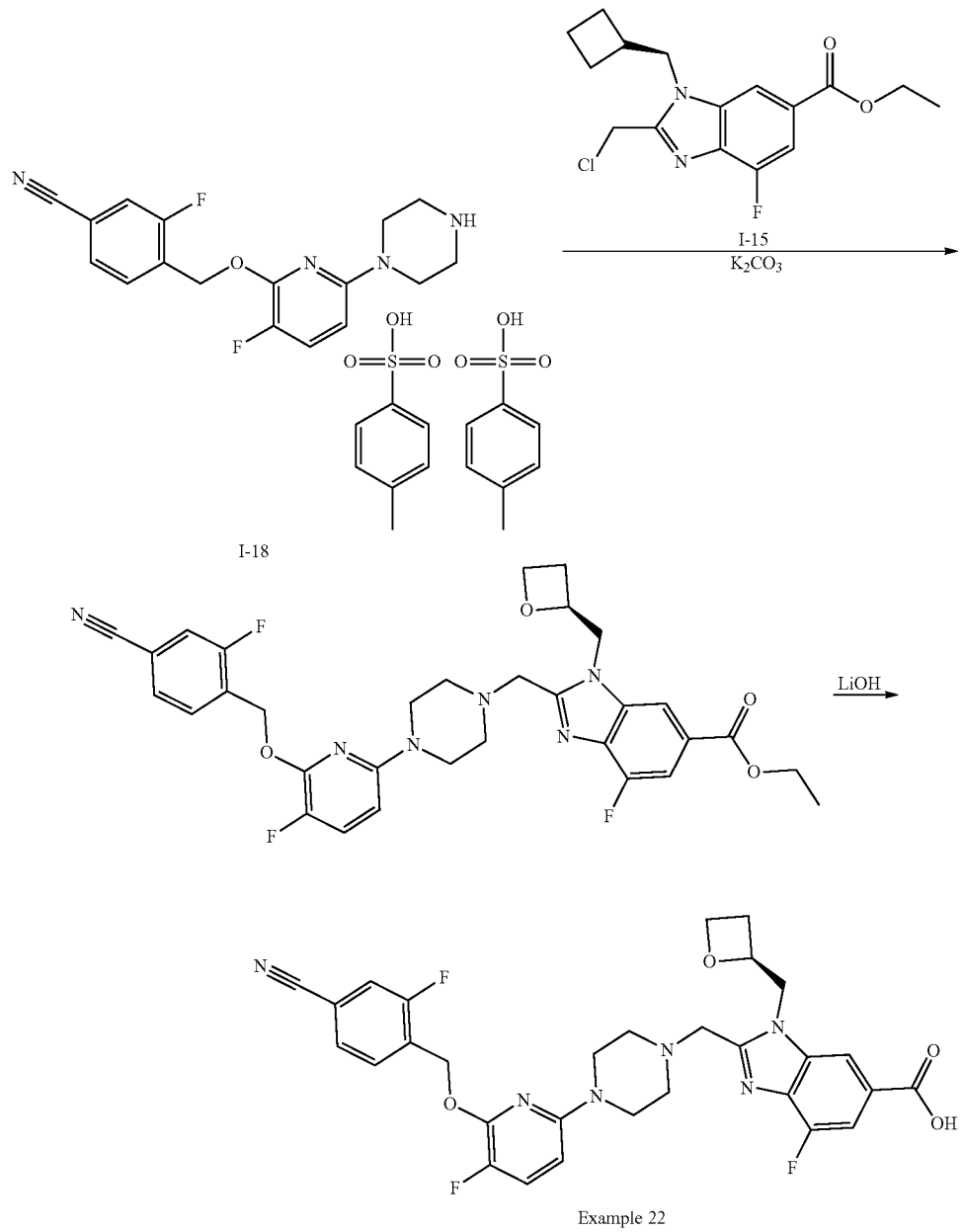

Procedure 14

Example 22 ethyl 2-[[4-[6-[(4-cyano-2-fluoro-phenyl)methoxy]-5-fluoro-2-pyridyl]-1-piperidyl]methyl]-7-fluoro-3-[[(2S)-oxetan-2-yl]methyl]benzimidazole-5-carboxylate To a solution of ethyl 2-(chloromethyl)-7-fluoro-3-[[(2S)-oxetan-2-yl]methyl]benzimidazole-5-carboxylate (I-15) (70.0 mg, 0.21 mmol) and 3-fluoro-4-[(3-fluoro-6-piperazin-1-yl-2-pyridyl)oxymethyl]benzonitrile; 4-methylbenzenesulfonic acid (I-18) (173 mg, 0.26 mmol) in acetonitrile (6 mL) was added potassium carbonate (148 mg, 1.07 mmol). The mixture was stirred at rt overnight. The reaction was partitioned between EtOAc and water, extracted twice with EtOAc, washed with brine, dried over MgSO$_4$, filtered, and concentrated. The crude material was purified by SiO$_2$ column chromatography with a gradient of 30-100% EtOAc/Hex to yield ethyl 2-[[4-[6-[(4-cyano-2-fluoro-phenyl)methoxy]-5-fluoro-2-pyridyl]piperazin-1-yl]methyl]-7-fluoro-3-[[(2S)-oxetan-2-yl]methyl]benzimidazole-5-carboxylate. ES/MS m/z: 621.2 (M+H$^+$).

2-[[4-[6-[(4-cyano-2-fluoro-phenyl)methoxy]-5-fluoro-2-pyridyl]piperazin-1-yl]methyl]-7-fluoro-3-[[(2S)-oxetan-2-yl]methyl]benzimidazole-5-carboxylic Acid (Example 22)

To a solution of ethyl 2-[[4-[6-[(4-cyano-2-fluoro-phenyl)methoxy]-5-fluoro-2-pyridyl]piperazin-1-yl]methyl]-7-fluoro-3-[[(2S)-oxetan-2-yl]methyl]benzimidazole-5-carboxylate (90 mg, 0.15 mmol) in a mixture of acetonitrile (3 mL) and water (1 mL) was added lithium hydroxide (10.4 mg, 0.43 mmol). The solution was heated to 100° C. for 3 minutes before being cooled to rt, having 1 drop of TFA and DMF (1 mL) added, and the solution was concentrated to remove the acetonitrile. Purification by reverse phase chromatography 10-58% ACN/H$_2$O with 0.1% TFA yielded 2-[[4-[6-[(4-cyano-2-fluoro-phenyl)methoxy]-5-fluoro-2-pyridyl]piperazin-1-yl]methyl]-7-fluoro-3-[[(2S)-oxetan-2-yl]methyl]benzimidazole-5-carboxylic acid (Example 22) as a mono TFA salt. ES/MS m/z: 593.2 (M+H$^+$); $^1$H NMR (400 MHz, CD3CN) δ 8.04 (s, 1H), 7.66 (t, J=7.6 Hz, 1H), 7.60-7.48 (m, 3H), 7.40 (dd, J=10.0, 8.6 Hz, 1H), 6.29 (dd, J=8.6, 1.8 Hz, 1H), 5.52 (s, 2H), 5.11 (d, J=7.3 Hz, 1H), 4.78 (dd, J=15.8, 7.2 Hz, 1H), 4.59 (d, J=7.2 Hz, 4H), 4.53-4.41 (m, 1H), 3.67 (s, 4H), 3.38 (s, 4H), 2.75 (q, J=8.6 Hz, 1H), 2.44 (t, J=9.8 Hz, 1H).

Example 24. 6-(tert-butoxycarbonylamino)-2-[[4-[6-[(4-cyano-2-fluoro-phenyl)methoxy]-2-pyridyl]-1-piperidyl]methyl]-3-[[(2S)-oxetan-2-yl]methyl]benzimidazole-5-carboxylic Acid Procedure 15

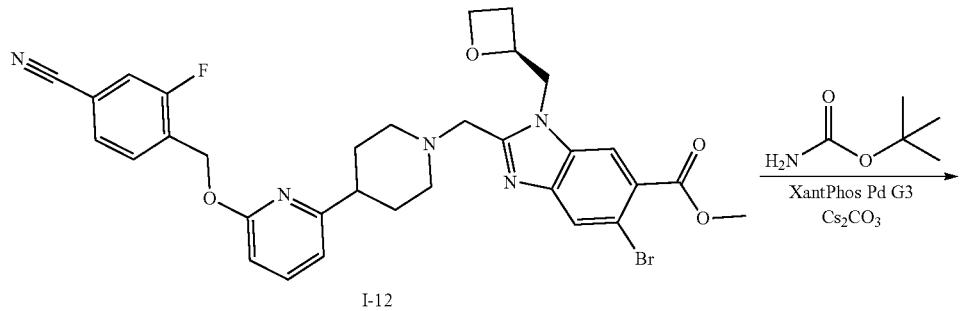

I-12

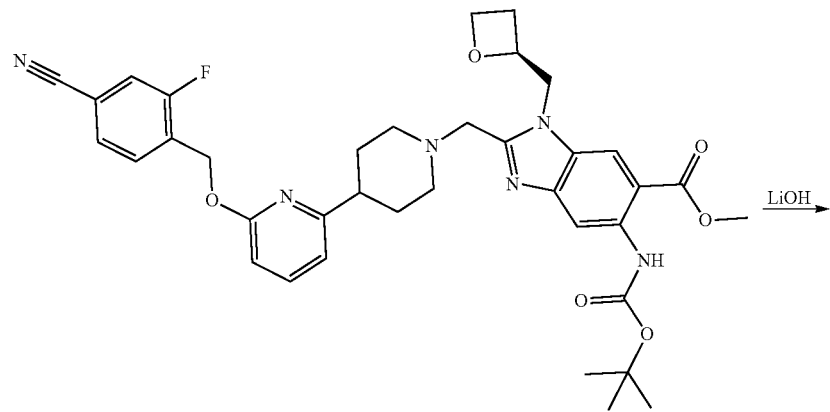

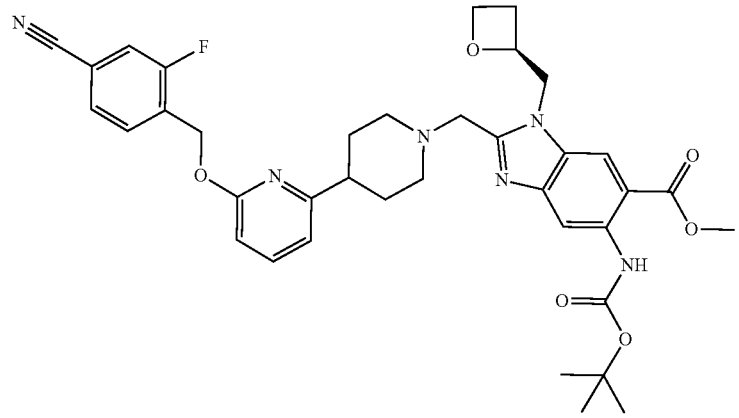

Example 24 methyl 6-(tert-butoxycarbonylamino)-2-[[4-[6-[(4-cyano-2-fluoro-phenyl)methoxy]-2-pyridyl]-1-piperidyl]methyl]-3-[[(2S)-oxetan-2-yl]methyl]benzimidazole-5-carboxylate To a 2 mL microwave vial containing 1,4-dioxane (4 mL) was added methyl 6-bromo-2-[[4-[6-[(4-cyano-2-fluoro-phenyl)methoxy]-2-pyridyl]-1-piperidyl]methyl]-3-[[(2S)-oxetan-2-yl]methyl]benzimidazole-5-carboxylate (I-12) (40.0 mg, 0.06 mmol), tert-butyl carbamate (10.8 mg, 0.09 mmol), cesium carbonate (51.6 mg, 0.16 mmol), and Xant-Phos Pd G3 (5.85 mg, 0.006 mmol). Argon was bubbled through this mixture for 5 minutes followed by heating to 130° C. for 2 hours. The mixture was diluted with EtOAc, filtered, concentrated, and purified by SiO$_2$ column chromatography with a gradient of 50-100% EtOAc/Hexanes to yield methyl 6-(tert-butoxycarbonylamino)-2-[[4-[6-[(4-cyano-2-fluoro-phenyl)methoxy]-2-pyridyl]-1-piperidyl]methyl]-3-[[(2S)-oxetan-2-yl]methyl]benzimidazole-5-carboxylate. ES/MS m/z: 593.2 (M+H$^+$).

6-(tert-butoxycarbonylamino)-2-[[4-[6-[(4-cyano-2-fluoro-phenyl)methoxy]-2-pyridyl]-1-piperidyl]methyl]-3-[[(2S)-oxetan-2-yl]methyl]benzimidazole-5-carboxylic Acid (Example 22)

To a solution of methyl 6-(tert-butoxycarbonylamino)-2-[[4-[6-[(4-cyano-2-fluoro-phenyl)methoxy]-2-pyridyl]-1-piperidyl]methyl]-3-[[(2S)-oxetan-2-yl]methyl]benzimidazole-5-carboxylate (25.2 mg, 0.04 mmol) in a mixture of acetonitrile (3 mL) and water (1 mL) was added lithium hydroxide (2.64 mg, 0.11 mmol). The solution was heated to 100° C. for 3 minutes before being cooled to rt, having 1 drop of TFA and DMF (1 mL) added, and the solution was concentrated to remove the acetonitrile. Purification by reverse phase chromatography 10-64% ACN/H$_2$O with 0.1% TFA yielded 6-(tert-butoxycarbonylamino)-2-[[4-[6-[(4-cyano-2-fluoro-phenyl)methoxy]-2-pyridyl]-1-piperidyl]methyl]-3-[[(2S)-oxetan-2-yl]methyl]benzimidazole-5-carboxylic acid (Example 22) as a mono TFA salt. ES/MS m/z: 671.2 (M+H$^+$); $^1$H NMR (400 MHz, CD3CN) δ 10.57 (s, 1H), 8.61 (s, 1H), 8.32 (s, 1H), 7.76-7.62 (m, 2H), 7.59-7.51 (m, 2H), 6.90 (d, J=7.3 Hz, 1H), 6.75 (d, J=8.2 Hz, 1H), 5.51 (s, 2H), 5.14 (d, J=7.3 Hz, 1H), 4.66 (s, 4H), 4.60-4.41 (m, 2H), 3.95-3.68 (m, 2H), 3.43-3.26 (m, 2H), 2.48 (s, 1H), 2.20-2.03 (m, 4H), 2.00 (d, J=2.8 Hz, 2H), 1.55 (s, 9H).

Example 25. 4-cyano-2-((4-(6-((4-cyano-2-fluorobenzyl)oxy)pyridin-2-yl)piperidin-1-yl)methyl)-1-(2-methoxyethyl)-1H-benzo[d]imidazole-6-carboxylic Acid Procedure 16

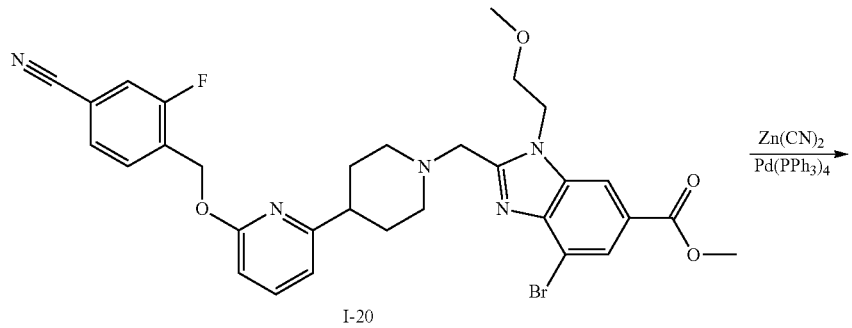

I-20

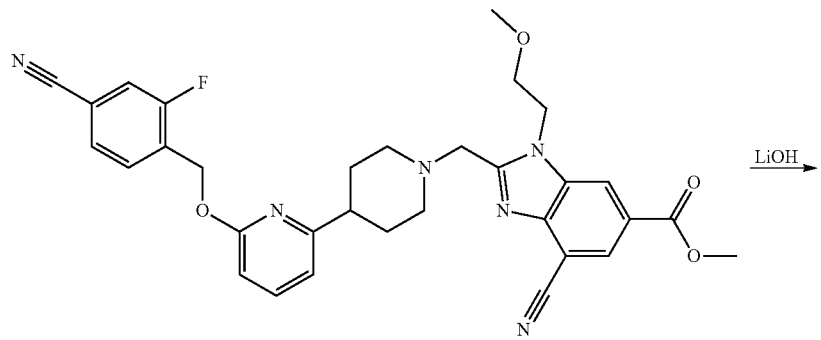

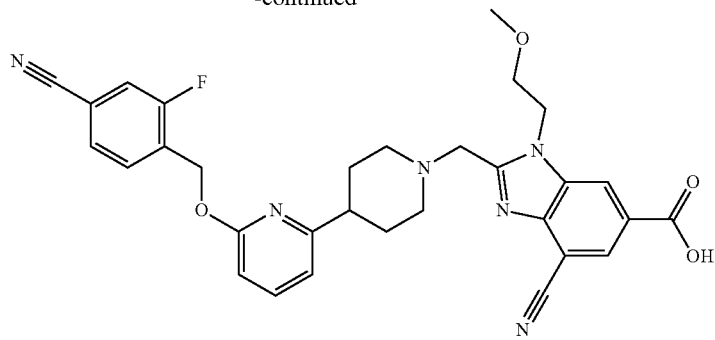

Example 25

Methyl 4-cyano-2-((4-(6-((4-cyano-2-fluorobenzyl)oxy)pyridin-2-yl)piperidin-1-yl)methyl)-1-(2-methoxyethyl)-1H-benzo[d]imidazole-6-carboxylate Methyl 4-bromo-2-((4-(6-((4-cyano-2-fluorobenzyl)oxy)pyridin-2-yl)piperidin-1-yl)methyl)-1-(2-methoxyethyl)-1H-benzo[d]imidazole-6-carboxylate (I-20) (30 mg, 0.047 mmol), tetrakis(triphenylphosphine)palladium(0) (5.5 mg, 0.0047 mmol), zinc cyanide (11.1 mg, 0.094 mmol) and NMP (1 mL) were combined in a 20 mL microwave vial under an atmosphere of argon. The mixture was heated to 150° C. for 90 minutes in a microwave reactor after which the reaction contents were poured into water (5 mL) and extracted with EtOAc (2×15 mL). The combined organic extracts were washed with brine (5 mL), dried over MgSO$_4$, and purified by silica gel chromatography (eluent: EtOAc/hexanes) to give the desired compound. ES/MS: 583.7 (M+H$^+$).

4-cyano-2-((4-(6-((4-cyano-2-fluorobenzyl)oxy)pyridin-2-yl)piperidin-1-yl)methyl)-1-(2-methoxyethyl)-1H-benzo[d]imidazole-6-carboxylic Acid (Example 25)

Example 25 was prepared from in a manner analogous to what is described for the final step of Procedure 15. ES/MS m/z: 569.7 (M+H$^+$); 1H NMR (400 MHz, Methanol-d4) δ 8.65 (d, J=1.3 Hz, 1H), 8.39 (d, J=1.3 Hz, 1H), 7.71 (td, J=7.7, 3.9 Hz, 2H), 7.62 (ddd, J=14.5, 8.9, 1.4 Hz, 2H), 6.98 (d, J=7.3 Hz, 1H), 6.82 (d, J=8.3 Hz, 1H), 5.59 (s, 2H), 4.91 (s, 2H), 4.68 (t, J=4.9 Hz, 2H), 4.08-3.87 (m, 2H), 3.77 (t, J=4.8 Hz, 2H), 3.50-3.37 (m, 2H), 3.33 (s, 3H), 3.12-3.01 (m, 1H), 2.42-2.13 (m, 4H).

Example 26. 2-((4-(6-((4-cyano-2-fluorobenzyl)oxy)pyridin-2-yl)piperidin-1-yl)methyl)-4-cyclopropyl-1-(2methoxyethyl)-1H-benzo[d]imidazole-6-carboxylic Acid Procedure 16

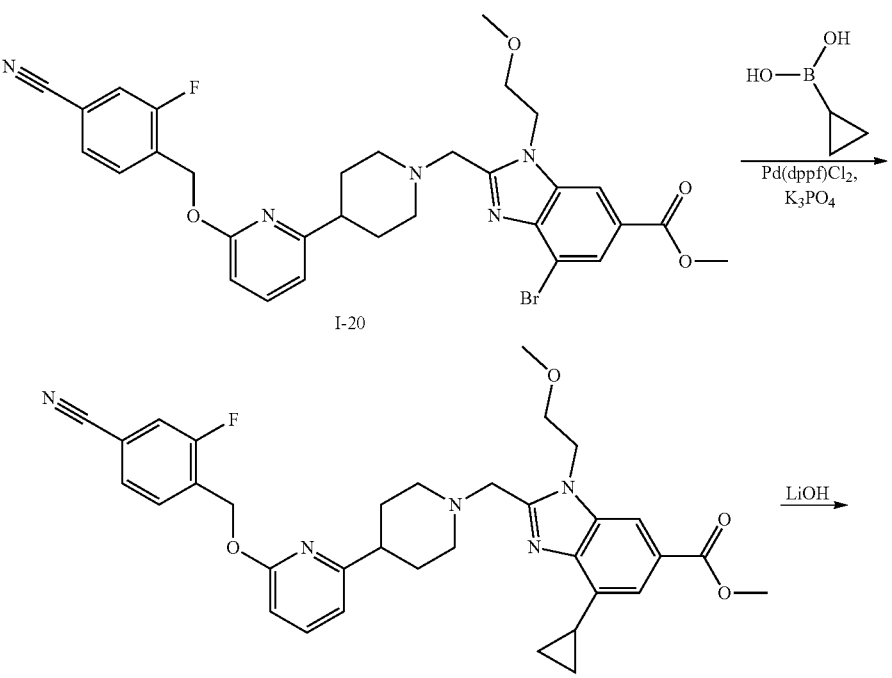

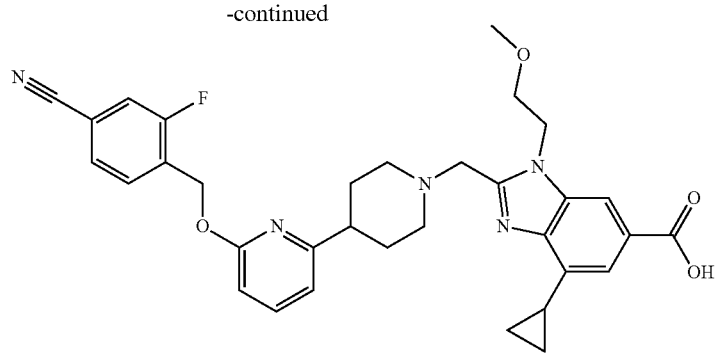

Example 26

Methyl 2-((4-(6-((4-cyano-2-fluorobenzyl)oxy)pyridin-2-yl)piperidin-1-yl)methyl)-4-cyclopropyl-1-(2-methoxyethyl)-1H-benzo[d]imidazole-6-carboxylate Methyl 4-bromo-2-((4-(6-((4-cyano-2-fluorobenzyl)oxy)pyridin-2-yl)piperidin-1-yl)methyl)-1-(2-methoxyethyl)-1H-benzo[d]imidazole-6-carboxylate (I-20) (30 mg, 0.047 mmol), 1,1'-Bis(diphenylphosphino)ferrocene dichloropalladium (II) (3.5 mg, 0.0047 mmol), cyclopropylboronic acid (8.1 mg, 0.094 mmol), $K_3PO_4$ (30 mg, 0.14 mmol) and dioxane (1 mL) were combined in a 4 mL vial under an atmosphere of argon. The mixture was heated to 90° C. for 2 hours after which the reaction contents were poured into water (5 mL) and extracted with EtOAc (2×15 mL). The combined organic extracts were washed with brine (5 mL), dried over $MgSO_4$, and concentrated to give the desired compound which was used without further purification. ES/MS: 598.5 (M+H$^+$).

2-((4-(6-((4-cyano-2-fluorobenzyl)oxy)pyridin-2-yl)piperidin-1-yl)methyl)-4-cyclopropyl-1-(2-methoxyethyl)-1H-benzo[d]imidazole-6-carboxylic Acid
(Example 26)

Example 26 was prepared in a manner analogous to what is described for the final step of Procedure 15. ES/MS m/z: 584.4 (M+H$^+$); 1H NMR (400 MHz, Methanol-d4) δ 8.10 (d, J=1.5 Hz, 1H), 7.71 (dd, J=8.3, 7.3 Hz, 2H), 7.66-7.52 (m, 3H), 6.98 (d, J=7.3 Hz, 1H), 6.81 (dd, J=8.3, 0.7 Hz, 1H), 5.57 (s, 2H), 4.82 (s, 2H), 4.61 (t, J=4.8 Hz, 2H), 3.95 (d, J=12.3 Hz, 2H), 3.76 (dd, J=5.3, 4.2 Hz, 2H), 3.49-3.38 (m, 2H), 3.33 (s, 3H), 3.09 (p, J=7.7 Hz, 1H), 2.70-2.56 (m, 1H), 2.23 (q, J=5.4, 5.0 Hz, 4H), 1.21-1.12 (m, 2H), 1.12-1.02 (m, 2H).

Example 27. 2-((4-(6-((4-cyano-2-fluorobenzyl)oxy)pyridin-2-yl)piperidin-1-yl)methyl)-1-(2-methoxyethyl)-4-(methoxymethyl)-1H-benzo[d]imidazole-6-carboxylic Acid Procedure 18

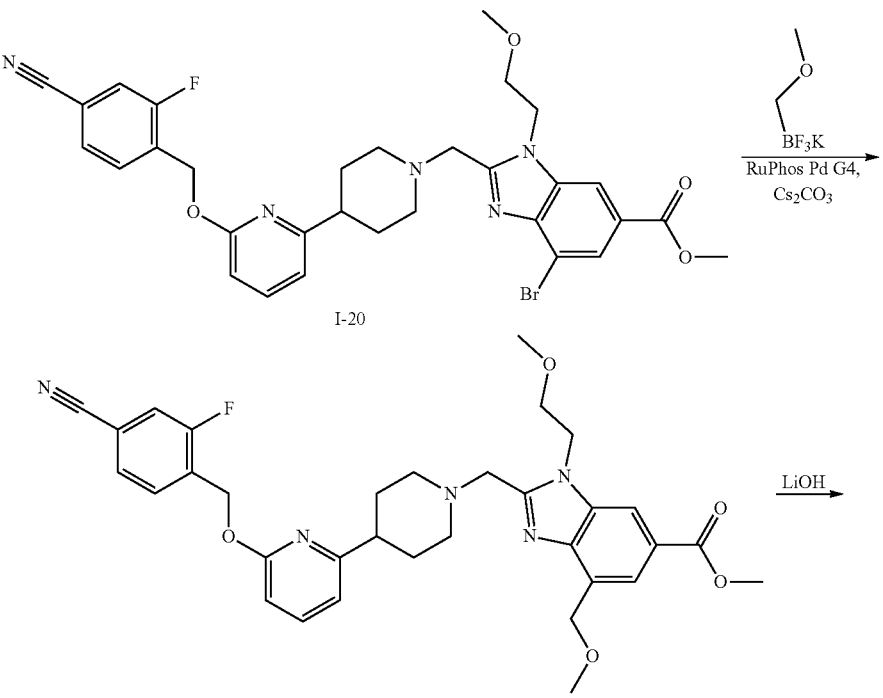

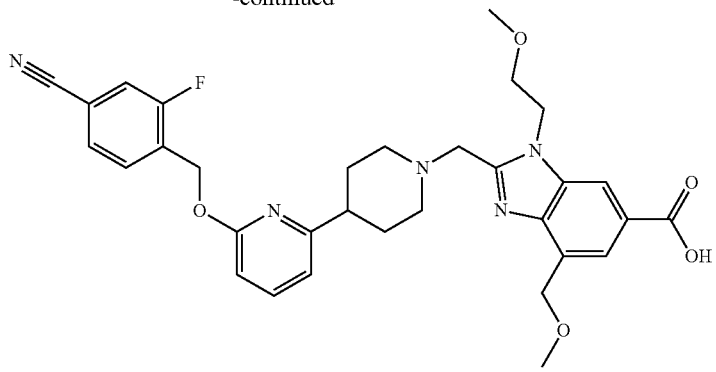

Example 27

Methyl 2-((4-(6-((4-cyano-2-fluorobenzyl)oxy)pyridin-2-yl)piperidin-1-yl)methyl)-1-(2-methoxyethyl)-4-(methoxymethyl)-1H-benzo[d]imidazole-6-carboxylate Methyl 4-bromo-2-((4-(6-((4-cyano-2-fluorobenzyl)oxy)pyridin-2-yl)piperidin-1-yl)methyl)-1-(2-methoxyethyl)-1H-benzo[d]imidazole-6-carboxylate (I-20) (30 mg, 0.047 mmol), RuPhos Pd G4 (12 mg, 0.014 mmol), Potassium (Methoxymethyl)trifluoroborate (71.6 mg, 0.47 mmol), $Cs_2CO_3$ (46 mg, 0.14 mmol), dioxane (1 mL) and water (0.1 mL) were combined in a 4 mL vial under an atmosphere of argon. The mixture was heated to 90° C. for 2 hours after which the reaction contents were poured into water (5 mL) and extracted with EtOAc (2×15 mL). The combined organic extracts were washed with brine (5 mL), dried over $MgSO_4$, and concentrated to give the desired compound which was used without further purification. ES/MS: 602.5 (M+H⁺).

2-((4-(6-((4-cyano-2-fluorobenzyl)oxy)pyridin-2-yl)piperidin-1-yl)methyl)-1-(2-methoxyethyl)-4-(methoxymethyl)-1H-benzo[d]imidazole-6-carboxylic Acid (Example 27)

Example 27 was prepared in a manner analogous to what is described for the final step of Procedure 15. ES/MS m/z: 588.5 (M+H⁺); 1H NMR (400 MHz, Methanol-d4) δ 8.30 (d, J=1.5 Hz, 1H), 8.06 (d, J=1.4 Hz, 1H), 7.78-7.66 (m, 2H), 7.66-7.53 (m, 2H), 6.98 (d, J=7.3 Hz, 1H), 6.88-6.75 (m, 1H), 5.58 (s, 2H), 4.96 (s, 2H), 4.84 (s, 2H), 4.63 (t, J=4.8 Hz, 2H), 3.92 (d, J=12.3 Hz, 2H), 3.85-3.71 (m, 2H), 3.49 (s, 3H), 3.47-3.40 (m, 2H), 3.32 (s, 3H), 3.14-3.01 (m, 1H), 2.40-2.15 (m, 4H).

Example 28. 2-((4-(6-((4-cyano-2-fluorobenzyl)oxy)pyridin-2-yl)piperidin-1-yl)methyl)-1-(2-methoxyethyl)-4-methyl-1H-benzo[d]imidazole-6-carboxylic Acid Procedure 19

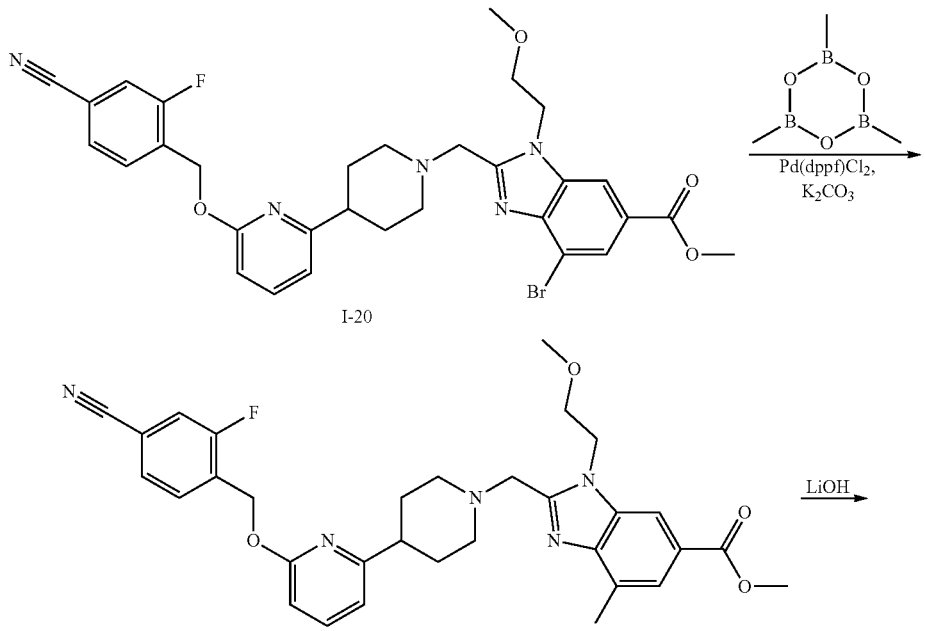

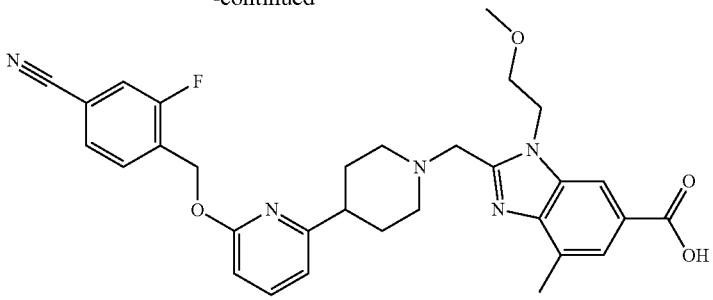

Example 28

Methyl 2-((4-(6-((4-cyano-2-fluorobenzyl)oxy)pyridin-2-yl)piperidin-1-yl)methyl)-1-(2-methoxyethyl)-4-methyl-1H-benzo[d]imidazole-6-carboxylate Methyl 4-bromo-2-((4-(6-((4-cyano-2-fluorobenzyl)oxy)pyridin-2-yl)piperidin-1-yl)methyl)-1-(2-methoxyethyl)-1H-benzo[d]imidazole-6-carboxylate (I-20) (30 mg, 0.047 mmol), 1,1'-Bis(diphenylphosphino)ferrocene dichloropalladium (II) (6.9 mg, 0.0094 mmol), 2,4,6-trimethyl-1,3,5,2,4,6-trioxatriborinane (11.8 mg, 0.094 mmol), K$_2$CO$_3$ (16.3 mg, 0.12 mmol), and dioxane (1.5 mL) were combined in a 4 mL vial under an atmosphere of argon. The mixture was heated to 90° C. for 2 hours after which the reaction contents were poured into water (5 mL) and extracted with EtOAc (2×15 mL). The combined organic extracts were washed with brine (5 mL), dried over MgSO$_4$, and concentrated to give the desired compound which was used without further purification. ES/MS: 572.7 (M+H$^+$).

2-((4-(6-((4-cyano-2-fluorobenzyl)oxy)pyridin-2-yl)piperidin-1-yl)methyl)-1-(2-methoxyethyl)-4-methyl-1H-benzo[d]imidazole-6-carboxylic Acid (Example 28)

Example 28 was prepared in a manner analogous to what is described for the final step of Procedure 15. ES/MS m/z: 558.6 (M+H$^+$); 1H NMR (400 MHz, Methanol-d4) δ 8.16 (t, J=1.0 Hz, 1H), 7.85 (t, J=1.2 Hz, 1H), 7.71 (ddd, J=8.3, 7.2, 1.6 Hz, 2H), 7.64-7.54 (m, 2H), 6.97 (d, J=7.3 Hz, 1H), 6.81 (dd, J=8.3, 0.7 Hz, 1H), 5.57 (s, 2H), 4.81 (s, 2H), 4.62 (t, J=4.8 Hz, 2H), 3.92 (d, J=12.4 Hz, 2H), 3.83-3.72 (m, 2H), 3.48-3.38 (m, 2H), 3.33 (s, 3H), 3.08 (p, J=7.7 Hz, 1H), 2.70 (s, 3H), 2.32-2.14 (m, 4H).

Example 29. 2-((4-(6-((4-cyano-2-fluorobenzyl)oxy)pyridin-2-yl)piperidin-1-yl)methyl)-1-(2-methoxyethyl)-4-(1-methyl-1H-pyrazol-4-yl)-1H-benzo[d]imidazole-6-carboxylic Acid Procedure 20

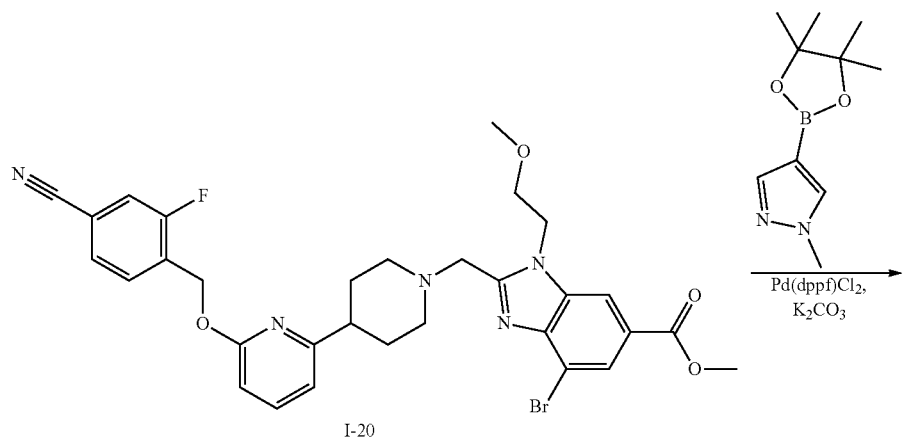

-continued

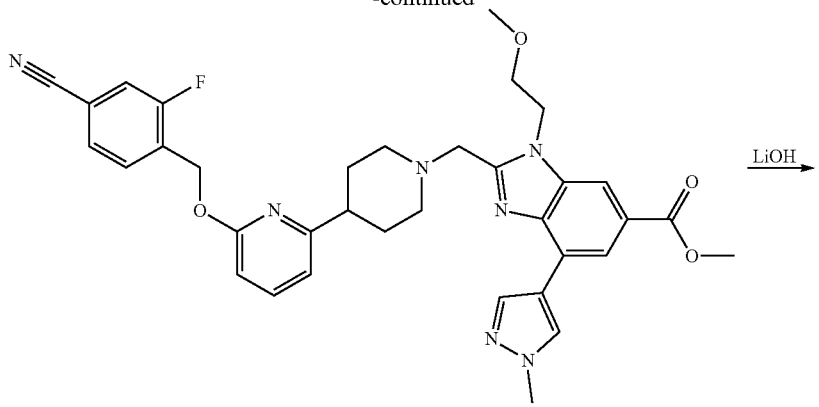

→ LiOH

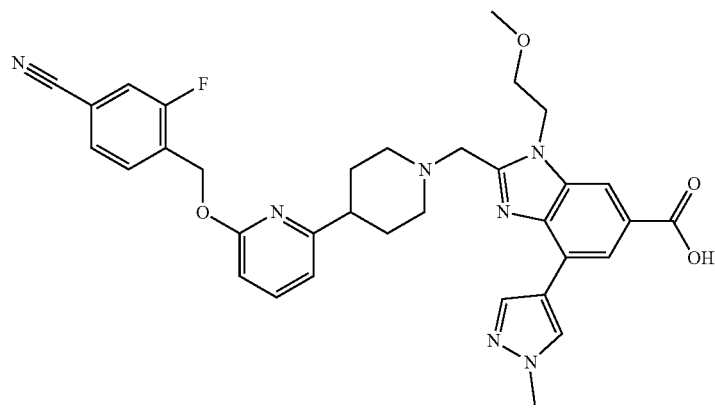

Example 29

Methyl 2-((4-(6-((4-cyano-2-fluorobenzyl)oxy)pyridin-2-yl)piperidin-1-yl)methyl)-1-(2-methoxyethyl)-4-(1-methyl-1H-pyrazol-4-yl)-1H-benzo[d]imidazole-6-carboxylate Methyl 4-bromo-2-((4-(6-((4-cyano-2-fluorobenzyl)oxy)pyridin-2-yl)piperidin-1-yl)methyl)-1-(2-methoxyethyl)-1H-benzo[d]imidazole-6-carboxylate (I-20) (30 mg, 0.047 mmol), 1,1'-Bis(diphenylphosphino)ferrocene dichloropalladium (II) (6.9 mg, 0.0094 mmol), 1-Methyl-4-(4,4,5,5-tetramethyl-1,3,2-dioxaborolan-2-yl)-1H-pyrazole, (14.7 mg, 0.071 mmol), $K_2CO_3$ (19.5 mg, 0.14 mmol), water (0.15 mL) and dioxane (1.5 mL) were combined in a 4 mL vial under an atmosphere of argon. The mixture was heated to 90° C. for 2 hours after which the reaction contents were poured into water (5 mL) and extracted with EtOAc (2×15 mL). The combined organic extracts were washed with brine (5 mL), dried over $MgSO_4$, and concentrated to give the desired compound which was used without further purification. ES/MS: 638.4 (M+H$^+$).

2-((4-(6-((4-cyano-2-fluorobenzyl)oxy)pyridin-2-yl)piperidin-1-yl)methyl)-1-(2-methoxyethyl)-4-(1-methyl-1H-pyrazol-4-yl)-1H-benzo[d]imidazole-6-carboxylic Acid (Example 29)

Example 29 was prepared in a manner analogous to what is described for the final step of Procedure 15. ES/MS m/z: 624.4 (M+H$^+$); 1H NMR (400 MHz, Methanol-d4) δ 8.52 (s, 1H), 8.42 (s, 1H), 8.24 (d, J=1.4 Hz, 1H), 8.17 (d, J=1.4 Hz, 1H), 7.72 (dd, J=8.2, 7.2 Hz, 2H), 7.66-7.54 (m, 2H), 6.99 (d, J=7.3 Hz, 1H), 6.82 (dd, J=8.3, 0.7 Hz, 1H), 5.56 (s, 2H), 4.89 (s, 2H), 4.64 (t, J=4.8 Hz, 2H), 4.04-3.98 (m, 2H), 4.01 (s, 3H), 3.85-3.74 (m, 2H), 3.56-3.43 (m, 2H), 3.33 (s, 3H), 3.14-3.06 (m, 2H), 2.37-2.17 (m, 4H).

Example 30. 2-[[4-[6-[(4-cyano-2-fluoro-phenyl)methoxy]-2-pyridyl]-1-piperidyl]methyl]-6-(1-methylpyrazol-3-yl)-3-[[(2S)-oxetan-2-yl]methyl]benzimidazole-5-carboxylic Acid

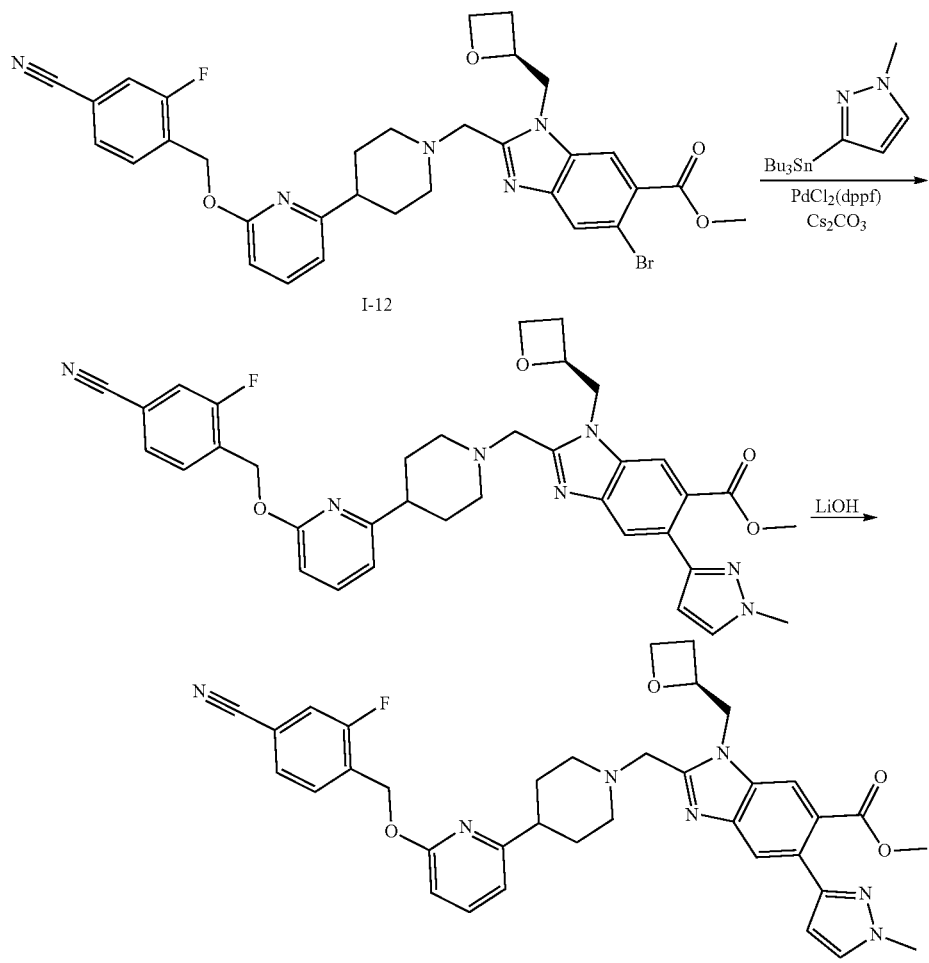

Example 30

Methyl 2-[[4-[6-[(4-cyano-2-fluoro-phenyl)methoxy]-2-pyridyl]-1-piperidyl]methyl]-6-(1-methylpyrazol-3-yl)-3-[[(2S)-oxetan-2-yl]methyl]benzimidazole-5-carboxylate To a 2 mL microwave vial containing DMF (4 mL) was added methyl 6-bromo-2-[[4-[6-[(4-cyano-2-fluoro-phenyl)methoxy]-2-pyridyl]-1-piperidyl]methyl]-3-[[(2S)-oxetan-2-yl]methyl]benzimidazole-5-carboxylate (60.0 mg, 0.09 mmol), tributyl-(1-methylpyrazol-3-yl)stannane (56.0 mg, 0.15 mmol), cesium carbonate (90.0 mg, 0.28 mmol), and [1,1'-Bis(diphenylphosphino)ferrocene] dichloropalladium (II) (6.60 mg, 0.009 mmol). Argon was bubbled through this mixture for 5 minutes followed by heating to 100° C. for 30 minutes. The mixture was diluted with EtOAc, filtered, concentrated, and purified by SiO₂ column chromatography with a gradient of 5-10% DCM/MeOH to yield methyl 2-[[4-[6-[(4-cyano-2-fluoro-phenyl)methoxy]-2-pyridyl]-1-piperidyl]methyl]-6-(1-methylpyrazol-3-yl)-3-[[(2S)-oxetan-2-yl]methyl]benzimidazole-5-carboxylate. ES/MS m/z: 650.2 (M+H⁺).

2-[[4-[6-[(4-cyano-2-fluoro-phenyl)methoxy]-2-pyridyl]-1-piperidyl]methyl]-6-(1-methylpyrazol-3-yl)-3-[[(2S)-oxetan-2-yl]methyl]benzimidazole-5-carboxylic Acid (Example 30)

To a solution of methyl 2-[[4-[6-[(4-cyano-2-fluoro-phenyl)methoxy]-2-pyridyl]-1-piperidyl]methyl]-6-(1-methylpyrazol-3-yl)-3-[[(2S)-oxetan-2-yl]methyl]benzimidazole-5-carboxylate (11.5 mg, 0.02 mmol) in a mixture of acetonitrile (3 mL) and water (1 mL) was added lithium hydroxide (1.27 mg, 0.05 mmol). The solution was heated to 100° C. for 20 minutes before being cooled to rt, having 1 drop of TFA and DMF (1 mL) added, and the solution was concentrated to remove the acetonitrile. Purification by reverse phase chromatography 10-48% ACN/H₂O with 0.1% TFA. Product containing fractions were combined and diluted with EtOAc. The aqueous layer was neutralized with sodium bicarbonate. When the layers were separated the product was not observed in the organic layer. A solid precipitated from the aqueous layer. The aqueous layer was passed through a membrane filter to yield 2-[[4-[6-[(4-cyano-2-fluoro-phenyl)methoxy]-2-pyridyl]-1-piperidyl]methyl]-6-(1-methylpyrazol-3-yl)-3-[[(2S)-oxetan-2-yl]methyl]benzimidazole-5-carboxylic acid (Example 30). ES/MS m/z: 636.2 (M+H$^+$); $^1$H NMR (400 MHz, DMSO) δ 7.90 (d, J=10.2 Hz, 2H), 7.71 (d, J=2.8 Hz, 2H), 7.65 (dd, J=8.2, 7.3 Hz, 1H), 7.56 (s, 2H), 7.53 (s, 1H), 6.89 (d, J=7.3 Hz, 1H), 6.72 (d, J=8.2 Hz, 1H), 5.48 (s, 2H), 5.10 (d, J=6.9 Hz, 1H), 4.65 (s, 2H), 4.57 (d, J=13.9 Hz, 1H), 4.49 (q, J=7.2 Hz, 1H), 4.39 (dt, J=9.1, 5.9 Hz, 1H), 3.88 (d, J=13.4 Hz, 1H), 3.74 (d, J=13.3 Hz, 1H), 3.66 (s, 3H), 2.97 (d, J=11.3 Hz, 1H), 2.85 (d, J=11.2 Hz, 1H), 2.59 (s, 1H), 2.26-2.09 (m, 2H), 1.86-1.61 (m, 5H).

Example 31. 2-(((1s,4s)-4-(6-((4-cyano-2-fluorobenzyl)oxy)pyridin-2-yl)cyclohexyl)methyl)-1-(2-methoxyethyl)-4-(1-methyl-1H-pyrazol-3-yl)-1H-benzo[d]imidazole-6-carboxylic Acid Example 32. 2-(((1r,4r)-4-(6-((4-cyano-2-fluorobenzyl)oxy)pyridin-2-yl)cyclohexyl)methyl)-1-(2-methoxyethyl)-4-(1-methyl-1H-pyrazol-3-yl)-1H-benzo[d]imidazole-6-carboxylic Acid Procedure 22

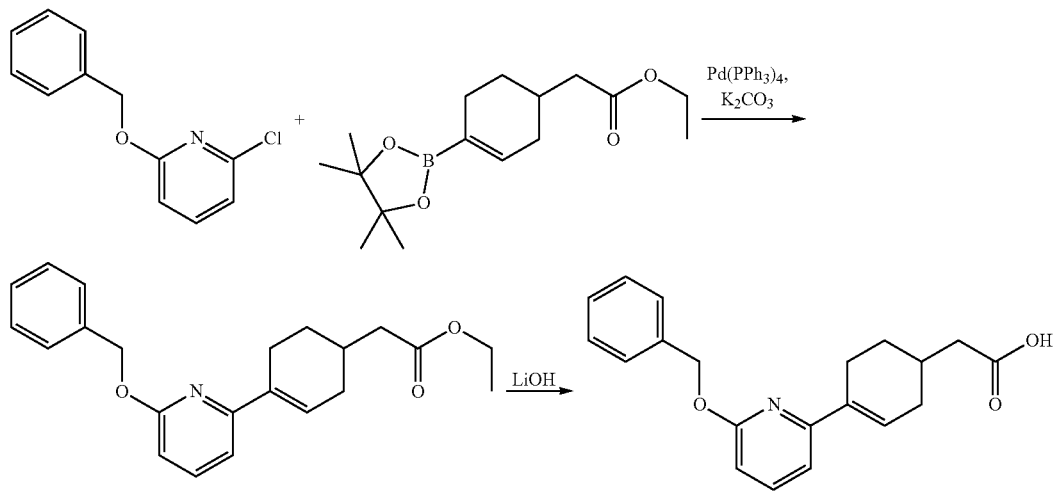

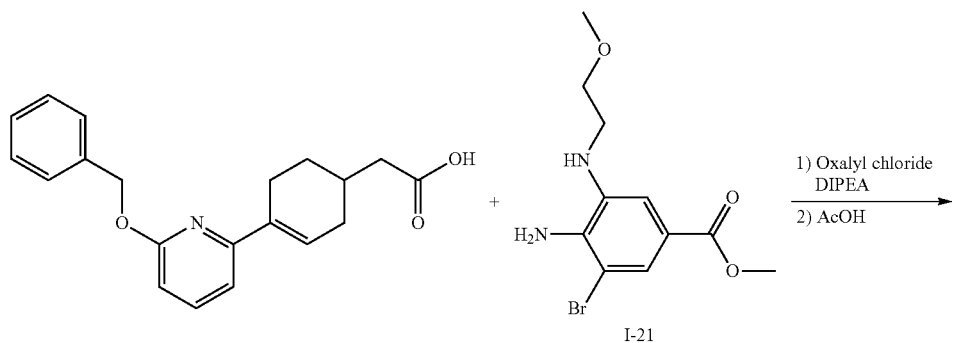

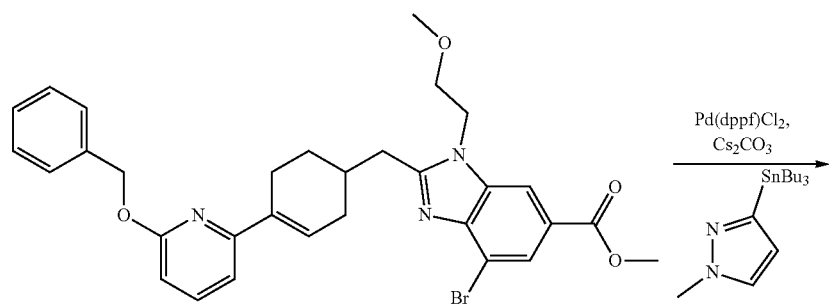

-continued
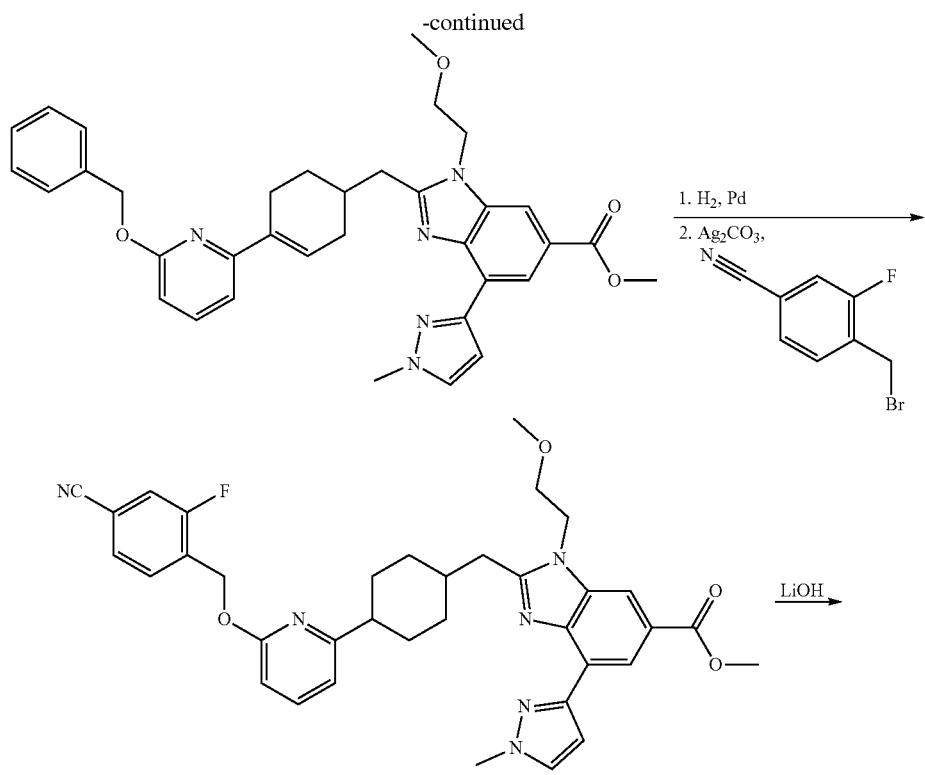
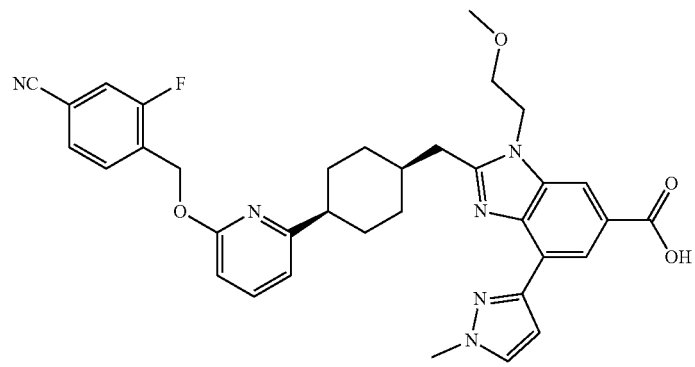
Example 31
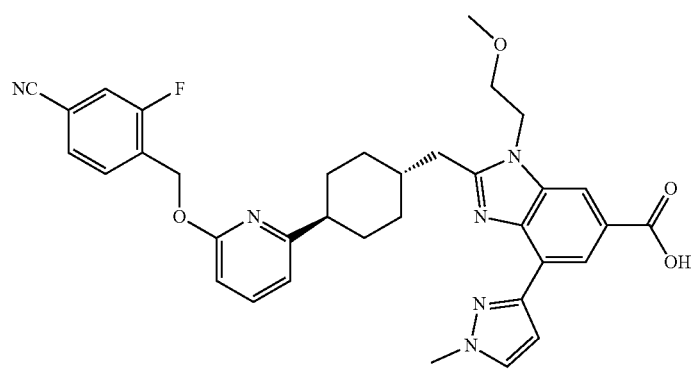
Example 32

Ethyl 2-(4-(6-(benzyloxy)pyridin-2-yl)cyclohex-3-en-1-yl)acetate

To a solution/suspension of ethyl 2-[4-(4,4,5,5-tetramethyl-1,3,2-dioxaborolan-2-yl)cyclohex-3-en-1-yl]acetate (2.00 g, 6.80 mmol), 2-benzyloxy-6-chloro-pyridine (1568 mg, 7.14 mmol), potassium carbonate (2M, 7.1 mL, 14.2 mmol) in 1,4-dioxane (12 mL) in a 20 mL microwave vial was added tetrakis(triphenylphosphine)palladium (413 mg, 0.36 mmol) after which the argon was bubbled through the reaction mixture for 2 minutes, the vial sealed and placed in a 140° C. heating block for 30 minutes. Upon completion the reaction contents were poured into water (20 mL) and extracted with EtOAc (2×50 mL). The combined organic extracts were washed with brine (20 mL), dried over MgSO$_4$, concentrated and purified by silica gel chromatography (eluent: EtOAc/hexanes) to give the desired compound. ES/MS m/z: 352.4 (M+H$^+$).

2-(4-(6-(benzyloxy)pyridin-2-yl)cyclohex-3-en-1-yl)acetic Acid

To a solution of ethyl 2-(4-(6-(benzyloxy)pyridin-2-yl)cyclohex-3-en-1-yl)acetate (1.20 g, 3.41 mmol) in acetonitrile (40 mL) was added lithium hydroxide (164 mg, 6.83 mmol) as a solution in water (8 mL) and the resultant mixture placed in a 100° C. heating block for 10 minutes. Upon completion EtOAc (30 mL) was added to the reaction mixture and the solid filtered and washed with EtOAc (1×10 mL). The resultant solid was used without further purification. ES/MS m/z: 324.2 (M+H$^+$).

Methyl 2-((4-(6-(benzyloxy)pyridin-2-yl)cyclohex-3-en-1-yl)methyl)-4-bromo-1-(2-methoxyethyl)-1H-benzo[d]imidazole-6-carboxylate To a suspension of 2-(4-(6-(benzyloxy)pyridin-2-yl)cyclohex-3-en-1-yl)acetic acid (150 mg, 0.46 mmol) in DCM (3 mL) was added oxalyl chloride (2M, 0.70 mL, 1.39 mmol) and the resultant mixture stirred at room temperature for 15 minutes. The mixture was concentrated directly and dried on a vacuum to produce the acyl chloride as a foam. The acyl chloride was then dissolved/suspended in DCM (2 mL) after which a separate solution of methyl 4-amino-3-bromo-5-((2-methoxyethyl)amino)benzoate (155 mg, 0.51 mmol) and diisopropylethylamine (0.33 mL, 1.86 mmol) in DCM (2 mL) was then added and the resultant mixture stirred at room temperature for 30 minutes. Upon completion the reaction contents were poured into water (10 mL) and extracted with EtOAc (2×25 mL). The combined organic extracts were washed with brine (5 mL), dried over MgSO$_4$, concentrated and purified by silica gel chromatography (eluent: EtOAc/hexanes) to give the amide product. This was then dissolved in neat acetic acid (4 mL) and placed in an 80° C. heating block for 4 hrs. Upon completion the reaction content were diluted with EtOAc (50 mL), washed with water (3×15 mL) and saturated aqueous NaHCO$_3$ (1×15 mL). The organic layer was dried over MgSO$_4$, concentrated and purified by silica gel chromatography (eluent: EtOAc/hexanes) to give the desired product. ES/MS m/z: 590.7 (M+H$^+$).

Methyl 2-((4-(6-(benzyloxy)pyridin-2-yl)cyclohex-3-en-1-yl)methyl)-1-(2-methoxyethyl)-4-(1-methyl-1H-pyrazol-3-yl)-1H-benzo[d]imidazole-6-carboxylate To a solution/suspension of methyl 2-((4-(6-(benzyloxy)pyridin-2-yl)cyclohex-3-en-1-yl)methyl)-4-bromo-1-(2-methoxyethyl)-1H-benzo[d]imidazole-6-carboxylate (81 mg, 0.14 mmol), tributyl-(1-methylpyrazol-3-yl)stannane (75 mg, 0.20 mmol), cesium carbonate (134 mg, 0.41 mmol) in DMF (1 mL) in a 2 mL microwave vial was added (1,1'-bis(diphenylphosphino)ferrocene)-dichloropalladium (II) (19.4 mg, 0.027 mmol) after which the argon was bubbled through the mixture for 2 minutes, the vial sealed and heated to 110° C. in a microwave reactor for 30 minutes. Upon completion the reaction contents were poured into water (5 mL) and extracted with EtOAc (2×15 mL). The combined organic extracts were washed with brine (5 mL), dried over MgSO$_4$, concentrated and purified by silica gel chromatography (eluent: EtOAc/hexanes) to give the desired compound. ES/MS m/z: 592.7 (M+H$^+$).

Methyl 2-((4-(6-((4-cyano-2-fluorobenzyl)oxy)pyridin-2-yl)cyclohexyl)methyl)-1-(2-methoxyethyl)-4-(1-methyl-1H-pyrazol-3-yl)-1H-benzo[d]imidazole-6-carboxylate To a solution of methyl 2-((4-(6-(benzyloxy)pyridin-2-yl)cyclohex-3-en-1-yl)methyl)-1-(2-methoxyethyl)-4-(1-methyl-1H-pyrazol-3-yl)-1H-benzo[d]imidazole-6-carboxylate (50 mg, 0.085 mmol) in a mixture of EtOAc (2 mL) and EtOH (4 mL) was added palladium on carbon (5%, 36 mg. 0.017 mmol). The resulting solution was stirred at room temperature under an atmosphere of hydrogen for 1 hour. The slurry was filtered through Celite, concentrated to dryness. The crude product was dissolved in toluene (2 mL) after which silver carbonate (71 mg, 0.25 mmol) and 4-(bromomethyl)-3-fluoro-benzonitrile (27.4 mg, 0.13 mmol) were added and the resultant mixture heated to 80° C. for 16 hrs. Upon completion the reaction content were diluted with EtOAc (50 mL), washed with water (3×15 mL) and saturated aqueous NaHCO$_3$ (1×15 mL). The organic layer was dried over MgSO$_4$, concentrated and purified by silica gel chromatography (eluent: EtOAc/hexanes) to give the desired product. ES/MS m/z: 637.8 (M+H$^+$).

2-(((1s,4s)-4-(6-((4-cyano-2-fluorobenzyl)oxy)pyridin-2-yl)cyclohexyl)methyl)-1-(2-methoxyethyl)-4-(1-methyl-1H-pyrazol-3-yl)-1H-benzo[d]imidazole-6-carboxylic acid (Example 31) and 2-(((1r,4r)-4-(6-((4-cyano-2-fluorobenzyl)oxy)pyridin-2-yl)cyclohexyl)methyl)-1-(2-methoxyethyl)-4-(1-methyl-1H-pyrazol-3-yl)-1H-benzo[d]imidazole-6-carboxylic Acid (Example 32)

Examples 31 and 32 were prepared in a manner analogous to what is described for the final step of Procedure 15. The two products separated upon purification with reverse phase preparative HPLC (eluent: ACN/H$_2$O with 0.1% TFA) with the trans isomer eluting first.

Example 31. ES/MS m/z: 623.7 (M+H$^+$). 1H NMR (400 MHz, DMSO-d6) δ 8.44 (d, J=1.5 Hz, 1H), 8.16 (s, 1H), 7.96-7.85 (m, 1H), 7.82 (d, J=2.2 Hz, 1H), 7.70 (dd, J=3.7, 1.0 Hz, 2H), 7.64 (dd, J=8.2, 7.3 Hz, 1H), 7.36 (s, 1H), 6.87 (d, J=7.3 Hz, 1H), 6.71 (d, J=8.2 Hz, 1H), 5.46 (s, 2H), 4.60 (s, 2H), 3.98 (s, 3H), 3.71 (t, J=5.0 Hz, 2H), 3.22 (s, 3H), 3.02 (s, 2H), 2.63-2.55 (m, 1H), 2.08 (s, 1H), 2.07-1.99 (m, 1H), 1.95-1.78 (m, 4H), 1.59-1.42 (m, 2H), 1.30 (q, J=12.8 Hz, 2H).

Example 32. ES/MS m/z: 623.6 (M+H$^+$). 1H NMR (400 MHz, DMSO-d6) δ 8.43 (d, J=1.5 Hz, 1H), 8.18 (s, 1H), 7.94-7.87 (m, 1H), 7.81 (d, J=2.2 Hz, 1H), 7.78-7.61 (m, 3H), 7.42-7.25 (m, 1H), 6.99 (d, J=7.3 Hz, 1H), 6.75 (d, J=8.2 Hz, 1H), 5.52 (s, 2H), 4.59 (d, J=5.5 Hz, 2H), 3.97 (s, 3H), 3.69 (t, J=5.0 Hz, 2H), 3.18 (s, 3H), 3.09 (d, J=7.3 Hz, 2H), 2.77 (s, 1H), 2.40 (s, 1H), 2.00 (d, J=7.7 Hz, 2H), 1.75-1.48 (m, 6H).

TABLE 2

| Ex. | Structure | Procedure | ES/MS m/z | ¹H NMR |
|---|---|---|---|---|
| 1 | 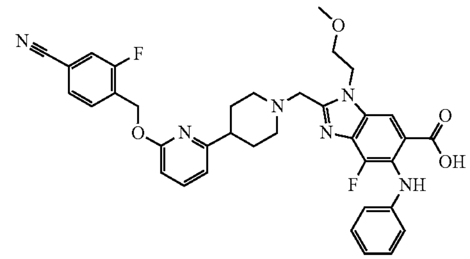 [SMILES: COCCn1c(CN2CCC(c3cccc(OCc4ccc(C#N)cc4F)n3)CC2)nc2c(F)c(Nc3ccccc3)c(C(=O)O)cc21] | 1 | 653.4 | 1H NMR (400 MHz, MeOD) δ 8.22 (s, 1H), 7.76 – 7.67 (m, 2H), 7.65 – 7.56 (m, 2H), 7.26 – 7.18 (m, 2H), 6.98 (d, J = 7.3 Hz, 1H), 6.93 – 6.87 (m, 1H), 6.87 – 6.83 (m, 2H), 6.81 (d, J = 8.2 Hz, 1H), 5.58 (s, 2H), 4.84 (s, 2H), 4.62 (t, J = 4.8 Hz, 2H), 3.94 (s, 2H), 3.78 (t, J = 4.7 Hz, 2H), 3.44 (s, 2H), 3.36 (s, 3H), 3.09 (s, 1H), 2.26 (d, J = 18.3 Hz, 4H). |
| 2 | 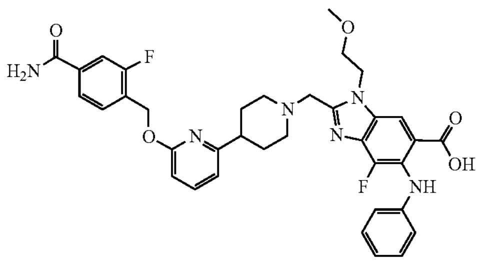 [SMILES: COCCn1c(CN2CCC(c3cccc(OCc4ccc(C(N)=O)cc4F)n3)CC2)nc2c(F)c(Nc3ccccc3)c(C(=O)O)cc21] | 1 | 671.2 | 1H NMR (400 MHz, MeOD) δ 8.16 (s, 1H), 7.64 (t, J = 8.5 Hz, 2H), 7.56 (dd, J = 14.4, 6.5 Hz, 2H), 7.16 (t, J = 7.8 Hz, 2H), 6.90 (d, J = 7.4 Hz, 1H), 6.87 – 6.76 (m, 3H), 6.74 (d, J = 8.3 Hz, 1H), 5.50 (s, 2H), 4.76 (s, 2H), 4.56 (s, 2H), 3.87 (s, 2H), 3.72 (s, 2H), 3.42 – 3.34 (m, 2H), 3.30 (d, J = 2.5 Hz, 3H), 3.03 (s, 1H), 2.19 (s, 4H). |
| 3 | 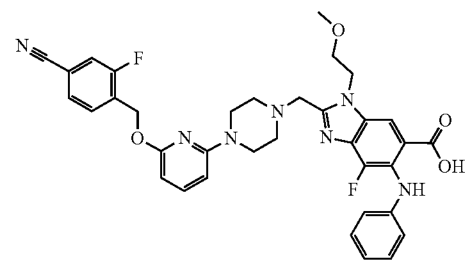 | 2 | 654.7 | 1H NMR (400 MHz, MeOD) δ 8.22 (d, J = 0.9 Hz, 1H), 7.68 (t, J = 7.5 Hz, 1H), 7.63 – 7.54 (m, 3H), 7.27 – 7.17 (m, 2H), 6.90 (tt, J = 7.4, 1.1 Hz, 1H), 6.85 (dq, J = 8.5, 1.1 Hz, 2H), 6.46 (d, J = 8.0 Hz, 1H), 6.31 (d, J = 7.9 Hz, 1H), 5.49 (s, 2H), 4.76 (s, 2H), 4.61 (t, J = 4.8 Hz, 2H), 3.85 (s, 4H), 3.80 – 3.73 (m, 2H), 3.52 (d, J = 6.2 Hz, 4H), 3.34 (s, 3H). |
| 4 | 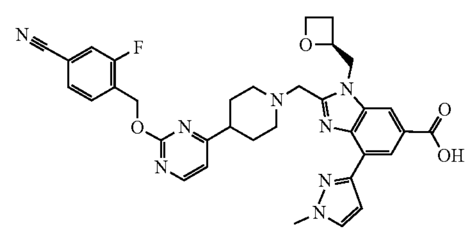 [SMILES: Cn1ccc(-c2cc(C(=O)O)cc3c2nc(CN2CCC(c4ccnc(OCc5ccc(C#N)cc5F)n4)CC2)n3C[C@@H]2CCO2)n1] | 3 | 637.2 | ¹H NMR (400 MHz, MeOH-d4) δ 8.59 – 8.51 (m, 2H), 8.28 (d, J = 1.5 Hz, 1H), 7.80 – 7.71 (m, 2H), 7.66 – 7.57 (m, 2H), 7.33 (d, J = 2.3 Hz, 1H), 7.16 (d, J = 5.1 Hz, 1H), 5.62 (s, 2H), 5.25 (qd, J = 7.0, 2.4 Hz, 1H), 4.95 (s, 2H), 4.79 (dd, J = 15.8, 6.7 Hz, 1H), 4.75 – 4.63 (m, 2H), 4.45 (dt, J = 9.3, 5.9 Hz, 1H), 4.04 (s, 3H), 4.04 – 3.90 (m, 2H), 3.58 – 3.40 (m, 2H), 3.17 (tt, J = 10.3, 4.7 Hz, 1H), 2.83 (dtd, J = 11.5, 8.2, 6.0 Hz, 1H), 2.52 (ddt, J = 11.5, 9.2, 7.4 Hz, 1H), 2.27 (d, J = 10.5 Hz, 4H). |
| 5 | 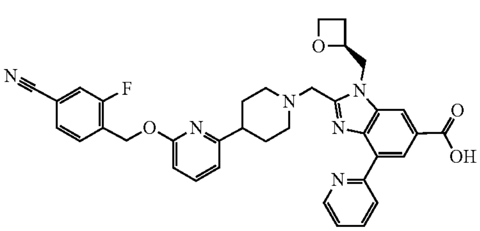 [SMILES: N#Cc1ccc(COc2cccc(C3CCN(Cc4nc5c(-c6ccccn6)cc(C(=O)O)cc5n4C[C@@H]4CCO4)CC3)n2)c(F)c1] | 4 | 633.2 | 1H NMR (400 MHz, DMSO-d6) δ 9.03 (d, J = 8.0 Hz, 1H), 8.87 (d, J = 1.5 Hz, 1H), 8.81 – 8.75 (m, 1H), 8.45 (d, J = 1.6 Hz, 1H), 7.97 (td, J = 7.8, 1.9 Hz, 1H), 7.91 (d, J = 9.9 Hz, 1H), 7.74 (d, J = 5.8 Hz, 3H), 7.48 – 7.42 (m, 1H), 6.97 (d, J = 7.4 Hz, 1H), 6.81 (d, J = 8.2 Hz, 1H), 5.50 (s, 2H), 5.13 – 5.04 (m, 1H), 4.93 (m, 3H), 4.78 (m, 2H), 2.96 (m, 1H), 2.75 (m, 1H), 2.39 (m, 2H), 2.08 (m, 5H). |
| 6 | 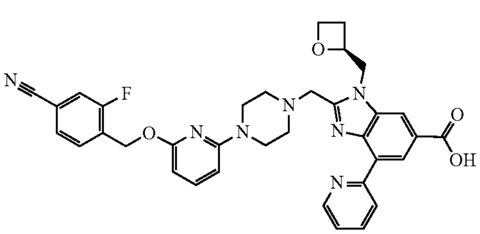 [SMILES: N#Cc1ccc(COc2cccc(N3CCN(Cc4nc5c(-c6ccccn6)cc(C(=O)O)cc5n4C[C@@H]4CCO4)CC3)n2)c(F)c1] | 4 | 634.2 | Multiplet Report 1H NMR (400 MHz, DMSO-d6) δ 9.01 (d, J = 7.9 Hz, 1H), 8.86 (d, J = 1.6 Hz, 1H), 8.82 – 8.72 (m, 1H), 8.45 (d, J = 1.6 Hz, 1H), 7.99 (td, J = 7.8, 1.8 Hz, 1H), 7.90 – 7.83 (m, 1H), 7.74 – 7.63 (m, 2H), 7.58 (t, J = 8.0 Hz, 1H), 7.49 – 7.41 (m, 1H), 6.48 (d, J = 8.1 Hz, 1H), 6.25 (d, J = 7.9 Hz, 1H), 5.43 (s, 2H), 5.08 (s, 2H), 4.95 – 4.72 (m, 5H), 4.52 (m, 2H), 4.39 (m, 3H), 2.81 – 2.70 (m, 2H), 2.39 (m, 3H). |

TABLE 2-continued

| Ex. | Structure | Procedure | ES/MS m/z | 1H NMR |
|---|---|---|---|---|
| 7 | mixture | 5 | 574.5 | 1H NMR (400 MHz, Methanol-d4) δ 8.15 (d, J = 1.2 Hz, 1H), 7.74 (dd, J = 11.1, 1.1 Hz, 1H), 7.59 (t, J = 7.6 Hz, 1H), 7.55 – 7.45 (m, 2H), 7.41 (t, J = 8.0 Hz, 1H), 6.29 (d, J = 8.2 Hz, 1H), 6.10 (d, J = 7.8 Hz, 1H), 5.50 – 5.29 (m, 2H), 4.73 – 4.51 (m, 2H), 4.02 (dt, J = 13.2, 4.5 Hz, 1H), 3.84 – 3.64 (m, 3H), 3.39 – 3.32 (m, 1H), 3.21 (ddd, J = 13.1, 9.9, 3.2 Hz, 1H), 3.10 (s, 3H), 2.44 (dd, J = 8.3, 5.7 Hz, 1H), 1.91 (ddd, J = 13.4, 9.8, 3.8 Hz, 1H), 1.79 (t, J = 5.5 Hz, 1H), 1.53 (ddd, J = 13.6, 9.7, 3.8 Hz, 1H), 1.40 (ddd, J = 13.6, 8.9, 4.8 Hz, 2H), 1.24 (td, J = 11.9, 10.0, 7.0 Hz, 1H). |
| 8 | 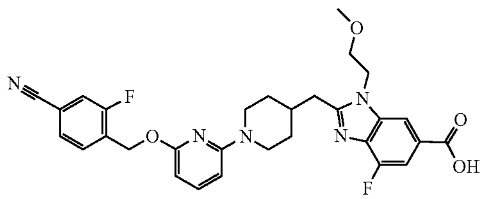 [SMILES: COCCn1c(CC2CCN(c3cccc(OCc4ccc(C#N)cc4F)n3)CC2)nc2c(F)cc(C(=O)O)cc21] | 5 | 562.2 | 1H NMR (400 MHz, Methanol-d4) δ 8.25 (d, J = 1.2 Hz, 1H), 7.81 (dd, J = 11.0, 1.1 Hz, 1H), 7.63 (t, J = 7.6 Hz, 1H), 7.58 – 7.50 (m, 2H), 7.45 (t, J = 8.0 Hz, 1H), 6.32 (d, J = 8.1 Hz, 1H), 6.14 (d, J = 7.8 Hz, 1H), 5.44 (s, 2H), 4.64 (t, J = 5.0 Hz, 2H), 4.24 (d, J = 13.2 Hz, 2H), 3.78 (t, J = 4.9 Hz, 2H), 3.27 (s, 3H), 3.08 (d, J = 7.4 Hz, 2H), 2.80 (t, J = 12.7 Hz, 2H), 2.39 – 2.19 (m, 1H), 1.74 (d, J = 12.9 Hz, 2H), 1.44 – 1.26 (m, 2H). |
| 9 | 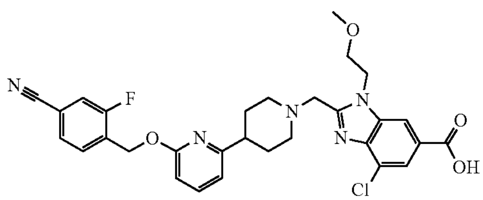 [SMILES: COCCn1c(CN2CCC(c3cccc(OCc4ccc(C#N)cc4F)n3)CC2)nc2c(Cl)cc(C(=O)O)cc21] | 6 | 578.3 | 1H NMR (400 MHz, Methanol-d4) δ 8.30 (d, J = 1.3 Hz, 1H), 8.03 (d, J = 1.3 Hz, 1H), 7.71 (dt, J = 8.3, 6.5 Hz, 2H), 7.66 – 7.55 (m, 2H), 6.97 (d, J = 7.3 Hz, 1H), 6.81 (d, J = 8.2 Hz, 1H), 5.58 (s, 2H), 4.86 (s, 2H), 4.64 (t, J = 4.8 Hz, 2H), 4.00 – 3.87 (m, 2H), 3.83 – 3.69 (m, 2H), 3.49 – 3.35 (m, 2H), 3.33 (s, 3H), 3.14 – 3.01 (m, 1H), 2.34 – 2.16 (m, 4H). |
| 10 | 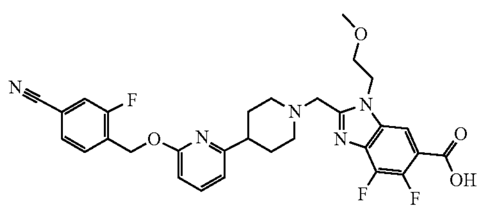 [SMILES: COCCn1c(CN2CCC(c3cccc(OCc4ccc(C#N)cc4F)n3)CC2)nc2c(F)c(F)c(C(=O)O)cc21] | 6 | 580.2 | 1H NMR (400 MHz, Methanol-d4) δ 8.07 (dd, J = 5.0, 1.6 Hz, 1H), 7.78 – 7.64 (m, 2H), 7.64 – 7.53 (m, 2H), 6.97 (d, J = 7.4 Hz, 1H), 6.81 (d, J = 8.2 Hz, 1H), 5.58 (s, 2H), 4.84 (s, 2H), 4.61 (t, J = 4.8 Hz, 2H), 3.95 (s, 2H), 3.75 (t, J = 4.8 Hz, 2H), 3.56 – 3.37 (m, 3H), 3.20 – 3.04 (m, 1H), 2.23 (s, 4H). |
| 11 | 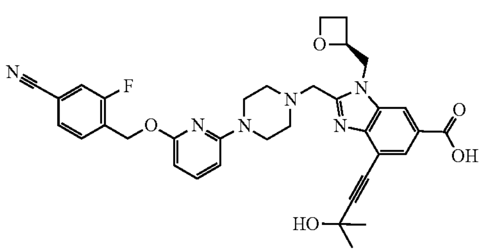 [SMILES: CC(C)(O)C#Cc1cc(C(=O)O)cc2c1nc(CN1CCN(c3cccc(OCc4ccc(C#N)cc4F)n3)CC1)n2C[C@@H]1CCO1] | 7 | 639.5 | 1H NMR (400 MHz, Methanol-d$_4$) δ 8.34 (d, J = 1.5 Hz, 1H), 8.08 (d, J = 1.4 Hz, 1H), 7.68 (t, J = 7.5 Hz, 1H), 7.64 – 7.50 (m, 3H), 6.46 (d, J = 8.1 Hz, 1H), 6.32 (d, J = 7.9 Hz, 1H), 5.49 (s, 2H), 5.22 (td, J = 7.7, 5.3 Hz, 1H), 4.85 – 4.75 (m, 3H), 4.68 (ddd, J = 13.7, 6.1, 3.1 Hz, 2H), 4.43 (dt, J = 9.2, 5.9 Hz, 1H), 3.83 (s, 4H), 3.52 (d, J = 18.8 Hz, 4H), 2.82 (dq, J = 13.8, 7.8 Hz, 1H), 2.61 – 2.29 (m, 1H), 1.65 (s, 6H). |
| 12 | 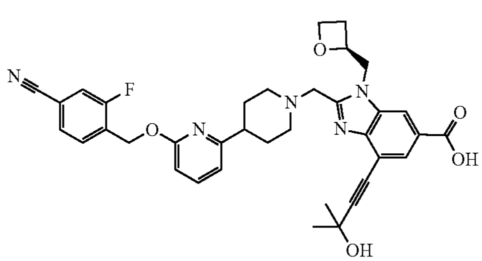 [SMILES: CC(C)(O)C#Cc1cc(C(=O)O)cc2c1nc(CN1CCC(c3cccc(OCc4ccc(C#N)cc4F)n3)CC1)n2C[C@@H]1CCO1] | 7 | 638.5 | $^1$H NMR (400 MHz, Methanol-d$_4$) δ 8.33 (d, J = 1.4 Hz, 1H), 8.08 (d, J = 1.4 Hz, 1H), 7.71 (dt, J = 8.3, 6.6 Hz, 2H), 7.66 – 7.54 (m, 2H), 6.96 (d, J = 7.3 Hz, 1H), 6.80 (dd, J = 8.3, 0.7 Hz, 1H), 5.57 (s, 2H), 5.24 (qd, J = 7.1, 2.4 Hz, 1H), 4.85 – 4.62 (m, 3H), 4.44 (dt, J = 9.3, 5.9 Hz, 1H), 3.92 (s, 2H), 3.51 – 3.38 (m, 2H), 3.33 (p, J = 1.7 Hz, 3H), 3.12 – 3.04 (m, 1H), 2.83 (ddt, J = 10.2, 5.6, 2.8 Hz, 1H), 2.50 (ddt, J = 11.6, 9.2, 7.4 Hz, 1H), 2.21 (s, 4H), 1.64 (s, 6H). |

TABLE 2-continued

| Ex. | Structure | Procedure | ES/MS m/z | ¹H NMR |
|---|---|---|---|---|
| 13 | 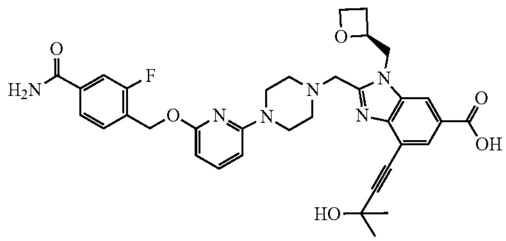 [SMILES: CC(C)(O)C#Cc1cc(C(=O)O)cc2c1nc(CN1CCN(c3cccc(OCc4ccc(C(N)=O)cc4F)n3)CC1)n2C[C@@H]1CCO1] | 7 | 657.4 | 1H NMR (400 MHz, Methanol-d4) δ 8.35 (d, J = 1.5 Hz, 1H), 8.09 (d, J = 1.4 Hz, 1H), 7.74 – 7.61 (m, 2H), 7.61 – 7.50 (m, 2H), 6.46 (d, J = 8.1 Hz, 1H), 6.32 (d, J = 7.9 Hz, 1H), 5.48 (s, 2H), 5.22 (q, J = 6.2 Hz, 1H), 4.87 (s, 2H), 4.79 (dd, J = 15.8, 6.9 Hz, 1H), 4.73 – 4.58 (m, 2H), 4.44 (dt, J = 9.2, 5.9 Hz, 1H), 3.87 (s, 4H), 3.58 (s, 4H), 2.89 – 2.71 (m, 1H), 2.49 (dt, J = 17.9, 8.1 Hz, 1H), 1.66 (s, 7H). |
| 14 | 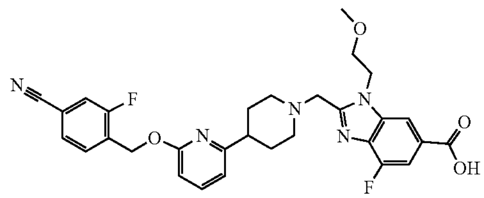 [SMILES: COCCn1c(CN2CCC(c3cccc(OCc4ccc(C#N)cc4F)n3)CC2)nc2c(F)cc(C(=O)O)cc21] | 8 | 562.4 | 1H NMR (400 MHz, Methanol-d4) δ 8.17 (d, J = 1.2 Hz, 1H), 7.69 (q, J = 6.4 Hz, 3H), 7.64 – 7.51 (m, 2H), 6.95 (d, J = 7.3 Hz, 1H), 6.79 (d, J = 8.3 Hz, 1H), 5.56 (s, 3H), 4.61 (t, J = 4.9 Hz, 2H), 3.91 (s, 2H), 3.74 (t, J = 4.8 Hz, 2H), 3.09 (d, J = 29.2 Hz, 2H), 2.20 (s, 5H), 1.43 – 1.19 (m, 2H). |
| 15 | 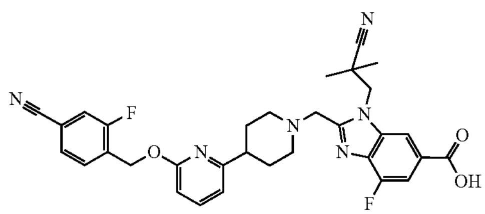 [SMILES: CC(C)(C#N)Cn1c(CN2CCC(c3cccc(OCc4ccc(C#N)cc4F)n3)CC2)nc2c(F)cc(C(=O)O)cc21] | 8 | 585.3 | 1H NMR (400 MHz, Methanol-d4) δ 8.27 (s, 1H), 7.78 – 7.63 (m, 3H), 7.63 – 7.51 (m, 2H), 6.94 (d, J = 7.3 Hz, 1H), 6.78 (d, J = 8.4 Hz, 1H), 5.56 (s, 2H), 4.94 (s, 2H), 4.67 (s, 2H), 4.00-3.90 (m, 1H), 2.15 (d, J = 40.0 Hz, 4H), 2.03 (s, 4H), 1.54 (s, 6H). |
| 16 | 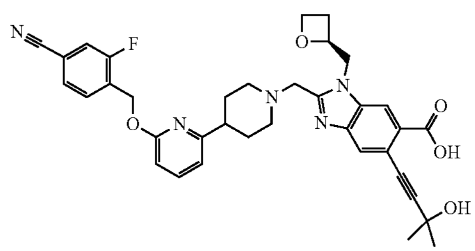 [SMILES: CC(C)(O)C#Cc1cc2nc(CN3CCC(c4cccc(OCc5ccc(C#N)cc5F)n4)CC3)n(C[C@@H]3CCO3)c2cc1C(=O)O] | 9 | 638.2 | ¹H NMR (400 MHz, DMSO-d6) δ 8.15 (s, 1H), 7.90 (d, J = 10.0 Hz, 1H), 7.77 – 7.58 (m, 4H), 6.89 (d, J = 7.4 Hz, 1H), 6.73 (d, J = 8.2 Hz, 1H), 5.48 (s, 2H), 5.10 (d, J = 5.5 Hz, 1H), 4.80 (dd, J = 15.1, 7.3 Hz, 1H), 4.65 (d, J = 14.1 Hz, 1H), 4.49 (q, J = 7.7, 7.0 Hz, 1H), 4.39 (dt, J = 8.9, 5.9 Hz, 1H), 3.94 (d, J = 13.5 Hz, 1H), 3.77 (d, J = 13.5 Hz, 1H), 2.98 (d, J = 11.0 Hz, 1H), 2.83 (d, J = 11.2 Hz, 1H), 2.76 – 2.65 (m, 1H), 2.42 (dd, J = 18.3, 8.5 Hz, 1H), 2.20 (dt, J = 25.0, 11.4 Hz, 2H), 1.84 – 1.57 (m, 4H), 1.48 (s, 6H), 1.42 – 1.28 (m, 1H). |
| 17 | 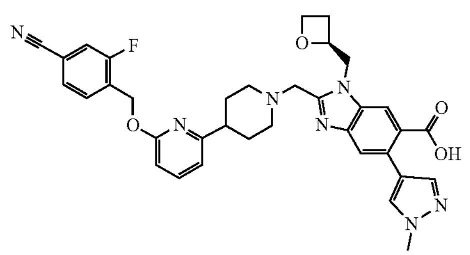 [SMILES: Cn1cc(-c2cc3nc(CN4CCC(c5cccc(OCc6ccc(C#N)cc6F)n5)CC4)n(C[C@@H]4CCO4)c3cc2C(=O)O)cn1] | 10 | 636.2 | ¹H NMR (400 MHz, DMSO-d6) δ 8.06 (s, 1H), 7.98 – 7.88 (m, 1H), 7.85 (s, 1H), 7.78 – 7.66 (m, 4H), 7.55 (s, 1H), 6.96 (d, J = 7.4 Hz, 1H), 6.81 (d, J = 8.2 Hz, 1H), 5.51 (s, 2H), 5.05 (d, J = 8.0 Hz, 1H), 4.94 – 4.73 (m, 3H), 4.64 (d, J = 15.3 Hz, 1H), 4.50 (q, J = 7.1 Hz, 1H), 4.40 – 4.27 (m, 1H), 3.88 (s, 3H), 3.32 (s, 3H), 2.95 (s, 1H), 2.80 – 2.69 (m, 1H), 2.40 – 2.28 (m, 1H), 2.08 (s, 4H), one signal overlapping with water. |
| 18 | 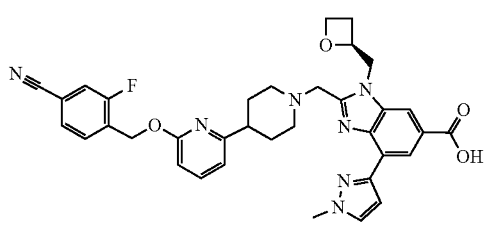 [SMILES: Cn1ccc(-c2cc(C(=O)O)cc3c2nc(CN2CCC(c4cccc(OCc5ccc(C#N)cc5F)n4)CC2)n3C[C@@H]2CCO2)n1] | 11 | 636.5 | ¹H NMR (400 MHz, CD3CN) δ 8.50 (s, 1H), 8.16 (s, 1H), 7.96 (s, 1H), 7.65 (t, J = 7.5 Hz, 1H), 7.62 – 7.56 (m, 2H), 7.52 (d, J = 8.9 Hz, 2H), 7.44 (d, J = 2.1 Hz, 1H), 6.81 (d, J = 7.2 Hz, 1H), 6.66 (d, J = 8.1 Hz, 1H), 5.48 (s, 2H), 5.16 (d, J = 7.3 Hz, 1H), 4.79 (dd, J = 14.7, 7.0 Hz, 1H), 4.71 – 4.51 (m, 2H), 4.44 (dd, J = 9.4, 5.6 Hz, 1H), 4.22 – 4.00 (m, 2H), 3.97 (s, 3H), 3.32 – 3.08 (m, 2H), 2.92 (s, 2H), 2.80 (d, J = 0.6 Hz, 2H), 2.78 – 2.61 (m, 1H), 2.48 (s, 3H), 1.85 (dt, J = 12.4, 7.8 Hz, 2H). |

TABLE 2-continued

Compounds

| Ex. | Structure | Procedure | ES/MS m/z | ¹H NMR |
|---|---|---|---|---|
| 19 | 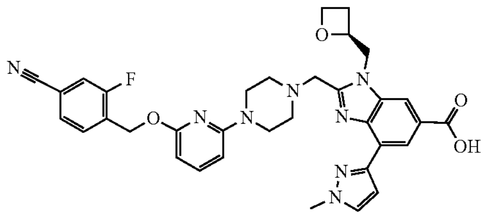 [SMILES: Cn1ccc(-c2cc(C(=O)O)cc3c2nc(CN2CCN(c4cccc(OCc5ccc(C#N)cc5F)n4)CC2)n3C[C@@H]2CCO2)n1] | 12 | 637.5 | ¹H NMR (400 MHz, CD3CN) δ 8.49 (s, 1H), 8.17 (s, 1H), 7.65 – 7.55 (m, 2H), 7.55 – 7.41 (m, 3H), 7.38 (d, J = 2.1 Hz, 1H), 6.25 (d, J = 8.0 Hz, 1H), 6.14 (d, J = 7.8 Hz, 1H), 5.42 (s, 2H), 5.15 (d, J = 7.2 Hz, 1H), 4.77 (dd, J = 15.4, 7.0 Hz, 1H), 4.68 – 4.50 (m, 2H), 4.43 (dt, J = 8.7, 5.7 Hz, 1H), 4.24 – 4.01 (m, 2H), 3.99 (s, 3H), 3.50 (d, J = 5.1 Hz, 4H), 2.73 (s, 5H), 2.55 – 2.33 (m, 1H). |
| 20 | 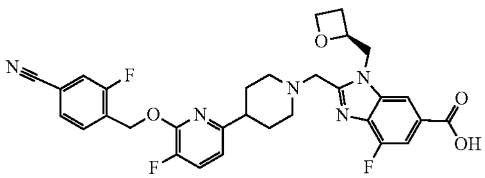 [SMILES: N#Cc1ccc(COc2nc(C3CCN(Cc4nc5c(F)cc(C(=O)O)cc5n4C[C@@H]4CCO4)CC3)ccc2F)c(F)c1] | 13 | 592.2 | ¹H NMR (400 MHz, DMSO) δ 8.28 (s, 2H), 7.93 (d, J = 9.9 Hz, 1H), 7.77 (d, J = 5.8 Hz, 2H), 7.73 – 7.66 (m, 1H), 7.63 (d, J = 11.1 Hz, 1H), 7.00 (s, 1H), 5.60 (s, 2H), 5.05 (d, J = 7.0 Hz, 2H), 4.85 (d, J = 15.6 Hz, 4H), 4.71 (d, J = 15.3 Hz, 1H), 4.49 (s, 2H), 4.43 – 4.23 (m, 2H), 2.92 (d, J = 16.8 Hz, 1H), 2.80 – 2.63 (m, 2H), 2.33 (s, 2H). |
| 21 | 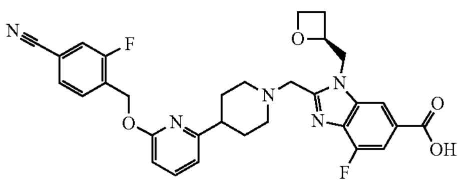 [SMILES: N#Cc1ccc(COc2cccc(C3CCN(Cc4nc5c(F)cc(C(=O)O)cc5n4C[C@@H]4CCO4)CC3)n2)c(F)c1] | 13 | 574.3 | 1H NMR (400 MHz, Methanol-d4) δ 8.19 (d, J = 1.3 Hz, 1H), 7.76 – 7.62 (m, 3H), 7.58 (td, J = 9.9, 1.5 Hz, 2H), 6.93 (d, J = 7.3 Hz, 1H), 6.78 (d, J = 8.2 Hz, 1H), 5.55 (s, 2H), 5.22 (qd, J = 7.1, 2.4 Hz, 1H), 4.86-4.71 (m, 2H), 4.72 – 4.59 (m, 2H), 4.44 (dd, J = 9.1, 5.6 Hz, 1H), 3.91 (s, 2H), 3.56 – 3.35 (m, 2H), 3.09 (d, J = 33.3 Hz, 1H), 2.81 (dtd, J = 11.6, 8.1, 5.9 Hz, 1H), 2.49 (tt, J = 10.6, 7.5 Hz, 1H), 2.17 (s, 4H). |
| 22 | 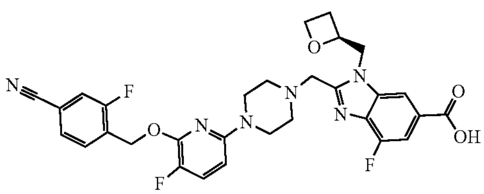 [SMILES: N#Cc1ccc(COc2nc(N3CCN(Cc4nc5c(F)cc(C(=O)O)cc5n4C[C@@H]4CCO4)CC3)ccc2F)c(F)c1] | 14 | 593.2 | ¹H NMR (400 MHz, CD3CN) δ 8.04 (s, 1H), 7.66 (t, J = 7.6 Hz, 1H), 7.60 – 7.48 (m, 3H), 7.40 (dd, J = 10.0, 8.6 Hz, 1H), 6.29 (dd, J = 8.6, 1.8 Hz, 1H), 5.52 (s, 2H), 5.11 (d, J = 7.3 Hz, 1H), 4.78 (dd, J = 15.8, 7.2 Hz, 1H), 4.59 (d, J = 7.2 Hz, 4H), 4.53 – 4.41 (m, 1H), 3.67 (s, 4H), 3.38 (s, 4H), 2.75 (q, J = 8.6 Hz, 1H), 2.44 (t, J = 9.8 Hz, 1H). |
| 23 | 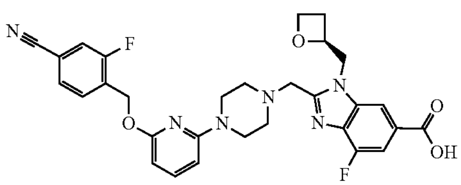 [SMILES: N#Cc1ccc(COc2cccc(N3CCN(Cc4nc5c(F)cc(C(=O)O)cc5n4C[C@@H]4CCO4)CC3)n2)c(F)c1] | 14 | 575.5 | 1H NMR (400 MHz, Methanol-d4) δ 8.22 (d, J = 1.2 Hz, 1H), 7.77 – 7.64 (m, 2H), 7.64 – 7.52 (m, 3H), 6.47 (d, J = 8.1 Hz, 1H), 6.32 (d, J = 7.9 Hz, 1H), 5.49 (s, 2H), 5.23 (qd, J = 7.1, 2.4 Hz, 1H), 4.79 (dd, J = 15.8, 6.9 Hz, 1H), 4.75 – 4.63 (m, 2H), 4.45 (dt, J = 9.3, 5.9 Hz, 1H), 3.86 (s, 4H), 3.61 (s, 4H), 2.83 (dtd, J = 11.5, 8.2, 6.0 Hz, 1H), 2.50 (ddt, J = 11.5, 9.2, 7.3 Hz, 1H). |
| 24 | 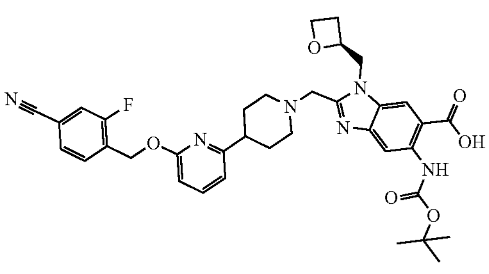 [SMILES: CC(C)(C)OC(=O)Nc1cc2nc(CN3CCC(c4cccc(OCc5ccc(C#N)cc5F)n4)CC3)n(C[C@@H]3CCO3)c2cc1C(=O)O] | 15 | 671.2 | ¹H NMR (400 MHz, CD3CN) 10.57 (s, 1H), 8.61 (s, 1H), 8.32 (s, 1H), 7.76 – 7.62 (m, 2H), 7.59 – 7.51 (m, 2H), 6.90 (d, J = 7.3 Hz, 1H), 6.75 (d, J = 8.2 Hz, 1H), 5.51 (s, 2H), 5.14 (d, J = 7.3 Hz, 1H), 4.66 (s, 4H), 4.60 – 4.41 (m, 2H), 3.95 – 3.68 (m, 2H), 3.43 – 3.26 (m, 2H), 2.48 (s, 1H), 2.20 – 2.03 (m, 4H), 2.00 (d, J = 2.8 Hz, 2H), 1.55 (s, 9H). |
| 25 | 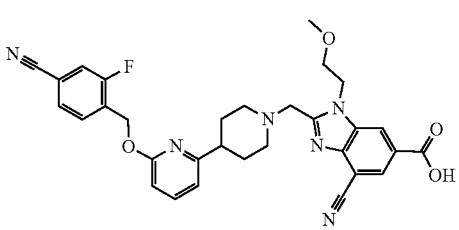 [SMILES: COCCn1c(CN2CCC(c3cccc(OCc4ccc(C#N)cc4F)n3)CC2)nc2c(C#N)cc(C(=O)O)cc21] | 16 | 569.7 | 1H NMR (400 MHz, Methanol-d4) δ 8.65 (d, J = 1.3 Hz, 1H), 8.39 (d, J = 1.3 Hz, 1H), 7.71 (td, J = 7.7, 3.9 Hz, 2H), 7.62 (ddd, J = 14.5, 8.9, 1.4 Hz, 2H), 6.98 (d, J = 7.3 Hz, 1H), 6.82 (d, J = 8.3 Hz, 1H), 5.59 (s, 2H), 4.91 (s, 2H), 4.68 (t, J = 4.9 Hz, 2H), 4.08 – 3.87 (m, 2H), 3.77 (t, J = 4.8 Hz, 2H), 3.50 – 3.37 (m, 2H), 3.33 (s, 3H), 3.12 – 3.01 (m, 1H), 2.42 – 2.13 (m, 4H). |

TABLE 2-continued

| Ex. | Structure | Procedure | ES/MS m/z | ¹H NMR |
|---|---|---|---|---|
| 26 | 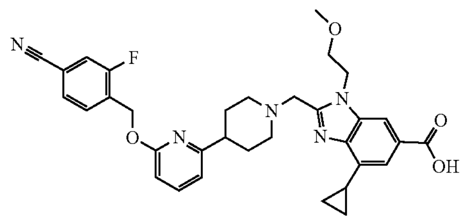 [SMILES: COCCn1c(CN2CCC(c3cccc(OCc4ccc(C#N)cc4F)n3)CC2)nc2c(C3CC3)cc(C(=O)O)cc21] | 17 | 584.4 | 1H NMR (400 MHz, Methanol-d4) δ 8.10 (d, J = 1.5 Hz, 1H), 7.71 (dd, J = 8.3, 7.3 Hz, 2H), 7.66 – 7.52 (m, 3H), 6.98 (d, J = 7.3 Hz, 1H), 6.81 (dd, J = 8.3, 0.7 Hz, 1H), 5.57 (s, 2H), 4.82 (s, 2H), 4.61 (t, J = 4.8 Hz, 2H), 3.95 (d, J = 12.3 Hz, 2H), 3.76 (dd, J = 5.3, 4.2 Hz, 2H), 3.49 – 3.38 (m, 2H), 3.33 (s, 3H), 3.09 (p, J = 7.7 Hz, 1H), 2.70 – 2.56 (m, 1H), 2.23 (q, J = 5.4, 5.0 Hz, 4H), 1.21 – 1.12 (m, 2H), 1.12 – 1.02 (m, 2H). |
| 27 | 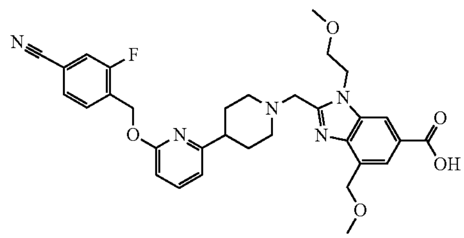 [SMILES: COCCn1c(CN2CCC(c3cccc(OCc4ccc(C#N)cc4F)n3)CC2)nc2c(COC)cc(C(=O)O)cc21] | 18 | 588.5 | 1H NMR (400 MHz, Methanol-d4) δ 8.30 (d, J = 1.5 Hz, 1H), 8.06 (d, J = 1.4 Hz, 1H), 7.78 – 7.66 (m, 2H), 7.66 – 7.53 (m, 2H), 6.98 (d, J = 7.3 Hz, 1H), 6.88 – 6.75 (m, 1H), 5.58 (s, 2H), 4.96 (s, 2H), 4.84 (s, 2H), 4.63 (t, J = 4.8 Hz, 2H), 3.92 (d, J = 12.3 Hz, 2H), 3.85 – 3.71 (m, 2H), 3.49 (s, 3H), 3.47 – 3.40 (m, 2H), 3.32 (s, 3H), 3.14 – 3.01 (m, 1H), 2.40 – 2.15 (m, 4H). |
| 28 | 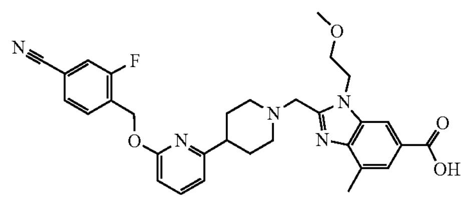 [SMILES: COCCn1c(CN2CCC(c3cccc(OCc4ccc(C#N)cc4F)n3)CC2)nc2c(C)cc(C(=O)O)cc21] | 19 | 558.6 | 1H NMR (400 MHz, Methanol-d4) δ 8.16 (t, J = 1.0 Hz, 1H), 7.85 (t, J = 1.2 Hz, 1H), 7.71 (ddd, J = 8.3, 7.2, 1.6 Hz, 2H), 7.64 – 7.54 (m, 2H), 6.97 (d, J = 7.3 Hz, 1H), 6.81 (dd, J = 8.3, 0.7 Hz, 1H), 5.57 (s, 2H), 4.81 (s, 2H), 4.62 (t, J = 4.8 Hz, 2H), 3.92 (d, J = 12.4 Hz, 2H), 3.83 – 3.72 (m, 2H), 3.48 – 3.38 (m, 2H), 3.33 (s, 3H), 3.08 (p, J = 7.7 Hz, 1H), 2.70 (s, 3H), 2.32 – 2.14 (m, 4H). |
| 29 | 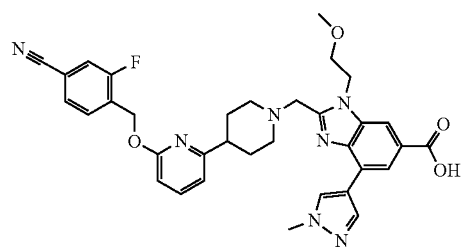 [SMILES: COCCn1c(CN2CCC(c3cccc(OCc4ccc(C#N)cc4F)n3)CC2)nc2c(-c3cnn(C)c3)cc(C(=O)O)cc21] | 20 | 624.4 | 1H NMR (400 MHz, Methanol-d4) δ 8.52 (s, 1H), 8.42 (s, 1H), 8.24 (d, J = 1.4 Hz, 1H), 8.17 (d, J = 1.4 Hz, 1H), 7.72 (dd, J = 8.2, 7.2 Hz, 2H), 7.66 – 7.54 (m, 2H), 6.99 (d, J = 7.3 Hz, 1H), 6.82 (dd, J = 8.3, 0.7 Hz, 1H), 5.56 (s, 2H), 4.89 (s, 2H), 4.64 (t, J = 4.8 Hz, 2H), 4.04 – 3.98 (m, 2H), 4.01 (s, 3H), 3.85 – 3.74 (m, 2H), 3.56 – 3.43 (m, 2H), 3.33 (s, 3H), 3.14 – 3.06 (m, 2H), 2.37 – 2.17 (m, 4H). |
| 30 | 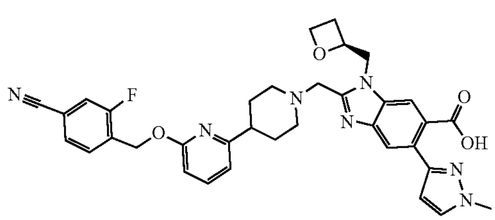 [SMILES: Cn1ccc(-c2cc3nc(CN4CCC(c5cccc(OCc6ccc(C#N)cc6F)n5)CC4)n(C[C@@H]4CCO4)c3cc2C(=O)O)n1] | 21 | 636.2 | ¹H NMR (400 MHz, DMSO) 7.90 (d, J = 10.2 Hz, 2H), 7.71 (d, J = 2.8 Hz, 2H), 7.65 (dd, J = 8.2, 7.3 Hz, 1H), 7.56 (s, 2H), 7.53 (s, 1H), 6.89 (d, J = 7.3 Hz, 1H), 6.72 (d, J = 8.2 Hz, 1H), 5.48 (s, 2H), 5.10 (d, J = 6.9 Hz, 1H), 4.65 (s, 2H), 4.57 (d, J = 13.9 Hz, 1H), 4.49 (q, J = 7.2 Hz, 1H), 4.39 (dt, J = 9.1, 5.9 Hz, 1H), 3.88 (d, J = 13.4 Hz, 1H), 3.74 (d, J = 13.3 Hz, 1H), 3.66 (s, 3H), 2.97 (d, J = 11.3 Hz, 1H), 2.85 (d, J = 11.2 Hz, 1H), 2.59 (s, 1H), 2.26 – 2.09 (m, 2H), 1.86 – 1.61 (m, 5H). |
| 31 | 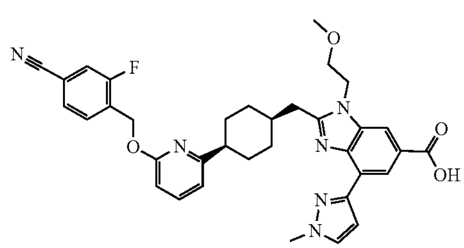 [SMILES: COCCn1c(C[C@H]2CC[C@@H](c3cccc(OCc4ccc(C#N)cc4F)n3)CC2)nc2c(-c3ccn(C)n3)cc(C(=O)O)cc21] | 22 | 623.7 | 1H NMR (400 MHz, DMSO-d6) δ 8.44(d, J = 1.5 Hz, 1H), 8.16 (s, 1H), 7.96– 7.85 (m, 1H), 7.82 (d, J = 2.2 Hz, 1H), 7.70 (dd, J = 3.7, 1.0 Hz, 2H), 7.64 (dd, J = 8.2, 7.3 Hz, 1H), 7.36 (s, 1H), 6.87 J = 7.3 Hz, 1H), 6.71 J = 8.2 Hz, 1H), 5.46 (s, 2H), 4.60 (s, 2H), 3.98 (s, 3H), 3.71 (t, J = 5.0 Hz, 2H), 3.22 (s, 3H), 3.02 (s, 2H), 2.63 – 2.55 (m, 1H), 2.08 (s, 1H), 2.07 – 1.99 (m, 1H), 1.95 – 1.78 (m, 4H), 1.59 – 1.42 (m, 2H), 1.30 (q, J = 12.8 Hz, 2H). |

TABLE 2-continued

Compounds

| Ex. | Structure | Procedure | ES/MS m/z | ¹H NMR |
|---|---|---|---|---|
| 32 | (structure) | 22 | 623.6 | 1H NMR (400 MHz, DMSO-d6) δ 8.43 (d, J = 1.5 Hz, 1H), 8.18 (s, 1H), 7.94 – 7.87 (m, 1H), 7.81 (d, J = 2.2 Hz, 1H), 7.78 – 7.61 (m, 3H), 7.42 – 7.25 (m, 1H), 6.99 (d, J = 7.3 Hz, 1H), 6.75 (d, J = 8.2 Hz, 1H), 5.52 (s, 2H), 4.59 (d, J = 5.5 Hz, 2H), 3.97 (s, 3H), 3.69 (t, J = 5.0 Hz, 2H), 3.18 (s, 3H), 3.09 (d, J = 7.3 Hz, 2H), 2.77 (s, 1H), 2.40 (s, 1H), 2.00 (d, J = 7.7 Hz, 2H), 1.75 – 1.48 (m, 6H). |

C. Biological Data

GLP-1R Activation—cAMP Assay 1

GLP-1R activation by a compound of the present disclosure was quantified by measuring cAMP increase in CHO cells stably expressing GLP-1R (MultiSpan product #C1267-1a). The cells were harvested and plated in growth medium (DMEM/F-12 (Corning product #10-090-CV) supplemented with 10% FBS (HyClone product #SH30071-03), penicillin/streptomycin (Corning product #30-002CI) and 10 g/ml puromycin (Gibco product #A11138-03)) at 1,000 cells/well in a 384-well plate (Greiner product #781080). The cells were then incubated overnight at 37° C., 5% $CO_2$. The next day, the medium was removed and the cells were washed with DPBS (Corning product #21-031-CM) before adding the assay medium (HBSS, Corning product #21-023-CV) with 20 mM Hepes (Gibco product #15630-080) and 0. 1% BSA (Rockland Immunochemicals product #BSA-1000)). Following the medium change, the cells were incubated for 1 hour at 37° C., 5% $CO_2$. The tested GLP-1 compound was added to the cells in a 10 point dose response followed by a 30 minutes incubation at 37° C., 5% $CO_2$. cAMP concentration increase was then detected using Cisbio's cAMP Gs Dynamic Kit (product #62AM4PEC) according to the manufacturer's protocol. The response was plotted against the log of the agonist concentration and fitted to a sigmoidal equation to determine the $EC_{50}$.

GLP-1R Activation—cAMP Assay 2

GLP-1R activation by small molecule agonists is quantified by measuring cAMP increase in CHO cells stably expressing GLP-1R (MultiSpan product #C1267-1a). 50 nL of agonists are pre-spotted in a 10 point dose response onto 384-well plate (Corning product #CL3826) using the Labcyte Echo System. The cells are harvested and plated in assay buffer (HBSS (Corning product #21-023-CV) with 20 mM Hepes (Gibco product #15630-080) and 0.1% BSA (Rockland Immunochemicals product #BSA-1000)) or 100% Human Plasma (Innovative Research product #50-643-396) at 1,000 cells/well, 10 L/well, onto the pre-spotted plates. The cells are then incubated for 30 minutes at 37° C., 5% $CO_2$. cAMP concentration increase is then detected using Cisbio's cAMP Gs Dynamic Kit (product #62AM4PEC) according to the manufacturer's protocol. The response is plotted against the log of the agonist concentration and fitted to a sigmoidal equation to determine the $EC_{50}$.

TABLE 3

| | Activity | |
|---|---|---|
| Example No. | GLP-1R Activation-Assay 1 EC50 (nm) | GLP-1R Activation-Assay 2 EC50 (nm) |
| 1 | | 15.1 |
| 2 | | 174.5 |
| 3 | | 1.9 |
| 4 | | 1.2 |
| 5 | | 9.8 |
| 6 | | 2.6 |
| 7 | 3.8 | 10.3 |
| 8 | 5.3 | 13.2 |
| 9 | 6.6 | 2.6 |
| 10 | 18.2 | 11.3 |
| 11 | | 1.7 |
| 12 | | 0.81 |
| 13 | | 31.9 |
| 14 | 1.04 | |
| 15 | 0.24 | |
| 16 | | 28.8 |
| 17 | | 13.3 |
| 18 | | 0.98 |
| 19 | | 0.3 |
| 20 | | 0.07 |
| 21 | | 0.038 |
| 22 | | 0.22 |
| 23 | | 0.031 |
| 24 | | 0.51 |
| 25 | 3.5 | 7.1 |
| 26 | 53.9 | 47.8 |
| 27 | 14.6 | |
| 28 | 21 | |
| 29 | 104.4 | |
| 30 | | 52.2 |
| 31 | | 133.6 |
| 32 | | 10.6 |

Although the foregoing has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A compound, or a pharmaceutically acceptable salt thereof, wherein the compound has the structure:
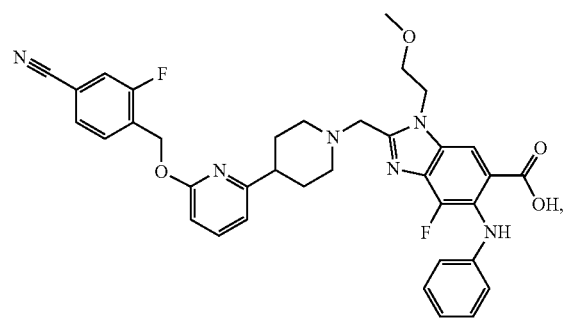
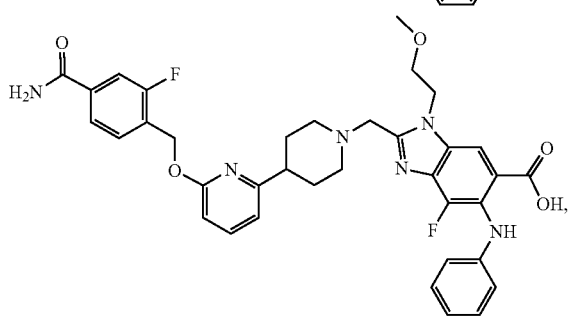
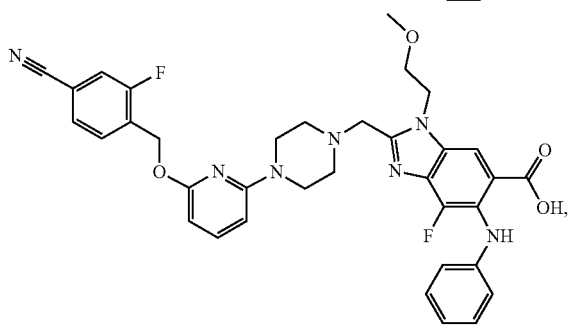
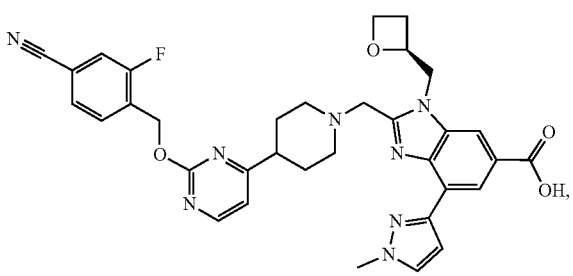
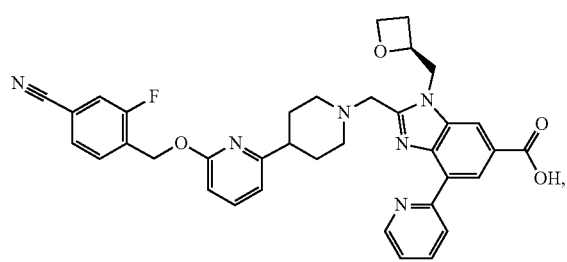
-continued
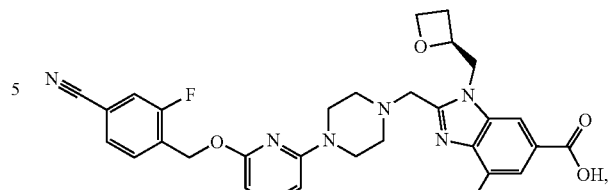
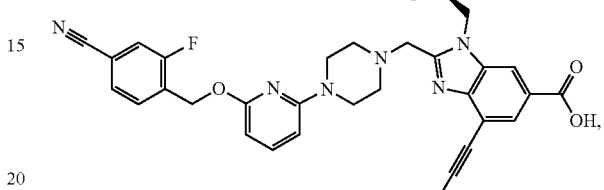
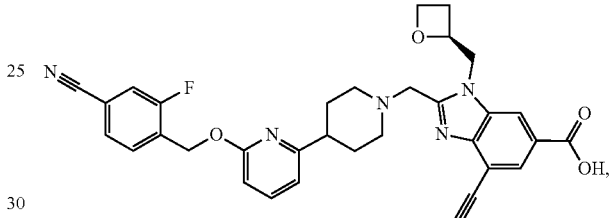
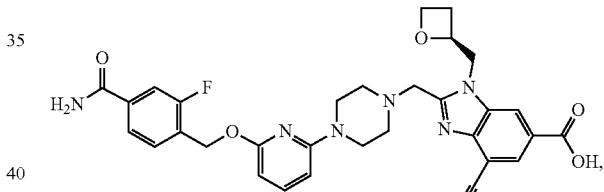
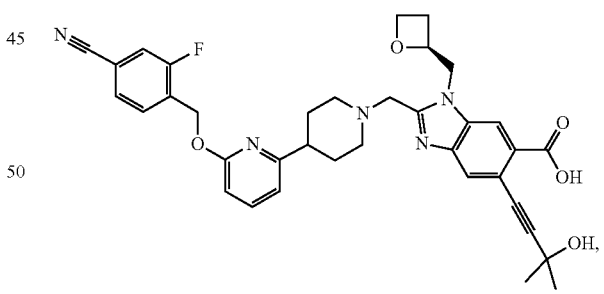
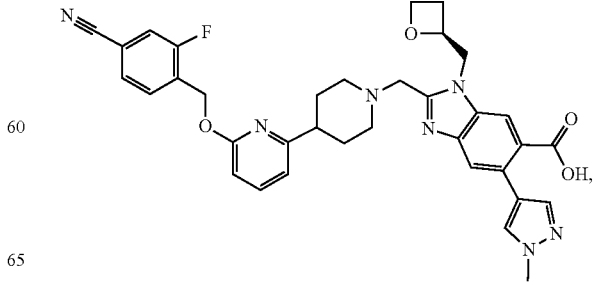

-continued

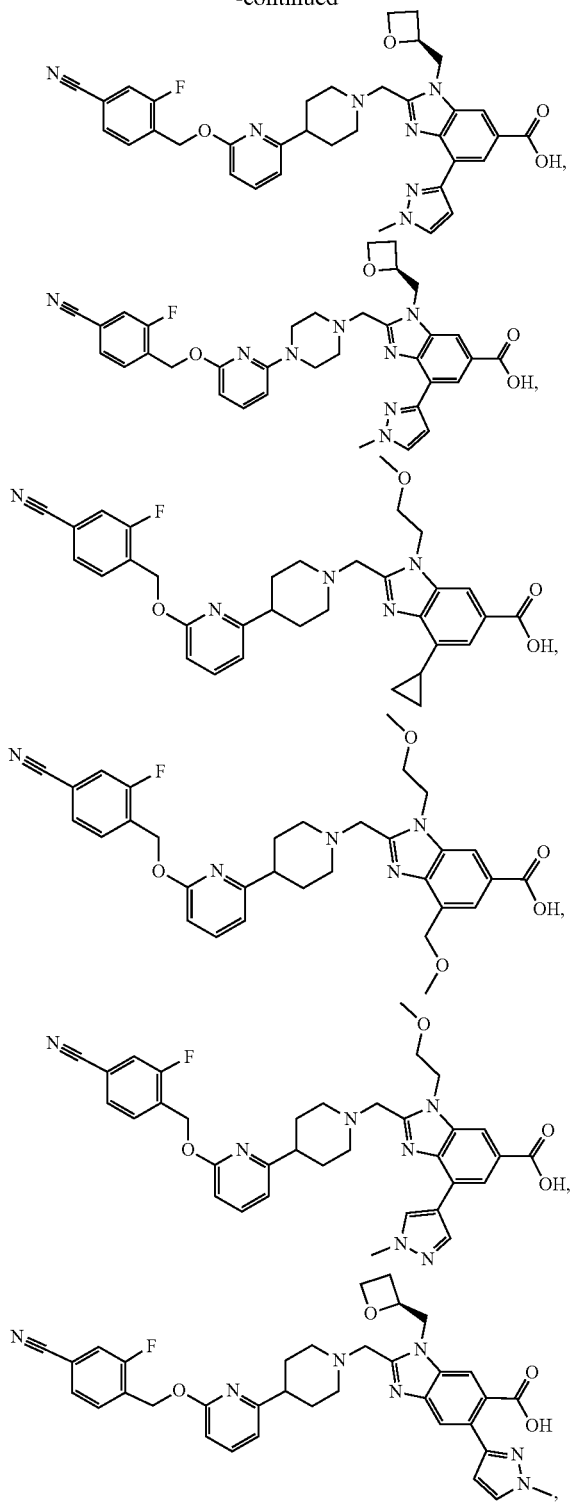

-continued

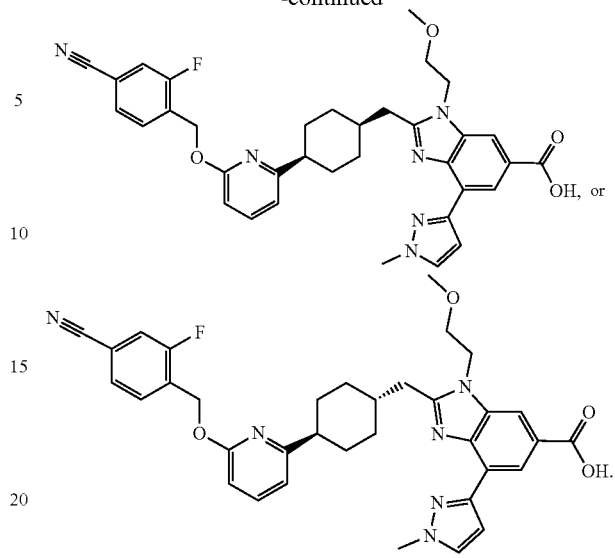

2. A pharmaceutical composition comprising a pharmaceutically effective amount of a compound of claim 1, or a pharmaceutically acceptable salt thereof, and a pharmaceutically acceptable carrier or excipient.

3. The pharmaceutical composition of claim 2 further comprising one or more additional therapeutic agents.

4. The pharmaceutical composition of claim 3, wherein the additional therapeutic agent comprises an anti-obesity agent selected from peptide YY , a neuropeptide Y receptor type 2 (NPYR2) agonist, a N PYR 1 agonist, an NPYR5 antagonist, a cannabinoid receptor type 1 (CB1 R) antagonist, a lipase inhibitor, a human proislet peptide (HIP), a melanocortin receptor 4 agonist (MC4R), a melanin concentrating hormone receptor 1 antagonist, a farnesoid X receptor (FXR) agonist, an apoptotic signal-regulating kinase (ASK-1) inhibitor, zonisamide, phentermine (alone or in combination with topiramate), a norepinephrine/dopa mine reuptake inhibitor, an opioid receptor antagonist, a combination of a norepinephrine/dopa mine reuptake inhibitor and an opioid receptor antagonist, sibutramine, a cholecystokinin agonist, amylin, leptin , a serotonergic agent, a methionine aminopeptidase 2 (MetAP2) inhibitor, phendimetrazine, diethylpropion, benzphetamine, an SGLT2 inhibitor , an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, a glucagon receptor agonist (alone or in combination with another GLP-1R agonist , a peroxisome proliferator-activated receptor alpha (PPARα) agonist, fish oil, an acetyl-coA carboxylase (ACC) inhibitor, a TGFβ antagonist, GFRAL agonist, and/or a pharmaceutically acceptable salt thereof.

* * * * *